:::
(12) United States Patent
Laing et al.

(10) Patent No.: US 9,157,088 B2
(45) Date of Patent: Oct. 13, 2015

(54) TRANSFERASES, EPIMERASES, POLYNUCLEOTIDES ENCODING THESE AND USES THEREOF

(75) Inventors: William Laing, Auckland (NZ); Sean Bulley, Auckland (NZ)

(73) Assignee: The New Zealand Institute for Plant and Food Research Limited, Auckland (NZ)

( * ) Notice: Subject to any disclaimer, the term of this patent is extended or adjusted under 35 U.S.C. 154(b) by 691 days.

(21) Appl. No.: 12/530,416

(22) PCT Filed: Mar. 7, 2008

(86) PCT No.: PCT/NZ2008/000042
§ 371 (c)(1),
(2), (4) Date: Nov. 20, 2009

(87) PCT Pub. No.: WO2008/108668
PCT Pub. Date: Sep. 12, 2008

(65) Prior Publication Data
US 2010/0077503 A1    Mar. 25, 2010

(30) Foreign Application Priority Data

Mar. 8, 2007 (NZ) .................................. 553705
Jul. 6, 2007 (NZ) .................................. 556389

(51) Int. Cl.
*C12N 15/82* (2006.01)
*C12N 9/12* (2006.01)
*C12N 9/90* (2006.01)

(52) U.S. Cl.
CPC .......... *C12N 15/8243* (2013.01); *C12N 9/1241* (2013.01); *C12N 9/90* (2013.01)

(58) Field of Classification Search
USPC ........................................................ 800/278
See application file for complete search history.

(56) References Cited

U.S. PATENT DOCUMENTS

| | | | |
|---|---|---|---|
| 4,795,855 A | 1/1989 | Fillatti et al. | |
| 5,004,863 A | 4/1991 | Umbeck | |
| 5,159,135 A | 10/1992 | Umbeck | |
| 5,177,010 A | 1/1993 | Goldman et al. | |
| 5,187,073 A | 2/1993 | Goldman et al. | |
| 5,188,958 A | 2/1993 | Moloney et al. | |
| 5,416,011 A | 5/1995 | Hinchee et al. | |
| 5,463,174 A | 10/1995 | Moloney et al. | |
| 5,563,055 A | 10/1996 | Townsend et al. | |
| 5,569,834 A | 10/1996 | Hinchee et al. | |
| 5,591,616 A | 1/1997 | Hiei et al. | |
| 5,750,871 A | 5/1998 | Moloney et al. | |
| 5,792,935 A | 8/1998 | Arntzen et al. | |
| 5,824,877 A | 10/1998 | Hinchee et al. | |
| 5,846,797 A | 12/1998 | Strickland | |
| 5,952,543 A | 9/1999 | Firoozabady et al. | |
| 5,968,830 A | 10/1999 | Dan et al. | |
| 5,981,840 A | 11/1999 | Zhao et al. | |
| 6,020,539 A | 2/2000 | Goldman et al. | |
| 6,037,522 A | 3/2000 | Dong et al. | |
| 6,074,877 A | 6/2000 | D'Halluin et al. | |
| 7,214,786 B2 | 5/2007 | Kovalic et al. | |
| 7,834,146 B2* | 11/2010 | Kovalic et al. | ................ 530/350 |
| 2004/0031072 A1 | 2/2004 | La Rosa et al. | |
| 2004/0034888 A1 | 2/2004 | Liu et al. | |
| 2004/0123343 A1 | 6/2004 | La Rosa et al. | |
| 2004/0172684 A1 | 9/2004 | Kovalic et al. | |
| 2004/0214272 A1 | 10/2004 | La Rosa et al. | |
| 2004/0216190 A1 | 10/2004 | Kovalic | |
| 2006/0021088 A1* | 1/2006 | Inze et al. | ..................... 800/281 |
| 2006/0048240 A1 | 3/2006 | Alexandrov et al. | |
| 2006/0123505 A1 | 6/2006 | Kikuchi et al. | |
| 2006/0150283 A1 | 7/2006 | Alexandrov et al. | |
| 2006/0236419 A1 | 10/2006 | La Rosa et al. | |

FOREIGN PATENT DOCUMENTS

| WO | 02/00894 | 1/2002 |
|---|---|---|
| WO | 03/057877 | 7/2003 |
| WO | 03/077648 | 9/2003 |

OTHER PUBLICATIONS

Thomas et al., Plant J., 2001, vol. 25.*
Klahre et al., PNAS, 2002, vol. 99.*
Jander et al., Plant Physiology, 2002, vol. 129.*
Major et al., Journal of American Chemical Society, 2005, vol. 127.*
Conklin et al., Genetics, 2000, vol. 154.*
Roberts, Fast-track applications: The potential for direct delivery of proteins and nucleic acids to plant cells for the discovery of gene function, 1 Plant Methods (2005).*
Chang et al., Cellular Internalization of Fluorescent Proteins via Arginine-rich Intracellular Delivery Peptide in Plant Cells, 46 Plant Cell Physiol. No. 3, 482-488 (2005)).*
Agius et al. (Engineering increased vitamin C levels in plants by overexpression of a D-galacturonic acid reductase, 21 Nature Biotech 177-181 (2003)).*
GenBank Database Accession No. CAG03444.1 (Mar. 17, 2004) "unnamed protein product [Tetraodon nigroviridis]".

(Continued)

*Primary Examiner* — Russell Kallis
(74) *Attorney, Agent, or Firm* — Lathrop & Gage LLP

(57) ABSTRACT

The invention provides compositions and methods for modulating GDP-L-Galactose Guanyltransferase (also known as GDP-L-Galactose phosphorylase) activity; and/or GDP-D-Mannose epimerase activity; and/or ascorbate content in plants. The invention provides plants and plant cells with increased GDP-L-Galactose Guanyltransferase activity; and/or GDP-D-Mannose epimerase activity. The invention provides plants and plant cells with increased ascorbate content as a result of: over-expression of GDP-L-Galactose Guanyltransferase; over-expression of GDP-D-Mannose epimerase; or in particular over-expression of a combination of GDP-L-Galactose Guanyltransferase and GDP-D-Mannose epimerase.

21 Claims, 40 Drawing Sheets

(56) References Cited

OTHER PUBLICATIONS

NCBI Database Accession No. NP_200323.1 (Aug. 21, 2009) "VTC5 (Vitamin C Defective 5); GDP-D-glucose phosphorylase/galactose-1-phosphate guanylyltransferase (GDP)/ quercetin 4'-Oglucosyltransferase [Arabidopsis thaliana]".
NCBI Database Accession No. NP_915203.1 (Nov. 9, 2004) "P0035F12.16 [Oryza sativa (japonica cultivar-group)]".
NCBI Database Accession No. XP_689388.1 (Jun. 30, 2005) "Predicted: similar to VTC2 like (52.7 kD) (5G449) [Danio rerio]".
NCBI Database Accession No. NP_001071021.1 (Nov. 18, 2006) "GDP-D-glucose phosphorylase C15orf58 homolog [Danio rerio]".
Buell et al. (Jul. 7, 2006) GenBank Database Accession No. ABA96028.1, "VTC2, putative, expressed [Oryza sativa Japonica Group]".
Carninci et al. (Oct. 6, 2010) GenBank Database Accession No. BAE25508.1, "unnamed protein product [Mus musculus]".
Kanehori et al. (Sep. 14, 2006) GenBank Database Accession No. BAC85370.1, "unnamed protein product [Homo sapiens]".
Kirkness et al. (May 11, 2004) GenBank Database Accession No. BT013858.1, "Lycopersicon esculentum clone 132824R, mRNA sequence".
Klein et al. (Jun. 9, 2008) GenBank Database Accession No. AAI21599.1, "UPF0580 protein [Xenopus (Silurana) tropicalis]".
Laing et al. (May 2, 2005) GenBank Database Accession No. AAO18639.1 "galactose dehydrogenase [Actinidia deliciosa]".
Matsumoto et al. (Aug. 7, 2009) GenBank Database Accession No. BAF29357.1, "Os12g0190000 [Oryza sativa Japonica Group]".
Shinn et al. (May 6, 2003) GenBank Database Accession No. AAP31933.1, "At4g26850 [Arabidopsis thaliana]".
Yamada et al. (Sep. 18, 2002) GenBank Database Accession No. AAM14224.1 "unknown protein [Arabidopsis thaliana]".
International Preliminary Report on Patentability, corresponding to International Application No. PCT/NZ2008/000042, parent of the present application, dated Jan. 13, 2009, 14 pp.
Search Report and Written Opinion corresponding to International Application No. PCT/NZ2008/000042, parent of the present application, dated Jun. 20, 2008, 11 pp.
Abbott et al. (2002) "Simultaneous Suppression of Multiple Genes by Single Transgenes. Down-Regulation of Three Unrelated Lignin Biosynthetic Genes in Tobacco," Plant Physiol. 128(3):844-853.
Agius et al. (2003) "Engineering increased vitamin C levels in plants by overexpression of a D-galacturonic acid reductase," Nat Biotechnol 21:177-181.
Alam et al. (1999) "Transgenic insect-resistant maintainer line (IR68899B) for improvement of hybrid rice," Plant Cell Reports 18:572-575.
Altschul et al. (1990) "Basic Local Alignment Search Tool," J. Mol. Biol. 215:403-410.
Altschul et al. (1997) "Gapped BLAST and PSI-BLAST: a new generation of protein database search programs," Nucleic Acids Res 25(17):3389-3402.
Bailey et al. (Aug. 1994) "Fitting a mixture model by expectation maximization to discover motifs in biopolymers," Proceedings of the Second International Conference on Intelligent Systems for Molecular Biology. AAAI Press, Menlo Park, California, pp. 28-36.
Bailey et al. (1994) "Fitting a mixture model by expectation maximization to discover motifs in biopolymers," UCSD Technical Report CS94-351, 33 pp.
Bartoli et al. (2005) "Ascorbate content of wheat leaves is not determined by maximal L-galactono-1,4-lactone dehydrogenase (GalLDH) activity under drought stress," Plant, Cell and Environment 28:1073-1081.
Birch, R.G. (1997) "Plant Transformation: Problems and Strategies for Practical Application," Ann Rev Plant Phys Plant Mol Biol 48:297-326.
Brenner et al. (Mar. 1997) "Crystal structures of HINT demonstrate that histidine triad proteins are GalT-related nucleotide-binding proteins," Nat Struct Biol 4(3):231-238.
Brenner (2002) "Hint, Fhit, and GalT: Function, Structure, Evolution, and Mechanism of Three Branches of the Histidine Triad Superfamily of Nucleotide Hydrolases and Transferases," Biochemistry 41(29):9003-9014.
Chen et al. (Mar. 2003) "Increasing vitamin C content of plants through enhanced ascorbate recycling," Proc Natl Acad Sci 100:3525-3530.
Clough et al. (1998) "Floral dip: a simplified method for *Agrobacterium*-mediated transformation of *Arabidopsis thaliana*," The Plant Journal 16(6):735-743.
Conklin (1998) "Vitamin C: a new pathway for an old antioxidant," Trends Plant Sci 3(9):329-330.
Conklin et al. (Mar. 1999) "Genetic evidence for the role of GDP-mannose in plant ascorbic acid (vitamin C) biosynthesis," Proc Natl Acad Sci USA 96:4198-4203.
Conklin et al. (Feb. 2000) "Identification of Ascorbic Acid-Deficient *Arabidopsis thaliana* Mutants," Genetics 154:847-856.
Conklin et al. (Jun. 9, 2006) "*Arabidopsis thaliana* VTC4 Encodes L-Galactose-1- p. Phosphatase, a Plant Ascorbic Acid Biosynthetic Enzyme," J. Biol. Chem. 281(23):15662-15670, published online Apr. 4, 2006.
Dan et al. (2006) "MicroTom—a high-throughput model transformation system for functional genomics," Plant Cell Reports 25:432-441.
Davey et al. (2003) "Rocket-powered high-performance liquid chromatographic analysis of plant ascorbate and glutathione," Analytical Biochemistry 316:74-81.
De Carvalho Niebel et al. (1995) "Post Transcriptional Cosuppression of β-1,3-Glucanase Genes Does Not Affect Accumulation of Transgene Nuclear mRNA," Plant Cell 7:347-358.
Ferguson et al. (1991) "Vitamin C in *Actinidia*" Acta Horticulture 297:481-487.
Folta et al. (2006) "Characterization of LF9, an octoploid strawberry genotype selected for rapid regeneration and transformation," Planta 224:1058-1067.
Gatzek et al. (2002) "Antisense suppression of L-galactose dehydrogenase in *Arabidopsis thaliana* provides evidence for its role in ascorbate synthesis and reveals light modulated L-galactose synthesis," Plant Journal 30(4):541-553.
Gonzalez Padilla et al. (2003) "Early antibiotic selection and efficient rooting and acclimatization improve the production of transgenic plum plants (*Prunus domestica* L.)," Plant Cell Reports 22(1):38-45.
Graham et al. (1995) "*Agrobacterium*-Mediated Transformation of Soft Fruit *Rubus, Ribes, and Fragaria*," Methods Mol Biol. 44:129-33.
Guerineau et al. (1990) "Sulfonamide resistance gene for plant transformation," Plant Molecular Biology 15:127-136.
Hellens et al. (2000) "pGreen: a versatile and flexible binary Ti vector for *Agrobacterium*-mediated plant transformation," Plant Mol Biol 42:819-832.
Hellens et al. (2005) "Transient expression vectors for functional genomics, quantification of promoter activity and RNA silencing in plants," Plant Methods 1:13, http://www.plantmethods.com/content/1/1/13.
Herrera-Estrella et al. (1983) "Expression of chimaeric genes transferred into plant cells using a Ti-plasmid-derived vector," Nature 303:209-213.
Herrera-Estrella et al. (1983) "Chimeric genes as dominant selectable markers in plant cells," The EMBO Journal 2(6):987-995.
Holden et al. (2003) "Structure and Function of Enzymes of the Leloir Pathway for Galactose Metabolism," J. Biol. Chem. 278(45):43885-43888.
Horsch et al. (1985) "A Simple and General Method for Transferring Genes into Plants," Science 227:1229-1231 with correction of authorship.
Imai et al. (1998) "L-Galactono-γ-lactone Dehydrogenase from Sweet Potato: Purification and cDNA Sequence Analysis," Plant Cell Physiology 39(12):1350-1358.
Ishikawa et al. (2006) "Progress in manipulating ascorbic acid biosynthesis and accumulation in plants," Physiologia Plantarum 126:343-355, published online Feb. 24, 2006.
Jander et al. (2002) "Arabidopsis Map-Based Cloning in the Post-Genome Era," Plant Physiol. 129:440-450.

(56) References Cited

OTHER PUBLICATIONS

Jeanmougin et al. (Oct. 1998) "Multiple sequence alignment with Clustal X," Trends Biochem Sci 23:403-405.

Jobling et al. (2003) "Immunomodulation of enzyme function in plants by single-domain antibody fragments," Nat. Biotechnol. 21(1):77-80.

Jones et al. (1998) "The effect of chimeric transgene architecture on co-ordinated gene silencing," Planta 204:499-505.

Jouvenot et al. (2003) "Targeted Regulation of Imprinted Genes by Synthetic Zinc-Finger Transcription Factors," Gene Therapy 10:513-522.

Keller et al. (1999) "Antisense inhibition of the GDP-mannose pyrophosphorylase reduces the ascorbate content in transgenic plants leading to developmental changes during senescence," Plant Journal 19(2):131-141.

Krens et al. (1997) "Transgenic caraway, *Carum carvi* L.: a model species for metabolic engineering," Plant Cell Reports 17:39-43.

Kumar et al. (1996) "Potato plants expressing antisense and sense S-adenosylmethionine decarboxylase (SAMDC) transgenes show altered levels of polyamines and ethylene: antisense plants display abnormal phenotypes," The Plant J. 9(2):147-158.

Laing et al. (Nov. 30, 2004) "A highly specific L-galactose-1-phosphate phosphatase on the path to ascorbate biosynthesis," PNAS USA 101(48):16976-16981.

Laing et al. (2004) "Kiwifruit L-galactose dehydrogenase; molecular, biochemical and physiological aspects of the enzyme," Functional Plant Biology 31:1015-1025.

Laing et al. (May 29, 2007) "The missing step of the L-galactose pathway of ascorbate biosynthesis in plants, an L-galactose guanyltransferase, increases leaf ascorbate content," PNAS USA 104(22):9534-9539.

Li et al. (1996) "Genetic transformation of cassava (*Manihot esculenta* Crantz)," Nature Biotechnology 14:736-740.

Li et al. (2001) "A fast neutron deletion mutagenesis-based reverse genetics system for plants," The Plant Journal 27(3):235-242.

Li et al. (2003) "Transgenic rose lines harboring an antimicrobial protein gene, *Ace-AMP1*, demonstrate enhanced resistance to powdery mildew (*Sphaerotheca pannosa*)," Planta 218(2):226-232.

Llave et al. (2002) "Cleavage of *Scarecrow-like* mRNA Targets Directed by a Class of *Arabidopsis* miRNA," Science 297:2053-2056.

Loewus et al. (1961) "The Metabolism of D-Galacturonic Acid and Its Methyl Ester in the Detached Ripening Strawberry," Arch. Biochem. Biophys. 95:483-493.

Lorence et al. (Mar. 2004) "*myo*-Inositol Oxygenase Offers a Possible Entry Point into Plant Ascorbate Biosynthesis," Plant Physiol. 134:1200-1205.

Matsuda et al. (2005) "Development of an *Agrobacterium*-mediated transformation method for pear (*Pyrus communis L.*) with leaf-section and axillary shoot-meristem explants," Plant Cell Reports 24(1):45-51.

Mcintyre et al. (1996) "Strategies for the suppression of peroxidase gene expression in tobacco. I. Designing efficient ribozymes," Transgenic Research 5:257-262.

Michelmore et al. (1987) "Transformation of lettuce (*Lactuca sativa*) mediated by *Agrobacterium tumefaciens*," Plant Cell Reports 6:439-442.

Napoli et al. (1990) "Introduction of a Chimeric Chalcone Synthase Gene into Petunia Results in Reversible Co-Suppression of Homologous Genes *in trans*," The Plant Cell 2:279-289.

Niu et al. (1998) "Transgenic peppermint (*Mentha x piperita* L.) plants obtained by cocultivation with *Agrobacterium tumefaciens*," Plant Cell Reports 17:165-171.

Oosumi et al. (2006) "High-efficiency transformation of the diploid strawberry (*Fragaria vesca*) for functional genomics," Planta 223(6):1219-1230, published online Dec. 1, 2005.

Ortiz et al. (1996) "Hygromycin resistance as an efficient selectable marker for wheat stable transformation," Plant Cell Reports 15:877-881.

Pena et al. (1995) "High efficiency *Agrobacterium*-mediated transformation and regeneration of citrus," Plant Science 104:183-191.

Piro et al. (1993) "Glucomannan synthesis in pea epicotyls: The mannose and glucose transferases," Planta 190:206-220.

Radzio et al. (2003) "L-Gulono-1,4-lactone oxidase expression rescues vitamin C-deficient *Arabidopsis* (*vtc*) mutants," Plant Mol Biol 53:837-844.

Ramesh et al. (2006) "Improved methods in *Agrobacterium*-mediated transformation of almond using positive (mannose/*pmi*) or negative (kanamycin resistance) selection-based protocols," Plant Cell Reports 25(8):821-828, published online Mar. 14, 2006.

Rassam et al. (2005) "Variation in Ascorbic Acid and Oxalate Levels in the Fruit of *Actinidia chinensis* Tissues and Genotypes," J. Agric. Food Chem. 53:2322-2326.

Redgwell, R.J. (1983) "Composition of *Actinidia* Mucilage," Phytochemistry 22(4):951-956.

Redgwell et al. (1990) "Cell Wall Changes in Kiwifruit Following Post Harvest Ethylene Treatment," Phytochemistry 29(2):399-407.

Schaffer et al. (2001) "Improving the accuracy of PSI-BLAST protein database searches with composition-based statistics and other refinements," Nucleic Acids Res 29(14):2994-3005.

Schrott, M. (1995) "Selectable Marker and Reporter Genes," In: Gene Transfer to Plants (Potrykus, T., Spangenberg. Eds) Springer Verlag. Berline, pp. 325-336.

Seifert, G. J. (2004) "Nucleotide sugar interconversions and cell wall biosynthesis: how to bring the inside to the outside," Current Opinion in Plant Biology 7:277-284.

Smirnoff, N. (2001) "L-Ascorbic Acid Biosynthesis," Vitamins and Hormones 61:241-266, Academic Press.

Song et al. (2006) "Transformation of Montmorency sour cherry (*Prunus cerasus* L.) and Gisela 6 (*P. cerasus* x *P. canescens*) cherry rootstock mediated by *Agrobacterium tumefaciens*," Plant Cell Reports 25(2):117-123, published online Dec. 21, 2005.

Tabata et al. (2001) "Generation and properties of ascorbic acid-deficient transgenic tobacco cells expressing antisense RNA for L-galactono-1,4-lactone dehydrogenase," The Plant Journal 27(2):139-148.

Till et al. (2003) "High-throughput TILLING for functional genomics," Methods Mol Biol 236:205-220. (Abstract only).

Tokunaga et al. (2005) "Generation and properties of ascorbic acid-overproducing transgenic tobacco cells expressing sense RNA for L-galactono-1,4-lactone dehydrogenase," Planta 220:854-863.

Valpuesta et al. (2004) "Biosynthesis of L-ascorbic acid in plants: new pathways for an old antioxidant," Trends in Plant Science 9(12):573-577.

Wang et al. (2006) "Transformation of *Actinidia eriantha*: A potential species for functional genomics studies in *Actinidia*," Plant Cell Reports 25(5):425-431, published online Jan. 11, 2006.

Watanabe et al. (2006) "Characterization of a GDP-D-mannose 3",5"-epimerase from rice," Phytochemistry 67:338-346.

Wheeler et al. (1998) "The biosynthetic pathway of vitamin C in higher plants," Nature 393:365-369.

Wolucka et al. (2001) "A High-Performance Liquid Chromatography Radio Method for Determination of L-Ascorbic Acid and Guanosine 5'-Diphosphate- L-Galactose, Key Metabolites of the Plant Vitamin C Pathway," Anal Biochem 294:161-168.

Wolucka et al. (Dec. 18, 2001) "Partial purification and identification of GDP-mannose 3 ",5 "-epimerase of *Arabidopsis thaliana*, a key enzyme of the plant vitamin C pathway," PNAS USA 98(26):14843-14848.

Wolucka et al. (2003) "GDP-Mannose 3',5'-Epimerase Forms GDP-L-gulose, a Putative Intermediate for the *de Novo* Biosynthesis of Vitamin C in Plants," J. Biol. Chem. 278(48):47483-47490.

Yao et al. (1995) "Regeneration of transgenic plants from the commercial apple cultivar Royal Gala," Plant Cell Reports 14:407-412.

\* cited by examiner

FIGURE 1A

|  |  |
|---|---|
| At4g26850 | (1) ------------------------------------------------------------------------- |
| At5g55120 | (1) -MLKIKRVPTVVSNYQKDDGAEDP---VGCGRNCLGACCLNGARLPIYACKNLVKS-GEKLVISHEAIEPPVAFL |
| 319998_KAZD | (1) MLLKIKRVPTVVSNYQKDETVEE----GGCGRNCLSKCCINGARLPIYTCKNLID----K--SVG-ENTESPVTFL |
| AT5G18200 | (1) -MLKIKRVPTVVSNFQKDEAEDGARSGGGGRNCLQKCCIQGAKIPLYAFKRVKEVVGEKGLLAVDDEEAPVAFL |
| Mm_74150758 | (1) ---------------------------MTSPSHASDRGG---GDGDSVENQSPE-----LR |
| | -MAVPHHLQETSYLLPEDPEDWEK----QGIPDFVYGQEDLVGKEVQWSRDSPSA---------VDT-----V-PLSRF |

|  |  |
|---|---|
| At4g26850 | (71) ESLVLGENEDRFORGLFRYDVTACETKVLGKYGFVAQLNEGNHLKKRPTEFRVDKVLQSFEG-----SKFNFTKV |
| At5g55120 | (65) ESLVIGENEDRFORGLFRYDVTACETKVLGKYGFIAQLNEGRHLKKRPTEFRVDKVLQPFDG-----NKFNFTKV |
| 319998_KAZD | (75) DSLLGEWEDRVQRGLFRYDVTACETKVLGEYGFIAQLNEGRHLKKRPTEFRVDKVLQPFDE-----SKFNFTKV |
| AT5G18200 | (27) KDPVTNRAVIFSPARAKPTDFKSKSPQNENPKPSSCPFCIGEQECAPELFRVPDHDPNWKLRVIENLYPALSR |
| Mm_74150758 | (60) DSAIRSARQRLELGLFKYRLEDLQTQILGSVGFVAQLNLEEGIQRRRPQ-NIRSVRQEFDP-----EQFNFNKI |

|  |  |
|---|---|
| At4g26850 | (142) GQEELLFQFEAG---EDAQVQFFPCMPIDPEN-SPSVVAINVSEIEYCHVLIPRVLDCLPQRIDHKSLLLAVHM |
| At5g55120 | (136) GQEELLFQFKASTNDPDSEIQELASMPLDADN-SPSVVAINVSHIEYSHVLIPRVLDCLPQRIDHKSLLLALQM |
| 319998_KAZD | (146) GQEEVLFQFEAS---DDNEVQFFPNAPVDVEN-SPSVVAINVSHIEYCHVLIPRILECLPQRIDRESFLLAHM |
| AT5G18200 | (102) NLETQSTQPETG---TSRTIVGFGFHDVVIESPVHSIQLSDIDPVGLCDIIAYKKR--------INQIA |
| Mm_74150758 | (130) RPGEVLFRMQRE------------PKGPATPKQEDDVLVVINVSLEWMHVLVPAPAQGLPQRLLPGVLRVGLEA |

HIT Triad

|  |  |
|---|---|
| At4g26850 | (213) AAEAANPYFRLGYNSLGAFTINHLLFQAYYLAMPFFPLEKAPTKKITTTVSGVKISELLSYPVRSLLFEGGSSMQ |
| At5g55120 | (210) AAEADNPYFRLGYNSLGAFTINHLLFQAYYLAMQFPIEKASSLKITTTNNGVKISKLLNYPVRGLLVEGGNTIK |
| 319998_KAZD | (217) AAEAGNPYFRLGYNSLGAFTINHLLFQAYYLAVPFPIEKAPTRKITTLNGGVKISDLLNYPVRGLVFEGGNSLE |
| AT5G18200 | (161) QHDSINYIQVFKNQGASAGASMSISHSQ--MMELPVVPPTVSSRLDGT--------KDYFEETGKCCLCEAKSKHF |
| Mm_74150758 | (194) VLLSLHPGFRVGFNSLGGIRSVNLILHCYYLAHPLRVEGAPSTPLDPKGCIHLLQALPAPGFLFYTSGPGPDLE |

|  |  |
|---|---|
| At4g26850 | (288) ELSDTVSDCCVCLQNNIPFNLLISDCG------RQIFLMPQCYAEKQALGEVSPEVLETQVNPAVWEISGHMVLK |
| At5g55120 | (285) DLADTVSDASVCLQNNIPFNLLISDSG------KRIFLLPQCYAEKQALGEVSSTLLDTQVNPAVWEMSGHMVLK |
| 319998_KAZD | (292) DLSNAVSDSSICLQGNNIPYNVLISDSG------KCIFLLPQCYAERKQAIGEVSSDLLDTQVNPAVWEISGHMVLK |
| AT5G18200 | (227) VIDESSHFVSVAPFAATYPFEIWLLPKD------HSSHEHHLDDVKAVDLGGLLKLMLQKIAKQLNDPPYNYMIHT |
| Mm_74150758 | (269) VLISRVCRATDYLSDREIAHNIFVTRGAPPGPTSSTSDLSGIRVILWARKSSFGIKESGAFNVALCELAGHLPVK |

FIGURE 1B

```
                    376                                                                                      450
At4g26850    (358)  RKEDYEGASEDNAWRLLAEAS SEERFKEVTALAFEAIGCSNQEEDLEGTIVHQQNSSGNVNQKSNRTHGGPITN
At5g55120    (355)  RKEDYEGASEEKAWRLLAEVS SEEREREVNTMFDAIGFSSHEEEEEELEEQNSMNGGS---ETIVHCPSVKE
319998_KAZD  (362)  RKEDYEEASEGNAWRLLAEVS SEERFEEVKALIFEAISCADDRSGSTAENLLEPDDNPQSRKVANDALNKGSH
AT5G18200    (297)  SP-----------LKVTESQ  PYTHWFLQIVPQLSGVGGFEIGTGCYINPVFPEDVAKVMREVSLT--------
Mm_74150758  (344)  TSQDFSSLTEAAAVALIQDCL PETQAGEVRAALVALMAQEEL-----------------------------------

451        464
At4g26850    (433)  GTAAECLVLQ---
At5g55120    (427)  EAVSN--------
319998_KAZD  (437)  RGMVPGKQECLVQH
AT5G18200    (352)  -------------
Mm_74150758  (387)  -------------
```

FIGURE 6A

```
                        75
244893_Ac        (1)  ---MLKIKRVPTVVSNFQKDEADDGARSG-GGCGRNCLQKCCIQGAKLPLYAFKRVNEVVGEKGVLALDNEEAPV
 24547_Ae        (1)  ---MLKIKRVPTVVSNFQKDEAEDGARSG-GGCGRNCLQKCCIQGAKLPLYAFKRVKEVVGEKGLIITVGDEEAPV
276582_Ae        (1)  ---MLKIKRVPTVVSNFQKDEAEDGARSG-GGCGRNCLQKCCIQGAKLPLYAFKRVKEVVGEKGLLAVGDEEAPV
319998_Ac        (1)  ---MLKIKRVPTVVSNFQKDEAEDGARSG-GGCGRNCLQKCCIQGAKLPLYAFKRVKEVVGEKGLLAVDDEEAPV
 82552_Md        (1)  ---LRIKRVPTVVSNYQKDEAEEVARRV-GGCGRNCLNQCCIPGAKLPLYAFKKLNVNDGDTGLLGREKREPPV
At4g26850        (1)  ---MLKIKRVPTVVSNYQKDDGAEDP----VGCGRNCLGACCLNGARLPLYACKNLIVKSGEKL-VISHEAIEPPV
At5g55120        (1)  ---MLLKIKRVPTVVSNYQKDETVEE----GGGCGRNCLSKCCINGARLPLYTCKNLDKSVG-----ENTESPV
BT013858_Le      (1)  ---MLTVKRVPTLVSNYQEDVLEGN-----VMGCGRKCLGKCCMPVSVLPLYAFKNDDNEPIENDVQTLPEEECQM
315905_Ms        (1)  ---MLRIKRVPTVVSNYQKDEAEEGARRV-KGCGRNCLNQCCIPGAKLPLYAFKKRNVNNGDTGVPGHDKREPPV
os12g01900000    (1)  MEMKLTIKRVPTVVSNYQEDAAATAGERPRAGCGRDCLGDCCLPDSKLPLYAFKASPKKPS------SQEDASND
Contig_St        (1)  ---MMLKIKRVPTIVSNFQKDEADEIGARG-AGCGRNCLRNCCLPGSKLPLYGFKNLSYGKS----VAADETKESPI
Consensus             GGCGRNCLQKCCIQGAKLPLYAFKRL     GE GVLA E EEAPV
                                                                                            150

244893_Ac       (72)  AFLDSLLLGEWEDRVQRGLFRYDVTACETKVIPGEYGFIAQLNEGRHLKKRPTEFRVDKVLQPFDGSKFNFTKVG
 24547_Ae       (72)  AFLDSLLLGEWEDRVQRGLFRYDVTACQTKVIPGEYGFIAQLNEGRHLKKRPTEFRVDKVLQPFDESKFNFTKVG
276582_Ae       (72)  AFLDSLLLGEWEDRVQRGLFRYDVTACETKVIPGEYGFIAQLNEGRHLKKRPTEFRVDKVLQPFDESKFNFTKVG
319998_Ac       (72)  AFLDSLLLGEWEDRVQRGLFRYDVTACETKVIPGEYGFIAQLNEGRHLKKRPTEFRVDKVLQPFDGSKFNFTKVG
 82552_Md       (71)  AFLDSLLLGEWEDRMQRGLFRYDVTACETKVIPGQFGFIAQLNEGRHLKKRPTEFRVDKVLQPFDGSKFNFTKVG
At4g26850       (68)  AFLESLVLGEWEDREFQRGLFRYDVTACETKVIPGKYGFVAQLNEGRHLKKRPTEFRVDKVLQSFDGSKFNFTKVG
At5g55120       (62)  TFLESLVIGEWEDRFQRGLFRYDVTTCETKVIPGRCGFIAQLNEGRHLKKRPTEFCIDKVLQPFDENKFNFTKVG
BT013858_Le     (69)  SFINDLLLGLMEERMSQGLFRYDVTACETKVIPGQYGFIAQLNEGRHLNKRPTEEFRVDKVLQPYDSNKFNFTKVG
315905_Ms       (72)  AFLDSLLLGEWEDRMARGLFRYDVTACETKVIPGNLGFVAQLNEGRHLKKRPTEFRVDRVLQPFDAAKFNFTKVG
os12g01900000   (70)  EFFVNLILGLWEDRQQKGLFRYDVTACETKVIPGEYGFVAQLNEGRHLKKRPTEFRVDKVLQPFDGSKFNFTKVG
Contig_St       (70)  DFLESLVIGEWEDRMQRGLFRYDVTACETKVIPG YGFTAQLNEGRHLKKRPTEFRVDKVLQPFDGSKFNFTKVG
Consensus       (76)
                                                                                            225
244893_Ac      (147)  QEEVLFQFEAS---NDNEVQFFPNAPVDVEN-SPSVVAINVSPIEYGHVLLIPSILECLPQRIDRESFLLALHMA
 24547_Ae      (147)  QEEVLFQFEAS---VDNEVQFFPNAPVDVEN-SPSVVAINVSPIEYGHVLLIPRILECLPQRIDRESFLLALHMA
276582_Ae      (147)  QEEVLFQFEAS---IDNEVQFFPNAPVDVEN-SPSVVAINVSPIEYGHVLLIPRILECLPQRIDRESFLLALHMA
319998_Ac      (147)  QEEVLFQFEAS---DDNEVQFFPNAPVDVEN-SPSVVAINVSPIEYGHVLLIPRILECLPQRIDRESFLLALHMA
 82552_Md      (146)  QEEVLFQFEAS---KDGEVQFFPSAPIDVES-SPSVVAINVSPIEYGHVLLIPHILERLPQRIDRESFLLALHMA
At4g26850      (143)  QEELLFQFEAG---EDAQVQFFPCMPIDPEN-SPSVVAINVSPIEYGHVLLIPRVLDCLPQRIDHKSLLLAVHMA
At5g55120      (137)  QEELLFQFKASTNDDDSEIQFLASMPLDADN-SPSVVAINVSPIEYGHVLLIPRVLDCLPQRIDHKSLLLALQMA
BT013858_Le    (144)  QEELLFRFFPS---TDYKAHYFSGMRVNSGI-SPSTVAINVSPIEYGHVLLIPRVLDCLPQRIDRDSFAIALHFA
315905_Ms      (147)  QEEVLFRFEAS---EDGEVHFFPSAPIDVEN-SPSVVAINVSPIEYGHVLLIPRIFERLPQRIDRESFLLALHMA
```

FIGURE 6B

```
os12g0190000   (145) QEEVLFQFENG----GGDDSFFVESSPISVADRAPNVVAINVSPIEYGHVLLIPRVLDRLPQRIDQESFLLALHMA
Contig_St      (145) QEELLFQFEAS----EEDEVQLYPNAPIDPEK-SPSVIAINVSPIEYGHVLLIEKVLECLPQRIDRDSFLLALHMA
Consensus      (151) QEEVLFQFEAS    D EVQFFP APIDVEN SPSVVAINVSPIEYGHVLLIPRILECLPQRIDRESFLLALHMA
                     226                                                                     300

244893_Ac      (218) AEAGNPYEFRLGYNSLGAFATINHLHFQAYYLAVPFPIEKAPTRKITTLN----GGVKISELLNYPVRGLVFEGGN
24547_Ae       (218) AEAGNPYEFRLGYNSLGAFATINHLHFQAYYLAVPFPIEKAPTRKITTLN----GGVKISELLNYPVRGLVFEGGN
276582_Ae      (218) AEAGNPYEFRLGYNSLGAFATINHLHFQAYYLAVPFPIEKAPTRKITTLN----GGVKISELLNYPVRGLVFEGGN
319998_Ac      (218) AEAGNPYEFRLGYNSLGAFATINHLHFQAYYLAVPFPIEKAPTRKITTLN----GGVKISDLLNYPVRGLVFEGGN
82552_Md       (217) AEAGNPYFRLGYNSLGAFATINHLHFQAYYLAVTFPIEKAPTKKISTLN-----AEVKVSELLNYPVRGLVFEGGN
At4g26850      (214) AEAANPYFRLGYNSLGAFATINHLHFQAYYLAMPFPLEKAPTKKITTV-----SGVKISELLSYPVRSLLFEGGS
At5g55120      (211) AEADNPYFRLGYNSLGAFATINHLHFQAYYLAMQFPIEKASSLKITTTN----NGVKLSKLLNYPVRGLLVEGGN
BT013858_Le    (215) REVADPFFRVGYNSLGAFATINHLHFQAYYLSVPFPVEKAPIQKILARKGLGGAGVIVSKLLNYPVRGEAFEGGN
315905_Ms      (218) AEAGSPYERLGYNSLGAFATINHLHFQAYYLAVTFPIEKAPTKKISTLN----AEVKVSELLNYPVRGLFFEGGN
os12g0190000   (217) AEAASPYERLGYNSLGAFATINHLHFQAYYLTVPFPVEKAATKRIFLAEGTMNSGVKVSKLMNYPVRGLVFEGGN
Contig_St      (216) AEAANPYERLGYNSLGAFATINHLHFQAYELAVQFPIEKAPTQKITVTD----TGVKISEMLNYPVRGLVFEGGN
Consensus      (226) AEAGNPYEFRLGYNSLGAFATINHLHFQAYYLAVPFPIEKAPTKKITTLN    GGVKISELLNYPVRGLVFEGGN
                     301                                                                     375

244893_Ac      (289) --TLEDLSNAVSDSSICLQGNNIPYNVLISDSGKRIFLLPQCYAEKQALGEVSSELLDTQVNPAVWEISGHMVLK
24547_Ae       (289) --SLEDLSNAVSDSSICLQCNNTPYNVLISDSGKRIFLLPQCYAEKQALGEVSSELLDTQVNPAVWEISGHMVLK
276582_Ae      (289) --SLEDLSNAVSDSSICLQCNNIPYNVLISDSGKRIFLLPQCYAEKQALGEVSSELLDTQVNPAVWEISGHMVLK
319998_Ac      (289) -SLEDLSNAVSDSSICLQGNNIPYNVLISDSGKCIFLLPQCYAEKQALGEVSSDILDTQVNPAVWEISGHMVLK
82552_Md       (288) -TLQDLSNTVSDACICLQENNIPYNVLISDSGKRIFLVPQCYGRQIFLMPQCYAEKQALGEVPEVLETQVNPAVWEISGHMVLK
At4g26850      (285) -SMQELSDTVSDCCVCLQNNNTPFNILISDCGRQIFLMPQCYAEKQALGEVSPEVLETQVNPAVWEISGHMVLK
At5g55120      (282) --TIKDLADTVSDAVVNSCISLQNKNIPFNILIAQCGKKIFLLPQCYAEKQALGEVSSTLLDTQVNPAVWEMSGHMVLK
BT013858_Le    (290) GSTARDLSDAVVNSCISLQNKNIPFNILIAQCGKKIFLLPQCYAEKQALGEVSSTLLDTQVNPAVWEISGHIVLK
315905_Ms      (289) --TLEDLSYTVSDACICLQENNVPYNVLISDCGKKIFLFPQCYAEKQALGEVSAEVLDTQVNPAVWEISGHMVLK
os12g0190000   (292) -SLSDLANVVSSACIWLQDMNVPYNVLISDCGKKIFLFPQCYAEKQALGEVSQELLDTQVNPAVWEISGHMVLK
Contig_St      (287) -TLEDIANVVSDSCICLQENNIPYNVLISDSGKRIFLIPQCYAEKQALGEVSAELLDTQVNPAVWEISGHMVLK
Consensus      (301) TLEDLSN VSDSCICLQ NNIPYNVLISDSGKRIFLLPQCYAEKQALGEVSSELLDTQVNPAVWEISGHMVLK
                     376                                                                     450

244893_Ac      (362) RKEDYEASEGNAWRLLAEVSLSGERFEEVKALIFEAISCADDRSSTAENLLEEPDDNP-QSREEANDALNKGS
24547_Ae       (362) RKEDYQEASEGNAWRLLAEVSLSEERFEEVKALIFEAISCADDRSGSTAENLLE----------
276582_Ae      (362) RKEDYQEASEGNAWRLLAEVSLSBERFEEVKALIFEAISCADDRSGSTAENLLEEPDNDP-QSREVANDALSKAS
319998_Ac      (362) RKEDYEEASEGNAWRLLAEVSLSEERFEEVKALIFEAISCADDRSGSTAENLLEEPDDNP-QSRKVANDALNKGS
82552_Md       (361) RKKDYDEASDENAWKLLAEVSLSEERFLEVNALIFEGIASGDNGN----ENLKDPEVKP-RSHEEVN-TINKRV
At4g26850      (358) RKEDYEGASEDNAWRLLAEASLSEERFKEVTALAFEAIGCSNQEED--LEGTIVHQQNSSGNVNQKSNRTHGGPI
At5g55120      (355) RKEDYEGASEEKAWRLLAEVSLSEERFREVNTMIFDAIGFSSHEEE--EEEELEEQNSMNGGS---FTIVHCPSV
BT013858_Le    (365) RTKDYNDASEEYAWKLLSEVSISEERFEEVKGYISEAADLQADEDENINPEKEIPDSPGPQVASHIPPDCLVLQ-
```

FIGURE 6C

```
315905_Ms       (362) RKKDYDEASDENAWKLLAEVSLSEERFQEVNALIFERIASGNNGN----ENLPEDPEVKP-RSHEEVDATINKSS
os12g0190000    (365) RRSDYEEASEASAWRLLAEVSLSEERFEEVKAYIFDAAGLVQSDEEVSEDEDATYTPVSIAPPAVAEGCLVLQ-
Contig_St       (360) RKEDYEGATEANAWRLLAEVSLSEARFQEVTALIFEAISLSVEENENANDGSPEDLDVTPPQPMEEID---GSHT
Consensus       (376)      ENLLEE  D   P   S            L 451                             465
244893_Ac       (436) HCGMVPGKQECLVQH
24547_Ae        (416) ---------------
276582_Ae       (436) HRGMVPGKQECLVQH
319998_Ac       (436) HRGMVPGKQECLVQH
82552_Md        (430) HCSAVNEQICRVFTM
At4g26850       (431) TNGTAAECLVLQ---
At5g55120       (425) KEEAVSN--------
BT013858_Le     (439) ---------------
315905_Ms       (432) RAAMVGETQECLVLQ
os12g0190000    (439) ---------------
Contig_St       (432) HSTMVPA--------
Consensus       (451)      V
```

FIGURE 7

| | 244893_Ac | 24547_Ae | 276582_Ae | 315905_Ms | 319998_Ac | 82552_Md | At4g26850 | At5g55120 | BT013858_Le | Contig_St | os12g0190000 |
|---|---|---|---|---|---|---|---|---|---|---|---|
| 244893_Ac | | 96 | 96 | 79 | 96 | 80 | 70 | 74 | 63 | 78 | 67 |
| 24547_Ae | | | 99 | 82 | 98 | 84 | 75 | 77 | 66 | 79 | 70 |
| 276582_Ae | | | | 78 | 97 | 80 | 70 | 74 | 64 | 77 | 68 |
| 315905_Ms | | | | | 78 | 89 | 69 | 71 | 63 | 74 | 67 |
| 319998_Ac | | | | | | 79 | 70 | 74 | 63 | 76 | 68 |
| 82552_Md | | | | | | | 70 | 73 | 62 | 75 | 68 |
| At4g26850 | | | | | | | | 76 | 59 | 72 | 65 |
| At5g55120 | | | | | | | | | 62 | 72 | 65 |
| BT013858_Le | | | | | | | | | | 62 | 64 |
| Contig_St | | | | | | | | | | | 67 |
| os12g0190000 | | | | | | | | | | | |

FIGURE 9A

```
                              817
                                                          748
    244893_KAIA    (558)  -------ATGTTGAAGATCAAGAGGGTTCCGACTGTTGTTTTCCAATTTCCAAAAGGATGAGGCCGAC-
     24547_KUFA    (650)  -------ATGTTGAAGATCAAGAGGGTTCCGACTGTTGTTTTCCAATTTCCAAAAGGATGAGGCCGAG-
  276582_KAJB_Ae   (297)  -------ATGTTGAAGATCAAGAGGGTTCCGACTGTGTTGTTTCCAATTCCAATTACCAGAAGATGAGGCGGAG-
  315905_ABOC     (395)  GGGAGCATGATGTTGAAGATCAAGAGGGTTCCCACCGTCTTTTGTCTCCAATTCCAATTACCAGAAGATGAGGCGGAG-
  319998_KAZD     (222)  -------ATGTTGAAGATCAAGAGGGTTCCGACTGTTGTCTCCAATTCCAATTCCAAGAAGACGATGAGGCCGAG-
    At4g26850    (505)  -------ATGTTGAAAATCAAAAGAGTTCCGACCGTTGTTTCGAACTACCAAGAAGACGATGAGGCCGAG-
    At5g55120    (421)  -------ATGTTGTTGAAGATCAAAAGAGTTGTATCGAATTATCAAAAGATGAGACAGTT-
 BT013858_tomato  (424)  -------ATGTTGACTGTAAAGAGGGTGCCTACACTGGTTTCCAACTATCAAGAGATGTTCTGAAG
 NM_001072870_Os  (434)  ATGGAGATGAAGCTGACCATCAAGCGGGTGCCCACCGTGGTTTCCAACTACCAGGAGATGCTGCGCCA
Potato VTC2 contig from ESTs (56)  -------ATCATGCTCAAGATTAAGAGGGTTCCTACACTTGTTTCTAACTTTCAAAAGATGAGGCTGAT-
    82552_AARA_NNT   (1)  -------TTGAGGATCAAGAGGGTTCGTGTTTCGAATTACCAGAAGATGAGGCGGAG-
                                                          887
                                                          818
    244893_KAIA    (618)  ---GACGGCGCTCGATCTGGCGGTGGTTGCGCGGTTGCCTCCAGAAGTGCCTCCAGAACTGCCTCCAGAAGTGTTGCATTCAAGGGGCAAA
     24547_KUFA    (710)  ---GACGGCGCTCGATCCGGCCGGCGGTGGTTGCGCGGTTGCCTCCAGAAGTGCCTCCAGAAGTGTTGCATTCAAGGGGCAAA
  276582_KAJB_Ae   (357)  ---GACGCGCTCGATCCGGCCGGCGGTGGTTGCGCGGTTGCCTCCAGAAGTGCCTCCAGAAACTGTTGCATTCAAGGGGCAAA
  315905_ABOC     (464)  ---GAGGGTGCTCGCCGATCGGCCGGCGGTGCGCGGTTGGCGCGGAAACTGCCCTAACCAATGTTGCTTCCAGAAGTGTTGCATTCAAGGGGCAAA
  319998_KAZD     (282)  ---GACGGCGCTCGATCGGCCGGCGGTGTGCGCGGGAATTGCCTCCAGAAACTGCCTCCGGCGCTTGTTGCCTTAACGGGGCTAG
    At4g26850    (565)  -------CGTCGGCTGTGACGGGAATTGCTCGGACGTGCCTGAGCAAGTGTTCTGAGCAAGTGTTCATCAATGGGCAAG
    At5g55120    (484)  ---GGTGGATGTGGTCGGAAGTGCCTCCGCAAAATGCTCATGCCTGTTTCAGT
 BT013858_tomato  (485)  GTAACGTC-------ATGGGTTGTGGCCGCAAGTGCCTCCGGAGGGATTGCCTCCGGGATTCGTGCCCGATTCCAA
 NM_001072870_Os  (504)  CCGCCGGCGAACGCCGCCCCCGCCGTGTGCCGCGGAGGGATTGCCTCCGGGATTCGTGCCCGATTCCAA
Potato VTC2 contig from ESTs (119)  ---GAAATTGGTGCTCGTCGTGGTGCGCCGTCGGCCGGCCAACCGCTGCCGGCCCTAACCAATGTTGCATTCCAGTTCAAA
    82552_AARA_NNT  (58)  ---GAAGTTGCTCGCCGCCGTCGGGCGGCCGTGCGCCGGCCAACCGCTGCCTAACCAATGTTGCATTCCAGTTCAAA
                                                          888
                                                          957
    244893_KAIA    (686)  GCTACCTCTCTGTATGCTTCAAGAGGTGAATGAGGTTGTTGGTGAAAGGGTGTGCTTGCCCTCGACAAC
     24547_KUFA    (778)  GCTACCTCTCTGTATGCTTCAAGAGGTGAAGCAGGTGTTGTTGGTGTTGCTTGCTTACCGTCGGCGAC
  276582_KAJB_Ae   (425)  GCTACCTCTCTGTATGCTTCAAGAGGTGAAGGAGGTGTTGGTGAAAGGGTTGCTTGCTTGCTTGCCTCGCGGCGAC
  315905_ABOC     (532)  ACTTCCATTGTTGCCTTCAAGAGGCGAACGTGAATAATGGTGAAGGGGTTGCCGAAACATGACAAA
  319998_KAZD     (350)  GCTACCTCTGTATGCTTCAAGAGGTGAAAGAGTTGTTGGTGAGAAAGGTTGCCGTCGACGAC
    At4g26850    (624)  GCTTCCATTGTATGCATGTAAGAATCG---GTAAAATCCGAGAAGAAGCTTGTAATCAGTCATGAGCT
    At5g55120    (540)  ACTTCCTTTATATACCTGCCAAGAATCTT---GATAAATCCGTCG--GA-------GAGAAC
 BT013858_tomato  (543)  ACTTCCTCTATATGCTTATCATCAAGAATGATGATAATGAGCCAATTGAAAATGATGTTCAAACTTGCCTGAG
 NM_001072870_Os  (574)  GCTTCCGCTGTATGCTTTCAAGGCGAGTC-CGAAAAAGCCGTCTTCGC--------AGGAG
Potato VTC2 contig from ESTs (187)  GCTGCCACTGTATGGTTTCAAAATTTG-------AGCTACGGC---AAGTCTGTTGCCGCCGATGAAACA
```

FIGURE 9B

```
82552_AARA_NNT          (126) ACTTCCATTGTATGCCTTCAAGAAGCTGAACGTAAATGATGGTGACACGGGTTTGCTAGGACGTGAGAAA
                              958                                                              1027
244893_KAIA             (756) GAAGAGGCTCCTCGTTGCTTTCTTTCTTGGATTCACTTCTCCTCGGGAGTGGAGGATCGTGTGCAGAGAGGAC
24547_KUFA              (848) GAAGAGGCTCCTCGTTGCTTTCTTTCTTGGATTCGCTTCTCGCTCTCGGGAGTGGAGGATCGTGTGCAGAGAGGAC
276582_KAJB_Ae          (495) GAAGAGGCCTCCCGTTGCTTTCTTTCTTGGATTCGCTTCTCGCTCTCGGGAGTGGAGGATCGTGTGCAGAGAGGAC
315905_ABOC             (602) AGAGAGGCCCTCCTGTTGCTTTCTTGGATTCACTTCTTCTGTTCTCGGAGAGTGGAGGATCGTGTGCAGAGGGC
319998_KAZD             (420) GAAGAGGCTCCTGTTGCTTTCTTGGATTCACTTCTTCTGTTCTCGGAGAGTGGAGGATAGGTTGCAAAGAGGAC
At4g26850               (691) ATAGAGCCTCCTGTAGCTTTCTCCGAGTCCTCGAATCCTTAGTATTGGAAGATCGTTTCCAAAGAGGTC
At5g55120               (589) ACAGAATCTCCGGTGACATGTCATTCTTGAACGATTCTTGTTGTTGGGCTTATGGAGGAGCGATGAGCCAGGAC
BT013858_tomato         (613) GAGGAGTGTCAAGATGTCATTCTTGAACGATTCTTGTTGTTGGGCTTATGGAGGAGCGATGAGCCAGGAC
NM_001072870_Os         (626) GATGCTTCCAACGATGAGTTCTTTGTCATTCTCCGCTCGGCCTGTGGGAAGACAGGATGGCCGAGTT
Potato VTC2 contig from ESTs (248) AAGGAATCTCCGATCGACTTTCTGGAATCCCTTGTTCTTGGGAATGGGAGGATCGTCAGCAGAAAGCC
82552_AARA_NNT          (196) AGAGAGCCTCCCGTTGCATTTCTTGACTCACTTGCTTCTCGGGGAGTGGGAGGATCGCATGCAGAGAGGC
                              1028                                                             1097
244893_KAIA             (826) TCTTTCGTTACGATGTCACTGCTTGCGAAACCAAGGTTATTCCGGGAGAGTATGGCTTCATTGCGCAGCT
24547_KUFA              (918) TCTTTCGCTACGATGTCACTGCTTGCCAAACCAAGGTTATTCCGGGAGAGTATGGCTTCATTGCGCAGCT
276582_KAJB_Ae          (565) TCTTTCGCTACGATGTCACTGCTTGCGAAACCAAGGTTATTCCGGGAGAGTATGGCTTCATTGCGCAGCT
315905_ABOC             (672) TATTTCGCTATGATGTCACTGCTTGTGAAACCAAGGTGATCCCAGGCAATATGGTTTCATTGCCCAGCT
319998_KAZD             (490) TCTTTCGCTACGATGTCACTGCTTGCGAAACCAAGGTTATTCCAGGAGAGTATGGCTTCATTGCGCAGTT
At4g26850               (761) TTTTTCGCTATGATGTCACTGCCCGCGAAACCAAGGTTATCCCGGGAGAAGTATGGCTTCATTGCTCAGCT
At5g55120               (659) TTTTTCGCTATGATGTCACCCGCTGCGAAACCAAGGTTATACCGGGAGTACGGTTTCATTGCGCAGCT
BT013858_tomato         (683) TATTTCGATATATGATGTGACAACCTGTGAGACGAAGGTCATTCCTGGAGATGTGTTTATTGCGCAACT
NM_001072870_Os         (696) TGTTCCGATATGATGTCACTGCCTGCTTGCGAGACCAAGGTTATCCCAGGCACCTTGGGTTTGTTGCACAACT
Potato VTC2 contig from ESTs (318) TCTTTCGCTACGATGATGTCACTGCTTGCGAAACCAAGGTGATTCCTGAGAATATGGTTTCGTTGCTCAACT
82552_AARA_NNT          (266) TATTTCGCTATGATGTCACTGCTTGTGAAACCAAGGTGATCCCAGGGCAATTTGGTTTCATAGCCCAGCT
                              1098                                                             1167
244893_KAIA             (896) GAACGAGGGTCGTCACCTTAAGAAGAGGCCAACTGAGTTTCGTGTTGATAAGGTCCTGCAGCCCTTCGAT
24547_KUFA              (988) GAACGAGGGTCGTCACCTTAAGAAGAGGCCAACTGAGTTTCGTGTTGATAAGGTCCTGCAGCCCTTCGAT
276582_KAJB_Ae          (635) GAACGAGGGTCGTCACCTTAAGAAGAGGCCAACTGAGTTTCGTGTTGATAAGGTCCTGCAGCCCTTCGAT
315905_ABOC             (742) GAACGAGGGTCGCCATCTTAAGAGAGAAGAGGCCAACTGAGTTTCGTGTTGATAAGGTCCTCCAGCCCTTTGAT
319998_KAZD             (560) GAACGAGGGTCGTCACCTTAAGAAGAGAAGAGGCCAACTGAGTTTCGTGTTGACAAGGTGTTGCAGCCCTTCGAT
At4g26850               (831) TAACGAGGGTCGGCATCTTGAAGAAGAGAAGAGACCAGTTCCGTGTTAGAGATAAGGTTGCAAAGTTCTTCAACCATTTGAT
At5g55120               (729) GAAAGAAGGTCGGGCGCCGCCACCTCAAAGAAGCGCCCAACAGAGTTTTGCATTGATAAGGTTCTTCAGCCTTTTGAC
BT013858_tomato         (753) GAATGAGGGGTCGCCGCCACCTCAAAGAAGCGCCCTACTGAATTCCGCGTGACCGAGTTTTCAACCATTTGAT
NM_001072870_Os         (766) GAATGAAGGACGCGCCACCTCAAAGAAGCGCCTACTGAATTCCGCGTGACCGAGTTTCTGCAGCCGTCGAC
Potato VTC2 contig from ESTs (388) GAATGAGGGAAGGCACCCACCTCAAGAAGAGGCCAACTGAGTTTCGAGTTTGATAAGGTTGATAAGGTTCGAGCCAGCCAGCT
```

FIGURE 9C

```
82552_AARA_NNT           (336)  GAATGAGGGTGCGCCATCTTAAGAAGCGGCCAACAGAGTTCGAGTTGATAAGGTCCTCCAGCCCTTTGAT
                                1168

244893_KAIA      (966)  GGGAGCAAATTCAACTTCACTAAAGTTGGACAGGAAGAGGTTCTGTTCCAGTTGAAGCAAG---------
         24547_KUFA     (1058)  GAGAGCAAATTCAACTTCACTAAAGTTGGACAGGAAGAGGTGCTCTTCCAGTTGAAGCAAG---------
       276582_KAJB_Ae    (705)  GAGAGCAAATTCAACTTCACTAAAGTTGGACAGGAAGAGGTGCTGTTCCAGTTTGAAGCAAG--------
        315905_ABOC      (812)  AGCAGCAAGTTTAACTTCAATTTCACTAAAGTTGGACAAGAGGAGGTTCTATTCCGGTTGAAGCCAG---
        319998_KAZD      (630)  GAGAGCAAATTCAATTTCACTAAAGTTGGACAAGAGAGAGGTGCTGTTCCAGTTTGAAGCAAG-------
          At4g26850      (901)  GGCAGCAAATTCAACTTCACTAAAGTTGGCCAAGAAGAGGAGTTGCTCTTCCAGTTTGAAGCTGG-----
          At5g55120      (799)  GGAAACAAATTCAATTTCACTAAAGTTGGTCAAGAAGAAGAGTTGCTTTTCCAGTTAAAGCTAGCACTAATG
        BT013858_tomato  (823)  GAGAACAAATTCAACTTCACCAAAGTGGGCCAGGAAGAGAAGTGCTTTTCAGGTTTGAACCAAG------
     NM_001072870_Os     (836)  GCTGCCAAGTTCAACTTCACCAAAGTTGGCCAGGACAGGAAGAGGTGCTCTTCCAATTTGAGAATGG---
Potato VTC2 contig from ESTs (458)  GGAAGCAAGTTCAACTTCACTAAGGTTGGACAGGTTGGACAAGAGGAAGAGTTGCTCTTCCAGTTTGAAGCAAG--
        82552_AARA_NNT   (406)  GGCAGCAAGTTCAACTTTAACTTCAGTTGGACAAGAGGAGGTTCTGTTCCAGTTTGAAGCCAG-------
                                1238

244893_KAIA     (1028)  -CAACGACAACGAAGTCCAGTTCTTCTCCCAAATGCACCTGT---TGATGTTGAGAATTCTCCCAGTGTTGT
         24547_KUFA     (1120)  -CGTCGACAATGAAGTCCAGTTCCTTTTCCCAAATGCACCTGT---TGATGTTGAGAATTCTCCCAGTGTTGT
       276582_KAJB_Ae    (767)  -CATCGACAATGAAGTCCAGTTTCACTTTCTCCCAAATGCACCTGT---TGATGTTGAAAATTCTCCGAGCGTTGT
        315905_ABOC      (874)  -TGAAGATGGTGAAGTCCAGTTCACTTTCTTCCCTAGTGCACCCAT---TGATGTTGAAAATTCTCCCAGTGTTGT
        319998_KAZD      (692)  -CGACGACAATGAAGTCCAGTTCAGTTCTTCCCAAATGCACCGGT---TGATGTTGAGAATTCTCCCAGTGTTGT
          At4g26850      (963)  -TGAAGATGCCCAAGTCGAAATTCAGTTCGTTCTTCGCGAGTGATGCCTCT---TGACCCTGAGAATTCTCCTAGCGTCGT
          At5g55120      (869)  ATGATGATAGTGAAGTCCAGTTCAGTTCAGGGCCCATTACTTTCCGGCCGAGT---AGACGCTGATAATTCTCACCTAGTATGT
        BT013858_tomato  (885)  -TACCGACTACAAGGCCCATTCAGTGAAATTCAGTTTTCCCGGAGAGCTCCCCAATCAGTCGTTGCTGATCGTGCTCCTAATGTTGT
     NM_001072870_Os     (898)  -TGGTGCTGATGACAGCTTCAGTTCCAGCTCTATCCAAATGCACCAAT---AAACAGTGGTATTTCACCTAGTATTGT
Potato VTC2 contig from ESTs (520)  -TGAGGAAGATGAAGTCCAGTCCAGTTCAGTTTCAGTTTCCCCAGCGCGACACCAAT---TGATCCTGAGAAATCTCCAAGTGTCAT
        82552_AARA_NNT   (468)  -CAAAGATGGTGAAGTTCAGTTTCAGTTTCCCCCAGCGCGACACCCAT---NGATGTTGAAAGTTCTCCGAGCGTTGT
                                1377

244893_KAIA     (1094)  GGCCATCAATGTTAGTCCTATTCCTATTGAATATGGTCACGTACTTCTCATCCCTTCGATTCTTGAATGCTGCCT
         24547_KUFA     (1186)  GGCCATCAATGTTAGTCCTATTCCTATTGAATATGGTCATGTACTTCTGATCCCTCCGGATTCTTGAATGCCTGCCT
       276582_KAJB_Ae    (833)  GGCCATCAATGTTAGTCCTATTCCTATTGAATATGGTCATGTACTTCTGATCCCTCCGGATTCTTGAATGCCTGCCT
        315905_ABOC      (940)  TGCCATTAATGTCAGTCCTATTCCTATTGAATATGGCCATGTGCTTGTGATTCCTCGGTGTTGATTTTGAGCGTTGCCA
        319998_KAZD      (758)  GGCCATCAATGTTAGTCCTATTCCTATTGAATATGGTCATGTACTTCTGATTCCTCCGGATTCTTGAATGCCTGCCT
          At4g26850     (1029)  TGCCATCAATGTTAGTCCGATAGAGTTAGTGAGTAGTGGCCATGTGCTTGTGATTCCTCGTGTTCCTGTTACTGCCT
          At5g55120      (936)  TGCCATCAATGTCGAGTCCGATTGAGTATGAGTATGGGGCACGTTCTTTTTGATACCTCCGAGTTCTTGATTGCTTACCT
        BT013858_tomato  (951)  TGCTATCAATGTGAGCCCCAATTGAGTTGAGTATGGGCACCATGCTTCTTCCTCTCATCCCCGTGACCGACGCTGCCT
     NM_001072870_Os     (967)  TGCAATCAATGAAGCCATTCCCATGGAGTACGACACGTGCTTTTCAGTACCCGTGTACTGGACCGCTGCCT
Potato VTC2 contig from ESTs (586)  TGCCATCAATGTCAGTCCCATGAGTGAGTACGACACGTGCTTTTGATCCCTAAGGTCCCTAAGGCCTTCCC
```

FIGURE 9D

```
82552_AARA_NNT           (534)  GGCCATTAATGTCAGTCCAATTGAATATGGCCATGTGCTGTGTTGATTCCTCACATTCTTGAGCGATTGCCT
                                1378                                                                1447

244893_KAIA              (1164) CAAAGGATTGACAGGGAGGAGAGAGCTTCTTGCTTGCTCTCTTCACATGGCCAGCAGAAGCTGGAAACCCGTACTTCC
24547_KUFA               (1256) CAGAGGATTGACAGGGAGGAGAGAGCTTCTTGCTTGCTCTCTTCACATGGCCAGCAGAAGCTGGAAACCCGTACTTCC
276582_KAJB_Ae           (903)  CAGAGGATTGACAGGGAGGAGAGAGCTTCTTGCTTGCTCTCTTCACATGGCCAGCAGAAGCTGGAAACCCGTACTTCC
315905_ABOC              (1010) CAAAGGATTGACCGGGAGGAGAAAGCTTCTTGCTTGCACTTCACATGGCCGGCTGGAGCTGGAAACCCGTACTTTC
319998_KAZD              (828)  CAAAGGATTGACAGGGAGGAGAGAGCTTCTTGCTTGCTCTTCACATGGCAGCAGAGAGCTGGAAACCCGTACTTCC
At4g26850                (1099) CAAAGGATCGATCACAAAAGCCTTTGCTTGCTTGCTTCACATGGCCTGCTGAGGCTGCTAATCCATACTTCA
At5g55120                (1006) CAAAGGATTGATCACAAAAGCCTTTTGCTTGCTTGCAATGGCCTGAAGCCGATAATCCGTATTTCC
BT013858_tomato          (1021) CAGAGAATTGATGCGTGATAGTTTTGCAATTGCTCTCCATTTTGCCAGAGAAGTGGCAGATCCTTCTTTA
NM_001072870_Os          (1037) CAGAGGATTGACCAGGGACAGGACAGCTTCCTGCTTGCACTTGCACATGGCGTGCTGAAGCACCAAGCCATACTTCA
Potato VTC2 contig from ESTs (656) CAGAGGATCGACAGGGACAGGAGAGCTTCCTGCTTGCATTGCACATGGCCTGCACATGCCGGAAGCAGCAAACCATACTTCC
82552_AARA_NNT           (604)  CAAAGGATTGACCGGGAAAGCTTCCTGCTTGCACTTCACATGGCGCGGCTGAAGCAGCAGGGAATCCTTACTTTC
                                1448                                                                1517

244893_KAIA              (1234) GATTGGGTTACAACAGCTTGGGTGCATTTGCCACTACAATCACCTTCATTTCCAGGCTTATTACTTAGC
24547_KUFA               (1326) GATTGGGTTACAACAGCTTGGGTGCATTTGCCACTACAATCACCTTCATTTCCAGGCTTATTACTTAGC
276582_KAJB_Ae           (973)  GATTGGGTTACAACAGCTTGGGTGCATTTGCCACTACAATCACCTTCATTTCCAGGCTTATTACTTAGC
315905_ABOC              (1080) GATTGGGTTACAACAGCTTGGGTGCATTTGCTACCATCAATCAATCACCTTCACTTCCAGGCTTACTACTTGGC
319998_KAZD              (898)  GATTGGGTTACAACAGCTTGGGTGCATTTGCCATTGCCAATCAATCAATCACCTACATTCCAGGCTTATTACTTAGC
At4g26850                (1169) GACTCGGTTACAACAGCTTGGGTGGTGCTTAGCGCGCTTTCTGCTACCATTAAACACCATCTCACTTTCACTTTCCAGGCTTACTATTTGGC
At5g55120                (1076) GACTTGGATACAACAACAGCTTGGGCGCCTTTGCTACTACCATTAACCATCCACCTCCACTTTCCAGGCGTATTACTTGTC
BT013858_tomato          (1091) GGGTAGGTTATAACAGTTTGGGCTTGGGTGCCTTTGCCTTTGCAACATCAACCATCCACCATCTCCACTTTCAGGCATACTACTTGAC
NM_001072870_Os          (1107) GGCTTGGCTATAATAGTTCAACAGCTTGGGTGCATTTGCCACCACAACCATCTTCACTTCCAGGCTTATTCTTGGC
Potato VTC2 contig from ESTs (726) GATTGGGTTACAACAGCTTGGGTGCATTTGCTACCACCATCAATCACCATCAATCACCTTCACTTCCAGGCTTACTACCTGGC
82552_AARA_NNT           (674)  GATTGGGTTACAACAGCTTGGGTGCATTTGCTACCACCATCAATCACCATCAATCACCTTCACTTCCAGGCTTACTACCTGGC
                                1518                                                                1587

244893_KAIA              (1304) CGTGGCCCTTCCCTATCGAGAAGGCTCCCACTAGGAAGAGATAACT------------ACTCTGAATGGTGGG
24547_KUFA               (1396) TGTGCCCCTTCCTATAGAGAAGGCTCCCACTAGGAAGAGATAACT------------ACTCTGAATGGTGGG
276582_KAJB_Ae           (1043) TGTGCCCCTTCCTATCGAGAAGGCTCCCACTAGGAAGAGATAACT------------ACTCTGAATGGTGGG
315905_ABOC              (1150) CGTGACCTTTCCCATTGAGAAGGCTCCCTACCAGGAAGAAAATATCC------------ACTCTGAATGCTGAG
319998_KAZD              (968)  TGTGCCCTTTCCTATCGAGAAGGCTCCCACTAGGAAGAGATAACT------------ACTCTGAATGGTGGG
At4g26850                (1239) CATGCCTTTCCCTGGAGAAGAGCTCCTACCAAGAAGAGATAACT------------ACCACTGTTAGTGGT
At5g55120                (1146) AATGCAATTCCGATAGAAGAAGCTCTTCCTGAAGATCACT------------ACCACCAATAATGGC
BT013858_tomato          (1161) AGTGCCATTTCCAGTTGAGAAGAAGCACCAATACAGAAAAATACTGGCAAGGAAGGGCTGGGTGGTGCTGAA
NM_001072870_Os          (1177) AGTGCCTTTCCCTGTTGAGAAGGCAGCTACCAAGAAGGATTTTCCTTGCTGAGGGCACAATGAATAGTGGA
Potato VTC2 contig from ESTs (796) TGTGCAATTCCCCATTGAGAAGGCCCAACTCAGAAGATAACC------------GTCACTGATACTGGA
```

FIGURE 9E

```
82552_AARA_NNT         (744)  CGTGACCTTTCCCATTGAGAGGCTCCTACCAAAAAAATATCC---------ACTTTGAATGCCGAG
                              1588                                                              1657
244893_KAIA           (1362)  GTGAAAAATCTCTGAGCTGCTGCTAAATTATCCAGTCAGGGGCTTGTTTTCGAGGGTGGAAAT-------ACTC
24547_KUFA            (1454)  GTGAAAAATCTCTGAGCTGCTGCTAAATTATCCAGTCAGAGAGGGCTTGTTTTCGAGGGTGGAAAT-------TCTC
276582_KAJB_Ae        (1101)  GTGAAAAATCTCTGAGCTGCTGCTAAATTATCCAGTCAGAGGGCTTGTTTTCGAGGGTGGAAAT-------TCTC
315905_ABOC           (1208)  GTGAAGGTCTCTGAGCTTCTGAACTATCCTGTCAGTCAGAGGTCTTTTTTTTGAGGGTGGAAAC-------ACTC
319998_KAZD           (1026)  GTGAAAAATCTCTGATCTGCTAAATTATCCAGTCAGTCAGAGGGCTTGTTTCGAGGGTGGAAAT-------TCTC
At4g26850             (1297)  GTCAAAATCTCAGAGCTTCTAAGTTACCCTGTGAGAAGTCTTCTTTGAAGGTGGAAGC-------TCTA
At5g55120             (1204)  GTCAAAATCTCTAAACTCTTGAATTATAAATTACCCCGTACGAGGGCTTCTAGTTGAAGGTGGAAAC-------ACCA
BT013858_tomato       (1231)  GTGATTGTATCTAAGTTATTAAATTACCCGTGATGAACTACCCTGTGAGGGACTGGTTTTTGAGGGAAGTACTG
NM_001072870_Os       (1247)  GTAAAGGCTGTCCAAGCTGATGAACGCTTAATTACCCAGTTCGAGGTCTCGTCTTTGAGGGTGGAAAT-------ACTT
Potato VTC2 contig from ESTs (854)  GTGAAGGCTCTCTGAGCTTCTGAATTATCCAGTCAGAGGTCTTGTTTTGAGGGTGGAAAT-------ACTC
82552_AARA_NNT         (802)                                                                    1727

244893_KAIA           (1426)  TGGAAGAGATTTGTCCAATGCCGTCTCTGATTCTCAAGGCAACAACAACATACCTTACAATGT
24547_KUFA            (1518)  TGGAAGAGATTTGTCCAATGCCGTCTCTGATTCTCAAGCAACAACAACATACCTTACAATGT
276582_KAJB_Ae        (1165)  TGGAAGAGATTTGTCTTCTACACCGTCTCTGATTGCCTGCATATGCCTTCAAGAAAACAACGTACCGTACAATGT
315905_ABOC           (1272)  TGGAAGAGATTTGTCCAATGCCGTCTCTGATTCCAGCATTGCCTTCAAGGCAACAACAACATACCTTACAATGT
319998_KAZD           (1090)  TGCAAGAACTATCTGATACTGTTTCAGACTGCTGTGTTTGCCTTCAAAACAACAACAACATTCCTTTCAACAT
At4g26850             (1361)  TTAAAGATCTGCAGATACTGTATCAGACGCATCCGTTTGTCTTCAGAACAACAATAAAACATCCCTTTCAACAT
At5g55120             (1268)  CCCGTGATTGTCTGATGCTGTTCTGTTGTGAATTCCTGCCGTTGTATCGGCTGCAGGAACAACAATGTGCCTTACAATGT
BT013858_tomato       (1301)  TGAGCGATCTGGCCAATGCCGTTGGTTTCCAAGCGTTCTGCATTTGTCTGCAAGAGAACAACATCCCTTACAATGT
NM_001072870_Os       (1311)  TGGAGGATTTGGCAATGCCGTCTCTGAGATTCTGTCATTTGTCCATATGCCTGCAAGAGAACAACAACATACCTTACAATGT
Potato VTC2 contig from ESTs (918)  TGCAAGAGATTTGTCAAACACCGTCTCTGATGCCTCTGATATGCCTTCAAGAGAACAACAACATACCTTACAATGT
82552_AARA_NNT         (866)                                                                    1797

244893_KAIA           (1496)  GCTTATCTCCGATTCTGAAAGCGTATCTTTCTTTTACCACAGTGTTACGCTGAGAAACAGGCTCTTGGA
24547_KUFA            (1588)  GCTTATCTCCGATTCTGAAAGCGCATCTTTCTCTTACCACAGTGTTATGCTGAGAAACAAGCTCTTGGA
276582_KAJB_Ae        (1235)  GCTTATCTCCGATTCTGAAAGCGAATCTTTCTCTTACCACAGTGTTATGCTGAGAAACAAGCTCTTGGA
315905_ABOC           (1342)  CCTTATCTCTGATTGTGAAAGCGAATCTTTCTTCCTGCCACAGTGTTATGCTGCACAGTGAGAAACAAGCTCTTGGA
319998_KAZD           (1160)  GCTTATCTCCGATTCTGAAAGTGTATCTTTCTCTTACGCTGCTACCCAGTGTTACGCTGAGAAACAGGCTCTTGGA
At4g26850             (1431)  TCTCATCTCTCCGATTGTGGAAGCAGACAGATCTTCTTAATGCCACAGAATCTTCCCCTCCAGTGTTACCGCACAGTGTTACCGAGAAACAGGCCTAGGT
At5g55120             (1338)  TCTCATCTCGACTCTGCAAACAAGAATCTTCCTCCCTTCCTTCTGCTTCCCCAGTGTTATGCCGAGCAGGCAAGCAGGCTTTAGGA
BT013858_tomato       (1371)  TCTCATTGCTCAGTGTCGCGCAAACAAAAGAATCTTCCTCCTTCCAGTGCTATGCCGAGCAGGCTTAGGA
NM_001072870_Os       (1381)  TCTTATCTCTGACTCCGATTCAGGAAGAAGAATCATTCTTCCCCACAGTGCTATGCCGAGCAGGCAAGCAGGCTGGGA
Potato VTC2 contig from ESTs (988)  CCTAATCTCCGATTCAGGAAATGCTTCCCCAGTGCTATGCAGAGAGAACAAGCTCTTGGA
```

FIGURE 9F

```
82552_AARA_NNT          (936)  CCTTATCTCTGACTCTGGAAAGGGAATCTTTCTCGTCGCCACAGTGTTATGCTGAGAAACAAGCTCTTGGG
                                                                                                      1867
244893_KAIA            (1566)  GAAGTGAGTTCTGAGCTTCTGGACACACAAGTGAACCCGGCAGTGTGGGAAATCAGCGGACATATGGTTT
24547_KUFA             (1658)  GAAGTGAGTTCCGAGCTTCTGGACACACAAGTGAACCCGGCAGTGTGGGAAATCAGCGGACATATGGTTT
276582_KAJB_Ae         (1305)  GAAGTGAGTTCCGAGCTTCTGGACACACAAGTGAACCCGGCAGTGTGGGAAATCAGCGGACATATGGTTT
315905_ABOC            (1412)  GAAGTGAGTGCAGAGTTCTGGATACACAGTGAACCAGCGTGTGGGAAATTAGTGGGCATATGGTCT
319998_KAZD            (1230)  GAAGTGAGTTCCGATCTTCTGGACACACAAGTGAACCCAGCCGTGTGGGAAATCAGCGGACATATGGTTT
At4g26850              (1501)  GAAGTGAGCCCGGAGTTATTGGAAAACAAGTGAACCAGCCGTGTGGGAGATAAGTGGTCACATGGTAC
At5g55120              (1408)  GAAGTTAGCTCAACGCTATTGGATACGCAAGTAATCAGCAGGTTTGGGAGATGAGTGGACACATGGTGT
BT013858_tomato        (1441)  GTTGTAGACCAAGAGCTCCTGGACACTCAGGTGAACCCTGCTGTATGGGAAATTAGTGGACATATAGTGC
NM_001072870_Os        (1451)  GAAGTGAGCCAGGAGCTACTGGACACACAGGTTAACCCAGCTGTGTGGGAGATCAGTGGCCACATCGTGC
Potato VTC2 contig from ESTs (1058) CAGGTCAGCGCTGAACTCCTGGACACCCAAGTCAATCCTGCTGTCTGTTTGGGAGATTAGTGGACATGGTCT
82552_AARA_NNT         (1006)  GAAGTGAGAGCAGAGATTCTGGATACACAGGTGAATCCAGCTGTGTGGGAAATTAGTGGGCATATGGTGC
                                                                                                      1937
244893_KAIA            (1636)  TGAAGAGGAAGGAG-GACTATGAGGAGGCCGTCTGAAGGAAATGCTTGGAGGCTCCTTGCTTGCTGAGGTCTCCC
24547_KUFA             (1728)  TGAAGAGGAAGGAG-GACTATCAGGAGGCCGTCTGAAGGAAATGCTTGGAGGCTCCTTGCTGCTGAGGTCTCCC
276582_KAJB_Ae         (1375)  TGAAGAGGAAGGAG-GACTATCAGGAGGCCGTCTGAAGGAAATGCTTGGAGGCTCCTTGCTGCTGAGGTCTCCC
315905_ABOC            (1482)  TGAAGAGGAAAAAG-GACTACGACGAGGCCGTCTCAGATGAAAATGCTTGGAGGCTCCTGGCAGAGGTTTCCC
319998_KAZD            (1300)  TGAAGAGGAGGAG-GACTATGAGGAGGCCGTCTGCTTCAGGAGCTCCAGCCGTGGAGGCTCCTTGCTGCTGAGGTCTCCC
At4g26850              (1571)  TGAAGAGGAAAGAG-GATTACGAAGGTGCTCAGAGAGCGTCAGAGGATAAACGCTGGAGGCTGGAGGCTCCTTGCGGAAGCTTCTC
At5g55120              (1478)  TGAAGAGGAAAGAA-GACTATGAGGAGCGTCAGAGAGAGGAATATGCATGGAGAAACTTCTTCTTCTGAGGTTTCTT
BT013858_tomato        (1511)  TTAAGCGAACAAAG-GATTACAATGATGCATGAGGAGGAGATAAGCTCCTCGCTCAGGACTCCTGAGGTTTCCA
NM_001072870_Os        (1521)  TGAA--ACGAAGGAGTGATTACGAGGAGGAGCTTCTCGCGTGGCAGACTCCTCGCTCGCCGAGGTCTCAC
Potato VTC2 contig from ESTs (1128) TGAAGAGGAAGGAG-GATTATGAGGGTGCAACTGAGGGTGCAAATGCAAATGAGGGCAAATGCATGGAGGCTTCTCGCGCCGAGGTCTCAC
82552_AARA_NNT         (1076)  TAAAGAGGAAAAAG-GACTATGATGAGGCGTCGGATGAAAATGCTTGAAGCTCCTGGAAGCTCCTGGCAGAGGTCTCCC
                                                                                                      2007
244893_KAIA            (1705)  TTTCGGGGAGGAGTTTGAAGAGAGTCAAGGCATTGATCTTTGAAGCCATCTCTTGTGCT-GATGAT-AGA
24547_KUFA             (1797)  TTTCGGAGGAGAGGTTCGAAGAAGTCAAGGCCATTGATCTCTTTGAAGCCATCTCTTGTGCT-GATGAT-AGA
276582_KAJB_Ae         (1444)  TTTCGGAGGAGAGGTTCGAAGAAGTCAAGGCCATTGATTCTTTTGAAGCCATCTCTTGTGCT-GATGAT-AGA
315905_ABOC            (1551)  TTCTCGGAGGAGAGGTCCAAGAAGAGTCCAAGAAGAATGCTCTTATTCGAACGTATTCCGGT-AATAAT-GGG
319998_KAZD            (1369)  TTTCGGAGGAGAGGTTCGAAGAAGTCAAGGCCATTGATTCTTGAAGCCATCTCTTGTGCT-GATGAT-AGA
At4g26850              (1640)  TGTCGGAGGAAAGGTTTTAAGGAGGTTACTGCTCCGCCCCTTTGAAGCCATAGGTTGTAGT-AACCA--AGA
At5g55120              (1547)  TATCAGAGGAGAGATTCAGAGAGTTAACACTATGATATTTGATGCCAAGCAGCTGATC-T------ACAAGCAGA
BT013858_tomato        (1580)  TATCAGAGGAGAGATTGAAGAAGTAAAGGGCTATATTTCTGAAGCAGCTGATC-T------ACAAGCAGA
NM_001072870_Os        (1590)  TGTCGGAGGAACGCTTCGAGGAAGTGAAGGCCTACTGCTCTCTCATGCTCATGCATGGAGCTATTAGTCTCAGT-GTTGAAGAGA
Potato VTC2 contig from ESTs (1197) TCTCTGAAGCAAGGTTCCAAGAAGTGACTGCTCTGCTCCATCTTTGAAGCTATTAGTCTCAGT-GTTGAAGAGA
```

FIGURE 9G

```
82552_AARA_NNT         (1145) TTTCTGAAGAAAGTTCCTAGAAGTGAATGCTCTTATTTCGAAGGTATTGCTTCGGGT-GATAACGGGA
                                                                                                  2077
244893_KAIA            (1773) AGCAGCAGCAC----AGCTGAGAACTTGCTTGAGGAGCCAGATGACAATCCTCAATCTC--GTGA-AGAA
24547_KUFA             (1865) AGCGGCAGCAC----GGCTGAGAACTTGCTTCGAG-------------------------------
276582_KAJB_Ae         (1512) AGCGGCAGCAC----AGCTGAGAACTTGCTCGAGGAGCCAGATAACGATCCTCAATCTC--GTGA-AGTA
315905_ABOC            (1619) AA-------------TGAAAATTGCCGGAGGAGATCCGAGGAGCCAGAAGTTAAGCCTGTTCTC--ATGA-AGAA
319998_KAZD            (1437) AGTGGCAGCAC----GGCTGAGAACTTGCTCGAGGAGCCAGAGCAGCCAGATGACAATCCACAATCTC--GCAA-AGTA
At4g26850              (1707) GGAGGATCT------TGAAGGACCATATTCATCAGCAGAAGAAAACTTAGTGGCAATGTTA--ACCAGAAAA
At5g55120              (1614) AGAAGA---------AGAAGAGAGGAGCTTGAAGAGCAGAATTC---------GAT-----------
BT013858_tomato        (1644) TGAGGA---------TGAAAACATCAATCCAGAGAAGAAAATTCCAGATTCCTGGTCC--------GCA
NM_001072870_Os        (1660) GGAGGAAGTCAGCGAAGACGGAGACGCCACCTACACGCCTGTCTCCATTGCCCCTCCTGCTGCGGAA
Potato VTC2 contig from ESTs (1266) ATGAGAACGCC----A-ATGAGGTTCTCCTGAGATCCTAGATGTCACACCTTCCACAGC---CCATGGAG
82552_AARA_NNT         (1214) AT-------------GAAAACTTGCTCAAGGATCCAAGAAGTTAAGCCTCGTTCTC----A--TGAA
                                                                                                  2147
244893_KAIA            (1836) GCAAATGATGCCCTAACAAAGCTCCCACTCTGGTATGGTGCCGGGAAAGCAAGAATGCCTAGT-TCAG
24547_KUFA             (1895) ----------------------------------------------------------------
276582_KAJB_Ae         (1575) GCGAATGATGCCCTAGCAAAGCCCTCCACCGAGTGGTGCCAGGGAAGCAAGAATGCCTAGT-TCAG
315905_ABOC            (1670) GTCGACGCTACCATTAACAAAGACCTCCCGCGCTGTCATGGTTGGTGAGACAAGAATGCATTGT-TCTG
319998_KAZD            (1500) GCGAATGATGCCCTTAACAAAGCCCTCCACCGAGGTATGGTGCCAGGGAAGCAAGAATGCCTAGT-TCAG
At4g26850              (1769) GCAACAGAACCCATGGAGGTCCGATCACAAATGGGACGGCCGC------------GAGTGCCTTGT-CCTT
At5g55120              (1653) GA-------------ATGGTGGCAGCTTCACAAT----------------------AGTGCATTGT-CCTT
BT013858_tomato        (1698) GG----TGGCCTCACATATTCCTCAGATTGTTTGGTGTTGCAGTGAAGAATTGTGGCTTGCTCTTG
NM_001072870_Os        (1730) GGCTGCCTCGTCCTTCAGTGAGACGGTAGAACAGGTTGTCGGCTGGTAAAGCGCTGCCCTTCGTC
Potato VTC2 contig from ESTs (1328) GAGATTGA-------TGGGTCTCACACCCATAGTACCATGGTTCC-----------CGCCTAGGTTTT
82552_AARA_NNT         (1261) GAAG-----------TCAACACCATCAACAAAA-----------------------GAGTGCATTGT-TCTG
                                                          2191
244893_KAIA            (1905) CACTGAGAATTTGGG-CATTGAAGAATGTTCAGTGGTTTGTGT
24547_KUFA             (1895) -----------------------------------------
276582_KAJB_Ae         (1644) CACTGAGAATTTGGG-CATTGAAGAATGTTCAGTGGTTTGTAT
315905_ABOC            (1739) CAGT---AAATGAGC-AGATTGGTGGGTGTTCAGTGGTTTACAA-TGTGAAT
319998_KAZD            (1569) CACTGAGAATTGGGG-CATTGAAGAATGTTCAGTGGTTTGTGT
At4g26850              (1828) CAGT--GAAC-----AATATGGTGACT---TGGTGGTTTGTAT
At5g55120              (1688) CAGT--GAAAG----AAGAGGCTGTCTC--TAATTGAGGCGCT
BT013858_tomato        (1762) CAAGATCTAATAAA-AGTTTGAAGTATTATCTAGTGTATGGTT
NM_001072870_Os        (1800) TTCTCATCAGTCTTCTTCAGTCTTCACCCGCTGGTCGCCTAGCT
Potato VTC2 contig from ESTs (1379) CACGGCCCAG-------CTCTGTGTTTTATCGCATGTATGATT
```

FIGURE 9H

82552_AARA_NNT (1298) CAGT----AAATGAGCAGAGATTGTGTCGGGTGTTTACAA-TGTGAAT

FIGURE 10

| | 244893_Ac | 24547_Ae | 276582_Ae | 315905_Ms | 319998_Ac | At4g26850 | At5g55120 | BT013858_Le | Os12g019000 | Contig-St | 82552_Md |
|---|---|---|---|---|---|---|---|---|---|---|---|
| 244893_Ac | | 95 | 95 | 73 | 95 | 65 | 64 | 57 | 57 | 74 | 72 |
| 24547_Ae | | | 100 | 79 | 98 | 68 | 68 | 62 | 62 | 75 | 81 |
| 276582_Ae | | | | 74 | 97 | 68 | 67 | 60 | 60 | 73 | 73 |
| 315905_Ms | | | | | 74 | 67 | 67 | 59 | 59 | 71 | 87 |
| 319998_Ac | | | | | | 67 | 66 | 60 | 61 | 73 | 74 |
| At4g26850 | | | | | | | 74 | 56 | 58 | 69 | 68 |
| At5g55120 | | | | | | | | 58 | 59 | 69 | 67 |
| BT013858_Le | | | | | | | | | 57 | 63 | 60 |
| Os12g019000 | | | | | | | | | | 64 | 60 |
| Contig-St | | | | | | | | | | | 73 |
| 82552_Md | | | | | | | | | | | |

| | Actinidia deliciosa 198296_KALA | Actinidia eriantha 169164 | Arabidopsis thaliana AT5G28840 | Malpighia glabra DQ229167 | Malus pumila 108403_AAOA | Ostreococcus lucimarinus XM_001422193 | Solanum tuberosum DQ268848 | Vitis vinifera EF554358 | Lycopersicon esculentum BT013590 | Oryza sativa AB193582 | Oryza sativa AB235855 |
|---|---|---|---|---|---|---|---|---|---|---|---|
| Actinidia deliciosa 198296_KALA | 100 | | | | | | | | | | |
| Actinidia eriantha 169164 | 98 | 100 | | | | | | | | | |
| Arabidopsis thaliana AT5G28840 | 90 | 90 | 100 | | | | | | | | |
| Malpighia glabra DQ229167 | 93 | 92 | 91 | 100 | | | | | | | |
| Malus pumila 108403_AAOA | 94 | 94 | 91 | 94 | 100 | | | | | | |
| Ostreococcus lucimarinus XM_001422193 | 69 | 69 | 70 | 69 | 69 | 100 | | | | | |
| Solanum tuberosum DQ268848 | 83 | 82 | 81 | 84 | 86 | 62 | 100 | | | | |
| Vitis vinifera EF554358 | 94 | 94 | 92 | 95 | 94 | 69 | 83 | 100 | | | |
| Lycopersicon esculentum BT013590 | 92 | 92 | 91 | 92 | 93 | 70 | 84 | 95 | 100 | | |
| Oryza sativa AB193582 | 92 | 91 | 90 | 93 | 90 | 69 | 82 | 92 | 90 | 100 | |
| Oryza sativa AB235855 | 64 | 64 | 65 | 64 | 64 | 62 | 58 | 64 | 64 | 64 | 100 |

```
                                                                                        158
         89
108403  (88)   TTT----CAGAATGGGAAGTACAGGCGAAATTAAGTATGGTGCGTATACCTATGAGAACCTCGAGAGGAGC
169164  (41)   TT-----CAGAATGGGAAGCACCGGTGAATCTAACTACGGATCGTACACCTATGAGAACCTTGAGAGGAAC
198296  (75)   TT-----CAGAATGGGAAGCAGCAGCTACCAATGAATCTAACTACGGATCGTACACCTATGAGAACCTCGAGAGGAAC
At5g28840 (80) TTCCTCAGAATGGGAACTACCAATGGAACAGACTATGGAGCATACATACAAGGAGCTAGAAAGAGAGC
                                                                                        228
         159
108403  (156)  CTTATTGGCCTTCTGAAAAGCTCCGAATTCCATTACCGGGGCAGGTGGTTTATCGCCTCCCACATTGC
169164  (108)  CCTACTGCCCGGAGGCGAAGCTCCGCATCTCCATAACCGGAGCCGGTCGCCCTCATTGCCTCACACATTGC
198296  (142)  CCTACTGCCCGGAGGCGAAGCTCCGCATCTCCATTCCGAGCCGGTCGCCGGTCATTGCCTCGCACATTGC
At5g28840 (150) AATATTGCCATCTGAGAATCTCAAGATATCAATAACAGGAGCTGGAGGTTTCATTGCATCTCACATTGC
                                                                                        298
         229
108403  (226)  CCGGAGATTGAAGAATGAGGGTCATTACATTATTGCTTCCGATTGGAAGAAGAATGAGCACATGACTGAA
169164  (178)  AAGGCGACTGAAGGGCGAGGGCATTACATCATTGCTTCTGACTGGAAGAAACGAGCACATGACCGAG
198296  (212)  AAGGCGACTGAAGGGGAGAGGGGCATTACATCATTGCTTCTGACTGGAAGAAAACGAGCACATGACCGAG
At5g28840 (220) TCGTCGTTTGAAGCACGAAGGTCATTACATTGATTGCTTGCTTCTGACTGGAAAAAAGAATGAACATGACTGAA
                                                                                        368
         299
108403  (296)  GACATGTTCTGCCATGAATTCCATCTTGCCGACCTCAGGGTCATGGATAATTGCTTGAAGGTTACAAAGA
169164  (248)  GACATGTTCTGTCACGAATTCCATCTTGTTGATCCATCTCAGGGTGATCTCAGGGTGATGGACAACTGCTTGAAAGTCACGACCA
198296  (282)  GACATGTTTTGTCACGAGTTCCATCTCGTTGATCCATCTCAGGGTGATCCAGGGTGATGGACAACTGCTTGAAAGTCACTACCG
At5g28840 (290) GACATGTTCTGTGATGAGTTCCATCTTGTTGATCCATCTTGTTGATCTTAGGGTTATGGAGAATTGTCTCAAAGTTACTGAAG
                                                                                        438
         369
108403  (366)  ATGTTGACCATGTGTTCAACCTGCAGCTGATATGGCGGAATGGGCTTCATTCAGTCCAACCATTCTGT
169164  (318)  GAGTTGATCATGTGTTCAATCTTGCTGCTGCTGCTGCTCAGCCTTCAGCTTCAATGGCTTCATTCATTCAGTCCAATCACTCAGT
198296  (352)  GAGTCGATCATGTGTTCAATCTTCAATCTTCAATCTTGCTGCTGCTGCTCAGCCTTCAGCTTCAATGGATTCATTCAGTCCAACCACTCGGT
At5g28840 (360) GAGTTGATCATCATGTTTTTAACTTAGCTGCTCAGTTGCTGATATGGGTTTTATCCAGAGTAATCACTCTGT
                                                                                        508
         439
108403  (436)  CATATTTTATAACAATACCATGATTAGTTTCAACATGGTCGAAGCTGCTAGGATCAATGACGTGAAGAGG
169164  (388)  CATTATGTATAACAACACAACAATGATCAGCTTCAACATGCTTGAAGCTGCTAGGGTCAATGGTATTAAGAGG
198296  (422)  CATTATGTATAACAACACGATGATCAGCTTCAACATGCTTGAAGCAGCTAGGGTCAATGGTGTTAAGAGG
At5g28840 (430) GATTATGTATAATAATACTATGATTAGTTTCAATATGATTGAGGCTGCTAGGATCAATGGGATTAAGAGG
                                                                                        578
         509
108403  (506)  TTTTTTCTATGCTTCTAGTGCTTGTATTTACCCTGAGTTTAAGCAGCTGGAAACCA---ATGTCAGCTTGA
169164  (458)  TTCTTTTATGCTTCTAGCGCTTGTATTTGTATTTACCCTGAATTTAAGCAGTTGGACACAA---ATGTGAGCTTGA
198296  (492)  TTCTTTTATGCTTCTAGCGCTTGCTTGTATTTATCCTGAATTTAAGCAGTTGGACACTA---ATGTGAGCTTGA
At5g28840 (500) TTCTTTTATGCTTGCTTCGAGTGCTTGCTTGATCTATCCAGAGTTTAAGCAGTTGGAGACTACTAATGTGAGCTTGA
```

FIGURE 13B

```
                579                                                                                          648
108403    (573) AGGAGTCTGATGCCTGGCCTGCAGAGAGCCTCAAGATGCTTATGGCCTGAGAAGCTTGCAACTGAGGAATT
169164    (525) AGGAATCTGATGCTTGGCCCCGTCGCCCCCTGAGCCTCAAGATGCTTATGGTTTAGAGAAGCTTGCAACCGAGGAGTT
198296    (559) AGGAGTCTGATGCTTGGCCTTGGCCCCTGGCCTGCAGAGCCTCAAGATGCTTATGGTTTAGGAGAAGCTTGCAACCGAGGAATT
At5g28840 (570) AGGAGTCAGATGCTTGGCCTTGCCTGCAGAGCCTCAAGATGCTTATGGTTTGGAGAAGCTTGCTACGGAGGAGTT
                649                                                                                          718
108403    (643) GTGCAAGCACTACACCAAAGACTTTGGAATCGAGTGCCGTATTGGAAGGTTCCACAACATTTATGGCCCT
169164    (595) ATGCAAGCACTACACCAAGGACTTTGGCATTGAATGGATTGGACGGTTTCACAACATCTATGGACCT
198296    (629) ATGCAAGCACTACACCAAGGAGATTTTGGCATTGAATGGATTGGAAGGTTCATAACATTTATGGACCT
At5g28840 (640) GTGTAAGCATTACAACAAGATATTTGGTATTGAGTGTCGAATTGGAAGGTTCCATAACATTTATGGTCCT
                719                                                                                          788
108403    (713) TTTGGAACCTGGAAAGTGGAAGGGAGAAGGCTCCTGCTGCGTTTGCAGAAAGACTCTCACTGCCACTG
169164    (665) TTTGGAACCTGGAAAGTGGGAGGGAGAAGGCTCCTGCTGCGTTTGCAGAAAGACCCTTACCTCCACTG
198296    (699) TTTGGAACATGGAAAGTGGAAGGGAGAAGGCTCCTGCATTCTGCAAACCGATCCCTTACCTCCACTG
At5g28840 (710) TTTGGAACATGGAAAGTGGAAGGGAGAAGGCTCCAGCTGCTTCAGACCCGATCCTCTTCACCTTTATTGATGAATGTGTAGAAGG
                789                                                                                          858
108403    (783) ATAAGTTTGAGATGTGGGGAGATGGGAGAGTCAGACTTCAGACCCGATCCTCACCTTTATTGATGAATGTGTAGAAGG
169164    (735) ATAGGTTTGAGATTGACGAAGTCAGAACTTCAGACCCGATCCTCACCTTCATTGATGAATGTGTCGAAGG
198296    (769) ATAGGTTTGAGATGTGGGAGACGGTCTGCAAACCGATCCTCACCTCCATTGATGAATGTGTCGAAGG
At5g28840 (780) ATAGGTTTGAGATGTGGGAGATGGGCTTCAGACCCGATCCTCACCTCCATTGATGAATGTGTCGAAGG
                859                                                                                          928
108403    (853) TGTACTTCGGTTGACGAAGTCAGACTTCCGTGAGCCAGTGAATATTGGAAGTGATGAGATGGTTAGCATG
169164    (805) TGTCCTAAGATTGACGAAGTCAGACTTCAGAGAACCAGTGAATATCGGAAGTGATGAGATGGTCAGCATG
198296    (839) TGTCCTAAGATTGACAAAATCAGACTTCAGAGAACCAGTGAATATAGGAAGCGATGAGATGGTCAGCATG
At5g28840 (850) TGTACTCAGGTTGACAAAATCAGATTTCCGTGAGCCGGTGAACATCGGAAGCGATGAGATGGTGAGCATG
                929                                                                                          998
108403    (923) AATGAGAATGGCTCAGATCGTTCTTAGCTTTGAGGACAAGAAGCTGCCCATCCAGCACATTCCTGGGCCAG
169164    (875) AATGAGAATGGCCGAGATCGTTCTCAGCTTCGAGAACAACAAGAAACTGCCCATCCATCACATTCCGGGGCCAG
198296    (909) AATGAGAATGGCCGAGATCGTTCTCAGCTTCGAGGACAACAAGAAGCTGCCCATCCATCACATTCCTGGCCAG
At5g28840 (920) AATGAGAATGGCCGAGATGGCTGAGATGGTTCAGCTTCCAGCTTTGCAGGAAAAGAAGCTTCCAATTCACCACATTCCTGGCCCG
                999                                                                                         1068
108403    (993) AGGGGTGTCCGTGGTCGTAACTCAGACAACACACTGATCAAAGAGAAACTTGTTGGGCTCCTACCATGAG
169164    (945) AGGGGCGTCCGTGGCCGTGACGAAAACTCGGACGAAACTCGGACAACAACCCTGATTAAGGAGAAGCTTGGTGGCCCAACTATGAA
198296    (979) AGGGGGTCCGTGGTCGTGACGAAAACTCGGACAACAACCCTGATTAAGGAGAAGCTTGGTGGCCCCAACTATGAA
At5g28840 (990) AAGGTGTTCGTGGTCGTAACTCAGACAACAACAATCTGATCAAAGAAAAGCTTGATCAAAGAAAAGCTTGGTGGCTCCTAATATGAG
                1069                                                                                        1138
```

FIGURE 13C

```
108403     (1063)  GTTGAAGGATGGTCTGAGAATTACATACTTCTGGATCAAGGAACAGATTGAGAAAGAGAAGGCACAAGGC
169164     (1015)  ACTGAAGGATGGGCTGAGATTCACATACTTTTGGATCAAGGAACAACTTGAGAAAGAGAAGGCTCGGGGC
198296     (1049)  ACTGAAGGATGGGCTGAGATTCACATACTTCTGGATCAAGGAGCAACTTGAGAAGAGAAGGCTCAGGGC
At5g28840  (1060)  ATTGAAGGAGGGGCTTAGAATAACCTACTTCTGGATAAAGGAACAGATCGAGAAGAGAAGCAAAGGGA
                                                                                       1208
108403     (1133)  GCTGACCTCTCGGTGTATGGCTCATCTAAGGTTGTGGGAACCCCAGTTCAACTTGGTTCGCTGC
169164     (1085)  ATCGATCTGTCAACTTATGGGTCATCAAAAGTTGTGGGAACGCAAGCCCAGTTCAGTTCAGTTGGGCTCTCTTC
198296     (1119)  ATCGATCTGTCAACTTATGGATCGTCAAAAGTTGTGGGAACGCAAGCCCGGTTCAGTTCAGTTGGGCTCTCTTC
At5g28840  (1130)  AGCGATGTGTCGCTTTACGGTCATCAAAGGTGGTTGGAACTCAAGCACCGGTTCAAGCTAGCCTAGGCTCACTCC
                         1209                                                        1233
108403     (1203)  GTGCTGCTGATGGCAAAGAATGAAG
169164     (1155)  GTGCTGCTGATGGCAAAGAATGAAG
198296     (1189)  GTGCTGCTGATGGCAAAGAATGAAG
At5g28840  (1200)  GCGCGGCTGATGAAAAGAGTGAAG
```

FIGURE 14

|           | 108403 | 169164 | 198296 | At5g28840 |
|-----------|--------|--------|--------|-----------|
| 108403    | 100    | 78     | 77     | 71        |
| 169164    |        | 100    | 94     | 74        |
| 198296    |        |        | 100    | 74        |
| At5g28840 |        |        |        | 100       |

FIGURE 16A

| Transferase EST | description | species | Vector | Agrobacterium | Epimerase added (169164) | leaf | mg asc/100g | relative to P19 control | average over all leaves | rel asc to average control P19 |
|---|---|---|---|---|---|---|---|---|---|---|
| none | control | | | | no | 1 | 33.8 | 1.0 | 35.4 | 1.0 |
| | | | | | | 2 | 36.0 | 1.0 | | |
| | | | | | | 3 | 36.5 | 1.0 | | |
| none | epimerase control 169164 | A. eriantha | pGreen | GV3101 | yes | 1 | 40.6 | 1.2 | 42.1 | 1.2 |
| | | | | | | 2 | 41.8 | 1.2 | | |
| | | | | | | 3 | 43.8 | 1.2 | | |
| 319998 | transferase | A. chinensis | pGreen | GV3101 | no | 1 | 91.1 | 2.7 | 150.2 | 4.2 |
| | | | | | | 2 | 144.6 | 4.0 | | |
| | | | | | | 3 | 214.9 | 5.9 | | |
| 319998 | transferase | A. chinensis | pGreen | GV3101 | yes | 1 | 152.8 | 4.5 | 303.9 | 8.6 |
| | | | | | | 2 | 306.3 | 8.5 | | |
| | | | | | | 3 | 452.5 | 12.4 | | |
| 319998 | transferase | A. chinensis | pHex2s | EHA105 | no | 1 | 104.3 | 3.1 | 166.3 | 4.7 |
| | | | | | | 2 | 130.5 | 3.6 | | |
| | | | | | | 3 | 264.3 | 7.2 | | |
| 319998 | transferase | A. chinensis | PHex2s | GV3101 | no | 1 | 90.2 | 2.7 | 153.5 | 4.3 |
| | | | | | | 2 | 130.1 | 3.6 | | |
| | | | | | | 3 | 240.2 | 6.6 | | |
| 142730 | transferase | apple | pGreen | GV3101 | no | 1 | 46.5 | 1.4 | 48.6 | 1.4 |
| | | | | | | 2 | 46.2 | 1.3 | | |

FIGURE 16B

| | | | | | | | |
|---|---|---|---|---|---|---|---|
| 142730 | transferase | apple | pGreen | GV3101 | yes | 3 | 53.3 | 1.5 |
| | | | | | | 1 | 57.5 | 1.7 | 75.7 | 2.1 |
| | | | | | | 2 | 75.0 | 2.1 |
| | | | | | | 3 | 94.6 | 2.6 |
| BTO13858 | transferase | Tomato | pGreen | GV3101 | no | 1 | 64.9 | 1.9 | 57.6 | 1.6 |
| | | | | | | 2 | 64.1 | 1.8 |
| | | | | | | 3 | 43.9 | 1.2 |
| BTO13858 | transferase | Tomato | pGreen | GV3101 | yes | 1 | 59.5 | 1.8 | 78.2 | 2.2 |
| | | | | | | 2 | 90.5 | 2.5 |
| | | | | | | 3 | 84.7 | 2.3 |

FIGURE 17A

| Transferase EST | description | species | Vector | Agrobacterium | Epimerase added (169164) | leaf | mg asc/100g control | relative average to P19 control | average over all leaves | rel asc to average control P19 |
|---|---|---|---|---|---|---|---|---|---|---|
| 319998 | transferase | His tagged 319998 pGreen | | GV3101 | | combined leaves | 134.1 | 2.5 | | |
| none | | control for His tagged | | | | combined leaves | 54.2 | | | |
| None | P19 control | | | | none | 1 | 32.4 | 1.0 | 28.0 | 1.0 |
| | | | | | | 2 | 28.3 | 1.0 | | |
| | | | | | | 3 | 23.4 | 1.0 | | |
| None | P19 + epimerase from Kiwifruit control | | | | 169164 | 1 | 37.7 | 1.2 | 29.4 | 1.1 |
| | | | | | | 2 | 22.2 | 0.8 | | |
| | | | | | | 3 | 28.3 | 1.2 | | |
| None | P19 + epimerase from apple control | | | | 108403 | 1 | 34.7 | 1.1 | 28.0 | 1.0 |
| | | | | | | 2 | 28.0 | 1.0 | | |
| | | | | | | 3 | 21.2 | 0.9 | | |
| 319998 | transferase | kiwifruit | pgreen | GV3101 | none | 1 | 116.4 | 3.6 | 77.4 | 2.8 |
| | | | | | | 2 | 75.7 | 2.7 | | |
| | | | | | | 3 | 40.2 | 1.7 | | |
| 319998 | transferase + KF epimerase | kiwifruit | pgreen | GV3101 | 169164 | 1 | 162.8 | 5.0 | 152.3 | 5.4 |
| | | | | | | 2 | 198.8 | 7.0 | | |
| | | | | | | 3 | 95.2 | 4.1 | | |
| 319998 | transferase + apple epimerase | kiwifruit | pgreen | GV3101 | 108403 | 1 | 95.3 | 2.9 | 78.7 | 2.8 |

FIGURE 17B

| | | | | | | | |
|---|---|---|---|---|---|---|---|
| 319998 | transferase | kiwifruit | Bar resistant pgreen GV3101 | none | 2 | 79.3 | 2.8 | |
| | | | | | 3 | 61.5 | 2.6 | |
| | | | | | 1 | 94.1 | 2.9 | 85.8 | 3.1 |
| | | | | | 2 | 106.2 | 3.8 | |
| | | | | | 3 | 57.3 | 2.4 | |
| 319998 | transferase + KF epimerase | kiwifruit | Bar resistant pgreen GV3101 | 169164 | 1 | 249.7 | 7.7 | |
| | | | | | 2 | 207.9 | 7.4 | 223.9 | 8.0 |
| | | | | | 3 | 214.0 | 9.2 | |
| 319998 | transferase + apple epimerase | kiwifruit | Bar resistant pgreen GV3101 | 108403 | 1 | 169.6 | 5.2 | |
| | | | | | 2 | 101.1 | 3.6 | 123.1 | 4.4 |
| | | | | | 3 | 98.5 | 4.2 | |

FIGURE 18A

| Line # | Number sensitive | Number resistant | Number expected | Chi statistic | Significant level? | Significant at 5% | Significant at 1% level? | # inserts |
|---|---|---|---|---|---|---|---|---|
| 1 | 18 | 142 | 40 | 12.1 | TRUE | TRUE | TRUE | |
| 2 | 8 | 59 | 16.75 | 4.6 | TRUE | TRUE | FALSE | |
| 3 | 5 | 12 | 4.25 | 0.13 | FALSE | FALSE | FALSE | |
| 5 | 12 | 162 | 44 | 22.8 | TRUE | TRUE | TRUE | |
| 6 | 41 | 167 | 52 | 2.3 | FALSE | FALSE | FALSE | one insert |
| 7 | 7 | 112 | 30 | 17.4 | TRUE | TRUE | TRUE | |
| 8 | 4 | 22 | 6.5 | 0.96 | FALSE | FALSE | FALSE | one insert |
| 9 | 0 | 130 | 33 | 32.5 | TRUE | TRUE | TRUE | |
| 10 | 0 | 47 | 11.75 | 11.8 | TRUE | TRUE | TRUE | >2 inserts |
| 11 | 7 | 315 | 81 | 67.1 | TRUE | TRUE | TRUE | |
| 12 | 3 | 121 | 31 | 25.3 | TRUE | TRUE | TRUE | |
| 13 | 7 | 82 | 22 | 10.5 | TRUE | TRUE | TRUE | |
| 14 | 17 | 171 | 47 | 19.1 | TRUE | TRUE | TRUE | |
| 16 | 17 | 199 | 54 | 25.4 | TRUE | TRUE | TRUE | |
| 17 | 0 | 6 | 1.5 | 1.5 | FALSE | FALSE | FALSE | contaminated |
| 18 | 2 | 62 | 16 | 12.3 | TRUE | TRUE | TRUE | |
| 19 | 18 | 320 | 85 | 52.3 | TRUE | TRUE | TRUE | |
| 20 | 0 | 189 | 47 | 47.3 | TRUE | TRUE | TRUE | >2 inserts |
| 21 | 0 | 187 | 47 | 46.8 | TRUE | TRUE | TRUE | >2 inserts |
| 25 | 13 | 110 | 31 | 10.2 | TRUE | TRUE | TRUE | |
| 26 | 7 | 234 | 60 | 47.1 | TRUE | TRUE | TRUE | |
| 33 | 22 | 335 | 89 | 50.7 | TRUE | TRUE | TRUE | |

FIGURE 18B

| | | | | | | |
|---|---|---|---|---|---|---|
| 34 | 5 | 12 | 4.25 | 0.13 | FALSE | FALSE | |
| 37 | 5 | 284 | 72 | 62.6 | TRUE | TRUE | |
| 38 | 2 | 83 | 21.25 | 17.4 | TRUE | TRUE | |
| 39 | 1 | 0 | 0.25 | 2.25 | FALSE | FALSE | |
| 40 | 5 | 105 | 27.5 | 18.4 | TRUE | TRUE | contaminated |
| 41 | 22 | 208 | 58 | 21.9 | TRUE | TRUE | |
| 43 | 6 | 23 | 7.25 | 0.22 | FALSE | FALSE | |
| 44 | 46 | 155 | 50 | 0.4 | FALSE | FALSE | one insert |
| 46 | 1 | 155 | 39 | 37.0 | TRUE | TRUE | |

FIGURE 19

| Line | # plants | mean ASC if ASC < 60 | # with ASC < 60 | mean ASC if ASC > 80 | # with ASC > 80 |
|---|---|---|---|---|---|
| 2 | 6 | 44 | 4 | 186 | 1 |
| 6 | 8 |  | 0 | 176 | 8 |
| 8 | 11 | 39 | 9 | 213 | 1 |
| 16 | 10 | 29 | 7 | 174 | 2 |
| 21 | 5 | 38 | 2 | 149 | 3 |
| 34 | 9 | 50 | 6 | 152 | 2 |
| 37 | 4 | 48 | 4 |  | 0 |
| 40 | 10 | 49 | 2 | 92 | 3 |
| 41 | 3 | 42 | 1 | 84 | 1 |
| 43 | 1 | 47 | 1 |  | 0 |
| 44 | 10 | 40 | 7 | 170 | 2 |
| phex1 | 8 | 51 (±3) | 8 |  | 0 |
| wt8 | 8 | 52 (±4) | 7 |  | 0 |

FIGURE 20A

| Line | mean ASC if ASC < 50 | SE | mean ASC if ASC > 80 | SE | max ASC | total # | # resistant to Kn | # with ascorbate > 80 | # asc < 50 |
|---|---|---|---|---|---|---|---|---|---|
| pHEX control | 50 | 2 | | | 60 | 20 | 20 | 0 | 8 |
| WT control | 53 | 2 | | | 70 | 11 | 11 | 0 | 5 |
| 2.1 | 41 | 2 | 122 | 21 | 154 | 11 | 11 | 3 | 7 |
| 2.7 | 42 | 1 | | | 48 | 12 | 12 | 0 | 12 |
| 6.19 | 43 | 2 | 140 | 12 | 184 | 12 | 12 | 6 | 3 |
| 6.21 | 44 | 2 | 101 | 7 | 124 | 10 | 10 | 5 | 4 |
| 8.12 | 42 | 2 | | | 65 | 12 | 12 | 0 | 8 |
| 8.7 | 34 | 4 | 95 | | 132 | 11 | 11 | 2 | 10 |
| 16.2 | 47 | 1 | 146 | 24 | 216 | 12 | 12 | 4 | 6 |
| 16.20 | 48 | | 128 | | 128 | 9 | 9 | 1 | 1 |
| 21.2 | 45 | 2 | 107 | 7 | 119 | 10 | 10 | 3 | 5 |
| 34.5 | | | 132 | 15 | 210 | 9 | 9 | 7 | 0 |
| 40.10 | 37 | 2 | | | 49 | 11 | 11 | 0 | 11 |
| 44.1 | 42 | 1 | | | 64 | 11 | 11 | 0 | 4 |
| 44.12 | 46 | 1 | 100 | 3 | 105 | 11 | 11 | 3 | 5 |

FIGURE 20B

| 44.2 | 49 | 0 | 164 | 23 | 204 | 11 | 11 | 2 | 4 |
| --- | --- | --- | --- | --- | --- | --- | --- | --- | --- |
| 44.3 | 41 | 1 | 105 | | 53 | 12 | 12 | 0 | 11 |
| 44.4 | 31 | 10 | | | 105 | 11 | 11 | 1 | 4 |

FIGURE 21

| Arabidopsis transgenic line | Ascorbate conc mg/100g FW | qPRC expression of 319998 |
|---|---|---|
| 2-1 10 | 30 | 0 |
| 2-1 11 | 130 | 8000 |
| 6-21 3 | 124 | 1500 |
| 6-21 5 | 41 | 0 |
| 34-5 3 | 55 | 0 |
| 34-5 5 | 133 | 4500 |
| 34-5 6 | 147 | 6500 |
| 34-5 8 | 118 | 6000 |
| 40-10 7 | 33 | 0 |
| 44-4 7 | 105 | 8500 |
| 44-12 4 | 105 | 5500 |
| 44-12 6 | 41 | 4500 |
| phex6 | 45 | 0 |
| wt6 | 48 | 0 |

FIGURE 22

| Sample number | 319998 PCR | ascorbate concentration (mg/100g FW) | Relative ascorbate |
|---|---|---|---|
| 1 | - | 31 | 0.9 |
| 2 | - | 39 | 1.2 |
| 3 | - | 29 | 0.9 |
| 4 | - | 35 | 1.1 |
| 5 | + | 29 | 0.9 |
| 6 | + | 28 | 0.8 |
| 7 | + | 38 | 1.1 |
| 8 | + | 52 | 1.6 |
| 9 | + | 29 | 0.9 |
| 10 | + | 53 | 1.6 |
| 11 | + | 29 | 0.9 |
| 12 | + | 33 | 1.0 |

FIGURE 23

| EST | species | F/min/uL | nmole/min/uL | ug protein/uL | nmoles/sec/mg protein | nmoles/sec/nmole | instrument |
|---|---|---|---|---|---|---|---|
| 73032 | A deliciosa | 4822 | 2.135 | 4.19 | 0.509 | 9.21 | new |
| 142730 | apple | 2043 | 0.905 | 2.80 | 0.323 | 5.84 | new |
| 315905 | Crab apple | 81 | 0.036 | 0.25 | 0.144 | 2.61 | new |
| 319998 | kiwifruit | 11097 | 2.824 | * | | | old |
| At5g55120 | arabidopsis | 2534 | 1.122 | 2.96 | 0.379 | 6.86 | new |
| BT013858 | Tomato | 82 | 0.036 | 0.28 | 0.129 | 2.33 | new |
| Potato | potato | 894 | 0.396 | 0.58 | 0.685 | 12.39 | new |
| No addition | bg | -1 | 0.000 | | | | old |
| Pet30 | empty vector control | 0 | 0.000 | 0.12 | -0.001 | -0.02 | new |

* protein not available but in Laing et al 2007, activity was 0.35 nmoles/mg/sec.

SEQUENCE LISTING

<160> NUMBER OF SEQ IDS NOS: 51

<210> SEQ ID NO 1
<211> LENGTH: 450
<212> TYPE: PRT
<213> ORGANISM: Actinidia chinensis

<400> SEQUENCE: 1

```
Met Leu Lys Ile Lys Arg Val Pro Thr Val Val Ser Asn Phe Gln Lys
1               5                   10                  15

Asp Glu Ala Glu Asp Gly Ala Arg Ser Gly Gly Gly Cys Gly Arg Asn
            20                  25                  30

Cys Leu Gln Lys Cys Cys Ile Gln Gly Ala Lys Leu Pro Leu Tyr Ala
        35                  40                  45

Phe Lys Arg Val Lys Glu Val Val Gly Glu Lys Gly Leu Leu Ala Val
    50                  55                  60

Asp Asp Glu Glu Ala Pro Val Ala Phe Leu Asp Ser Leu Leu Leu Gly
65                  70                  75                  80

Glu Trp Glu Asp Arg Val Gln Arg Gly Leu Phe Arg Tyr Asp Val Thr
                85                  90                  95

Ala Cys Glu Thr Lys Val Ile Pro Gly Tyr Gly Phe Ile Ala Gln
            100                 105                 110

Leu Asn Glu Gly Arg His Leu Lys Lys Arg Pro Thr Glu Phe Arg Val
        115                 120                 125
```

```
Asp Lys Val Leu Gln Pro Phe Asp Glu Ser Lys Phe Asn Phe Thr Lys
    130                 135                 140

Val Gly Gln Glu Glu Val Leu Phe Gln Phe Glu Ala Ser Asp Asp Asn
145                 150                 155                 160

Glu Val Gln Phe Phe Pro Asn Ala Pro Val Asp Val Glu Asn Ser Pro
                165                 170                 175

Ser Val Val Ala Ile Asn Val Ser Pro Ile Glu Tyr Gly His Val Leu
            180                 185                 190

Leu Ile Pro Arg Ile Leu Glu Cys Leu Pro Gln Arg Ile Asp Arg Glu
        195                 200                 205

Ser Phe Leu Leu Ala Leu His Met Ala Ala Glu Ala Gly Asn Pro Tyr
210                 215                 220

Phe Arg Leu Gly Tyr Asn Ser Leu Gly Ala Phe Ala Thr Ile Asn His
225                 230                 235                 240

Leu His Phe Gln Ala Tyr Tyr Leu Ala Val Pro Phe Pro Ile Glu Lys
                245                 250                 255

Ala Pro Thr Arg Lys Ile Thr Thr Leu Asn Gly Gly Val Lys Ile Ser
            260                 265                 270

Asp Leu Leu Asn Tyr Pro Val Arg Gly Leu Val Phe Glu Gly Gly Asn
        275                 280                 285

Ser Leu Glu Asp Leu Ser Asn Ala Val Ser Asp Ser Ser Ile Cys Leu
290                 295                 300

Gln Gly Asn Asn Ile Pro Tyr Asn Val Leu Ile Ser Asp Ser Gly Lys
305                 310                 315                 320

Cys Ile Phe Leu Leu Pro Gln Cys Tyr Ala Glu Lys Gln Ala Leu Gly
                325                 330                 335

Glu Val Ser Ser Asp Leu Leu Asp Thr Gln Val Asn Pro Ala Val Trp
            340                 345                 350

Glu Ile Ser Gly His Met Val Leu Lys Arg Lys Glu Asp Tyr Glu Glu
        355                 360                 365

Ala Ser Glu Gly Asn Ala Trp Arg Leu Leu Ala Glu Val Ser Leu Ser
370                 375                 380

Glu Glu Arg Phe Glu Glu Val Lys Ala Leu Ile Phe Glu Ala Ile Ser
385                 390                 395                 400

Cys Ala Asp Asp Arg Ser Gly Ser Thr Ala Glu Asn Leu Leu Glu Glu
                405                 410                 415

Pro Asp Asp Asn Pro Gln Ser Arg Lys Val Ala Asn Asp Ala Leu Asn
            420                 425                 430

Lys Gly Ser His Arg Gly Met Val Pro Gly Lys Gln Glu Cys Leu Val
        435                 440                 445

Gln His
    450

<210> SEQ ID NO 2
<211> LENGTH: 445
<212> TYPE: PRT
<213> ORGANISM: Malus x domesticus

<400> SEQUENCE: 2

Met Leu Arg Ile Lys Arg Val Pro Thr Val Val Ser Asn Tyr Gln Lys
1               5                   10                  15

Asp Glu Ala Glu Glu Val Ala Arg Arg Val Gly Gly Cys Gly Arg Asn
            20                  25                  30

Cys Leu Asn Gln Cys Cys Ile Pro Gly Ala Lys Leu Pro Leu Tyr Ala
        35                  40                  45
```

-continued

```
Phe Lys Lys Leu Asn Val Asn Asp Gly Asp Thr Gly Leu Leu Gly Arg
    50                  55                  60

Glu Lys Arg Glu Pro Val Ala Phe Leu Asp Ser Leu Leu Leu Gly
65                  70                  75                  80

Glu Trp Glu Asp Arg Met Gln Arg Gly Leu Phe Arg Tyr Asp Val Thr
                    85                  90                  95

Ala Cys Glu Thr Lys Val Ile Pro Gly Gln Phe Gly Phe Ile Ala Gln
                100                 105                 110

Leu Asn Glu Gly Arg His Leu Lys Lys Arg Pro Thr Glu Phe Arg Val
                115                 120                 125

Asp Lys Val Leu Gln Pro Phe Asp Gly Ser Lys Phe Asn Phe Thr Lys
            130                 135                 140

Val Gly Gln Glu Val Leu Phe Gln Phe Glu Ala Ser Lys Asp Gly
145                 150                 155                 160

Glu Val Gln Phe Phe Pro Ser Ala Pro Ile Asp Val Glu Ser Ser Pro
                165                 170                 175

Ser Val Val Ala Ile Asn Val Ser Pro Ile Glu Tyr Gly His Val Leu
                180                 185                 190

Leu Ile Pro His Ile Leu Glu Arg Leu Pro Gln Arg Ile Asp Arg Glu
            195                 200                 205

Ser Phe Leu Leu Ala Leu His Met Ala Ala Glu Ala Gly Asn Pro Tyr
    210                 215                 220

Phe Arg Leu Gly Tyr Asn Ser Leu Gly Ala Phe Ala Thr Ile Asn His
225                 230                 235                 240

Leu His Phe Gln Ala Tyr Tyr Leu Ala Val Thr Phe Pro Ile Glu Lys
                245                 250                 255

Ala Pro Thr Lys Lys Ile Ser Thr Leu Asn Ala Glu Val Lys Val Ser
                260                 265                 270

Glu Leu Leu Asn Tyr Pro Val Arg Gly Leu Val Phe Glu Gly Gly Asn
            275                 280                 285

Thr Leu Gln Asp Leu Ser Asn Thr Val Ser Asp Ala Cys Ile Cys Leu
290                 295                 300

Gln Glu Asn Asn Ile Pro Tyr Asn Val Leu Ile Ser Asp Ser Gly Lys
305                 310                 315                 320

Arg Ile Phe Leu Val Pro Gln Cys Tyr Ala Glu Lys Gln Ala Leu Gly
                325                 330                 335

Glu Val Arg Ala Glu Ile Leu Asp Thr Gln Val Asn Pro Ala Val Trp
                340                 345                 350

Glu Ile Ser Gly His Met Val Leu Lys Arg Lys Lys Asp Tyr Asp Glu
            355                 360                 365

Ala Ser Asp Glu Asn Ala Trp Lys Leu Leu Ala Glu Val Ser Leu Ser
    370                 375                 380

Glu Glu Arg Phe Leu Glu Val Asn Ala Leu Ile Phe Glu Gly Ile Ala
385                 390                 395                 400

Ser Gly Asp Asn Gly Asn Glu Asn Leu Leu Lys Asp Pro Glu Val Lys
                405                 410                 415

Pro Arg Ser His Glu Glu Val Asn Thr Ile Asn Lys Arg Val His Cys
                420                 425                 430

Ser Ala Val Asn Glu Gln Ile Cys Arg Val Phe Thr Met
            435                 440                 445

<210> SEQ ID NO 3
<211> LENGTH: 450
```

<212> TYPE: PRT
<213> ORGANISM: Actinidia chinensis

<400> SEQUENCE: 3

```
Met Leu Lys Ile Lys Arg Val Pro Thr Val Val Ser Asn Phe Gln Lys
1               5                   10                  15

Asp Glu Ala Asp Gly Ala Arg Ser Gly Gly Cys Gly Arg Asn
            20                  25                  30

Cys Leu Gln Lys Cys Cys Ile Gln Gly Ala Lys Leu Pro Leu Tyr Ala
            35                  40                  45

Phe Lys Arg Val Asn Glu Val Gly Glu Lys Gly Val Leu Ala Leu
    50                  55                  60

Asp Asn Glu Glu Ala Pro Val Ala Phe Leu Asp Ser Leu Leu Leu Gly
65                  70                  75                  80

Glu Trp Glu Asp Arg Val Gln Arg Gly Leu Phe Arg Tyr Asp Val Thr
                85                  90                  95

Ala Cys Glu Thr Lys Val Ile Pro Gly Glu Tyr Gly Phe Ile Ala Gln
                100                 105                 110

Leu Asn Glu Gly Arg His Leu Lys Lys Arg Pro Thr Glu Phe Arg Val
            115                 120                 125

Asp Lys Val Leu Gln Pro Phe Asp Gly Ser Lys Phe Asn Phe Thr Lys
130                 135                 140

Val Gly Gln Glu Glu Val Leu Phe Gln Phe Glu Ala Ser Asn Asp Asn
145                 150                 155                 160

Glu Val Gln Phe Phe Pro Asn Ala Pro Val Asp Val Glu Asn Ser Pro
                165                 170                 175

Ser Val Val Ala Ile Asn Val Ser Pro Ile Glu Tyr Gly His Val Leu
            180                 185                 190

Leu Ile Pro Ser Ile Leu Glu Cys Leu Pro Gln Arg Ile Asp Arg Glu
        195                 200                 205

Ser Phe Leu Leu Ala Leu His Met Ala Ala Glu Ala Gly Asn Pro Tyr
210                 215                 220

Phe Arg Leu Gly Tyr Asn Ser Leu Gly Ala Phe Ala Thr Ile Asn His
225                 230                 235                 240

Leu His Phe Gln Ala Tyr Tyr Leu Ala Val Pro Phe Pro Ile Glu Lys
                245                 250                 255

Ala Pro Thr Arg Lys Ile Thr Thr Leu Asn Gly Gly Val Lys Ile Ser
                260                 265                 270

Glu Leu Leu Asn Tyr Pro Val Arg Gly Leu Val Phe Glu Gly Gly Asn
        275                 280                 285

Thr Leu Glu Asp Leu Ser Asn Ala Val Ser Asp Ser Ile Cys Leu
290                 295                 300

Gln Gly Asn Asn Ile Pro Tyr Asn Val Leu Ile Ser Asp Ser Gly Lys
305                 310                 315                 320

Arg Ile Phe Leu Leu Pro Gln Cys Tyr Ala Glu Lys Gln Ala Leu Gly
                325                 330                 335

Glu Val Ser Ser Glu Leu Leu Asp Thr Gln Val Asn Pro Ala Val Trp
            340                 345                 350

Glu Ile Ser Gly His Met Val Leu Lys Arg Lys Glu Asp Tyr Glu Glu
            355                 360                 365

Ala Ser Glu Gly Asn Ala Trp Arg Leu Leu Ala Glu Val Ser Leu Ser
    370                 375                 380

Gly Glu Arg Phe Glu Glu Val Lys Ala Leu Ile Phe Glu Ala Ile Ser
385                 390                 395                 400
```

```
Cys Ala Asp Asp Arg Ser Ser Thr Ala Glu Asn Leu Leu Glu Glu
            405                 410                 415

Pro Asp Asp Asn Pro Gln Ser Arg Glu Ala Asn Asp Ala Leu Asn
        420                 425                 430

Lys Gly Ser His Cys Gly Met Val Pro Gly Lys Gln Glu Cys Leu Val
        435                 440                 445

Gln His
    450

<210> SEQ ID NO 4
<211> LENGTH: 415
<212> TYPE: PRT
<213> ORGANISM: Actinidia eriantha

<400> SEQUENCE: 4

Met Leu Lys Ile Lys Arg Val Pro Thr Val Ser Asn Phe Gln Lys
1               5                   10                  15

Asp Glu Ala Glu Asp Gly Ala Arg Ser Gly Gly Cys Gly Arg Asn
            20                  25                  30

Cys Leu Gln Lys Cys Cys Ile Gln Gly Ala Lys Leu Pro Leu Tyr Ala
        35                  40                  45

Phe Lys Arg Val Lys Glu Val Val Gly Glu Lys Gly Leu Leu Thr Val
50                  55                  60

Gly Asp Glu Glu Ala Pro Val Ala Phe Leu Asp Ser Leu Leu Leu Gly
65                  70                  75                  80

Glu Trp Glu Asp Arg Val Gln Arg Gly Leu Phe Arg Tyr Asp Val Thr
                85                  90                  95

Ala Cys Gln Thr Lys Val Ile Pro Gly Glu Tyr Gly Phe Ile Ala Gln
            100                 105                 110

Leu Asn Glu Gly Arg His Leu Lys Lys Arg Pro Thr Glu Phe Arg Val
        115                 120                 125

Asp Lys Val Leu Gln Pro Phe Asp Glu Ser Lys Phe Asn Phe Thr Lys
    130                 135                 140

Val Gly Gln Glu Glu Val Leu Phe Gln Phe Glu Ala Ser Val Asp Asn
145                 150                 155                 160

Glu Val Gln Phe Phe Pro Asn Ala Pro Val Asp Val Glu Asn Ser Pro
                165                 170                 175

Ser Val Val Ala Ile Asn Val Ser Pro Ile Glu Tyr Gly His Val Leu
            180                 185                 190

Leu Ile Pro Arg Ile Leu Glu Cys Leu Pro Gln Arg Ile Asp Arg Glu
        195                 200                 205

Ser Phe Leu Leu Ala Leu His Met Ala Ala Glu Ala Gly Asn Pro Tyr
    210                 215                 220

Phe Arg Leu Gly Tyr Asn Ser Leu Gly Ala Phe Ala Thr Ile Asn His
225                 230                 235                 240

Leu His Phe Gln Ala Tyr Tyr Leu Ala Val Pro Phe Pro Ile Glu Lys
                245                 250                 255

Ala Pro Thr Arg Lys Ile Thr Thr Leu Asn Gly Gly Val Lys Ile Ser
            260                 265                 270

Glu Leu Leu Asn Tyr Pro Val Arg Gly Leu Val Phe Glu Gly Gly Asn
        275                 280                 285

Ser Leu Glu Asp Leu Ser Asn Ala Val Ser Asp Ser Ser Ile Cys Leu
    290                 295                 300

Gln Cys Asn Asn Ile Pro Tyr Asn Val Leu Ile Ser Asp Ser Gly Lys
```

```
              305                 310                 315                 320
Arg Ile Phe Leu Leu Pro Gln Cys Tyr Ala Glu Lys Gln Ala Leu Gly
                325                 330                 335

Glu Val Ser Ser Glu Leu Leu Asp Thr Gln Val Asn Pro Ala Val Trp
                340                 345                 350

Glu Ile Ser Gly His Met Val Leu Lys Arg Lys Glu Asp Tyr Gln Glu
                355                 360                 365

Ala Ser Glu Gly Asn Ala Trp Arg Leu Leu Ala Glu Val Ser Leu Ser
370                 375                 380

Glu Glu Arg Phe Glu Glu Val Lys Ala Leu Ile Phe Glu Ala Ile Ser
385                 390                 395                 400

Cys Ala Asp Asp Arg Ser Gly Ser Thr Ala Glu Asn Leu Leu Glu
                405                 410                 415

<210> SEQ ID NO 5
<211> LENGTH: 450
<212> TYPE: PRT
<213> ORGANISM: Actinidia eriantha

<400> SEQUENCE: 5

Met Leu Lys Ile Lys Arg Val Pro Thr Val Ser Asn Phe Gln Lys
1               5                   10                  15

Asp Glu Ala Glu Asp Gly Ala Arg Ser Gly Gly Gly Cys Gly Arg Asn
                20                  25                  30

Cys Leu Gln Lys Cys Cys Ile Gln Gly Ala Lys Leu Pro Leu Tyr Ala
                35                  40                  45

Phe Lys Arg Val Lys Glu Val Val Gly Glu Lys Gly Leu Leu Ala Val
50                  55                  60

Gly Asp Glu Glu Ala Pro Val Ala Phe Leu Asp Ser Leu Leu Leu Gly
65                  70                  75                  80

Glu Trp Glu Asp Arg Val Gln Arg Gly Leu Phe Arg Tyr Asp Val Thr
                85                  90                  95

Ala Cys Glu Thr Lys Val Ile Pro Gly Glu Tyr Gly Phe Ile Ala Gln
                100                 105                 110

Leu Asn Glu Gly Arg His Leu Lys Lys Arg Pro Thr Glu Phe Arg Val
                115                 120                 125

Asp Lys Val Leu Gln Pro Phe Asp Glu Ser Lys Phe Asn Phe Thr Lys
130                 135                 140

Val Gly Gln Glu Glu Val Leu Phe Gln Phe Glu Ala Ser Ile Asp Asn
145                 150                 155                 160

Glu Val Gln Phe Phe Pro Asn Ala Pro Val Asp Val Glu Asn Ser Pro
                165                 170                 175

Ser Val Val Ala Ile Asn Val Ser Pro Ile Glu Tyr Gly His Val Leu
                180                 185                 190

Leu Ile Pro Arg Ile Leu Glu Cys Leu Pro Gln Arg Ile Asp Arg Glu
                195                 200                 205

Ser Phe Leu Leu Ala Leu His Met Ala Ala Glu Ala Gly Asn Pro Tyr
                210                 215                 220

Phe Arg Leu Gly Tyr Asn Ser Leu Gly Ala Phe Ala Thr Ile Asn His
225                 230                 235                 240

Leu His Phe Gln Ala Tyr Tyr Leu Ala Val Pro Phe Pro Ile Glu Lys
                245                 250                 255

Ala Pro Thr Arg Lys Ile Thr Thr Leu Asn Gly Gly Val Lys Ile Ser
                260                 265                 270
```

```
Glu Leu Leu Asn Tyr Pro Val Arg Gly Leu Val Phe Glu Gly Gly Asn
            275                 280                 285

Ser Leu Glu Asp Leu Ser Asn Ala Val Ser Asp Ser Ile Cys Leu
        290                 295                 300

Gln Cys Asn Asn Ile Pro Tyr Asn Val Leu Ile Ser Asp Ser Gly Lys
305                 310                 315                 320

Arg Ile Phe Leu Leu Pro Gln Cys Tyr Ala Glu Lys Gln Ala Leu Gly
                325                 330                 335

Glu Val Ser Ser Glu Leu Leu Asp Thr Gln Val Asn Pro Ala Val Trp
            340                 345                 350

Glu Ile Ser Gly His Met Val Leu Lys Arg Lys Glu Asp Tyr Gln Glu
        355                 360                 365

Ala Ser Glu Gly Asn Ala Trp Arg Leu Leu Ala Glu Val Ser Leu Ser
    370                 375                 380

Glu Glu Arg Phe Glu Glu Val Lys Ala Leu Ile Phe Glu Ala Ile Ser
385                 390                 395                 400

Cys Ala Asp Asp Arg Ser Gly Ser Thr Ala Glu Asn Leu Leu Glu Glu
                405                 410                 415

Pro Asp Asn Asp Pro Gln Ser Arg Glu Val Ala Asn Asp Ala Leu Ser
            420                 425                 430

Lys Ala Ser His Arg Gly Met Val Pro Gly Lys Gln Glu Cys Leu Val
        435                 440                 445

Gln His
    450

<210> SEQ ID NO 6
<211> LENGTH: 447
<212> TYPE: PRT
<213> ORGANISM: Malus sieboldii

<400> SEQUENCE: 6

Met Met Leu Arg Ile Lys Arg Val Pro Thr Val Phe Ser Asn Tyr Gln
1               5                   10                  15

Lys Asp Glu Ala Glu Glu Gly Ala Arg Arg Val Glu Gly Cys Gly Arg
            20                  25                  30

Asn Cys Leu Asn Gln Cys Cys Ile Pro Gly Ala Lys Leu Pro Leu Tyr
        35                  40                  45

Ala Phe Lys Lys Arg Asn Val Asn Asn Gly Asp Thr Gly Val Pro Gly
    50                  55                  60

His Asp Lys Arg Glu Pro Pro Val Ala Phe Leu Asp Ser Leu Leu Leu
65                  70                  75                  80

Gly Glu Trp Glu Asp Arg Met Gln Arg Gly Leu Phe Arg Tyr Asp Val
                85                  90                  95

Thr Ala Cys Glu Thr Lys Val Ile Pro Gly Gln Tyr Gly Phe Ile Ala
            100                 105                 110

Gln Leu Asn Glu Gly Arg His Leu Lys Lys Arg Pro Thr Glu Phe Arg
        115                 120                 125

Val Asp Lys Val Leu Gln Pro Phe Asp Ser Ser Lys Phe Asn Phe Thr
    130                 135                 140

Lys Val Gly Gln Glu Glu Val Leu Phe Arg Phe Glu Ala Ser Glu Asp
145                 150                 155                 160

Gly Glu Val His Phe Phe Pro Ser Ala Pro Ile Asp Val Glu Asn Ser
                165                 170                 175

Pro Ser Val Val Ala Ile Asn Val Ser Pro Ile Glu Tyr Gly His Val
            180                 185                 190
```

```
Leu Leu Ile Pro Arg Ile Phe Glu Arg Leu Pro Gln Arg Ile Asp Arg
            195                 200                 205

Glu Ser Phe Leu Leu Ala Leu His Met Ala Ala Glu Ala Gly Ser Pro
210                 215                 220

Tyr Phe Arg Leu Gly Tyr Asn Ser Leu Gly Ala Phe Ala Thr Ile Asn
225                 230                 235                 240

His Leu His Phe Gln Ala Tyr Tyr Leu Ala Val Thr Phe Pro Ile Glu
            245                 250                 255

Lys Ala Pro Thr Lys Lys Ile Ser Thr Leu Asn Ala Glu Val Lys Val
            260                 265                 270

Ser Glu Leu Leu Asn Tyr Pro Val Arg Gly Leu Phe Glu Gly Gly
            275                 280                 285

Asn Thr Leu Glu Asp Leu Ser Tyr Thr Val Ser Asp Ala Cys Ile Cys
290                 295                 300

Leu Gln Glu Asn Asn Val Pro Tyr Asn Val Leu Ile Ser Asp Cys Gly
305                 310                 315                 320

Lys Arg Ile Phe Leu Leu Pro Gln Cys Tyr Ala Glu Lys Gln Ala Leu
            325                 330                 335

Gly Glu Val Ser Ala Glu Val Leu Asp Thr Gln Val Asn Pro Ala Val
            340                 345                 350

Trp Glu Ile Ser Gly His Met Val Leu Lys Arg Lys Lys Asp Tyr Asp
            355                 360                 365

Glu Ala Ser Asp Glu Asn Ala Trp Lys Leu Leu Ala Glu Val Ser Leu
370                 375                 380

Ser Glu Glu Arg Phe Gln Glu Val Asn Ala Leu Ile Phe Glu Arg Ile
385                 390                 395                 400

Ala Ser Gly Asn Asn Gly Asn Glu Asn Leu Pro Glu Asp Pro Glu Val
            405                 410                 415

Lys Pro Arg Ser His Glu Val Asp Ala Thr Ile Asn Lys Ser Ser
            420                 425                 430

Arg Ala Ala Met Val Gly Glu Thr Gln Glu Cys Ile Val Leu Gln
            435                 440                 445

<210> SEQ ID NO 7
<211> LENGTH: 438
<212> TYPE: PRT
<213> ORGANISM: Solanum tuberosum

<400> SEQUENCE: 7

Met Met Leu Lys Ile Lys Arg Val Pro Thr Leu Val Ser Asn Phe Gln
1               5                   10                  15

Lys Asp Glu Ala Asp Glu Ile Gly Ala Arg Gly Ala Cys Gly Arg
            20                  25                  30

Asn Cys Leu Arg Asn Cys Cys Leu Pro Gly Ser Lys Leu Pro Leu Tyr
            35                  40                  45

Gly Phe Lys Asn Leu Ser Tyr Gly Lys Ser Val Ala Ala Asp Glu Thr
50                  55                  60

Lys Glu Ser Pro Ile Asp Phe Leu Glu Ser Leu Val Leu Gly Glu Trp
65                  70                  75                  80

Glu Asp Arg Gln Gln Lys Gly Leu Phe Arg Tyr Asp Val Thr Ala Cys
                85                  90                  95

Glu Thr Lys Val Ile Pro Gly Leu Tyr Gly Phe Val Ala Gln Leu Asn
            100                 105                 110

Glu Gly Arg His Leu Lys Lys Arg Pro Thr Glu Phe Arg Val Asp Lys
```

```
                    115                 120                 125
Val Leu Gln Pro Phe Asp Gly Ser Lys Phe Asn Phe Thr Lys Val Gly
        130                 135                 140

Gln Glu Glu Leu Leu Phe Gln Phe Glu Ala Ser Glu Glu Asp Glu Val
145                 150                 155                 160

Gln Leu Tyr Pro Asn Ala Pro Ile Asp Pro Glu Lys Ser Pro Ser Val
                165                 170                 175

Ile Ala Ile Asn Val Ser Pro Ile Glu Tyr Gly His Val Leu Leu Ile
            180                 185                 190

Pro Lys Val Leu Glu Cys Leu Pro Gln Arg Ile Asp Arg Asp Ser Phe
        195                 200                 205

Leu Leu Ala Leu His Met Ala Ala Glu Ala Ala Asn Pro Tyr Phe Arg
210                 215                 220

Leu Gly Tyr Asn Ser Leu Gly Ala Phe Ala Thr Ile Asn His Leu His
225                 230                 235                 240

Phe Gln Ala Tyr Phe Leu Ala Val Gln Phe Pro Ile Glu Lys Ala Pro
                245                 250                 255

Thr Gln Lys Ile Thr Val Thr Asp Thr Gly Val Lys Ile Ser Glu Met
            260                 265                 270

Leu Asn Tyr Pro Val Arg Gly Leu Val Phe Glu Gly Asn Thr Leu
        275                 280                 285

Glu Asp Leu Ala Asn Val Val Ser Asp Ser Cys Ile Cys Leu Gln Glu
290                 295                 300

Asn Asn Ile Pro Tyr Asn Val Leu Ile Ser Asp Ser Gly Lys Arg Ile
305                 310                 315                 320

Phe Ile Leu Pro Gln Cys Tyr Ala Glu Lys Gln Ala Leu Gly Glu Val
                325                 330                 335

Ser Ala Glu Leu Leu Asp Thr Gln Val Asn Pro Ala Val Trp Glu Ile
            340                 345                 350

Ser Gly His Met Val Leu Lys Arg Lys Glu Asp Tyr Glu Gly Ala Thr
        355                 360                 365

Glu Ala Asn Ala Trp Arg Leu Leu Ala Glu Val Ser Leu Ser Glu Ala
370                 375                 380

Arg Phe Gln Glu Val Thr Ala Leu Ile Phe Glu Ala Ile Ser Leu Ser
385                 390                 395                 400

Val Glu Glu Asn Glu Asn Ala Asn Asp Gly Ser Pro Glu Asp Leu Asp
                405                 410                 415

Val Thr Pro Pro Gln Pro Met Glu Glu Ile Asp Gly Ser His Thr His
            420                 425                 430

Ser Thr Met Val Pro Ala
        435

<210> SEQ ID NO 8
<211> LENGTH: 442
<212> TYPE: PRT
<213> ORGANISM: Arabidopsis thaliana

<400> SEQUENCE: 8

Met Leu Lys Ile Lys Arg Val Pro Thr Val Val Ser Asn Tyr Gln Lys
1               5                   10                  15

Asp Asp Gly Ala Glu Asp Pro Val Gly Cys Gly Arg Asn Cys Leu Gly
                20                  25                  30

Ala Cys Cys Leu Asn Gly Ala Arg Leu Pro Leu Tyr Ala Cys Lys Asn
            35                  40                  45
```

```
Leu Val Lys Ser Gly Glu Lys Leu Val Ile Ser His Glu Ala Ile Glu
 50                  55                  60

Pro Pro Val Ala Phe Leu Glu Ser Leu Val Leu Gly Glu Trp Glu Asp
 65                  70                  75                  80

Arg Phe Gln Arg Gly Leu Phe Arg Tyr Asp Val Thr Ala Cys Glu Thr
                 85                  90                  95

Lys Val Ile Pro Gly Lys Tyr Gly Phe Val Ala Gln Leu Asn Glu Gly
                100                 105                 110

Arg His Leu Lys Lys Arg Pro Thr Glu Phe Arg Val Asp Lys Val Leu
                115                 120                 125

Gln Ser Phe Asp Gly Ser Lys Phe Asn Phe Thr Lys Val Gly Gln Glu
130                 135                 140

Glu Leu Leu Phe Gln Phe Glu Ala Gly Glu Asp Ala Gln Val Gln Phe
145                 150                 155                 160

Phe Pro Cys Met Pro Ile Asp Pro Glu Asn Ser Pro Ser Val Val Ala
                165                 170                 175

Ile Asn Val Ser Pro Ile Glu Tyr Gly His Val Leu Leu Ile Pro Arg
                180                 185                 190

Val Leu Asp Cys Leu Pro Gln Arg Ile Asp His Lys Ser Leu Leu Leu
                195                 200                 205

Ala Val His Met Ala Ala Glu Ala Ala Asn Pro Tyr Phe Arg Leu Gly
                210                 215                 220

Tyr Asn Ser Leu Gly Ala Phe Ala Thr Ile Asn His Leu His Phe Gln
225                 230                 235                 240

Ala Tyr Tyr Leu Ala Met Pro Phe Pro Leu Glu Lys Ala Pro Thr Lys
                245                 250                 255

Lys Ile Thr Thr Thr Val Ser Gly Val Lys Ile Ser Glu Leu Leu Ser
                260                 265                 270

Tyr Pro Val Arg Ser Leu Leu Phe Glu Gly Gly Ser Ser Met Gln Glu
                275                 280                 285

Leu Ser Asp Thr Val Ser Asp Cys Cys Val Cys Leu Gln Asn Asn Asn
290                 295                 300

Ile Pro Phe Asn Ile Leu Ile Ser Asp Cys Gly Arg Gln Ile Phe Leu
305                 310                 315                 320

Met Pro Gln Cys Tyr Ala Glu Lys Gln Ala Leu Gly Glu Val Ser Pro
                325                 330                 335

Glu Val Leu Glu Thr Gln Val Asn Pro Ala Val Trp Glu Ile Ser Gly
                340                 345                 350

His Met Val Leu Lys Arg Lys Glu Asp Tyr Glu Gly Ala Ser Glu Asp
                355                 360                 365

Asn Ala Trp Arg Leu Leu Ala Glu Ala Ser Leu Ser Glu Glu Arg Phe
370                 375                 380

Lys Glu Val Thr Ala Leu Ala Phe Glu Ala Ile Gly Cys Ser Asn Gln
385                 390                 395                 400

Glu Glu Asp Leu Glu Gly Thr Ile Val His Gln Gln Asn Ser Ser Gly
                405                 410                 415

Asn Val Asn Gln Lys Ser Asn Arg Thr His Gly Gly Pro Ile Thr Asn
                420                 425                 430

Gly Thr Ala Ala Glu Cys Leu Val Leu Gln
                435                 440

<210> SEQ ID NO 9
<211> LENGTH: 431
<212> TYPE: PRT
```

<213> ORGANISM: Arabidopsis thaliana

<400> SEQUENCE: 9

```
Met Leu Leu Lys Ile Lys Arg Val Pro Thr Val Val Ser Asn Tyr Gln
1               5                   10                  15

Lys Asp Glu Thr Val Glu Glu Gly Gly Cys Gly Arg Asn Cys Leu Ser
            20                  25                  30

Lys Cys Cys Ile Asn Gly Ala Arg Leu Pro Leu Tyr Thr Cys Lys Asn
        35                  40                  45

Leu Asp Lys Ser Val Gly Glu Asn Thr Glu Ser Pro Val Thr Phe Leu
    50                  55                  60

Glu Ser Leu Val Ile Gly Glu Trp Glu Asp Arg Phe Gln Arg Gly Leu
65                  70                  75                  80

Phe Arg Tyr Asp Val Thr Ala Cys Glu Thr Lys Val Ile Pro Gly Lys
                85                  90                  95

Tyr Gly Phe Ile Ala Gln Leu Asn Glu Gly Arg His Leu Lys Lys Arg
            100                 105                 110

Pro Thr Glu Phe Arg Val Asp Lys Val Leu Gln Pro Phe Asp Gly Asn
        115                 120                 125

Lys Phe Asn Phe Thr Lys Val Gly Gln Glu Glu Leu Leu Phe Gln Phe
    130                 135                 140

Lys Ala Ser Thr Asn Asp Asp Ser Glu Ile Gln Phe Leu Ala Ser
145                 150                 155                 160

Met Pro Leu Asp Ala Asp Asn Ser Pro Ser Val Val Ala Ile Asn Val
                165                 170                 175

Ser Pro Ile Glu Tyr Gly His Val Leu Leu Ile Pro Arg Val Leu Asp
            180                 185                 190

Cys Leu Pro Gln Arg Ile Asp His Lys Ser Leu Leu Leu Ala Leu Gln
        195                 200                 205

Met Ala Ala Glu Ala Asp Asn Pro Tyr Phe Arg Leu Gly Tyr Asn Ser
    210                 215                 220

Leu Gly Ala Phe Ala Thr Ile Asn His Leu His Phe Gln Ala Tyr Tyr
225                 230                 235                 240

Leu Ala Met Gln Phe Pro Ile Glu Lys Ala Ser Ser Leu Lys Ile Thr
                245                 250                 255

Thr Thr Asn Asn Gly Val Lys Ile Ser Lys Leu Leu Asn Tyr Pro Val
            260                 265                 270

Arg Gly Leu Leu Val Glu Gly Gly Asn Thr Ile Lys Asp Leu Ala Asp
        275                 280                 285

Thr Val Ser Asp Ala Ser Val Cys Leu Gln Asn Asn Asn Ile Pro Phe
    290                 295                 300

Asn Ile Leu Ile Ser Asp Ser Gly Lys Arg Ile Phe Leu Leu Pro Gln
305                 310                 315                 320

Cys Tyr Ala Glu Lys Gln Ala Leu Gly Glu Val Ser Ser Thr Leu Leu
                325                 330                 335

Asp Thr Gln Val Asn Pro Ala Val Trp Glu Met Ser Gly His Met Val
            340                 345                 350

Leu Lys Arg Lys Glu Asp Tyr Glu Gly Ala Ser Glu Glu Lys Ala Trp
        355                 360                 365

Arg Leu Leu Ala Glu Val Ser Leu Ser Glu Glu Arg Phe Arg Glu Val
    370                 375                 380

Asn Thr Met Ile Phe Asp Ala Ile Gly Phe Ser Ser His Glu Glu Glu
385                 390                 395                 400
```

Glu Glu Glu Glu Leu Glu Gln Asn Ser Met Asn Gly Gly Ser Phe
            405                 410                 415

Thr Ile Val His Cys Pro Ser Val Lys Glu Glu Ala Val Ser Asn
        420                 425                 430

<210> SEQ ID NO 10
<211> LENGTH: 438
<212> TYPE: PRT
<213> ORGANISM: Lycopersicon esculentum

<400> SEQUENCE: 10

Met Leu Thr Val Lys Arg Val Pro Thr Leu Val Ser Asn Tyr Gln Glu
1               5                   10                  15

Asp Val Leu Glu Gly Asn Val Met Gly Cys Gly Arg Lys Cys Leu Gly
            20                  25                  30

Lys Cys Cys Met Pro Val Ser Val Leu Pro Leu Tyr Ala Phe Lys Asn
        35                  40                  45

Asp Asp Asn Glu Pro Ile Glu Asn Asp Val Gln Thr Leu Pro Glu Glu
    50                  55                  60

Glu Cys Gln Met Ser Phe Leu Asn Asp Leu Leu Gly Leu Trp Glu
65                  70                  75                  80

Glu Arg Met Ser Gln Gly Leu Phe Arg Tyr Asp Val Thr Thr Cys Glu
                85                  90                  95

Thr Lys Val Ile Pro Gly Arg Cys Gly Phe Ile Ala Gln Leu Asn Glu
            100                 105                 110

Gly Arg His Leu Lys Lys Arg Pro Thr Glu Phe Cys Ile Asp Lys Val
        115                 120                 125

Leu Gln Pro Phe Asp Glu Asn Lys Phe Asn Phe Thr Lys Val Gly Gln
    130                 135                 140

Glu Glu Val Leu Phe Arg Phe Glu Pro Ser Thr Asp Tyr Lys Ala His
145                 150                 155                 160

Tyr Phe Ser Gly Met Arg Val Asn Ser Gly Ile Ser Pro Ser Ile Val
                165                 170                 175

Ala Ile Asn Val Ser Pro Ile Glu Tyr Gly His Val Leu Leu Ile Pro
            180                 185                 190

Arg Val Leu Asp Cys Leu Pro Gln Arg Ile Asp Arg Asp Ser Phe Ala
        195                 200                 205

Ile Ala Leu His Phe Ala Arg Glu Val Ala Asp Pro Phe Phe Arg Val
    210                 215                 220

Gly Tyr Asn Ser Leu Gly Ala Phe Ala Thr Ile Asn His Leu His Phe
225                 230                 235                 240

Gln Ala Tyr Tyr Leu Ser Val Pro Phe Pro Val Glu Lys Ala Pro Ile
                245                 250                 255

Gln Lys Ile Leu Ala Arg Lys Gly Leu Gly Gly Ala Gly Val Ile Val
            260                 265                 270

Ser Lys Leu Leu Asn Tyr Pro Val Arg Gly Phe Ala Phe Glu Gly Gly
        275                 280                 285

Asn Gly Ser Thr Ala Arg Asp Leu Ser Asp Ala Val Val Asn Ser Cys
    290                 295                 300

Ile Ser Leu Gln Asn Lys Asn Ile Pro Phe Asn Ile Leu Ile Ala Gln
305                 310                 315                 320

Cys Gly Lys Lys Ile Phe Leu Leu Pro Gln Cys Tyr Ala Glu Lys Gln
                325                 330                 335

Ala Leu Gly Val Val Asp Gln Glu Leu Leu Asp Thr Gln Val Asn Pro
            340                 345                 350

```
Ala Val Trp Glu Ile Ser Gly His Ile Val Leu Lys Arg Thr Lys Asp
            355                 360                 365

Tyr Asn Asp Ala Ser Glu Glu Tyr Ala Trp Lys Leu Leu Ser Glu Val
            370                 375                 380

Ser Ile Ser Glu Glu Arg Phe Glu Val Lys Gly Tyr Ile Ser Glu
385                 390                 395                 400

Ala Ala Asp Leu Gln Ala Asp Glu Asp Glu Asn Ile Asn Pro Glu Lys
                405                 410                 415

Glu Ile Pro Asp Ser Pro Gly Pro Gln Val Ala Ser His Ile Pro Pro
            420                 425                 430

Asp Cys Leu Val Leu Gln
            435

<210> SEQ ID NO 11
<211> LENGTH: 438
<212> TYPE: PRT
<213> ORGANISM: Oryza sativa

<400> SEQUENCE: 11

Met Glu Met Lys Leu Thr Ile Lys Arg Val Pro Thr Val Ser Asn
1               5                   10                  15

Tyr Gln Glu Asp Ala Ala Thr Ala Gly Glu Arg Pro Arg Ala Gly
                20                  25                  30

Cys Gly Arg Asp Cys Leu Gly Asp Cys Cys Leu Pro Asp Ser Lys Leu
            35                  40                  45

Pro Leu Tyr Ala Phe Lys Ala Ser Pro Lys Pro Ser Ser Gln Glu
50                  55                  60

Asp Ala Ser Asn Asp Glu Phe Phe Val Asn Leu Leu Leu Gly Leu Trp
65                  70                  75                  80

Glu Asp Arg Met Ala Arg Gly Leu Phe Arg Tyr Asp Val Thr Ala Cys
                85                  90                  95

Glu Thr Lys Val Ile Pro Gly Asn Leu Gly Phe Val Ala Gln Leu Asn
            100                 105                 110

Glu Gly Arg His Leu Lys Lys Arg Pro Thr Glu Phe Arg Val Asp Arg
            115                 120                 125

Val Leu Gln Pro Phe Asp Ala Ala Lys Phe Asn Phe Thr Lys Val Gly
130                 135                 140

Gln Glu Glu Val Leu Phe Gln Phe Glu Asn Gly Gly Asp Asp Ser
145                 150                 155                 160

Phe Phe Val Glu Ser Ser Pro Ile Ser Val Ala Asp Arg Ala Pro Asn
                165                 170                 175

Val Val Ala Ile Asn Val Ser Pro Ile Glu Tyr Gly His Val Leu Leu
            180                 185                 190

Ile Pro Arg Val Leu Asp Arg Leu Pro Gln Arg Ile Asp Gln Glu Ser
            195                 200                 205

Phe Leu Leu Ala Leu His Met Ala Ala Glu Ala Ala Ser Pro Tyr Phe
            210                 215                 220

Arg Leu Gly Tyr Asn Ser Leu Gly Ala Phe Ala Thr Ile Asn His Leu
225                 230                 235                 240

His Phe Gln Ala Tyr Tyr Leu Thr Val Pro Phe Pro Val Glu Lys Ala
                245                 250                 255

Ala Thr Lys Arg Ile Phe Leu Ala Glu Gly Thr Met Asn Ser Gly Val
            260                 265                 270

Lys Val Ser Lys Leu Met Asn Tyr Pro Val Arg Gly Leu Val Phe Glu
```

```
                275                 280                 285
Gly Gly Asn Ser Leu Ser Asp Leu Ala Asn Val Val Ser Ser Ala Cys
        290                 295                 300
Ile Trp Leu Gln Asp Asn Asn Val Pro Tyr Asn Val Leu Ile Ser Asp
305                 310                 315                 320
Cys Gly Lys Lys Ile Phe Leu Phe Pro Gln Cys Tyr Ala Glu Lys Gln
                325                 330                 335
Ala Leu Gly Glu Val Ser Gln Glu Leu Leu Asp Thr Gln Val Asn Pro
            340                 345                 350
Ala Val Trp Glu Ile Ser Gly His Ile Val Leu Lys Arg Arg Ser Asp
            355                 360                 365
Tyr Glu Glu Ala Ser Glu Ala Ser Ala Trp Arg Leu Leu Ala Glu Val
            370                 375                 380
Ser Leu Ser Glu Glu Arg Phe Glu Glu Val Lys Ala Tyr Ile Phe Asp
385                 390                 395                 400
Ala Ala Gly Leu Val Gln Ser Asp Glu Glu Val Ser Glu Asp Glu
                405                 410                 415
Asp Ala Thr Tyr Thr Pro Val Ser Ile Ala Pro Pro Ala Val Ala Glu
            420                 425                 430
Gly Cys Leu Val Leu Gln
        435

<210> SEQ ID NO 12
<211> LENGTH: 16
<212> TYPE: PRT
<213> ORGANISM: Artificial Sequence
<220> FEATURE:
<223> OTHER INFORMATION: Synthetic construct: conserved transferase
      motif 1

<400> SEQUENCE: 12

Ala Ile Asn Val Ser Pro Ile Glu Tyr Gly His Val Leu Leu Ile Pro
1               5                   10                  15

<210> SEQ ID NO 13
<211> LENGTH: 19
<212> TYPE: PRT
<213> ORGANISM: Artificial Sequence
<220> FEATURE:
<223> OTHER INFORMATION: Synthetic construct:  conserved transferase
      motif 2

<400> SEQUENCE: 13

Gly Tyr Asn Ser Leu Gly Ala Phe Ala Thr Ile Asn His Leu His Phe
1               5                   10                  15

Gln Ala Tyr

<210> SEQ ID NO 14
<211> LENGTH: 1800
<212> TYPE: DNA
<213> ORGANISM: Actinidia chinensis

<400> SEQUENCE: 14
gcggacgtgg cgccttgccg tccgaaggcg gtagcccctc cgacctcctc ttcctcgccg    60
gcggcggtca cttcgctttc tccgtctact agcttattag gtttattctt acttagtgag   120
taattcgtcc tattatagtt cgtaagttca tcaaagatct gttacttgat tcgtctttcg   180
ttgctcgagt cttggtgttt tttgcgtttt ctgagttcga gatgttgaag atcaagaggg   240
ttccgactgt tgtctccaat ttccaaaagg atgaggccga ggacggcgct cgatccggcg   300
```

```
gtggttgcgg ccgaaactgc ctccagaagt gttgcattca aggggcaaag ctacctctgt      360
atgctttcaa gagggtgaaa gaggttgttg gtgaaaaggg tttgcttgcc gtcgacgacg      420
aagaggctcc tgttgctttc ttggattcac ttcttctcgg ggagtgggag gatcgtgtgc      480
agagaggact ctttcgctac gatgtcactg cttgcgaaac caaggttatt ccaggagagt      540
atggcttcat tgcgcagttg aacgagggtc gtcaccttaa gaagaggcca actgagtttc      600
gtgttgacaa ggtcctgcag cccttcgatg agagcaaatt caatttcact aaagttggac      660
aggaagaggt gctgttccag tttgaagcaa gcgacgacaa tgaagtccag ttcttcccaa      720
atgcaccggt tgatgttgag aattctccca gtgttgtggc catcaatgtt agtcctattg      780
aatatggtca tgtacttctg atccctcgga ttcttgaatg cctgcctcag aggattgaca      840
gggagagctt cttgcttgct ctcacatgg cagcagaagc tggaaacccg tacttccgat      900
tgggttacaa cagcttgggt gcatttgcca ctatcaatca cctacatttc caggcttatt      960
acttagctgt gcccttttcct atcgagaagg ctcccactag gaagataact actctgaatg     1020
gtggggtgaa aatctctgat ctgctaaatt atccagtcag agggcttgtt ttcgagggtg     1080
gaaattctct ggaagatttg tccaatgccg tctctgattc cagcatttgc cttcaaggca     1140
acaacatacc ttacaatgtg cttatctccg attctggaaa gtgtatcttt ctcttaccgc     1200
agtgctacgc tgagaaacag gctcttggag aagtgagttc cgatcttctg gacacacaag     1260
tgaacccggc agtgtgggaa atcagcggac atatggtttt gaagaggaag gaggactatg     1320
aggaggcgtc tgaaggaaat gcttggaggc tccttgctga ggtctccctt tcggaggaga     1380
ggttcgaaga agtcaaggca ttgatctttg aagccatctc ttgtgctgat gatagaagtg     1440
gcagcacggc tgaaacttg ctcgaggagc cagatgacaa tccacaatct cgcaaagtag     1500
cgaatgatgc ccttaacaaa ggctcccacc gaggtatggt gccagggaag caagaatgcc     1560
tagttcagca ctgagaattg gggcattga agaatgttca gtggtttgtg tgcgtctta     1620
attaaatatg gtattactac tctctgggaa tttgcttgtt aatgttaaac atccctaaat     1680
aaggcaaact aggtttgcgt tgttgttgtt gttgttgttg ttgttgcagt tgcttctgtt     1740
ctggggattt gctgtggtaa tctgttttta cttgtcgctt gtgggcatat gtaaaaatac     1800
```

<210> SEQ ID NO 15
<211> LENGTH: 1593
<212> TYPE: DNA
<213> ORGANISM: Malus x domesticus

<400> SEQUENCE: 15

```
ttgaggatca gagggttcc caccgtcgtt tcgaattacc agaaagatga ggcggaggaa       60
gttgctcgcc gcgtcggggg ctgtggccgc aactgcctta accatgttg cattccaggt      120
gcaaaacttc cattgtatgc cttcaagaag ctgaacgtaa atgatggtga cacgggtttg      180
ctaggacgtg agaaaagaga gcctcccgtt gcatttcttg actcactgct ctcggggag      240
tgggaggatc gcatgcagag agggctattt cgctatgatg tcactgcttg tgaaaccaag      300
gtgatcccag gcaatttgg tttcatagcc cagctgaatg agggtcgcca tcttaagaag      360
cggccaacag agtttcgagt tgataaggtc ctccagccct tgatggcag caagtttaac      420
ttcactaaag ttggacaaga ggaggttctg ttccagtttg aagccagcaa agatggtgaa      480
gttcagtttt tccccagcgc acccattgat gttgaaagtt ctccgagcgt tgtggccatt      540
aatgtcagtc caattgaata tggccatgtg ctgttgattc ctcacattct tgagcgattg      600
```

| | |
|---|---|
| cctcaaagga ttgaccggga aagcttcttg cttgcacttc acatggcggc tgaagcaggg | 660 |
| aatccttact ttcgattggg ttacaacagc ttgggtgcat ttgctaccat caatcacctt | 720 |
| cacttccagg cttactacct ggccgtgacc tttcccattg agaaggctcc taccaaaaaa | 780 |
| atatccactt tgaatgccga ggtgaaggtc tctgagcttc tgaattatcc agtcagaggt | 840 |
| cttgttttg agggtggaaa tactctgcaa gatttgtcaa acaccgtctc tgatgcctgc | 900 |
| atatgccttc aagagaacaa cataccttac aatgtcctta tctctgactc tggaaagcga | 960 |
| atctttctcg tgccacagtg ttatgctgag aaacaagctc ttggggaagt gagagcagag | 1020 |
| attctggata cacaggtgaa tccagctgtg tgggaaatta gtgggcatat ggtgctaaag | 1080 |
| aggaaaaagg actatgatga ggcgtcggat gaaaatgctt ggaagctcct ggcagaggtc | 1140 |
| tcccttctg aagaaaggtt cctagaagtg aatgctctta ttttcgaagg tattgcttcg | 1200 |
| ggtgataacg ggaatgaaaa cttgctcaag gatccagaag ttaagcctcg ttctcatgaa | 1260 |
| gaagtcaaca ccatcaacaa aagagtgcat tgttctgcag taaatgagca gatttgtcgg | 1320 |
| gtgtttacaa tgtgaatcta ctattgccgt ttacgatttg ggttaatgtc tctactttc | 1380 |
| ttggatgcta ccgatgcct aaataagcaa aactggtttt gcagctttc attgtttgca | 1440 |
| gtgtgttgtg catgtatact gcataacaac attgatctat tttagggtgg tttatggata | 1500 |
| tgtaaaatgc tttattgtgg tggtttcgtt tgtggctgaa taaaaggcca gtaggctcta | 1560 |
| ttatggggtc atagcttcac caaaaaaaaa aaa | 1593 |

<210> SEQ ID NO 16
<211> LENGTH: 2201
<212> TYPE: DNA
<213> ORGANISM: Actinidia chinensis

<400> SEQUENCE: 16

| | |
|---|---|
| ctctctctcc ctccctcttc tctatctata tatcccccaa tctggcctct cctcacctca | 60 |
| cccccaaagt ctacacagaa tcaacccttc atctcacgca caggcctcca aaacccactt | 120 |
| cttctccaca atccagagtc ccagacacac ctcgagtggc cggagttgag agagagagag | 180 |
| agagagagag agatttttctg cttcgatcgg gggtaaaacc cggtgtttga caagttgtag | 240 |
| acatcacggc tatattcgga gtttctcgtg ccctcataca tgtccggtct gtacgacgca | 300 |
| agggttgtgt agtcgagaga aacccttcgc cgcacggcgg acgtggcgcc ttgccgtctg | 360 |
| aaggcggtag cccctctgat ctcctattcc tcgccggcgg cggtcacttc gctttctccg | 420 |
| tctactagct taataggttt attcttagtt agtgagtaaa tacgtcttac tatagttcgt | 480 |
| aagattatcg aagatctgtt gcttgattcg tctttcgtag ctcgagtctt ggtgttttg | 540 |
| cgttttctga gttcgagatg ttgaagatca agagggttcc gactgttgtt tccaatttcc | 600 |
| aaaaggatga ggccgacgac ggcgctcgat ctggcggtgg ttgcggccga aactgcctcc | 660 |
| agaagtgttg cattcaaggg gcaaagctac ctctgtatgc tttcaagagg gtgaatgagg | 720 |
| ttgttggtga aaagggtgtg cttgccctcg acaacgaaga ggctcctgtt gctttcttgg | 780 |
| attcacttct cctcggggag tgggaggatc gtgtgcagag aggactcttt cgttacgatg | 840 |
| tcactgcttg cgaaaccaag gttattccgg gagagtatgg cttcattgcg cagctgaacg | 900 |
| agggtcgtca ccttaagaag aggccaactg agtttcgtgt tgataaggtc ctgcagccct | 960 |
| tcgatgggag caaattcaac ttcactaaag ttggacagga agaggttctg ttccagtttg | 1020 |
| aagcaagcaa cgacaacgaa gtccagttct tcccaaatgc acctgttgat gttgagaatt | 1080 |
| ctcccagtgt tgtggccatc aatgttagtc ctattgaata tggtcacgta cttctcatcc | 1140 |

```
cttcgattct tgaatgcctg cctcaaagga ttgacaggga gagcttcttg cttgctcttc    1200
acatggcagc agaagctgga aacccgtact tccgattggg ttacaacagc ttgggtgcat    1260
ttgccactat caatcacctt catttccagg cttattactt agccgtgccc ttccctatcg    1320
agaaggctcc cactaggaag ataactactc tgaatggtgg ggtgaaaatc tctgagctgc    1380
taaattatcc agtcaggggg cttgttttcg agggtggaaa tactctggaa gatttgtcca    1440
atgccgtctc tgattccagc atttgccttc aaggcaacaa catacCttac aatgtgctta    1500
tctccgattc tggaaagcgt atctttcttt taccacagtg ttacgctgag aaacaggctc    1560
ttggagaagt gagttctgag cttctggaca cacaagtgaa cccggcagtg tgggaaatca    1620
gcggacatat ggttttgaag aggaaggagg actatgagga ggcgtctgaa ggaaatgctt    1680
ggaggctcct tgctgaggtc tccCttcgg gggagaggtt tgaagaagtc aaggcattga    1740
tctttgaagc catctcttgt gctgatgata gaagcagcag cacagctgag aacttgcttg    1800
aggagccaga tgacaatcct caatctcgtg aagaagcaaa tgatgccctt aacaaaggct    1860
cccactgtgg tatggtgccg ggaaagcaag aatgcctagt tcagcactga gaatttgggc    1920
atttgaagaa tgttcagtgg tttgtgtgca tctttaatta aataaggtac tactacgctg    1980
tgggaatttg catgttcatg tttaattaaa taaggcaaac taggtttgcg ttgttgttgt    2040
tgttgctgct gctgctgctg ctgaagttgc ttctgttatg gcgacttgct ttcgtaatcg    2100
cttttacttg tcccttctgg gcgtatgtaa aaatactatg tcgatttcgc tctcatgagc    2160
taatgaatgc ttgtatgatt tggtattgta aaaaaaaaa a                        2201

<210> SEQ ID NO 17
<211> LENGTH: 1894
<212> TYPE: DNA
<213> ORGANISM: Actinidia eriantha

<400> SEQUENCE: 17
tctctccgtc cctctcaata gttgtctcca ttcgcagtaa aatcactaag gccgctcgtc      60
cctcagtgca caccacggcc cctccacagc cgcattcacc tctctctctc tctctctgct     120
ctatctatat atccccccaa tctggcctct cttcacctca cccccaaaat ctacacaaaa     180
tcaatccttc atcatccaca tcggcctcca aaacccacct cttctccaca atccagacac     240
accttgagcg gctggcgttg agcgaataga tagatagata gagagatttt ctgcttcgat     300
cgggggtaaa acccggtgtt tgacaagttg tagacatcac ggctatactc ggagtttctc     360
ggccgctcat acatgtccgg tctgtacgac gcaagggttg tgtagtcgag agcaacccctt     420 cgccgcacgg aggacgtggc gccttgccgt ccgaaggcgg tagcccctcc gacctcctct     480
tcctcgccgg cggcggtcac ttcgctttct ccgtctacta gcttattagg tttattctta     540
cttagtgagt aattcgtcct attatagttc gtaagtttat cgaagatctg ttacttgatt     600
cgtctttcgt tgctcgagtc ttggtgtttt tgcgttttct gagttcgaga tgttgaagat     660
caagagggtt ccgactgttg tttccaattt ccaaaaggat gaggccgagg acggcgctcg     720 atccggcgt ggttgcggcc gaaactgtct ccagaagtgt tgcattcaag ggcaaagct      780 acctctgtat gctttcaaga gggtgaagga ggttgttggt gaaaagggtt tgcttaccgt     840
cggcgacgaa gaggctcctg ttgctttctt ggattcgctt cttctcgggg agtgggagga     900
tcgtgtgcag agaggactct ttcgctacga tgtcactgct tgccaaacca aggttattcc     960
gggagagtat ggcttcattg cgcagctgaa cgagggtcgt caccttaaga agaggccaac    1020
```

```
tgagtttcgt gttgataagg tcctgcagcc cttcgatgag agcaaattca acttcactaa    1080
agttggacag gaagaggtgc tgttccagtt tgaagcaagc gtcgacaatg aagtccagtt    1140
tttcccaaat gcacctgttg atgttgagaa ttctcccagt gttgtggcca tcaatgttag    1200
tcctattgaa tatggtcatg tacttctgat ccctcggatt cttgaatgcc tgcctcagag    1260
gattgacagg gagagcttct tgcttgctct tcacatggca gcagaagctg gaaacccgta    1320
cttccgattg ggttacaaca gcttgggtgc atttgccact atcaatcacc ttcatttcca    1380
ggcttattac ttagctgtgc cctttcctat agagaaggct cccactagga agataactac    1440
tctgaatggt ggggtgaaaa tctctgagct gctaaattat ccagtcagag ggcttgtttt    1500
cgagggtgga aattctctgg aagatttgtc caatgccgtc tctgattcca gcatttgcct    1560
tcaatgcaac aacataccct acaatgtgct tatctccgat tctggaaagc gcatctttct    1620
cttaccacag tgttatgctg agaaacaagc tcttggagaa gtgagttccg agcttctgga    1680
cacacaagtg aacccggcag tgtgggaaat cagcggacat atggttttga agaggaagga    1740
ggactatcag gaggcgtctg aaggaaatgc ttggaggctc cttgctgagg tctccctttc    1800
ggaggagagg ttcgaagaag tcaaggcatt gatctttgaa gccatctctt gtgctgatga    1860
tagaagcggc agcacggctg agaacttgct cgag                                1894

<210> SEQ ID NO 18
<211> LENGTH: 1941
<212> TYPE: DNA
<213> ORGANISM: Actinidia eriantha

<400> SEQUENCE: 18
gtttctcggc cgctcataca tgtccggtct gtacgacgca agggttgtgt agtcgagagc      60
aacccttcgc cgcacggagg acgtggcgcc ttgccgtccg aaggcggtag cccctccgac     120
ctcctcttcc tcgccggtgg cggtcacttc gctttctccg tctactagct tattaggttt     180
attcttactt agtgagtaat tcgtcctatt atagttcgta agtttatcga agatctgtta     240
cttgattcgt ctttcgttgc tcgagtcttg gtgtttttgc gttttctgag ttcgagatgt     300
tgaagatcaa gagggttccg actgttgttt ccaatttcca aaaggatgag gccgaggacg     360
gcgctcgatc cggcggtggt tgcggccgaa actgtctcca gaagtgttgc attcaagggg     420
caaagctacc tctgtatgct ttcaagaggg tgaaggaggt tgttggtgaa aagggtttgc     480
ttgccgtcgg cgacgaagag gctcctgttg ctttcttgga ttcgcttctt ctcggggagt     540
gggaggatcg tgtgcagaga ggactctttc gctacgatgt cactgcttgc gaaaccaagg     600
ttattccggg agagtatggc ttcattgcgc agctgaacga gggtcgtcac cttaagaaga     660
ggccaactga gtttcgtgtt gataaggtcc tgcagccctt cgatgagagc aaattcaact     720
tcactaaagt tggacaggaa gaggtgctgt tccagtttga agcaagcatc gacaatgaag     780
tccagttttt cccaaatgca cctgttgatg ttgagaattc tcccagtgtt gtggccatca     840
atgttagtcc tattgaatat ggtcatgtac ttctgatccc tcggattctt gaatgcctgc     900
ctcagaggat tgacagggag agcttcttgc ttgctcttca catggcagca gaagctggaa     960
acccgtactt ccgattgggt tacaacagct tgggtgcatt tgccactatc aatcaccttc    1020
atttccaggc ttattactta gctgtgccct ttcctatcga aaggctcccc actaggaaga    1080
taactactct gaatggtggg gtgaaaatct ctgagctgct aaattatcca gtcagagggc    1140
ttgttttcga gggtggaaat tctctggaag atttgtccaa tgccgtctct gattccagca    1200
tttgccttca atgcaacaac ataccttaca atgtgcttat ctccgattct ggaaagcgca    1260
```

```
tctttctctt accacagtgt tatgctgaga aacaagctct tggagaagtg agttccgagc      1320
ttctggacac acaagtgaac ccggcagtgt gggaaatcag cggacatatg gttttgaaga      1380
ggaaggagga ctatcaggag gcgtctgaag gaaatgcttg gaggctcctt gctgaggtct      1440 cccttcgga ggagaggttc gaagaagtca aggcattgat ctttgaagcc atctcttgtg       1500
ctgatgatag aagcggcagc acagctgaga acttgctcga ggagccagat aacgatcctc      1560
aatctcgtga agtagcgaat gatgccctta gcaaagcctc ccaccgaggt atggtgccag      1620
ggaagcaaga atgcctagtt cagcactgag aatttgggca tttgaagaat gttcagtggt      1680
ttgtatgcgt ctttaattaa atatggtatt actactatct gggaatttgc ttgttaatgt      1740
taaatatccc taaataaggc aaactaggtt tgcgttgttg ttgttgttgt tgttgttgaa      1800
gttgcttctg ttctggggat ttgctgttgt aatctgtttt tacttgtcgc ttgtgcccat      1860
atgtaaaaat actgtggatt tcactctcac gagctaatga atgcttgtat gatttggtat      1920
tgtaatttca aaaaaaaaa a                                                1941
```

<210> SEQ ID NO 19
<211> LENGTH: 2010
<212> TYPE: DNA
<213> ORGANISM: Malus sieboldii

<400> SEQUENCE: 19

```
caggttcgac gagttgtaga catcacggct atacacggag ctccttggcc gctcattcat       60
gtccgggctg tccgacgaaa gggttgtgta attgagagca accctcgcc gcacggcggg       120 cgtggcgctt tgccttccga aggcggtagc ccctccgacc tgctcttcct ggctggtggc      180
ggttctgcat cctctgtttt tctcttctgc ttatattagc ttttttagac tttcttggtt      240
agattcttag aagattttag agattttttt cttctataaa gtgcacgagt agatcatatt      300
gttgttttcg ggggttttg ggtttggtgg tgtttgattt tactgagaat taagaaaaaa       360
aaagggaaaa aaaagagagg gagaaagaag gggagggagc atgatgttga ggatcaagag      420
ggttcccacc gtcttttcga attaccagaa agatgaggcg gaggagggtg ctcgccgcgt      480
cgagggttgt ggccgcaatt gccttaacca atgttgcatt ccaggggcaa aacttccatt      540
gtatgccttc aagaagcgga acgtgaataa tggtgacacg ggtgtgcccg gacatgacaa      600
aagagagcct cccgttgcgt ttcttgactc gctgcttctc ggggagtggg aggatcgcat      660
gcagagaggg ctatttcgct atgatgtcac tgcttgtgaa accaaggtga tcccagggca      720
atatggtttc attgcccagc tgaatgaggg tcgccatctt aagaagagac caactgagtt      780
tcgagttgat aaggtcctcc agcccttga tagcagcaag tttaacttca ctaaagttgg      840
acaagaggag gttctattcc ggtttgaagc cagtgaagat ggtgaagttc acttttccc       900 tagtgcaccc attgatgttg aaaattctcc gagcgttgtt gccattaatg tcagtcctat      960
tgaatatggc catgtgctgt tgattcctcg tatttttgag cgtttgccac aaaggattga      1020
ccgggaaagc ttcttgcttg cacttcacat ggcggctgaa gctgggagtc cttactttcg      1080
attgggttac aacagcttgg gtgcatttgc taccatcaat caccttcact tccaggctta      1140
ctacttggcc gtgaccttc ccattgagaa ggctcctacc aagaaaatat ccactctgaa       1200
tgctgaggtg aaggtctctg agcttctgaa ctatcctgtc agaggtcttt ttttgaggg       1260 tggaaacact ctggaagatt tgtcttacac cgtctctgat gcctgcatat gccttcaaga      1320
aaacaacgta ccgtacaatg tccttatctc tgattgtgga aagcgaatct ttctcctgcc      1380
```

```
acagtgttat gctgagaaac aagctcttgg agaagtgagt gcagaggttc tggatacaca    1440
ggtgaatcca gcggtgtggg aaattagtgg gcatatggtc ttgaagagga aaaaggacta    1500
cgacgaggct tcagatgaaa atgcttggaa gctcctggca gaggtttccc tttctgaaga    1560
gaggttccaa gaagtgaatg ctcttatttt cgaacgtatt gcttccggta ataatgggaa    1620
tgaaaatttg ccggaggatc cagaagttaa gcctcgttct catgaagaag tcgacgctac    1680
cattaacaaa agctcccgcg ctgctatggt tggtgagaca caagaatgca ttgttctgca    1740
gtaaatgagc agattggtgg gtgtttacaa tgtgaatcta gtattgcagt attcgatttg    1800
ggttaatgtc tgtacctttt attggatgct agccgatgcc taaataagca aaactggttt    1860
tgcatagtca gctgttcatg gtttgcagtg tttgtgtatt ctgcgtaaca acttcgatct    1920
atttgtttag ggtgctttat ggatacgtaa aatcccttgt ggttactatt gtgggtgaat    1980
aaatgttatt ttctgtgtaa aaaaaaaaaa                                     2010
```

<210> SEQ ID NO 20
<211> LENGTH: 1425
<212> TYPE: DNA
<213> ORGANISM: Solanum tuberosum

<400> SEQUENCE: 20

```
ttacgtacag ttctatctag tattctcttg attattcgaa gaaaacacaa aaagatgat      60
gctcaagatt aagagggttc ctacacttgt ttctaacttt caaaggatg aggctgatga     120
aattggtgct cgtggtgctg gttgtggccg gaattgcctc aggaattgct gccttccagg    180
ttcaaagctg ccactgtatg gtttcaaaaa tttgagctac ggcaagtctg ttgccgccga    240
tgaaacaaag gaatctccga tcgactttct ggaatccctt gttcttgggg aatgggagga    300
tcgtcagcag aaaggcctct ttcgctatga tgtcactgct tgcgaaacca aggtgattcc    360
tggagaatat ggtttcgttg ctcaactgaa tgagggaagg cacctcaaga gaggccaac    420
tgagtttcga gttgataagg tgctgcagcc ttttgatgga agcaagttca acttcactaa    480
ggttggacag gaagagttgc tctttcagtt tgaagcaagt gaggaagatg aagtccagct    540
ctatccaaat gcaccaattg atcctgagaa atctccaagt gtcattgcca tcaatgtcag    600
tcccattgag tacggacacg tgcttttgat ccctaaggtc cttgaatgcc ttccccagag    660
gatcgacagg gacagcttcc tgcttgcatt gcacatggct gctgaagcag caaacccata    720
cttccgattg ggttacaaca gcttgggtgc atttgccacc atcaaccatc ttcacttcca    780
ggcttatttc ttggctgtgc aattcccat tgagaaggcc ccaactcaga agataaccgt    840
cactgatact ggagtgaaga tatcggagat gcttaattac ccagttcgag gtctcgtctt    900
tgagggtgga aatactttgg aggatttggc caatgtcgtc tcagattctt gcatttgtct    960
gcaagagaac aacatcccctt acaatgtcct aatctccgat tcaggaaaaa ggatattcat   1020
tctcccacag tgctatgcag agaaacaagc tcttggagag tcagcgctg aactcctcga   1080
cacccaagtc aatcctgctg tttgggagat tagtggacac atggtcttga agaggaagga   1140
ggattatgag ggtgcaactg aggcaaatgc atggaggctt ctcgccgagg tctcactctc   1200
tgaagcaagg ttccaagaag tgactgctct catctttgaa gctattagtc tcagtgttga   1260
agagaatgag aacgccaatg atggttctcc tgaggatcta gatgtcacac ctccacagcc   1320
catggaggag attgatgggt ctcacaccca tagtaccatg gttcccgcct agggttttca   1380
cggcccagct ctggtgtttt atcgcatgta tgatttcatg aattt                   1425
```

<210> SEQ ID NO 21
<211> LENGTH: 2043
<212> TYPE: DNA
<213> ORGANISM: Arabidopsis thaliana

<400> SEQUENCE: 21

| | | | | | |
|---|---|---|---|---|---|
| ggtatcatca | aaaacacct | caaagaatta | ttcattcagg | catcttctca | aattttttgtt | 60 |
| tgtgaaaaaa | acccacatca | aaagatctct | catttattcg | tttcgtttct | gctgttttga | 120 |
| gtgtcgggtt | cgttttagct | gtaatctttt | tttccggcgt | tcgatttgaa | aaaatccggg | 180 |
| gaacaggtga | tcggaatcac | ggctatacac | gggatatcac | ggggtgttag | ctcacatgtc | 240 |
| catattgtcc | gacagaaggg | ttgtttaatc | gaaactaatc | ctttgccgca | cggaggacgt | 300 |
| ggagctctgc | cgtctgaagg | cggcagcccct | tccgatctcc | tctttctcgc | cggtggcggt | 360 |
| tccagcttta | acttcttttc | ctttaggttt | taggagttag | ggtttgttag | tgttttttcc | 420 |
| ttcttctttt | tttggtgctc | ttgaatcgct | tttttcttgg | gggaagtttt | tcttttgct | 480 |
| cttcgaaatt | tgtcttttt | gagaatgttg | aaaatcaaaa | gagttccgac | cgttgtttcg | 540 |
| aactaccaga | aggacgatgg | agcggaggat | cccgtcggct | gtggacggaa | ttgcctcggc | 600 |
| gcttgttgcc | ttaacggggc | taggcttcca | ttgtatgcat | gtaagaatct | ggtaaaatcc | 660 |
| ggagagaagc | ttgtaatcag | tcatgaggct | atagagcctc | ctgtagcttt | tctcgagtcc | 720 |
| cttgttctcg | gagagtggga | ggataggttc | caaagaggac | ttttttcgcta | tgatgtcact | 780 |
| gcctgcgaaa | ccaaagttat | cccggggaag | tatggtttcg | ttgctcagct | taacgagggt | 840 |
| cgtcacttga | agaagaggcc | aactgagttc | cgtgtagata | aggtgttgca | gtcttttgat | 900 |
| ggcagcaaat | tcaacttcac | taaagttggc | caagaagagt | tgctcttcca | gtttgaagct | 960 |
| ggtgaagatg | cccaagttca | gttcttccct | tgcatgccta | ttgaccctga | gaattctccc | 1020 |
| agtgttgttg | ccatcaatgt | tagtccgata | gagtatggcc | atgtgctgct | gattcctcgt | 1080 |
| gttcttgact | gcttgcctca | aaggatcgat | cacaaaagcc | ttttgcttgc | agttcacatg | 1140 |
| gctgctgagg | ctgctaatcc | atacttcaga | ctcggttaca | acagcttggg | tgcttttgcc | 1200 |
| actatcaatc | atctccactt | tcaggcttat | tacttggcca | tgccttttccc | actggagaaa | 1260 |
| gctcctacca | agaagataac | taccactgtt | agtggtgtca | aaatctcaga | gcttctaagt | 1320 |
| taccctgtga | gaagtcttct | ctttgaaggt | ggaagctcta | tgcaagaact | atctgatact | 1380 |
| gtttcagact | gctgtgtttg | ccttcaaaac | aacaacattc | ctttcaacat | tctcatctct | 1440 |
| gattgtggaa | ggcagatctt | cttaatgcca | cagtgttacg | cagagaaaca | ggctctaggt | 1500 |
| gaagtgagcc | cggaggtatt | ggaaacacaa | gtgaacccag | ccgtgtggga | gataagtggt | 1560 |
| cacatggtac | tgaagaggaa | agaggattac | gaaggtgctt | cagaggataa | cgcgtggagg | 1620 |
| ctccttgcgg | aagcttctct | gtcggaggaa | aggtttaagg | aggttactgc | tctcgcccttt | 1680 |
| gaagccatag | gttgtagtaa | ccaagaggag | gatcttgaag | gaaccatagt | tcatcagcaa | 1740 |
| aactctagtg | gcaatgttaa | ccagaaaagc | aacagaaccc | atggaggtcc | gatcacaaat | 1800 |
| gggacggccg | ccgagtgcct | tgtccttcag | tgaacaatat | ggtgacttgg | tggtttgtat | 1860 |
| gtataattaa | aagcctaaat | aagcaaactc | tctttgtagt | tgcatttgaa | gcttcttggt | 1920 |
| ttatgtatga | tggttgtggg | cattttgtgc | ctagacttct | ggttctttgt | tttttgttat | 1980 |
| gagttggtgt | ttatgaatta | tatatgttct | tcactaatat | gattattatt | tgtataaaaa | 2040 |
| aag | | | | | 2043 |

<210> SEQ ID NO 22

<211> LENGTH: 1874
<212> TYPE: DNA
<213> ORGANISM: Arabidopsis thaliana

<400> SEQUENCE: 22

```
caaaatctca cacatcaaac acgtgaattt gctctctttc tggttcactc acctaccatt     60
actataagtc tgaaagagtg attgaaaccc acctcgaaaa atctatcctt ttttttgttt    120
tccttctccg gcgaatcccc ggggagattg gtaatcggta atcacggcta tttacgggat    180
aaagccacgg cctttgagct ttcatgtcca acgaaagggt tgtttaatca taactaatcc    240
tttgcctcac ggaggacgtg gagctctgcc gtctgaaggc ggcagtccct ccgatctcct    300
cttcctcgcc ggaggcggtt ccacaaatag ccactaaccc taacccttt tctaattagg    360
tttttagttc ttagagtcct gtattaatct gttatttcga gattataata tttgtgagca    420
atgttgttga agatcaaaag agttccaaca gttgtatcga attatcaaaa agatgagaca    480
gttgaagaag gtggatgtgg tcggaattgt ctgagcaagt gttgcatcaa tgggcaaga    540
cttcctttat atacctgcaa gaatcttgat aaatccgtcg agagaacac agaatctccg    600
gtgacgttcc tcgaatcctt agttattgga gagtgggaag atcgtttcca agaggtctt    660
tttcgctatg atgtcaccgc ctgcgaaacc aaggttatac cggggaagta cggtttcatt    720
gcgcagctga atgaaggtcg gcatctcaag aagagaccaa ccgagttccg tgttgacaaa    780
gttcttcaac catttgatgg aaacaaattc aatttcacta aagttggtca agaagagttg    840
cttttccagt ttaaagctag cactaatgat gatgatagtg aaattcagtt cttggcgagt    900
atgcctctag acgctgataa ttctcctagc gtcgttgcaa tcaatgtgag tccgattgag    960
tatgggcatg tgttgctgat tcctcgtgtt cttgattgct tacctcaaag gattgatcac   1020
aaaagccttt tgcttgctct tcaaatggcg gctgaagccg ataatccgta tttccgactt   1080
ggatacaaca gtctaggcgc tttcgctacc attaaccatc ttcactttca ggcttactat   1140
ttggcaatgc aattcccgat agagaaagct tcttccttga agatcactac caccaataat   1200
ggcgtcaaaa tctctaaact cttgaattac cctgtgagag gtcttctagt tgaaggtgga   1260
aacaccatta aagatctcgc agatactgta tcagacgcat ccgtttgtct tcagaacaac   1320
aacattcctt tcaacattct catctctgac tctggcaaac gaatcttcct tctccctcag   1380
tgttacgcag agaaacaggc tttaggagaa gttagctcaa cgctattgga tacgcaagtg   1440
aatccagcgg tttgggagat gagtggacac atggtgttga agaggaaaga agactatgaa   1500
ggagcgtcag aagagaaggc atggaggtta ctagctgaag tttctttatc agaggagaga   1560
ttcagagaag ttaacactat gatatttgat gccatcggtt ttagtagtca cgaagaagaa   1620
gaagaagagg agcttgaaga gcagaattcg atgaatggtg gcagcttcac aatagtgcat   1680
tgtccttcag tgaaagaaga ggctgtctct aattgaggcg ctttataact aaaagcaaaa   1740
acataactgt cgtcgtgatt ttgcataact tgtgtttgac attttactgt tttgtagttt   1800
ttttcttttc ttcttggctt tgttacgtct ttgttcgaac cttttgaatc aataaaaatcg   1860
aaatcgccta attc                                                     1874
```

<210> SEQ ID NO 23
<211> LENGTH: 2013
<212> TYPE: DNA
<213> ORGANISM: Lycopersicon esculentum

<400> SEQUENCE: 23

```
gattgaccaa aatacgtgtg caagagagag accaccggag caccaaacgc cacccaacaa     60
```

```
ccacccattc aattcttcta gaaaagaaca tcttcctcaa aattatcgat gaaggatcgc      120
tcctcagtaa ttgttcgttg atcctacaaa ttcaatcacg gctcttcttg aatctttcgt      180
ttgtattctc acaattcatc atcaccgcaa agtgttgacc cttaatccaa ctcttctggt      240
ggacgataag caccggaccc cttcccctca cggaggtagg ggtgcctcac ccgctgaagg      300
cggttgcccc tccgatctcc tcttcctcgc cggcggcggt ccaattcttc ctttctcttt      360
ttccttctcc taattttttcg tataagagtt gtattttttga ttatccatcc aagaacagga     420
ccgatgttga ctgtaaagag ggtgcctaca ctggtttcca actatcaaga ggatgttctc      480
gaaggtaacg tcatgggttg tggccgcaag tgcctcggaa aatgctgcat gcctgtttca      540
gtacttcctc tatatgcatt caagaatgat gataatgagc caattgaaaa tgatgttcaa      600
accttgcctg aggaggagtg tcagatgtca ttcttgaacg atttgttgtt gggcttatgg      660
gaggagcgga tgagccaggg actatttcga tatgatgtga caacctgtga gacgaaggtc      720
attcctggga gatgtggttt tattgcgcaa ctgaatgagg ggcgccacct aaagaagcgc      780
ccaacagagt tttgcattga taaggttctt cagccttttg acgagaacaa attcaacttt      840
accaaagtgg gccaggaaga agtgcttttc aggtttgaac caagtaccga ctacaaggcc      900
cattactttt ccggcatgcg agtaaacagt ggtatttcac ctagtattgt tgctatcaat      960
gtgagcccaa ttgagtatgg gcacgttctt ttgatacctc gagttcttga ttgcttacct     1020
cagagaattg atcgtgatag ttttgcaatt gctctccatt ttgccagaga agtggcagat     1080
cctttcttta gggtaggtta taacagtttg ggcgcttttg ctaccattaa ccacctccac     1140
ttccaggcgt attacttgtc agtgccattt ccagttgaga aagcaccaat acagaaaata     1200
ctggcaagga aggggctggg tggtgctgga gtgattgtat ctaagttatt aaattacccc     1260
gtacgaggtt ttgcttttga gggaggaaat ggaagtactg cccgtgattt gtctgatgct     1320
gttgtgaatt cctgcatttc ccttcagaat aaaaacatcc ctttcaacat tctcattgct     1380
cagtgtggaa agaagatttt tctgcttccc cagtgttatg cagagaagca agcactagga     1440
gttgtagacc aagagctcct ggacactcag gtgaaccctg ctgtatggga aattagtgga     1500
catatagtgc ttaagcgaac aaaggattac aatgatgcat cagagaaata tgcatggaaa     1560
cttctttctg aggtttccat atcagaggag agatttgaag aagtaaaggg ctatatttct     1620
gaagcagctg atctacaagc agatgaggat gaaaacatca atccagagaa ggaaattcca     1680
gattctcctg gtccgcaggt ggcctcacat attcctccag attgtttggt gttgcagtga     1740
agaatttgtg gcttgctctt gcaagatcta ataaagtttt gaagtattat ctagtgtatg     1800
gttgaaattt tgtgtgtttg ttttttccagc atcttgtttg atgcatactg ttgtcttggt     1860
tggaggttgt aatccccaaa tagtgttaaa cgtcatggct gcaagctgtg gtctttggca     1920 ggattgtttta cagtacccttt tttgttggtg ttttgactgt gctagcaaat gttcctaata     1980
ataacaccag tgtaggacca aaaaaaaaaa aaa                                   2013

<210> SEQ ID NO 24
<211> LENGTH: 2086
<212> TYPE: DNA
<213> ORGANISM: Oryza sativa

<400> SEQUENCE: 24
accaccacca ccgtcgccgc cgccgccgac tgagaagagg aagaggaaga ggggagattc       60
cgccgccgac gagaggtggg ggggagtggg ttgtgatcgt gaggagggct ctcatcccta      120
```

| | |
|---|---|
| gacgggcgag ttgaaaggcg gcaaagacgg ctagcgttga agcggtcggg cgcggccacg | 180 |
| cagctgcgcc gcccacgccc agtgggggag ccatcgcttc tccggcgacg gcgtccagcc | 240 |
| cagccccgca cggcggccgc ggggcgcttc cctcggccgg cggcagcccc tctgacctcc | 300 |
| tcttcctcgc cggcggcggt cgcctctgag accgctcgcc cccccatcc accttctcta | 360 |
| acatccaatc aacaaaaatc tttcgctgac ctgaccctga ccccgagaga gaggaaggaa | 420 |
| ttgagattta atcatggaga tgaagctgac atcaagcgg gtgcccaccg tggtttccaa | 480 |
| ctaccaggag gatgctgccg ccaccgccgg cgaacgcccc cgcgccggct gcgggaggga | 540 |
| ttgcctcggg gattgctgct tgcccgattc aagcttccg ctgtatgctt caaggcgag | 600 |
| tccgaaaaag ccgtcttcgc aggaggatgc ttccaacgat gagttctttg tcaatctcct | 660 |
| gctcggcctg tgggaagaca ggatggcccg aggtttgttc cgatatgatg tcactgcctg | 720 |
| tgagaccaag gttatcccag gcaaccttgg gtttgttgca caactgaatg aaggacgcca | 780 |
| cctcaagaag cgccctactg aattccgcgt ggaccgtgtg cttcaaccat ttgatgctgc | 840 |
| caagttcaac ttcaccaaag ttggccagga ggaggtgctc ttccaatttg agaatggtgg | 900 |
| tggtgatgac agcttctttg tggagagctc cccaatcagt gttgctgatc gtgctcctaa | 960 |
| tgttgttgca atcaatgtaa gcccaattga atatggccat gttcttctca ttccccgtgt | 1020 |
| actggaccgc ctgcctcaga ggattgacca ggagagcttc ttgcttgcac tgcacatggc | 1080 |
| tgctgaagcc gcaagcccat acttcaggct tggctataat agtttgggtg cctttgcaac | 1140 |
| catcaaccac ctccactttc aggcatacta cttgacagtg cctttccctg ttgagaaggc | 1200 |
| agctaccaag aggattttcc ttgctgaggg cacaatgaat agtggagtaa aggtgtccaa | 1260 |
| gctgatgaac taccctgtga ggggactggt ttttgaggga ggcaactcac tgagcgatct | 1320 |
| ggccaatgtg gtttccagcg cttgtatctg gctgcaggac aacaatgtgc cttacaatgt | 1380 |
| tcttatctct gactgcggca aaaagatctt cctcttccct cagtgctatg ccgagaagca | 1440 |
| ggctctggga gaagtgagcc aggagctact ggacacgcag gttaacccag ctgtgtggga | 1500 |
| gatcagtggc cacatcgtgc tgaaacgaag gagtgattac gaggaggcat cagaagcttc | 1560 |
| tgcgtggaga ctcctcgctg aggtttccct gtcggaggaa cgcttcgagg aagtgaaggc | 1620 |
| ctacatcttt gatgccgctg gtctggttca gtccgacgag gaggaagtca gcgaagacga | 1680 |
| ggacgccacc tacacgcctg tctccattgc ccctcctgct gtcgcggaag gctgcctcgt | 1740 |
| ccttcagtga gacggtagaa caggttgtcg gcctggtaaa gcgctgtgcc gccttcgtct | 1800 |
| tctcatcagt cttcttcagt cttcacccgc tggtcgccta gcttcgtcat agttatggtt | 1860 |
| gctggtcttt tataaggatc aatgtaatcg aactgcctgg agtcttgtgt ctgaacctgc | 1920 |
| atgctacttg ctcctccctt ccctgctgct ctgatattca gactctgcaa atattaagca | 1980 |
| gagaaactgt gaaactgttt gtattgtttg tgctgttgag cactggatct aatgtgatga | 2040 |
| acattgttaa taactacaca tcttccctga tctgtttgct tgtttt | 2086 |

<210> SEQ ID NO 25
<211> LENGTH: 376
<212> TYPE: PRT
<213> ORGANISM: Actinidia eriantha

<400> SEQUENCE: 25

Met Gly Ser Thr Gly Glu Ser Asn Tyr Gly Ser Tyr Thr Tyr Glu Asn
1               5                   10                  15

Leu Glu Arg Glu Pro Tyr Trp Pro Glu Ala Lys Leu Arg Ile Ser Ile
            20                  25                  30

```
Thr Gly Ala Gly Gly Phe Ile Ala Ser His Ile Ala Arg Arg Leu Lys
        35                  40                  45

Gly Glu Gly His Tyr Ile Ile Ala Ser Asp Trp Lys Lys Asn Glu His
    50                  55                  60

Met Thr Glu Asp Met Phe Cys His Glu Phe His Leu Val Asp Leu Arg
65                  70                  75                  80

Val Met Asp Asn Cys Leu Lys Val Thr Thr Arg Val Asp His Val Phe
                85                  90                  95

Asn Leu Ala Ala Asp Met Gly Gly Met Gly Phe Ile Gln Ser Asn His
            100                 105                 110

Ser Val Ile Met Tyr Asn Asn Thr Met Ile Ser Phe Asn Met Leu Glu
        115                 120                 125

Ala Ala Arg Val Asn Gly Ile Lys Arg Phe Phe Tyr Ala Ser Ser Ala
    130                 135                 140

Cys Ile Tyr Pro Glu Phe Lys Gln Leu Asp Thr Asn Val Ser Leu Lys
145                 150                 155                 160

Glu Ser Asp Ala Trp Pro Ala Glu Pro Gln Asp Ala Tyr Gly Leu Glu
                165                 170                 175

Lys Leu Ala Thr Glu Glu Leu Cys Lys His Tyr Thr Lys Asp Phe Gly
            180                 185                 190

Ile Glu Cys Arg Ile Gly Arg Phe His Asn Ile Tyr Gly Pro Phe Gly
        195                 200                 205

Thr Trp Lys Gly Gly Arg Glu Lys Ala Pro Ala Ala Phe Cys Arg Lys
    210                 215                 220

Thr Leu Thr Ser Thr Asp Arg Phe Glu Met Trp Gly Asp Gly Leu Gln
225                 230                 235                 240

Thr Arg Ser Phe Thr Phe Ile Asp Glu Cys Val Glu Gly Val Leu Arg
                245                 250                 255

Leu Thr Lys Ser Asp Phe Arg Glu Pro Val Asn Ile Gly Ser Asp Glu
            260                 265                 270

Met Val Ser Met Asn Glu Met Ala Glu Ile Val Leu Ser Phe Glu Asn
        275                 280                 285

Lys Lys Leu Pro Ile His His Ile Pro Gly Pro Glu Gly Val Arg Gly
    290                 295                 300

Arg Asn Ser Asp Asn Thr Leu Ile Lys Glu Lys Leu Gly Trp Ala Pro
305                 310                 315                 320

Thr Met Lys Leu Lys Asp Gly Leu Arg Phe Thr Tyr Phe Trp Ile Lys
                325                 330                 335

Glu Gln Leu Glu Lys Glu Lys Ala Arg Gly Ile Asp Leu Ser Thr Tyr
            340                 345                 350

Gly Ser Lys Val Val Gly Thr Gln Ala Pro Val Gln Leu Gly Ser
        355                 360                 365

Leu Arg Ala Ala Asp Gly Lys Glu
    370                 375

<210> SEQ ID NO 26
<211> LENGTH: 376
<212> TYPE: PRT
<213> ORGANISM: Actinidia deliciosa

<400> SEQUENCE: 26

Met Gly Ser Ser Ser Glu Ser Asn Tyr Gly Ser Tyr Thr Tyr Glu Asn
1               5                   10                  15

Leu Glu Arg Glu Pro Tyr Trp Pro Glu Ala Lys Leu Arg Ile Ser Ile
```

```
                20                  25                  30
Thr Gly Ala Gly Gly Phe Ile Ala Ser His Ile Ala Arg Arg Leu Lys
            35                  40                  45
Gly Glu Gly His Tyr Ile Ile Ala Ser Asp Trp Lys Lys Asn Glu His
        50                  55                  60
Met Thr Glu Asp Met Phe Cys His Glu Phe His Leu Val Asp Leu Arg
65                  70                  75                  80
Val Met Asp Asn Cys Leu Lys Val Thr Thr Gly Val Asp His Val Phe
                85                  90                  95
Asn Leu Ala Ala Asp Met Gly Gly Met Gly Phe Ile Gln Ser Asn His
            100                 105                 110
Ser Val Ile Met Tyr Asn Asn Thr Met Ile Ser Phe Asn Met Leu Glu
        115                 120                 125
Ala Ala Arg Val Asn Gly Val Lys Arg Phe Phe Tyr Ala Ser Ser Ala
    130                 135                 140
Cys Ile Tyr Pro Glu Phe Lys Gln Leu Asp Thr Asn Val Ser Leu Lys
145                 150                 155                 160
Glu Ser Asp Ala Trp Pro Ala Glu Pro Gln Asp Ala Tyr Gly Leu Glu
                165                 170                 175
Lys Leu Ala Thr Glu Glu Leu Cys Lys His Tyr Thr Lys Asp Phe Gly
            180                 185                 190
Ile Glu Cys Arg Ile Gly Arg Phe His Asn Ile Tyr Gly Pro Phe Gly
        195                 200                 205
Thr Trp Lys Gly Gly Arg Glu Lys Ala Pro Ala Ala Phe Cys Arg Lys
    210                 215                 220
Thr Leu Thr Ser Thr Asp Arg Phe Glu Met Trp Gly Asp Gly Leu Gln
225                 230                 235                 240
Thr Arg Ser Phe Thr Phe Ile Asp Glu Cys Val Glu Gly Val Leu Arg
                245                 250                 255
Leu Thr Lys Ser Asp Phe Arg Glu Pro Val Asn Ile Gly Ser Asp Glu
            260                 265                 270
Met Val Ser Met Asn Glu Met Ala Glu Ile Val Leu Ser Phe Glu Asp
        275                 280                 285
Lys Lys Leu Pro Ile His His Ile Pro Gly Pro Glu Gly Val Arg Gly
    290                 295                 300
Arg Asn Ser Asp Asn Thr Leu Ile Lys Glu Lys Leu Gly Trp Ala Pro
305                 310                 315                 320
Thr Met Lys Leu Lys Asp Gly Leu Arg Phe Thr Tyr Phe Trp Ile Lys
                325                 330                 335
Glu Gln Leu Glu Lys Glu Lys Ala Gln Gly Ile Asp Leu Ser Thr Tyr
            340                 345                 350
Gly Ser Ser Lys Val Val Gly Thr Gln Ala Pro Val Gln Leu Gly Ser
        355                 360                 365
Leu Arg Ala Ala Asp Gly Lys Glu
    370                 375

<210> SEQ ID NO 27
<211> LENGTH: 376
<212> TYPE: PRT
<213> ORGANISM: Malus x domesticus

<400> SEQUENCE: 27

Met Gly Ser Thr Gly Glu Ile Lys Tyr Gly Ala Tyr Thr Tyr Glu Asn
1               5                   10                  15
```

Leu Glu Arg Glu Pro Tyr Trp Pro Ser Glu Lys Leu Arg Ile Ser Ile
            20                  25                  30

Thr Gly Ala Gly Gly Phe Ile Ala Ser His Ile Ala Arg Arg Leu Lys
            35                  40                  45

Asn Glu Gly His Tyr Ile Ile Ala Ser Asp Trp Lys Lys Asn Glu His
        50                  55                  60

Met Thr Glu Asp Met Phe Cys His Glu Phe His Leu Ala Asp Leu Arg
 65                  70                  75                  80

Val Met Asp Asn Cys Leu Lys Val Thr Lys Asn Val Asp His Val Phe
                    85                  90                  95

Asn Leu Ala Ala Asp Met Gly Gly Met Gly Phe Ile Gln Ser Asn His
                100                 105                 110

Ser Val Ile Phe Tyr Asn Asn Thr Met Ile Ser Phe Asn Met Val Glu
                115                 120                 125

Ala Ala Arg Ile Asn Asp Val Lys Arg Phe Phe Tyr Ala Ser Ser Ala
            130                 135                 140

Cys Ile Tyr Pro Glu Phe Lys Gln Leu Glu Thr Asn Val Ser Leu Lys
145                 150                 155                 160

Glu Ser Asp Ala Trp Pro Ala Glu Pro Gln Asp Ala Tyr Gly Leu Glu
                165                 170                 175

Lys Leu Ala Thr Glu Glu Leu Cys Lys His Tyr Thr Lys Asp Phe Gly
            180                 185                 190

Ile Glu Cys Arg Ile Gly Arg Phe His Asn Ile Tyr Gly Pro Phe Gly
            195                 200                 205

Thr Trp Lys Gly Gly Arg Glu Lys Ala Pro Ala Ala Phe Cys Arg Lys
        210                 215                 220

Thr Leu Thr Ala Thr Asp Lys Phe Glu Met Trp Gly Asp Gly Leu Gln
225                 230                 235                 240

Thr Arg Ser Phe Thr Phe Ile Asp Glu Cys Val Glu Gly Val Leu Arg
                245                 250                 255

Leu Thr Lys Ser Asp Phe Arg Glu Pro Val Asn Ile Gly Ser Asp Glu
            260                 265                 270

Met Val Ser Met Asn Glu Met Ala Glu Ile Val Leu Ser Phe Glu Asp
            275                 280                 285

Lys Lys Leu Pro Ile Gln His Ile Pro Gly Pro Glu Gly Val Arg Gly
        290                 295                 300

Arg Asn Ser Asp Asn Thr Leu Ile Lys Glu Lys Leu Gly Trp Ala Pro
305                 310                 315                 320

Thr Met Arg Leu Lys Asp Gly Leu Arg Ile Thr Tyr Phe Trp Ile Lys
                325                 330                 335

Glu Gln Ile Glu Lys Glu Lys Ala Gln Gly Ala Asp Leu Ser Val Tyr
            340                 345                 350

Gly Ser Ser Lys Val Val Gly Thr Gln Ala Pro Val Gln Leu Gly Ser
        355                 360                 365

Leu Arg Ala Ala Asp Gly Lys Glu
        370                 375

<210> SEQ ID NO 28
<211> LENGTH: 377
<212> TYPE: PRT
<213> ORGANISM: Arabidopsis thaliana

<400> SEQUENCE: 28

Met Gly Thr Thr Asn Gly Thr Asp Tyr Gly Ala Tyr Tyr Lys Glu
 1               5                  10                  15

Leu Glu Arg Glu Gln Tyr Trp Pro Ser Glu Asn Leu Lys Ile Ser Ile
         20                  25                  30

Thr Gly Ala Gly Gly Phe Ile Ala Ser His Ile Ala Arg Leu Lys
         35                  40                  45

His Glu Gly His Tyr Val Ile Ala Ser Asp Trp Lys Lys Asn Glu His
 50                  55                  60

Met Thr Glu Asp Met Phe Cys Asp Glu Phe His Leu Val Asp Leu Arg
 65                  70                  75                  80

Val Met Glu Asn Cys Leu Lys Val Thr Glu Gly Val Asp His Val Phe
                 85                  90                  95

Asn Leu Ala Ala Asp Met Gly Gly Met Gly Phe Ile Gln Ser Asn His
             100                 105                 110

Ser Val Ile Met Tyr Asn Asn Thr Met Ile Ser Phe Asn Met Ile Glu
         115                 120                 125

Ala Ala Arg Ile Asn Gly Ile Lys Arg Phe Phe Tyr Ala Ser Ser Ala
130                 135                 140

Cys Ile Tyr Pro Glu Phe Lys Gln Leu Glu Thr Thr Asn Val Ser Leu
145                 150                 155                 160

Lys Glu Ser Asp Ala Trp Pro Ala Glu Pro Gln Asp Ala Tyr Gly Leu
                 165                 170                 175

Glu Lys Leu Ala Thr Glu Glu Leu Cys Lys His Tyr Asn Lys Asp Phe
             180                 185                 190

Gly Ile Glu Cys Arg Ile Gly Arg Phe His Asn Ile Tyr Gly Pro Phe
         195                 200                 205

Gly Thr Trp Lys Gly Gly Arg Glu Lys Ala Pro Ala Ala Phe Cys Arg
     210                 215                 220

Lys Ala Gln Thr Ser Thr Asp Arg Phe Glu Met Trp Gly Asp Gly Leu
225                 230                 235                 240

Gln Thr Arg Ser Phe Thr Phe Ile Asp Glu Cys Val Glu Gly Val Leu
                 245                 250                 255

Arg Leu Thr Lys Ser Asp Phe Arg Glu Pro Val Asn Ile Gly Ser Asp
             260                 265                 270

Glu Met Val Ser Met Asn Glu Met Ala Glu Met Val Leu Ser Phe Glu
         275                 280                 285

Glu Lys Lys Leu Pro Ile His His Ile Pro Gly Pro Glu Gly Val Arg
     290                 295                 300

Gly Arg Asn Ser Asp Asn Asn Leu Ile Lys Glu Lys Leu Gly Trp Ala
305                 310                 315                 320

Pro Asn Met Arg Leu Lys Glu Gly Leu Arg Ile Thr Tyr Phe Trp Ile
                 325                 330                 335

Lys Glu Gln Ile Glu Lys Glu Lys Ala Lys Gly Ser Asp Val Ser Leu
             340                 345                 350

Tyr Gly Ser Ser Lys Val Val Gly Thr Gln Ala Pro Val Gln Leu Gly
         355                 360                 365

Ser Leu Arg Ala Ala Asp Gly Lys Glu
     370                 375

<210> SEQ ID NO 29
<211> LENGTH: 376
<212> TYPE: PRT
<213> ORGANISM: Malpighia glabra

<400> SEQUENCE: 29

Met Glu Ser Ser Asp Gly Thr Asp Tyr Gly Ala Tyr Thr Tyr Lys Glu

```
  1               5                  10                 15
Leu Glu Arg Glu Pro Tyr Trp Pro Ser Glu Lys Leu Arg Ile Ser Ile
                20                  25                  30

Thr Gly Ala Gly Gly Phe Ile Ala Ser His Ile Ala Arg Arg Leu Lys
                35                  40                  45

Ser Glu Gly His Tyr Ile Ile Ala Ser Asp Trp Lys Lys Asn Glu His
    50                      55                  60

Met Thr Glu Asp Met Phe Cys His Glu Phe His Leu Val Asp Leu Arg
65                  70                      75                  80

Val Met Asp Asn Cys Leu Lys Val Thr Lys Asp Ala Asp His Val Phe
                85                  90                  95

Asn Leu Ala Ala Asp Met Gly Gly Met Gly Phe Ile Gln Ser Asn His
                100                 105                 110

Ser Val Ile Met Tyr Asn Asn Thr Met Ile Ser Phe Asn Met Leu Glu
                115                 120                 125

Ala Ser Arg Ile Ser Gly Val Lys Arg Phe Phe Tyr Ala Ser Ser Ala
                130                 135                 140

Cys Ile Tyr Pro Glu Phe Lys Gln Leu Glu Thr Asn Val Ser Leu Lys
145                 150                 155                 160

Glu Ser Asp Ala Trp Pro Ala Glu Pro Gln Asp Ala Tyr Gly Leu Glu
                165                 170                 175

Lys Leu Ala Thr Glu Glu Leu Cys Lys His Tyr Thr Lys Asp Phe Gly
                180                 185                 190

Ile Glu Cys Arg Val Gly Arg Phe His Asn Ile Tyr Gly Pro Phe Gly
                195                 200                 205

Thr Trp Lys Gly Gly Arg Glu Lys Ala Pro Ala Ala Phe Cys Arg Lys
                210                 215                 220

Ala Ile Thr Ser Val Asp Lys Phe Glu Met Trp Gly Asp Gly Leu Gln
225                 230                 235                 240

Thr Arg Ser Phe Thr Phe Ile Asp Glu Cys Val Glu Gly Val Leu Arg
                245                 250                 255

Leu Thr Lys Ser Asp Phe Arg Glu Pro Val Asn Ile Gly Ser Asp Glu
                260                 265                 270

Met Val Ser Met Asn Glu Met Ala Glu Ile Val Leu Ser Phe Glu Asp
                275                 280                 285

Lys Lys Leu Pro Ile His His Ile Pro Gly Pro Glu Gly Val Arg Gly
                290                 295                 300

Arg Asn Ser Asp Asn Thr Leu Ile Lys Glu Lys Leu Gly Trp Ala Pro
305                 310                 315                 320

Thr Met Arg Leu Lys Asp Gly Leu Arg Ile Thr Tyr Phe Trp Ile Lys
                325                 330                 335

Glu Gln Ile Glu Lys Glu Lys Ala Gln Gly Ile Asp Leu Ala Val Tyr
                340                 345                 350

Gly Ser Ser Lys Val Val Gly Thr Gln Ala Pro Val Gln Leu Gly Ser
                355                 360                 365

Leu Arg Ala Ala Asp Gly Lys Glu
                370                 375

<210> SEQ ID NO 30
<211> LENGTH: 378
<212> TYPE: PRT
<213> ORGANISM: Oryza sativa

<400> SEQUENCE: 30
```

```
Met Gly Ser Ser Glu Lys Asn Gly Thr Ala Tyr Gly Glu Tyr Thr Tyr
  1               5                  10                  15

Ala Glu Leu Glu Arg Glu Gln Tyr Trp Pro Ser Glu Lys Leu Arg Ile
             20                  25                  30

Ser Ile Thr Gly Ala Gly Gly Phe Ile Gly Ser His Ile Ala Arg Arg
         35                  40                  45

Leu Lys Ser Glu Gly His Tyr Ile Ile Ala Ser Asp Trp Lys Lys Asn
 50                  55                  60

Glu His Met Thr Glu Asp Met Phe Cys His Glu Phe His Leu Val Asp
 65                  70                  75                  80

Leu Arg Val Met Asp Asn Cys Leu Lys Val Thr Asn Gly Val Asp His
             85                  90                  95

Val Phe Asn Leu Ala Ala Asp Met Gly Gly Met Gly Phe Ile Gln Ser
            100                 105                 110

Asn His Ser Val Ile Met Tyr Asn Asn Thr Met Ile Ser Phe Asn Met
            115                 120                 125

Leu Glu Ala Ala Arg Ile Asn Gly Val Lys Arg Phe Phe Tyr Ala Ser
130                 135                 140

Ser Ala Cys Ile Tyr Pro Glu Phe Lys Gln Leu Glu Thr Asn Val Ser
145                 150                 155                 160

Leu Lys Glu Ser Asp Ala Trp Pro Ala Glu Pro Gln Asp Ala Tyr Gly
            165                 170                 175

Leu Glu Lys Leu Ala Thr Glu Glu Leu Cys Lys His Tyr Thr Lys Asp
            180                 185                 190

Phe Gly Ile Glu Cys Arg Val Gly Arg Phe His Asn Ile Tyr Gly Pro
            195                 200                 205

Phe Gly Thr Trp Lys Gly Gly Arg Glu Lys Ala Pro Ala Ala Phe Cys
            210                 215                 220

Arg Lys Ala Gln Thr Ser Thr Asp Arg Phe Glu Met Trp Gly Asp Gly
225                 230                 235                 240

Leu Gln Thr Arg Ser Phe Thr Phe Ile Asp Glu Cys Val Glu Gly Val
            245                 250                 255

Leu Arg Leu Thr Lys Ser Asp Phe Arg Glu Pro Val Asn Ile Gly Ser
            260                 265                 270

Asp Glu Met Val Ser Met Asn Glu Met Ala Glu Ile Ile Leu Ser Phe
            275                 280                 285

Glu Asp Arg Glu Leu Pro Ile His His Ile Pro Gly Pro Glu Gly Val
            290                 295                 300

Arg Gly Arg Asn Ser Asp Asn Thr Leu Ile Lys Glu Lys Leu Gly Trp
305                 310                 315                 320

Ala Pro Thr Met Lys Leu Lys Asp Gly Leu Arg Phe Thr Tyr Phe Trp
            325                 330                 335

Ile Lys Glu Gln Ile Glu Lys Glu Lys Thr Gln Gly Val Asp Ile Ala
            340                 345                 350

Gly Tyr Gly Ser Ser Lys Val Val Ser Thr Gln Ala Pro Val Gln Leu
            355                 360                 365

Gly Ser Leu Arg Ala Ala Asp Gly Lys Glu
370                 375

<210> SEQ ID NO 31
<211> LENGTH: 350
<212> TYPE: PRT
<213> ORGANISM: Oryza sativa

<400> SEQUENCE: 31
```

Met Ala Thr Lys Thr Lys Leu Arg Ile Phe Val Ala Gly Gly Gly
1               5                   10                  15

Phe Ile Gly Ser His Thr Ala Lys Arg Leu Lys Glu Glu Gly His Phe
            20                  25                  30

Val Arg Val Ala Asp Trp Lys Arg Gln His Tyr Phe Glu Asp Ser Gln
            35                  40                  45

Ile Cys Asp Glu Phe His Asp Val Asp Leu Arg Asp Leu Asn Asn Cys
50                  55                  60

Ile Lys Met Cys Glu Gly Met Asp Glu Val Tyr Asp Phe Ala Ala Asp
65                  70                  75                  80

Met Gly Gly Met Gly Phe Ile Gln Ser Asn His Ser Val Ile Leu Tyr
                85                  90                  95

Asn Asn Ile Met Ile Ser Phe Asn Met Val Glu Ala Ala Arg Arg Ser
                100                 105                 110

Gly Ser Val Lys Arg Phe Phe Tyr Ser Ser Ala Cys Ile Tyr Pro
            115                 120                 125

Glu Tyr Arg Gln Leu Glu Thr Ala Asn Pro Gly Leu Lys Glu Ser Asp
    130                 135                 140

Ala Trp Pro Ala Gln Pro Gln Asp Ala Tyr Gly Leu Glu Lys Leu Val
145                 150                 155                 160

Thr Glu Glu Phe Cys Lys Tyr Tyr Asn Lys Asp Phe Gly Ile Glu Phe
                165                 170                 175

Arg Ile Gly Arg Phe His Asn Ile Tyr Gly Pro His Gly Thr Trp Lys
                180                 185                 190

Gly Gly Arg Glu Lys Ala Pro Ala Phe Cys Arg Lys Ala Leu Val
            195                 200                 205

Cys Gly Asp Val Phe Glu Met Trp Gly Asp Gly Glu Gln Thr Arg Ser
210                 215                 220

Phe Cys Tyr Ile Asp Asp Cys Val Glu Gly Val Leu Arg Leu Met Arg
225                 230                 235                 240

Ser Asp Val Arg Glu Pro Ile Asn Ile Gly Ser Glu Met Val Ser
            245                 250                 255

Met Asn Asp Met Ala His Leu Val Leu Asp Phe Ala Gly Lys Lys Asp
            260                 265                 270

Ser Thr Lys Leu His His Ile Pro Gly Pro Glu Gly Val Arg Gly Arg
    275                 280                 285

Asn Ser Asp Asn Thr Leu Ile Arg Glu Lys Leu Gly Trp Ala Pro Ile
    290                 295                 300

Ile Asn Leu Lys Asp Gly Leu Lys Arg Thr Phe Asp Trp Ile Lys Ile
305                 310                 315                 320

Gln Ile Glu Asn Glu Lys Ala Gln Gly Val Asp Val Ser Gln Tyr Ser
                325                 330                 335

Gln Ser His Val Val Asn Gln Lys Pro Thr Asp Phe Thr Lys
            340                 345                 350

<210> SEQ ID NO 32
<211> LENGTH: 376
<212> TYPE: PRT
<213> ORGANISM: Ostreococcus lucimarinus

<400> SEQUENCE: 32

Met Ala Ala Ala Gly Tyr Glu Leu Arg Gly Ile Tyr Gly Thr Glu Glu
1               5                   10                  15

Tyr Trp Pro Glu Lys Lys Leu Lys Ile Cys Val Thr Gly Ala Gly Gly

```
                20                  25                  30
Phe Ile Gly Ser His Leu Ala Lys Arg Leu Lys Glu Glu Gly His His
             35                  40                  45
Val Val Ala Cys Asp Trp Lys Arg Asn Glu His Met Glu Glu Ala Met
         50                  55                  60
Phe Cys Asp Glu Phe Ile Leu Ala Asp Leu Arg Leu Tyr Glu Asn Cys
 65                  70                  75                  80
Lys Lys Val Leu Glu Gly Cys Asp His Cys Phe Asn Leu Ala Ala Asp
                 85                  90                  95
Met Gly Gly Met Gly Phe Ile Gln Ser Asn His Ser Val Ile Phe Tyr
            100                 105                 110
Asn Asn Val Met Ile Ser Phe Asn Met Met Glu Ala Met Arg Val Gln
        115                 120                 125
Gly Val Thr Arg Cys Phe Tyr Ala Ser Ser Ala Cys Ile Tyr Pro Glu
        130                 135                 140
Gly Thr Gln Leu Ser Thr Glu Met Gln Asp Gly Leu Lys Glu Ala Ser
145                 150                 155                 160
Ala Trp Pro Ala Gln Pro Gln Asp Ala Tyr Gly Leu Glu Lys Leu Ala
                165                 170                 175
Ser Glu Glu Val Tyr Lys His Tyr Gln Gln Asp Phe Gly Ile Gln Thr
            180                 185                 190
Arg Ile Gly Arg Phe His Asn Ile Tyr Gly Pro Tyr Gly Thr Trp Lys
        195                 200                 205
Gly Gly Arg Glu Lys Ala Pro Ala Ala Phe Cys Arg Lys Ala Ala Thr
        210                 215                 220
Ala Glu Ser Glu Val Glu Met Trp Gly Asp Gly Lys Gln Thr Arg Ser
225                 230                 235                 240
Phe Thr Tyr Ile Asp Asp Cys Val Glu Gly Ile Leu Arg Leu Thr Lys
                245                 250                 255
Ser Asp Phe Ala Glu Pro Val Asn Ile Gly Ser Asp Glu Met Ile Ser
            260                 265                 270
Met Asn Asp Met Gln Ala Met Thr Leu Lys Phe Ala Gly Lys Asp Leu
        275                 280                 285
Pro Ile Lys His Ile Pro Gly Pro Glu Gly Val Arg Gly Arg Asn Ser
        290                 295                 300
Asn Asn Glu Leu Ile Lys Glu Lys Leu Gly Trp Ala Pro Ser Val Lys
305                 310                 315                 320
Leu Ala Asp Gly Leu Lys Val Thr Phe Glu Trp Ile Ser Ser Lys Ile
                325                 330                 335
Ala Glu Glu Lys Ala Lys Gly Val Asp Thr Ala Ala Ala Phe Gly Lys
            340                 345                 350
Ser Thr Ile Cys Gly Thr Gln Ala Pro Thr Glu Leu Gly Gln Leu Arg
        355                 360                 365
Ala Ala Asp Gly Asp Glu Lys Leu
    370                 375

<210> SEQ ID NO 33
<211> LENGTH: 403
<212> TYPE: PRT
<213> ORGANISM: Solanum tuberosum

<400> SEQUENCE: 33

Met Gly Ser Ser Gly Gly Ile Asn Tyr Gly Ser Tyr Thr Tyr Glu Asn
 1               5                  10                  15
```

Leu Glu Arg Glu Pro Tyr Trp Pro Ser Glu Lys Leu Arg Ile Ser Ile
            20                  25                  30

Thr Gly Ala Gly Gly Phe Ile Ala Ser His Ile Ala Arg Arg Leu Lys
        35                  40                  45

Ser Glu Gly His Tyr Ile Ile Ala Ser Asp Trp Lys Lys Asn Glu His
    50                  55                  60

Met Thr Glu Asp Met Phe Cys His Glu Phe His Leu Ala Asp Leu Arg
65                  70                  75                  80

Val Met Asp Asn Cys Leu Lys Val Thr Lys Gly Val Asp His Val Phe
                85                  90                  95

Asn Leu Ala Ala Asp Met Gly Gly Met Gly Phe Ile Gln Ser Asn His
            100                 105                 110

Ser Val Ile Phe Tyr Asn Asn Thr Met Ile Ser Phe Asn Met Met Glu
        115                 120                 125

Ala Ala Arg Ile Asn Ser Val Lys Arg Phe Phe Tyr Ala Ser Ser Ala
    130                 135                 140

Cys Ile Tyr Pro Glu Phe Lys Gln Leu Glu Thr Asn Val Ser Leu Lys
145                 150                 155                 160

Glu Ala Asp Ala Trp Pro Ala Glu Pro Gln Asp Ala Tyr Gly Leu Glu
                165                 170                 175

Lys Leu Ala Thr Glu Glu Leu Cys Lys His Tyr Asn Lys Asp Phe Gly
            180                 185                 190

Ile Glu Cys Arg Ile Gly Arg Phe His Asn Ile Tyr Gly Pro Phe Gly
        195                 200                 205

Thr Trp Lys Gly Gly Arg Glu Lys Ala Pro Ala Ala Phe Cys Arg Lys
210                 215                 220

Ala Gln Thr Ala Thr Asp Lys Phe Glu Met Trp Gly Asp Gly Leu Gln
225                 230                 235                 240

Thr Arg Ser Phe Thr Phe Ile Asp Glu Cys Val Glu Gly Val Leu Arg
                245                 250                 255

Leu Thr Lys Ser Asp Phe Arg Glu Pro Val Asn Ile Gly Ser Asp Glu
            260                 265                 270

Met Val Ser Met Asn Glu Met Ala Glu Met Val Leu Ser Phe Glu Asp
        275                 280                 285

Lys Lys Leu Ala Val Gln His Ile Pro Gly Pro Glu Gly Val Arg Gly
290                 295                 300

Arg Asn Ser Asp Asn Thr Leu Ile Lys Glu Lys Leu Gly Trp Ala Pro
305                 310                 315                 320

Thr Met Arg Leu Lys Asp Gly Leu Arg Ile Thr Tyr Phe Trp Ile Lys
                325                 330                 335

Glu Gln Ile Glu Lys Glu Lys Ser Gln Gly Val Asp Thr Ala Thr Tyr
            340                 345                 350

Gly Ser Ser Lys Val Val Gly Thr Gln Ala Pro Val Glu Leu Val Pro
        355                 360                 365

Phe Val Leu Leu Met Ala Arg Asn Lys Phe Ile Pro Ser Val Ile Ile
    370                 375                 380

Ser Thr Gly Ser Gln Ser Leu Cys Tyr Asp Ile Ala Ala Leu Cys Ile
385                 390                 395                 400

Met Ala Ser

<210> SEQ ID NO 34
<211> LENGTH: 376
<212> TYPE: PRT
<213> ORGANISM: Vitis vinifera

<400> SEQUENCE: 34

```
Met Gly Ser Asn Asp Gly Thr Thr Tyr Gly Ala Tyr Thr Tyr Glu Glu
1               5                   10                  15

Leu Glu Arg Glu Pro Tyr Trp Gln Ser Glu Lys Leu Arg Ile Ser Ile
            20                  25                  30

Thr Gly Ala Gly Gly Phe Ile Ala Ser His Ile Ala Arg Arg Leu Lys
        35                  40                  45

Thr Glu Gly His Tyr Ile Ile Ala Ser Asp Trp Lys Lys Asn Glu His
50                  55                  60

Met Thr Glu Asp Met Phe Cys His Glu Phe Arg Leu Val Asp Leu Arg
65                  70                  75                  80

Val Met Asp Asn Cys Leu Lys Val Thr Thr Gly Val Asp His Val Phe
                85                  90                  95

Asn Leu Ala Ala Asp Met Gly Met Gly Phe Ile Gln Ser Asn His
                100                 105                 110

Ser Val Ile Met Tyr Asn Asn Thr Met Ile Ser Phe Asn Met Leu Glu
            115                 120                 125

Ala Ser Arg Ile Asn Gly Val Lys Arg Phe Phe Tyr Ala Ser Ser Ala
        130                 135                 140

Cys Ile Tyr Pro Glu Phe Lys Gln Leu Glu Thr Asn Val Ser Leu Lys
145                 150                 155                 160

Glu Ser Asp Ala Trp Pro Ala Glu Pro Gln Asp Ala Tyr Gly Leu Glu
                165                 170                 175

Lys Leu Ala Thr Glu Glu Leu Cys Lys His Tyr Thr Lys Asp Phe Gly
            180                 185                 190

Ile Glu Cys Arg Ile Gly Arg Phe His Asn Ile Tyr Gly Pro Phe Gly
        195                 200                 205

Thr Trp Lys Gly Gly Arg Glu Lys Ala Pro Ala Ala Phe Cys Arg Lys
210                 215                 220

Ala Leu Thr Ser Thr Asp Lys Phe Glu Met Trp Gly Asp Gly Leu Gln
225                 230                 235                 240

Thr Arg Ser Phe Thr Phe Ile Asp Glu Cys Val Glu Gly Val Leu Arg
                245                 250                 255

Leu Thr Lys Ser Asp Phe Arg Glu Pro Val Asn Ile Gly Ser Asp Glu
            260                 265                 270

Met Val Ser Met Asn Glu Met Ala Glu Ile Val Leu Ser Phe Glu Asn
        275                 280                 285

Lys Asn Leu Pro Ile His His Ile Pro Gly Pro Glu Gly Val Arg Gly
290                 295                 300

Arg Asn Ser Asp Asn Thr Leu Ile Lys Glu Lys Leu Gly Trp Ala Pro
305                 310                 315                 320

Thr Met Lys Leu Lys Asp Gly Leu Arg Ile Thr Tyr Phe Trp Ile Lys
                325                 330                 335

Glu Gln Ile Glu Lys Glu Lys Val Lys Gly Ile Asp Leu Ser Ile Tyr
            340                 345                 350

Gly Ser Ser Lys Val Val Gly Thr Gln Ala Pro Val Gln Leu Gly Ser
        355                 360                 365

Leu Arg Ala Ala Asp Gly Lys Glu
370                 375
```

<210> SEQ ID NO 35
<211> LENGTH: 376
<212> TYPE: PRT

<213> ORGANISM: Lycopersicon esculentum

<400> SEQUENCE: 35

```
Met Gly Thr Ser Val Glu Thr Thr Tyr Gly Glu Tyr Thr Tyr Glu Asn
1               5                   10                  15

Leu Glu Arg Glu Pro Tyr Trp Pro Ser Glu Lys Leu Arg Val Ser Ile
            20                  25                  30

Thr Gly Ala Gly Gly Phe Ile Ala Ser His Ile Ala Arg Arg Leu Lys
        35                  40                  45

Thr Glu Gly His Tyr Ile Ile Ala Ser Asp Trp Lys Lys Asn Glu His
    50                  55                  60

Met Ser Glu Asp Met Phe Cys His Glu Phe His Leu Val Asp Leu Arg
65                  70                  75                  80

Val Met Asp Asn Cys Leu Lys Val Thr Lys Gly Val Asp His Val Phe
                85                  90                  95

Asn Leu Ala Ala Asp Met Gly Gly Met Gly Phe Ile Gln Ser Asn His
            100                 105                 110

Ser Val Ile Met Tyr Asn Asn Thr Met Ile Ser Phe Asn Met Met Glu
        115                 120                 125

Ala Ser Arg Ile Asn Ser Val Lys Arg Phe Phe Tyr Ala Ser Ser Ala
    130                 135                 140

Cys Ile Tyr Pro Glu Phe Lys Gln Leu Glu Thr Asn Val Ser Leu Lys
145                 150                 155                 160

Glu Ser Asp Ala Trp Pro Ala Glu Pro Gln Asp Ala Tyr Gly Leu Glu
                165                 170                 175

Lys Leu Ala Thr Glu Glu Leu Cys Lys His Tyr Asn Lys Asp Phe Gly
            180                 185                 190

Ile Glu Cys Arg Ile Gly Arg Phe His Asn Ile Tyr Gly Pro Phe Gly
        195                 200                 205

Thr Trp Lys Gly Gly Arg Glu Lys Ala Pro Ala Ala Phe Cys Arg Lys
    210                 215                 220

Ala Leu Thr Ser Thr Asp Lys Phe Glu Met Trp Gly Asp Gly Lys Gln
225                 230                 235                 240

Thr Arg Ser Phe Thr Phe Ile Asp Glu Cys Val Glu Gly Val Leu Arg
                245                 250                 255

Leu Thr Lys Ser Asp Phe Arg Glu Pro Val Asn Ile Gly Ser Asp Glu
            260                 265                 270

Met Val Ser Met Asn Glu Met Ala Glu Ile Val Leu Ser Phe Asp Gly
        275                 280                 285

Lys Asn Leu Pro Ile His His Ile Pro Gly Pro Glu Gly Val Arg Gly
    290                 295                 300

Arg Asn Ser Asp Asn Thr Leu Ile Lys Glu Lys Leu Gly Trp Ala Pro
305                 310                 315                 320

Asn Met Lys Leu Lys Asp Gly Leu Arg Ile Thr Tyr Phe Trp Ile Lys
                325                 330                 335

Glu Gln Ile Glu Lys Glu Lys Val Lys Gly Ala Asp Val Ser Thr Tyr
            340                 345                 350

Gly Ser Ser Lys Val Val Gly Thr Gln Ala Pro Val Glu Leu Gly Ser
        355                 360                 365

Leu Arg Ala Ala Asp Gly Lys Glu
    370                 375
```

<210> SEQ ID NO 36
<211> LENGTH: 28

```
<212> TYPE: PRT
<213> ORGANISM: Artificial Sequence
<220> FEATURE:
<223> OTHER INFORMATION: Synthetic construct: conserved epimerase
      motif 1

<400> SEQUENCE: 36

Val Leu Arg Leu Thr Lys Ser Asp Phe Arg Glu Pro Val Asn Ile Gly
 1               5                  10                  15

Ser Asp Glu Met Val Ser Met Asn Glu Met Ala Glu
             20                  25

<210> SEQ ID NO 37
<211> LENGTH: 27
<212> TYPE: PRT
<213> ORGANISM: Artificial Sequence
<220> FEATURE:
<223> OTHER INFORMATION: Synthetic construct: conserved epimerase
      motif 1

<400> SEQUENCE: 37

Gly Arg Phe His Asn Ile Tyr Gly Pro Phe Gly Thr Trp Lys Gly Gly
 1               5                  10                  15

Arg Glu Lys Ala Pro Ala Ala Phe Cys Arg Lys
             20                  25

<210> SEQ ID NO 38
<211> LENGTH: 1384
<212> TYPE: DNA
<213> ORGANISM: Actinidia eriantha

<400> SEQUENCE: 38
agagagagag agcattacat agattcggta ctcgaactct ttcagaatgg gaagcaccgg      60
tgaatctaac tacggatcgt acacctatga gaaccttgag agggaaccct actggccgga    120
ggcgaagctc cgcatctcca taaccggagc cggtgggttc attgcctcac acattgcaag    180
gcgactgaag ggcgagggc attacatcat tgcttctgac tggaagaaaa acgagcacat     240
gaccgaggac atgttctgtc acgaattcca tcttgttgat ctcagggtga tggacaactg    300
cttgaaagtc acgaccagag ttgatcatgt gttcaatctt gctgctgata tgggtgggat    360
gggcttcatt cagtccaatc actcagtcat tatgtataac aacacaatga tcagcttcaa    420
catgcttgaa gctgctaggg tcaatggtat taagaggttc ttttatgctt ctagcgcttg    480
tatttaccct gaatttaagc agttggacac aaatgtgagc ttgaaggaat ctgatgcttg    540
gcccgctgag cctcaagatg cttatggttt agagaagctt gcaaccgagg agttatgcaa    600
gcactacacc aaggactttg gcattgaatg taggattgga cggtttcaca acatctatgg    660
acctttggga acctggaaag gtgggaggga gaaagcccct gctgcattct gcagaaagac    720
ccttacctcc actgataggt ttgagatgtg gggagacggt ctgcaaaccc gatctttcac    780
cttcattgat gaatgtgtcg aaggtgtcct aagattgacg aagtcagact tcagagaacc    840
agtgaatatc ggaagtgatg agatggtcag catgaatgag atggccgaga tcgttctcag    900
cttcgagaac aagaaactgc ccatccatca cattccgggc ccagagggcg tccgtggacg    960
aaactcggac aacaccctga ttaaggagaa gcttgggtgg gccccaacta tgaaactgaa   1020
ggatgggctg agattcacat acttttggat caaggaacaa cttgagaaag agaaggctcg   1080
gggcatcgat ctgtcaactt atgggtcatc aaaagttgtg gaacgcaag ccccagttca    1140 gttgggctct cttcgtgctg ctgatggcaa agaatgaagt ggataagacc gagcaggcta   1200
```

| | |
|---|---:|
| tccggtgaac ttgaggccga ggtttaattt atgattgttt tcgtgggatt tatgtacaag | 1260 |
| ggttgtcgtt taaattgcaa tctgctgttt ctttctgcta taattgttat tgtacggcga | 1320 |
| aagatgccct actcttggat ccgtatctt gttgagagta ggcttctgtt gtaaaaaaaa | 1380 |
| aaaa | 1384 |

<210> SEQ ID NO 39
<211> LENGTH: 1388
<212> TYPE: DNA
<213> ORGANISM: Actinidia deliciosa

<400> SEQUENCE: 39

| | |
|---|---:|
| gtcttgagag agagagagag agagagagat ttactttggg agagcgaaat ttatagctac | 60 |
| ggcactcgat ctctttcaga atgggaagca gcagtgaatc taactacgga tcgtacacct | 120 |
| atgagaacct cgagagggaa ccctactggc cggaggcgaa gctccgcatc tccattaccg | 180 |
| gagccggtgg gttcattgcc tcgcacattg caaggcgact gaaggagag gggcattaca | 240 |
| tcattgcttc tgactggaag aaaaacgagc acatgaccga ggacatgttt tgtcacgagt | 300 |
| tccatctcgt tgatctcagg gtgatggaca actgcttgaa agtcactacc ggagtcgatc | 360 |
| atgtgttcaa tcttgctgct gatatgggtg gtatgggatt cattcagtcc aaccactcgg | 420 |
| tcattatgta taacaacacg atgatcagct tcaacatgct tgaagcagct agggtcaatg | 480 |
| gtgttaagag gttcttttat gcttctagcg cttgtattta tcctgaattt aagcagttgg | 540 |
| acactaatgt gagcttgaag gagtctgatg cttggcccgc tgagcctcaa gatgcttatg | 600 |
| gtttagagaa gcttgcaacc gaggaattat gcaagcacta caccaaggat tttggcattg | 660 |
| aatgtaggat tggaaggttt cataacattt atggaccttt tggaacatgg aaaggtggaa | 720 |
| gggagaaagc ccctgctgca ttctgcagaa agacccttac ctccactgat aggttgaga | 780 |
| tgtggggaga cggtctgcaa acccgatctt tcaccttcat tgatgaatgt gtcgaaggtg | 840 |
| tcctaagatt gacaaaatca gacttcagag aaccagtgaa tataggaagc gatgagatgg | 900 |
| tcagcatgaa tgagatggcc gagatcgttc tcagcttcga ggacaagaag ctgcccatcc | 960 |
| atcacattcc tggcccagag ggggtccgtg gtcgaaactc ggacaacacc ctgattaagg | 1020 |
| agaagcttgg gtgggcccca actatgaaac tgaaggatgg gctgagattc acatacttct | 1080 |
| ggatcaagga gcaacttgag aaagagaagg ctcagggcat cgatctgtca acttatggat | 1140 |
| cgtcaaaagt tgtgggaacg caagccccgg ttcagttggg ctctcttcgt gctgctgatg | 1200 |
| gcaaagaatg aagcagataa gaatctgtcc agtgaaatcg agggcaaggt ttaatttatg | 1260 |
| attgttttag tgggatttat gcatatgggt tgtctttaaa ttgcaatctg ctgtttcttt | 1320 |
| ctgccataat tattattgta cgtcgaaaga caccctgctc ttggatttcg tatcttaaaa | 1380 |
| aaaaaaaa | 1388 |

<210> SEQ ID NO 40
<211> LENGTH: 1592
<212> TYPE: DNA
<213> ORGANISM: Malus x domesticus

<400> SEQUENCE: 40

| | |
|---|---:|
| atcatctatc ccctcgaacc caacttttgt ctatcatttt cttcttccca actcctcaaa | 60 |
| atcttcaaag ctccaaactt ttgctctttt cagaatggga agtacaggcg aaattaagta | 120 |
| tggtgcgtat acctatgaga acctcgagag ggagccttat tggcccttctg aaaagctccg | 180 |
| aatttccatt accggggcag gtggttttat cgcctccac attgcccgga gattgaagaa | 240 |

```
tgagggtcat tacattattg cttccgattg gaagaagaat gagcacatga ctgaagacat    300
gttctgccat gaattccatc ttgccgacct cagggtcatg gataattgct tgaaggttac    360
aaagaatgtt gaccatgtgt tcaacctcgc agctgatatg gcggaatgg gcttcattca    420 gtccaaccat tctgtcatat tttataacaa taccatgatt agtttcaaca tggtcgaagc    480
tgctaggatc aatgacgtga agaggttttt ctatgcttct agtgcttgta tttaccctga    540
gtttaagcag ctggaaacca atgtcagctt gaaggagtct gatgcctggc ctgcagagcc    600
tcaagatgct tatggcctgg agaagcttgc aactgaggaa ttgtgcaagc actacaccaa    660
agactttgga atcgagtgcc gtattggaag gttccacaac atttatggcc cttttggaac    720
ctggaaaggt ggaagggaga aggctcctgc tgcgttttgc agaaagactc tcactgccac    780
tgataagttt gagatgtggg gagatggact tcagacccga tccttcacct ttattgatga    840
atgtgtagaa ggtgtacttc ggttgacgaa gtcagacttc cgtgagccag tgaatattgg    900
aagtgatgag atggttagca tgaatgagat ggctgagatc gttcttagct ttgaggacaa    960
gaagctgccc atccagcaca ttcctgggcc agagggtgtc cgtggtcgta actcagacaa   1020
cacactgatc aaagagaaac ttggttgggc tcctaccatg aggttgaagg atggtctgag   1080
aattacatac ttctggatca aggaacagat tgagaaagag aaggcacaag gcgctgacct   1140
ctcggtgtat ggctcatcta aggttgtggg aacccaagcc ccagttcaac ttggttcgct   1200
gcgtgctgct gatggcaaag aatgaagggt ccgacaaaac tgcaccagaa aatatgatat   1260
ccagtagttc tggttatgat agcgcggcac attctatgtg cgtgaacaat aaggcgggaa   1320
gcttttgttc cgctcccgtt gtatatctag cttgttagtt aaatctgcca ccttaggatt   1380
gcctttgtat tttgtttccc taccttagc attattcagt ttatgagttc agttgatcgt   1440
ttataagatt tttttcggg ttcaaatttc aatatcgacc tgtcccgaat gttgagaccg   1500
gctgtattca accggcgggc aatcggagat gtgctcgtct gagttatgct gttttatgct   1560
tgcaaaaatt gatctttggt aaaaaaaaaa aa                                 1592

<210> SEQ ID NO 41
<211> LENGTH: 1611
<212> TYPE: DNA
<213> ORGANISM: Arabidopsis thaliana

<400> SEQUENCE: 41
aataccaata ggagttggaa aactaaaaca acgagtggtg ttgctctctc catcttcctc     60
ttcatcttct tctgttctct ctctataaat acaagtttac tcttcctctt cctcaaatct    120
ctgactcttc tctgcattat ctcttcgatc tctccaactc tccaaaacct tcctcagaat    180
gggaactacc aatggaacag actatggagc atacacatac aaggagctag aaagagagca    240
atattggcca tctgagaatc tcaagatatc aataacagga gctggaggtt tcattgcatc    300
tcacattgct cgtcgtttga agcacgaagg tcattacgtg attgcttctg actggaaaaa    360
gaatgaacac atgactgaag acatgttctg tgatgagttc catcttgttg atcttagggt    420
tatggagaat tgtctcaaag ttactgaagg agttgatcat gttttttaact tagctgctga    480 tatgggtggt atgggttttta tccagagtaa tcactctgtg attatgtata ataatactat    540
gattagtttc aatatgattg aggctgctag gatcaatggg attaagaggt tctttttatgc    600 ttcgagtgct tgtatctatc cagagtttaa gcagttggag actactaatg tgagcttgaa    660
ggagtcagat gcttggcctg cagagcctca agatgcttat ggtttggaga agcttgctac    720
```

-continued

```
ggaggagttg tgtaagcatt acaacaaaga ttttggtatt gagtgtcgaa ttggaaggtt      780
ccataacatt tatggtcctt ttggaacatg gaaaggtgga agggagaagg ctccagctgc      840
tttctgtagg aaggctcaga cttccactga taggtttgag atgtggggag atgggcttca      900
gacccgttct tttaccttta tcgatgagtg tgttgaaggt gtactcaggt tgacaaaatc      960
agatttccgt gagccggtga acatcggaag cgatgagatg gtgagcatga atgagatggc     1020
tgagatggtt ctcagctttg aggaaaagaa gcttccaatt caccacattc ctggcccgga     1080
aggtgttcgt ggtcgtaact cagacaacaa tctgatcaaa gaaaagcttg gttgggctcc     1140
taatatgaga ttgaaggagg ggcttagaat aacctacttc tggataaagg aacagatcga     1200
gaaagagaaa gcaagggaa gcgatgtgtc gctttacggg tcatcaaagg tggttggaac     1260
tcaagcaccg gttcagctag gctcactccg cgcggctgat ggaaaagagt gaagttcacc     1320
aaagtataag tcaagctcaa atatggcctt ttaagttcag caaaatgttt agatatattt     1380
ttaggtagct tcctattaaa aaagcaataa taagtgtttt ggattttggt tccttctatt     1440
ctgctaatcc ttgtttatgt ttagttgaaa aagtttgctt gcattgttaa gtctgttatc     1500
atattattgt ggtcctttca ttcacagtat gtatgtttat catcatagtc aagttgatgt     1560
cgtggtcctc tcacggacca gtacaagtaa gtggcttgtg ttttttcttg c              1611
```

<210> SEQ ID NO 42
<211> LENGTH: 1372
<212> TYPE: DNA
<213> ORGANISM: Malpighia glabra

<400> SEQUENCE: 42

```
aattatttga aagagatcac agtttcagga tggagagtag cgatggaact gattacggag       60
catacacata caaggagctt gagagggaac cctactggcc ctcagaaaag cttcgaattt      120
cgattactgg tgctggtgga tttattgcct cgcacatagc tcgtcgcttg aagagtgaag      180
gccattatat tattgcttct gattggaaga agaatgagca catgactgaa gatatgttct      240
gtcatgaatt ccatcttgtt gatctcaggg ttatggataa ttgcttgaag gttactaaag      300
atgccgacca tgttttcaac cttgctgctg atatgggtgg aatgggtttc atccaatcaa      360
atcattccgt catcatgtat aacaacacga tgatcagctt taacatgctt gaagcatcca      420
gaatcagcgg agtcaagagg ttcttttatg cctctagtgc ttgcatctat cctgagttca      480
agcaattgga aactaatgtg agcttgaagg agtctgatgc ctggccagct gagccgcaag      540
atgcttacgg cttggagaag ctagctacag aagagttgtg caagcactat accaaagact      600
tcggaattga atgccgtgtt ggaaggttcc ataacattta tggtcctttt ggaacatgga      660
aagtggcag ggaaaaggca cctgctgctt tttgcagaaa ggcgattacc tctgttgaca      720
agtttgagat gtgggggat ggactacaaa cccgatcctt cacgtttatt gatgaatgcg      780
tggaaggagt gcttagattg accaagtctg acttccgcga gccagtgaac attggaagtg      840
atgagatggt tagcatgaat gagatggctg aaattgttct cagctttgag gacaagaagc      900
ttcccatcca ccacattcct ggaccagaag gtgtccgagg tcgtaactcc gacaacactc      960
taatcaaaga gaagcttggt tgggcaccta caatgaggtt gaaggatgga cttagaatta     1020
catacttctg gatcaaggaa cagatcgaga aggagaaggc tcaaggaatc gatctcgcag     1080
tttatggatc atcgaaagtg gtgggaaccc aagcaccggt tcaactgggt tctctccgtg     1140
ccgcagacgc caaagaatga ggtggttgta agtgcaagca gattagtctt tgttgcagtc     1200
aagaaagccg aggttcattt ttaaatatga gatggctggc atatgttgtc gcaataagtg     1260
```

| | |
|---|---|
| gtgttgattg tgttgaattt tcattgaggt tctgtgttgt ctgtagcaat gttctttatt | 1320 |
| tccttaatga tttgtactat gattgatatg aatgaggagt gaagcttcca tc | 1372 |

<210> SEQ ID NO 43
<211> LENGTH: 1212
<212> TYPE: DNA
<213> ORGANISM: Oryza sativa

<400> SEQUENCE: 43

| | |
|---|---|
| gatccctctc cgaccgacca agcgccgcct ccaagaatgg ggagctcgga gaagaacgga | 60 |
| actgcttatg gcgagtacac ctatgctgaa ctggagaggg agcagtactg gccgtctgag | 120 |
| aagctgagga tatcgatcac cggagctggt ggtttcattg gatcccacat tgctcgccgt | 180 |
| ctgaagagcg aggggcatta catcatcgcc tccgactgga agaagaatga gcacatgact | 240 |
| gaggacatgt tctgccatga gttccacctt gttgacctta gggtcatgga caactgcctc | 300 |
| aaggtcacca acgcgtcga ccatgtgttc aaccttgccg ctgatatggg tggtatgggg | 360 |
| ttcattcagt ccaaccactc tgtgatcatg tacaacaaca ccatgatcag tttcaacatg | 420 |
| ctcgaggctg cacgtatcaa tggtgtgaag aggttcttct atgcctcaag tgcatgcatt | 480 |
| taccctgaat tcaagcagct tgaaactaac gttagcctga aggaatctga tgcctggcct | 540 |
| gctgagcctc aagatgccta tggtttggag aagcttgcaa ctgaggagct ctgcaagcac | 600 |
| tacaccaagg actttggcat tgagtgccgt gttggccgct ccacaacat atatggcccc | 660 |
| tttggaacat ggaaaggtgg ccgtgagaag gcaccagctg cattctgcag gaaggctcag | 720 |
| acttccactg acaggtttga gatgtgggt gatggcctcc agacccggtc cttcacattc | 780 |
| atagatgagt gtgttgaggg tgttctgagg ttgacaaagt cggacttccg tgagccagtg | 840 |
| aacattggaa gcgatgaaat ggtaagcatg aacgagatgg ctgaaatcat tctcagcttc | 900 |
| gaggataggg agctgcccat ccaccacatc cctggacccg agggtgtccg tggccgtaac | 960 |
| tccgacaaca ccctcatcaa ggagaagctt ggctgggcac ccacaatgaa gctcaaggac | 1020 |
| gggctgaggt tcacctactt ctggatcaag gagcagatag agaaggagaa gacccagggc | 1080 |
| gtcgacatcg cggggttacgg ctcatccaag gtggtgtcca cccaggcccc ggttcagctg | 1140 |
| ggctccctcc gtgctgccga tgcaaggag taatttcaaa gctgctacac catgaagatc | 1200 |
| aatcagctcc tc | 1212 |

<210> SEQ ID NO 44
<211> LENGTH: 1053
<212> TYPE: DNA
<213> ORGANISM: Oryza sativa

<400> SEQUENCE: 44

| | |
|---|---|
| atggcaacta aaactaaact ccgtattttc gtcgctggtg gtggtggctt cattggtagt | 60 |
| cacactgcta agcgtctcaa ggaagagggt cacttcgtgc gcgtggctga ctggaagaga | 120 |
| caacactact ttgaggacag ccaaatatgc gacgagttcc atgacgtgga cttgcgtgat | 180 |
| ttgaacaatt gtattaagat gtgcgaaggc atggacgaag tctacgactt tgctgcagat | 240 |
| atgggcggta tgggttttat tcaatccaac cactctgtta tcttgtacaa caatattatg | 300 |
| atcagcttca acatggtgga ggctgctcgt cgctctggtt ctgtcaagcg attcttctac | 360 |
| agctcctcag cttgcatcta ccccgaatac cgtcaattgg aaactgccaa tcccggtttg | 420 |
| aaggagtctg atgcttggcc cgcgcaacct caagatgcct atggtcttga aaagctcgtt | 480 |

-continued

| | |
|---|---|
| accgaagagt tctgcaagta ctacaacaag actttggca ttgagttccg cattggtcgc | 540 |
| ttccacaaca tctacggccc ccacggcact tggaagggtg gtcgcgagaa ggcccccgct | 600 |
| gccttttgtc gcaaggccct ggtgtgcggc gatgtgttcg agatgtgggg tgacggcgaa | 660 |
| cagacgcgct ccttctgcta cattgacgac tgcgtggagg gtgtgttgcg attgatgcgc | 720 |
| agcgatgtgc gcgagccgat caacattggc agcgaggaga tggtgagcat gaacgacatg | 780 |
| gcacacctcg tgctcgactt tgcgggcaag aaggacagca ccaagttgca tcacattccg | 840 |
| ggacctgaag gtgtgcgcgg tcgtaacagc gacaacaccc tcatccgcga aagttgggc | 900 |
| tgggctccta tcatcaattt gaaggacggc ttgaagcgca cttttgactg gatcaagatc | 960 |
| cagatcgaga acgagaaggc gcaaggagtc gatgtgtcgc agtacagcca atcacacgtc | 1020 |
| gtcaatcaga agcccactga cttcactaaa taa | 1053 |

<210> SEQ ID NO 45
<211> LENGTH: 1131
<212> TYPE: DNA
<213> ORGANISM: Ostreococcus lucimarinus

<400> SEQUENCE: 45

| | |
|---|---|
| atggcggccg ccgggtacga attgcgcggg atttacggca cggaggagta ctggccggag | 60 |
| aagaagctga agatttgcgt gacgggcgcg ggaggtttca tcgggtcgca tctcgcgaaa | 120 |
| cgattgaaag aggagggaca tcacgtcgtg gcgtgcgatt ggaagcgcaa tgaacacatg | 180 |
| gaagaggcga tgttctgcga tgagttcatc ttggctgatt tgaggctgta cgaaaactgt | 240 |
| aaaaaggttc tcgaggggtg cgaccactgc ttcaacctcg cggcggacat gggagggatg | 300 |
| ggattcattc agtccaacca ctccgtcatc ttctacaaca acgtgatgat ttccttcaat | 360 |
| atgatggaag cgatgcgggt gcagggcgtg acgcgatgct tttacgcgtc gagcgcgtgc | 420 |
| atctacccgg agggcacgca gttgagcacg gagatgcaag acgggttgaa ggaagcgagc | 480 |
| gcgtggccgg cgcagccgca agacgcgtat ggtctcgaaa agctcgcgag cgaggaagtg | 540 |
| tacaagcact accagcaaga ttttggtatt cagacgcgca tcggtcgatt ccacaacatt | 600 |
| tacggtccgt acggcacgtg gaagggcggt gcgaaaaagg cgccggcggc gttctgccgt | 660 |
| aaggctgcga cggctgaaag cgaagtcgaa atgtggggtg acggtaagca aacgcgctct | 720 |
| ttcacctaca tcgacgattg cgtcgagggc atcttgcgtc tcaccaagag cgacttcgcc | 780 |
| gagccggtga acatcggttc cgacgaaatg atctccatga acgatatgca agccatgacg | 840 |
| ttgaagttcg cgggcaagga cttgccaatc aagcatattc cgggtccgga aggtgtgcgc | 900 |
| ggtcgcaact ccaacaacga actcatcaag gaaaagctcg gttgggcgcc gtctgtcaag | 960 |
| ctcgcggacg gcttgaaggt tacgtttgag tggatctcga gcaagattgc cgaagagaag | 1020 |
| gccaagggtg ttgacaccgc cgccgctttc ggtaagtcca ccatctgtgg cacgcaagcg | 1080 |
| ccgaccgaac tcggtcagtt gcgcgctgcg gacggcgacg aaaagctgta a | 1131 |

<210> SEQ ID NO 46
<211> LENGTH: 1521
<212> TYPE: DNA
<213> ORGANISM: Solanum tuberosum

<400> SEQUENCE: 46

| | |
|---|---|
| ttttctcctg catactttta gagaatggga agctctggtg gtattaacta tggttcttac | 60 |
| acttatgaga atcttgagag ggaaccttac tggccatctg agaaactccg tatttccatt | 120 |
| actggggctg gaggatttat cgcttctcac attgctcgtc gtttgaagag cgagggccac | 180 |

```
tacataattg cctccgattg aagaagaat gagcacatga cagaggatat gttctgtcat      240
gagtttcatc ttgcggatct tagggttatg gataattgct tgaaggtaac aaaaggtgtt    300
gaccatgtct tcaatctcgc tgctgatatg ggtggcatgg gtttcattca gtccaaccac    360
tcggttatct tctataacaa cactatgatc agcttcaata tgatggaagc tgctaggatt    420
aacagtgtca aaggttctt ctatgcatct agtgcttgca tatacccga gttcaaacaa      480 ctcgaaacaa atgtcagcct gaaagaagct gatgcttggc ctgcagagcc tcaagatgca    540
tacggcttgg aaaagcttgc cacagaagaa ctgtgcaaac attacaacaa ggattttgga    600
attgaatgtc gtattggaag gttccataac atctatggac ttttggaac ttggaaaggt     660 ggaagggaaa aagctcctgc cgcttttgt agaaaagcac aaactgcaac ggataagttt     720
gaaatgtggg gagatggact tcaaacacgt tcattcacct tcattgatga gtgtgttgaa    780
ggggttctta gattgacaaa atccgactc cgagagccag tgaacatagg aagtgatgag     840
atggtcagca tgaatgagat ggctgagatg gttctcagct tgaggacaa gaagcttgct     900 gtccaacaca ttccaggccc agaaggcgtc cgtggtcgca actcagacaa cacactgata    960
aaagagaagc ttggttgggc tccaacaatg agattgaagg atggtctgag aattacatac   1020
ttctggatca aggagcagat cgagaaagag aaatctcaag gagttgatac tgcaacctat   1080
ggatcttcca aggtggtggg cacccaagct ccagttgagc tagttccctt cgtgctgctg   1140
atggcaagga ataagttcat tccttctgtc atcatttcaa ctggaagcca atccctctgc   1200
tatgacattg ctgcattatg tattatgcg tcgtagaaga tgtgttaagt tctggtaatt    1260 gttggcttt cttggtttta gtttgaacat gtcaatgtaa tctattaccc cttggtcttg    1320 tgaagggat gatagtttaa tagtatattt atcagtcgtt cgagaagatc tcaatgtgag    1380
aattgaataa ctgccagtgg atcctctctt gtttttttta cctagttcag gatcttgctg    1440
ttgatgatca tgtaatcaaa attttaatct tgttaaggtt tatatgtaag atttcattgc    1500
aaagtaaaaa aaaaaaaaaa a                                             1521
```

<210> SEQ ID NO 47
<211> LENGTH: 1211
<212> TYPE: DNA
<213> ORGANISM: Vitis vinifera

<400> SEQUENCE: 47

```
cccttgagag cttcacatta tcttcttct ctaaatcttg agaatgggaa gtaacgatgg       60
aaccacttat ggtgcgtaca cctatgagga gcttgagagg gaaccatact ggcaatctga    120
aaagctccgg atttcaatca ctggtgctgg tggttttatt gcctctcaca ttgctcggcg    180
tctgaagacc gagggccact acattattgc ttctgactgg aagaagaacg agcacatgac    240
tgaagatatg ttctgtcatg aatttcgtct tgttgatctc agggtgatgg ataactgctt    300
gaaggtcact acaggagttg accatgtgtt taaccttgct gctgatatgg gtggaatggg    360
gttcatccag tccaaccatt cagttattat gtacaataac acaatgatca gcttcaacat    420
gcttgaggct tctaggatca atggggttaa gaggttcttc tatgcctcta gtgcttgcat    480
ctaccctgaa tttaagcagt tggaaactaa tgtgagcttg aaggagtctg atgcatggcc    540
tgcagagcct caagatgctt atggattgga gaaacttgct acggaggagt tgtgtaagca    600
ctataccaaa gactttggaa ttgaatgtcg tattggaaga ttccataaca tttatggacc    660
ttttggaaca tggaaaggtg ggagagagaa ggctcctgct gcttttgcc gaaaggctct    720
```

```
cacttccacc gacaagtttg aaatgtgggg agacggactt caaactcgtt ctttcacctt      780
cattgatgaa tgtgtagaag gtgtcctcag gctgacaaag tcagacttcc gggagccagt      840
gaacattgga agtgatgaga tggttagcat gaatgagatg gccgagattg ttctcagctt      900
tgagaacaag aaccttccca tccatcacat tccaggccca gagggtgtgc gtggtcgtaa      960
ctcagacaac acactgatca agagaagct cggttgggct ccaacaatga aattgaagga      1020
tgggctgaga attacatact tctggatcaa ggaacagatt gagaaagaga agttaaggg      1080 cattgatctg tctatttatg ggtcatccaa ggtggtgggt acccaagccc cggttcagct      1140
aggctcactt cgtgctgctg atggcaaaga gtgaagctgt tgaggccaac agctctggta      1200
gcttatgcca t                                                          1211

<210> SEQ ID NO 48
<211> LENGTH: 1880
<212> TYPE: DNA
<213> ORGANISM: Lycopersicon esculentum

<400> SEQUENCE: 48
ggtatttact ataattatct tcaaccaaga aaccccttca acttggaaat tattgagtag       60
ctctataaag atagagatct attaccaaaa aaaaacatca aaaaaataaa taaaaagcat      120
agcctcttgg cccttatcat tttttgagttt ctccatcttc gagacccttta aagttcaagt   180 ttttcaagaa tgggaacttc tgttgaaacc acttatggag aatacacata tgaaaaccett   240 gagagggagc cctactggcc ttcagagaag cttcgggtct ctattacagg tgctggtgga      300
tttattgcct cacacattgc gaggcgtctg aagactgagg ggcattacat tattgcttcc      360
gactggaaga agaatgagca catgtctgag gacatgtttt gtcatgagtt ccatcttgtt      420
gatctcaggg tgatggataa ctgtttgaaa gtcacaaaag gagttgatca tgtgttcaat      480
ctcgctgctg atatgggagg tatgggcttc attcagtcga accactcggt gatcatgtat      540
aacaacacta tgatcagctt taacatgatg gaggcttcaa gaataaatag tgttaagagg      600
ttcttttatg catccagtgc ttgcatctac cctgaattta gcaattgga aactaacgtg       660 agcttaaagg agtctgatgc ttggcctgca gagcctcaag atgcttatgg cttagaaaag      720
ctagcaacag aggagttgtg taagcactac aacaaggact ttggaattga atgtcgcatt      780
ggccgtttcc ataacattta tggcccattt ggaacatgga aaggcggacg tgagaaagca      840
ccagcagctt tttgtagaaa agccctcact tccactgaca aattcgagat gtggggagat      900
ggaaagcaaa ctcgatcttt caccttcatt gatgagtgtg ttgaaggtgt cctgaggtta      960
acaaaatccg acttcagaga gcctgtgaac atcggaagtg atgagatggt aagcatgaat     1020
gagatggcag agatagtcct cagctttgat ggcaagaacc ttccgatcca tcacattcca     1080
ggaccagagg gtgtgcgtgg tcgaaactct gacaacactc tcatcaagga aaagcttggc     1140
tgggctccta atatgaagtt gaaggatggg ttgaggatta cgtatttctg gataaaggaa     1200
caaattgaga aagagaaggt gaagggtgcc gatgtgtcca cttatggatc atccaaagtt     1260
gtgggaacac aagctccagt tgaattaggc tccctccgtg ctgccgatgg caaagagtga     1320
agtatagatg aagccaagtg attatcattc ggtatgcact atggccatct gttagttcca     1380
ccatgttttg ttcgcgtgga atgtttactt attattgata tatctatata ttacgcgcta     1440
aagcagtcct ttttccccca catcccctca ttgcacctac caaataatac tcaagagatg     1500
tggtagtcca gtaatgcttg catttttgtga tttcttttttg ctacctcaat gcatttgtgg    1560
tattctctga gttttgtatg agacaatagc catttgctat cgatctatca ttttcttgct     1620
```

```
cctcgactct gtaacattac actgtctttg ctgcaatacc agtgttcaat gttcaaatcg   1680
cgatgacaac aaaataacta cattggtaga gctacctaga tgttgtaata gtgggaggta   1740
gtagtaagta tctgatgaaa tagttgaggc gatctaaact cattcatctc tactcgtgta   1800
tgcttagaga tataccgttg atacattata tatacgtatc aatatattac atatacatat   1860
tgtccaaaaa aaaaaaaaaa                                                1880

<210> SEQ ID NO 49
<211> LENGTH: 351
<212> TYPE: PRT
<213> ORGANISM: Arabidopsis thaliana

<400> SEQUENCE: 49

Met Thr Ser Pro Ser His Ala Ser Asp Arg Gly Gly Asp Gly Asp
1               5                   10                  15

Ser Val Glu Asn Gln Ser Pro Glu Leu Arg Lys Asp Pro Val Thr Asn
            20                  25                  30

Arg Trp Val Ile Phe Ser Pro Ala Arg Ala Lys Arg Pro Thr Asp Phe
        35                  40                  45

Lys Ser Lys Ser Pro Gln Asn Pro Asn Pro Lys Pro Ser Ser Cys Pro
    50                  55                  60

Phe Cys Ile Gly Arg Glu Gln Glu Cys Ala Pro Glu Leu Phe Arg Val
65                  70                  75                  80

Pro Asp His Asp Pro Asn Trp Lys Leu Arg Val Ile Glu Asn Leu Tyr
                85                  90                  95

Pro Ala Leu Ser Arg Asn Leu Glu Thr Gln Ser Thr Gln Pro Glu Thr
            100                 105                 110

Gly Thr Ser Arg Thr Ile Val Gly Phe Gly Phe His Asp Val Val Ile
        115                 120                 125

Glu Ser Pro Val His Ser Ile Gln Leu Ser Asp Ile Asp Pro Val Gly
    130                 135                 140

Ile Gly Asp Ile Leu Ile Ala Tyr Lys Lys Arg Ile Asn Gln Ile Ala
145                 150                 155                 160

Gln His Asp Ser Ile Asn Tyr Ile Gln Val Phe Lys Asn Gln Gly Ala
                165                 170                 175

Ser Ala Gly Ala Ser Met Ser His Ser His Ser Gln Met Met Ala Leu
            180                 185                 190

Pro Val Val Pro Pro Thr Val Ser Ser Arg Leu Asp Gly Thr Lys Asp
        195                 200                 205

Tyr Phe Glu Glu Thr Gly Lys Cys Cys Leu Cys Glu Ala Lys Ser Lys
    210                 215                 220

His Phe Val Ile Asp Glu Ser Ser His Phe Val Ser Val Ala Pro Phe
225                 230                 235                 240

Ala Ala Thr Tyr Pro Phe Glu Ile Trp Ile Ile Pro Lys Asp His Ser
                245                 250                 255

Ser His Phe His His Leu Asp Asp Val Lys Ala Val Asp Leu Gly Gly
            260                 265                 270

Leu Leu Lys Leu Met Leu Gln Lys Ile Ala Lys Gln Leu Asn Asp Pro
        275                 280                 285

Pro Tyr Asn Tyr Met Ile His Thr Ser Pro Leu Lys Val Thr Glu Ser
    290                 295                 300

Gln Leu Pro Tyr Thr His Trp Phe Leu Gln Ile Val Pro Gln Leu Ser
305                 310                 315                 320
```

```
Gly Val Gly Gly Phe Glu Ile Gly Thr Gly Cys Tyr Ile Asn Pro Val
                325                 330                 335

Phe Pro Glu Asp Val Ala Lys Val Met Arg Glu Val Ser Leu Thr
            340                 345                 350

<210> SEQ ID NO 50
<211> LENGTH: 386
<212> TYPE: PRT
<213> ORGANISM: Mus musculus

<400> SEQUENCE: 50

Met Ala Val Pro His His Leu Gln Glu Thr Ser Tyr Leu Leu Pro Pro
1               5                   10                  15

Asp Pro Glu Asp Trp Glu Lys Gln Gly Ile Pro Asp Phe Val Tyr Gly
            20                  25                  30

Gln Glu Asp Leu Val Gly Lys Glu Val Gln Trp Ser Arg Asp Ser Pro
        35                  40                  45

Ser Ala Val Asp Thr Val Pro Leu Ser Arg Phe Asp Ser Ala Leu Arg
50                  55                  60

Ser Ala Trp Arg Gln Arg Leu Glu Leu Gly Leu Phe Arg Tyr Arg Leu
65                  70                  75                  80

Glu Asp Leu Gln Thr Gln Ile Leu Pro Gly Ser Val Gly Phe Val Ala
                85                  90                  95

Gln Leu Asn Ile Glu Arg Gly Ile Gln Arg Arg Pro Gln Asn Ile
            100                 105                 110

Arg Ser Val Arg Gln Glu Phe Asp Pro Glu Gln Phe Asn Phe Asn Lys
        115                 120                 125

Ile Arg Pro Gly Glu Val Leu Phe Arg Met Gln Arg Glu Pro Lys Gly
130                 135                 140

Pro Ala Thr Pro Lys Gln Glu Asp Val Leu Val Ile Asn Val
145                 150                 155                 160

Ser Pro Leu Glu Trp Gly His Val Leu Leu Val Pro Ala Pro Ala Gln
                165                 170                 175

Gly Leu Pro Gln Arg Leu Leu Pro Gly Val Leu Arg Val Gly Leu Glu
            180                 185                 190

Ala Val Leu Leu Ser Leu His Pro Gly Phe Arg Val Gly Phe Asn Ser
        195                 200                 205

Leu Gly Gly Leu Ala Ser Val Asn His Leu His Leu His Cys Tyr Tyr
210                 215                 220

Leu Ala His Pro Leu Pro Val Glu Gly Ala Pro Ser Thr Pro Leu Asp
225                 230                 235                 240

Pro Lys Gly Cys Ile His Leu Leu Gln Ala Leu Pro Ala Pro Gly Phe
                245                 250                 255

Leu Phe Tyr Thr Ser Gly Pro Gly Pro Asp Leu Glu Val Leu Ile Ser
            260                 265                 270

Arg Val Cys Arg Ala Thr Asp Tyr Leu Ser Asp Arg Glu Ile Ala His
        275                 280                 285

Asn Leu Phe Val Thr Arg Gly Ala Pro Pro Gly Pro Thr Ser Ser Thr
290                 295                 300

Ser Asp Leu Ser Gly Ile Arg Val Ile Leu Trp Ala Arg Lys Ser Ser
305                 310                 315                 320

Phe Gly Ile Lys Glu Ser Gly Ala Phe Asn Val Ala Leu Cys Glu Leu
                325                 330                 335

Ala Gly His Leu Pro Val Lys Thr Ser Gln Asp Phe Ser Ser Leu Thr
            340                 345                 350
```

```
Glu Ala Ala Ala Val Ala Leu Ile Gln Asp Cys Leu Leu Pro Glu Thr
            355                 360                 365
Gln Ala Gly Glu Val Arg Ala Ala Leu Val Ala Leu Met Ala Gln Glu
        370                 375                 380
Glu Leu
385

<210> SEQ ID NO 51
<211> LENGTH: 1337
<212> TYPE: DNA
<213> ORGANISM: Malus x domestica

<400> SEQUENCE: 51
ttgaggatca agagggttcc caccgtcgtt tcgaattacc agaaagatga ggcggaggaa      60
gttgctcgcc gcgtcggggg ctgtggccgc aactgcctta accaatgttg cattccaggt     120
gcaaaacttc cattgtatgc cttcaagaag ctgaacgtaa atgatggtga cacgggtttg     180
ctaggacgtg agaaaagaga gcctcccgtt gcatttcttg actcactgct tctcggggag     240
tgggaggatc gcatgcagag agggctattt cgctatgatg tcactgcttg tgaaaccaag     300
gtgatcccag ggcaatttgg tttcatagcc agctgaatg agggtcgcca tcttaagaag      360
cggccaacag agtttcgagt tgataaggtc ctccagccct tgatggcag caagtttaac      420 ttcactaaag ttggacaaga ggaggttctg ttccagtttg aagccagcaa agatggtgaa     480
gttcagtttt tccccagcgc acccattgat gttgaaagtt ctccgagcgt tgtggccatt     540
aatgtcagtc caattgaata tggccatgtg ctgttgattc ctcacattct tgagcgattg     600
cctcaaagga ttgaccggga aagcttcttg cttgcacttc acatggcggc tgaagcaggg     660
aatccttact ttcgattggg ttacaacagc ttgggtgcat ttgctaccat caatcaccttt    720 cacttccagg cttactacct ggccgtgacc tttcccattg agaaggctcc taccaaaaaa     780
atatccactt tgaatgccga ggtgaaggtc tctgagcttc tgaattatcc agtcagaggt     840
cttgtttttg agggtggaaa tactctgcaa gatttgtcaa acaccgtctc tgatgcctgc     900
atatgccttc aagagaacaa cataccttac aatgtcctta tctctgactc tggaaagcga     960
atctttctcg tgccacagtg ttatgctgag aaacaagctc ttggggaagt gagagcagag    1020
attctggata cacaggtgaa tccagctgtg tgggaaatta gtgggcatat ggtgctaaag    1080
aggaaaaagg actatgatga ggcgtcggat gaaaatgctt ggaagctcct ggcagaggtc    1140
tccctttctg aagaaaggtt cctagaagtg aatgctctta ttttcgaagg tattgcttcg    1200
ggtgataacg ggaatgaaaa cttgctcaag gatccagaag ttaagcctcg ttctcatgaa    1260
gaagtcaaca ccatcaacaa aagagtgcat tgttctgcag taaatgagca gatttgtcgg    1320
gtgtttacaa tgtgaat                                                   1337
```

TRANSFERASES, EPIMERASES, POLYNUCLEOTIDES ENCODING THESE AND USES THEREOF

CROSS-REFERENCE TO RELATED APPLICATIONS

This is application is a National Stage Application filed under 35 U.S.C. §371 of PCT Application No. PCT/NZ2008/000042, filed on Mar. 7, 2008 and published in English on Sep. 12, 2008 as WO 2008/108668, which claims priority to New Zealand patent application 553705, filed on Mar. 8, 2007 and to New Zealand patent application 556389, filed on Jul. 6, 2007, all of which are incorporated by reference in their entireties to the extent there is no inconsistency with the present disclosure.

TECHNICAL FIELD

The present invention relates to compositions and methods for producing plants with altered GDP-L-Galactose Guanyltransferase activity; and/or altered GDP-D-Mannose epimerase activity; and/or altered ascorbic acid content.

BACKGROUND ART

Ascorbate is the most abundant soluble antioxidant in plants and is also an essential nutrient for humans and a few other animals. Ascorbate contributes significantly to the overall intake of "free radical scavengers" or "anti-oxidative metabolites" in the human diet. Convincing evidence now shows that such metabolites either singly or in combination, benefit health and well-being, acting as anti-cancer forming agents and protecting against coronary heart disease.

Almost all of the dietary ascorbate intake in humans is derived from plant products. The ascorbate content of plant tissues however, is remarkably variable. Whilst leaf ascorbate content is generally high and relatively uniform in herbaceous and woody plants, a huge and unexplained variability in ascorbate content found is in non-green edible plant tissues. For example, in fruits, the levels vary from up to 30 mg gFW-1 AsA in the camu camu of *Mirciaria dubia*, to less than 3 μg gFW-1 AsA in the medlar of *Mespilus germanica* (Rodriguez et al. 1992, J Chromatogr Sci, 30:433-437). A range of values for ascorbate have been reported in kiwifruit (Ferguson, A. R., Botanical nomenclature: *Actinidia chinensis, Actinidia deliciosa*, and *Actinidia setosa*. Kiwifruit: science and management, ed. I. J. Warrington and G. C. Weston. 1990, Palmerston North; New Zealand: New Zealand Society for Horticultural Science. 576. Beever, D. J. and G. Hopkirk, Fruit development and fruit physiology. Kiwifruit: science and management, ed. I. J. Warrington and G. C. Weston. 1990, Palmerston North; New Zealand: New Zealand Society for Horticultural Science. 576.) Ascorbate content of fruits from different vines range for *A. deliciosa*, 30-400 mg/100 g (Ferguson, A. R., 1991 Acta Hort. 290: p. 603-656, Spano, D., et al., 1997 Acta Hort., 444: p. 501-506.) while for the cultivar 'Hayward' the reported range is 80-120 mg/100 g (Beever, D. J. and G. Hopkirk, Fruit development and fruit physiology. Kiwifruit: science and management, ed. I. J. Warrington and G. C. Weston. 1990, Palmerston North; New Zealand: New Zealand Society for Horticultural Science. 576). Higher concentrations of ascorbate are reported in fruit of, *A. arguta, A. chinensis* (Muggleston, S., et al., Orchardist, 1998. 71(8): p. 38-40, Chen, Q. and Q. Chen, Crop Genetic Resources, 1998 (2): p. 3, Coggiatti, S., 1971 Ital Agr, October, 108(10): p. 935-941) *A. chrysantha* and *A. polygama* with very high levels in *A. eriantha*, and *A. latifolia* (>1% fresh weight) (Ferguson 1991 Acta Hort. 290: p. 603-656. and *A. kolomikta* (Kola, J. and J. Pavelka, 1988 Nahrung, 32(5): p. 513-515).

Three pathways of biosynthesis of ascorbic acid have been proposed in plants, one through L-Gal (Wheeler et al., 1998, Nature 393, 365-369), another from myoinositol (Loewus & Kelly, 1961, Arch. Biochem. Biophys. 95, 483-493; Lorence et al., (2004) Plant Physiol. 134, 1200-1205) and a third through Galacturonic acid (Agius et al., 2003, Nat Biotechnol 21, 177-81). The L-Gal pathway proceeds through L-Gal to galactono-1,4-lactone and thence to ascorbate (Wheeler et aL, 1998, Nature 393, 365-369).

To date, all the genes encoding enzymes, and their associated enzymatic activities, for the L-Galactose pathway have been identified and at least partially characterised, except for one, a postulated enzyme to convert GDP-L-Galactose to L-Galactose-1-Phosphate.

The characterised genes and enzyme activities include the GDP-D-Mannose Pyrophosphorylase (Conklin, 1998; Conklin et al., 1999; Keller et al., 1999), the GDP-D-Mannose 3',5'-Epimerase (Wolucka et al., 2001; Wolucka and Van Montagu, 2003; Watanabe et al., 2006), the L-Galactose-1-P Phosphatase (Laing et al., 2004; Conklin et al., 2006), L-Galactose Dehydrogenase (Wheeler et al., 1998; Gatzek et al., 2002; Laing et al., 2004), and L-Galactono-1,4-lactone Dehydrogenase (Imai et al., 1998; Bartoli et al., 2005).

The missing enzyme, which (to the best of the applicant's knowledge) has not been reported as being assayed either as an extracted or purified enzyme activity or as an expressed gene, catalyses the second committed step to ascorbic acid biosynthesis.

The VTC2 mutant of *Arabidopsis thaliana* was identified in a screen for resistance to ozone, and is also characterised as showing especially low ascorbic acid levels (Conklin et al., 2000). The mutated gene was cloned using a map based approach (Jander et al., 2002) and identified as a gene (At4g26850) encoding a novel protein. However this gene was reported to show no homology to other genes in *Arabidopsis* except for the similarly uncharacterised At5g55120 and other uncharacterised genes from other species. The encoded protein was reported to be most similar to *Arabidopsis* protein MC015.7, *Caenorhabitis elegans* protein C10F3.4, and fruitfly (*Drosophila melanogaster*) protein CG3552, none of which had a demonstrated function.

Although the *Arabidopsis* gene (At Ag26850) was reported to complement four alleles of the VTC2 mutant, no details were provided (Jander et al., 2002). In addition the authors commented that "although we have a phenotype associated with mutations in VTC2, the regulatory or biosynthetic pathways leading to the reduced vitamin C levels in these mutants remain to be discovered."

Identification of genes encoding enzymes in the biosynthetic pathway for ascorbate production provides the opportunity for gene-based approaches to manipulation of ascorbate content in plants.

However, although transgenic plants, or mutants, with changed expression of different genes in the L-Galactose pathway have been generated for many of the steps of the L-galactose pathway of ascorbate biosynthesis, and decreased gene expression (and enzyme levels) can result in reduced ascorbate, over expression has not resulted in increased ascorbate in leaves (Ishikawa et al., 2006 and Conklin et al., 2006).

It is an object of the invention to provide improved compositions and methods for modulating GDP-L-Galactose Guanyltransferase (also known as GDP-L-Galactose phosphorylase) activity; and/or GDP-D-Mannose epimerase

SUMMARY OF THE INVENTION

In a first aspect the invention provides a method for producing a plant cell or plant with increased GDP-L-Galactose Guanyltransferase activity (also known as GDP-L-Galactose phosphorylase), the method comprising transformation of a plant cell or plant with a polynucleotide encoding a polypeptide with the amino acid sequence of any one of SEQ ID NO:1 to 11, or a variant of the polypeptide, wherein the variant has the activity of an GDP-L-Galactose Guanyltransferase.

In one embodiment the variant comprises the amino acid sequence:

```
AINVSPIEYGHVLLIP.          (SEQ ID NO: 12)
```

In a further embodiment the variant comprises the amino acid sequence:

```
GYNSLGAFATINHLHFQAY.       (SEQ ID NO: 13)
```

In a further embodiment the variant comprises the sequences of both SEQ ID NO:12 and SEQ ID NO:13.

In a further embodiment the variant has at least 60% sequence identity to a polypeptide with the amino acid sequence of any one of SEQ ID NO:1 to 11.

In a further embodiment the polynucleotide encodes a polypeptide with the amino acid sequence of any one of SEQ ID NO:1 to 11.

In a further embodiment the variant has at least 60% sequence identity to a polypeptide with the amino acid sequence of SEQ ID NO:1.

In a further embodiment the polynucleotide of a) encodes a polypeptide with the amino acid sequence of SEQ ID NO:1.

In a further embodiment the variant has at least 60% sequence identity to a polypeptide with the amino acid sequence of SEQ ID NO:6.

In a further embodiment the polynucleotide of a) encodes a polypeptide with the amino acid sequence of SEQ ID NO:6.

In a further embodiment the variant has at least 60% sequence identity to a polypeptide with the amino acid sequence of SEQ ID NO:7.

In a further embodiment the polynucleotide of a) encodes a polypeptide with the amino acid sequence of SEQ ID NO:7.

In a further embodiment the variant has at least 60% sequence identity to a polypeptide with the amino acid sequence of SEQ ID NO:8.

In a further embodiment the polynucleotide of a) encodes a polypeptide with the amino acid sequence of SEQ ID NO:8.

In a further embodiment the variant has at least 60% sequence identity to a polypeptide with the amino acid sequence of SEQ ID NO:9.

In a further embodiment the polynucleotide of a) encodes a polypeptide with the amino acid sequence of SEQ ID NO:9.

In a further embodiment the variant has at least 60% sequence identity to a polypeptide with the amino acid sequence of SEQ ID NO:10.

In a further embodiment the polynucleotide of a) encodes a polypeptide with the amino acid sequence of SEQ ID NO:10.

In a further aspect the invention provides a method of producing a plant cell or plant with increased GDP-L-Galactose Guanyltransferase activity, the method comprising transformation of a plant cell or plant with a polynucleotide comprising a nucleotide sequence selected from any one the sequences of SEQ ID NO: 14 to 24, or a variant thereof, wherein the variant encodes a polypeptide which has the activity of an GDP-L-Galactose Guanyltransferase.

In one embodiment the variant comprises a sequence with at least 60% sequence identity to any one of the sequences of SEQ ID NO: 14 to 24.

In a further embodiment the polynucleotide of a) comprises any one the sequences of SEQ ID NO:14 to 24.

In a further embodiment the polynucleotide of a) comprises the full-length coding sequence of any one of SEQ ID NO:14 to 24.

In one further embodiment the variant comprises a sequence with at least 60% sequence identity to the sequence of SEQ ID NO: 14.

In a further embodiment the polynucleotide of a) comprises the sequence of SEQ ID NO: 14.

In one further embodiment the variant comprises a sequence with at least 60% sequence identity to the full-length coding sequence of SEQ ID NO: 14.

In a further embodiment the polynucleotide of a) comprises the full-length coding sequence of SEQ ID NO: 14.

In one further embodiment the variant comprises a sequence with at least 60% sequence identity to the sequence of SEQ ID NO: 19.

In a further embodiment the polynucleotide of a) comprises the sequence of SEQ ID NO: 19.

In one further embodiment the variant comprises a sequence with at least 60% sequence identity to the full-length coding sequence of SEQ ID NO: 19.

In a further embodiment the polynucleotide of a) comprises the full-length coding sequence of SEQ ID NO: 19.

In one further embodiment the variant comprises a sequence with at least 60% sequence identity to the sequence of SEQ ID NO: 20.

In a further embodiment the polynucleotide of a) comprises the sequence of SEQ ID NO: 20.

In one further embodiment the variant comprises a sequence with at least 60% sequence identity to the full-length coding sequence of SEQ ID NO: 20.

In a further embodiment the polynucleotide of a) comprises the full-length coding sequence of SEQ ID NO: 20.

In one further embodiment the variant comprises a sequence with at least 60% sequence identity to the sequence of SEQ ID NO: 21.

In a further embodiment the polynucleotide of a) comprises the sequence of SEQ ID NO:21.

In one further embodiment the variant comprises a sequence with at least 60% sequence identity to the full-length coding sequence of SEQ ID NO: 21.

In a further embodiment the polynucleotide of a) comprises the full-length coding sequence of SEQ ID NO:21.

In one further embodiment the variant comprises a sequence with at least 60% sequence identity to the sequence of SEQ ID NO: 22.

In a further embodiment the polynucleotide of a) comprises the sequence of SEQ ID NO:22.

In one further embodiment the variant comprises a sequence with at least 60% sequence identity to the full-length coding sequence of SEQ ID NO: 22.

In a further embodiment the polynucleotide of a) comprises the full-length coding sequence of SEQ ID NO:22.

In one further embodiment the variant comprises a sequence with at least 60% sequence identity to the sequence of SEQ ID NO: 23.

In a further embodiment the polynucleotide of a) comprises the sequence of SEQ ID NO:23.

In one further embodiment the variant comprises a sequence with at least 60% sequence identity to the full-length coding sequence of SEQ ID NO: 23.

In a further embodiment the polynucleotide of a) comprises the full-length coding sequence of SEQ ID NO:23.

Preferably the plant or plant cell with increased GDP-L-Galactose Guanyltransferase activity produced by the methods of the invention also have increased ascorbate content.

In a further aspect the invention provides a method for producing a plant cell or plant with increased ascorbate, the method comprising transformation of a plant cell or plant with a polynucleotide encoding a polypeptide with the amino acid sequence of any one of SEQ ID NO:1 to 11, or a variant of the polypeptide, wherein the variant has the activity of an GDP-L-Galactose Guanyltransferase.

In one embodiment the variant comprises the amino acid sequence:

AINVSPIEYGHVLLIP.        (SEQ ID NO: 12)

In a further embodiment the variant comprises the amino acid sequence:

GYNSLGAFATINHLHFQAY.     (SEQ ID NO: 13)

In a further embodiment the variant comprises the sequences of both SEQ ID NO:12 and SEQ ID NO:13.

In a further embodiment the variant has at least 60% sequence identity to a polypeptide with the amino acid sequence of any one of SEQ ID NO:1 to 11.

In a further embodiment the polynucleotide encodes a polypeptide with the amino acid sequence of any one of SEQ ID NO:1 to 11.

In a further embodiment the variant has at least 60% sequence identity to a polypeptide with the amino acid sequence of SEQ ID NO:1.

In a further embodiment the polynucleotide of a) encodes a polypeptide with the amino acid sequence of SEQ ID NO:1.

In a further embodiment the variant has at least 60% sequence identity to a polypeptide with the amino acid sequence of SEQ ID NO:6.

In a further embodiment the polynucleotide of a) encodes a polypeptide with the amino acid sequence of SEQ ID NO:6.

In a further embodiment the variant has at least 60% sequence identity to a polypeptide with the amino acid sequence of SEQ ID NO:7.

In a further embodiment the polynucleotide of a) encodes a polypeptide with the amino acid sequence of SEQ ID NO:7.

In a further embodiment the variant has at least 60% sequence identity to a polypeptide with the amino acid sequence of SEQ ID NO:8.

In a further embodiment the polynucleotide of a) encodes a polypeptide with the amino acid sequence of SEQ ID NO:8.

In a further embodiment the variant has at least 60% sequence identity to a polypeptide with the amino acid sequence of SEQ ID NO:9.

In a further embodiment the polynucleotide of a) encodes a polypeptide with the amino acid sequence of SEQ ID NO:9.

In a further embodiment the variant has at least 60% sequence identity to a polypeptide with the amino acid sequence of SEQ ID NO:10.

In a further embodiment the polynucleotide of a) encodes a polypeptide with the amino acid sequence of SEQ ID NO:10.

In a preferred embodiment the method further comprises transformation of the plant cell or plant with a polynucleotide encoding a polypeptide with the amino acid sequence of any one of SEQ ID NO: 25 to 35, or a variant of the polypeptide, wherein the variant has the activity of GDP-D-Mannose epimerase.

In one embodiment the variant comprises the amino acid sequence:

AADMGGMGFIQSNHSVI.       (SEQ ID NO: 36)

In a further embodiment the variant comprises the amino acid sequence:

GTWKGGREKAPAAFCRK.       (SEQ ID NO: 37)

In a further embodiment the variant comprises the sequences of both SEQ ID NO: 36 and SEQ ID NO: 37.

In a further embodiment the variant has at least 70% sequence identity to a polypeptide with the amino acid sequence of any one of SEQ ID NO: 25 to 35.

In a further embodiment the polynucleotide encodes a polypeptide with the amino acid sequence of any one of SEQ ID NO: 25 to 35.

In a further embodiment the variant has at least 70% sequence identity to a polypeptide with the amino acid sequence of SEQ ID NO: 25.

In a further embodiment the polynucleotide of a) encodes a polypeptide with the amino acid sequence of SEQ ID NO: 25.

In a further embodiment the variant has at least 70% sequence identity to a polypeptide with the amino acid sequence of SEQ ID NO: 26.

In a further embodiment the polynucleotide of a) encodes a polypeptide with the amino acid sequence of SEQ ID NO: 26.

In a further embodiment the variant has at least 70% sequence identity to a polypeptide with the amino acid sequence of SEQ ID NO: 27.

In a further embodiment the polynucleotide of a) encodes a polypeptide with the amino acid sequence of SEQ ID NO: 27.

Transformation with the transferase and epimerase may be sequential, in either order. Alternatively transformation with the epimerase and transferase may be simultaneous. When simultaneous, sequences encoding the epimerase and transferase may be on the same or separate constructs or vectors.

In a further aspect the invention provides a method of producing a plant cell or plant with increased ascorbate, the method comprising transformation of a plant cell or plant with a polynucleotide comprising a nucleotide sequence selected from any one the sequences of SEQ ID NO: 14 to 24, or a variant thereof, wherein the variant encodes a polypeptide which has the activity of an GDP-L-Galactose Guanyltransferase.

In one embodiment the variant comprises a sequence with at least 60% sequence identity to any one of the sequences of SEQ ID NO: 14 to 24.

In a further embodiment the polynucleotide of a) comprises any one the sequences of SEQ ID NO:14 to 24.

In a further embodiment the polynucleotide of a) comprises the full-length coding sequence of any one of SEQ ID NO:14 to 24.

In one further embodiment the variant comprises a sequence with at least 60% sequence identity to the sequence of SEQ ID NO: 14.

In a further embodiment the polynucleotide of a) comprises the sequence of SEQ ID NO: 14.

In one further embodiment the variant comprises a sequence with at least 60% sequence identity to the full-length coding sequence of SEQ ID NO: 14.

In a further embodiment the polynucleotide of a) comprises the full-length coding sequence of SEQ ID NO: 14.

In one further embodiment the variant comprises a sequence with at least 60% sequence identity to the sequence of SEQ ID NO: 19.

In a further embodiment the polynucleotide of a) comprises the sequence of SEQ ID NO: 19.

In one further embodiment the variant comprises a sequence with at least 60% sequence identity to the full-length coding sequence of SEQ ID NO: 19.

In a further embodiment the polynucleotide of a) comprises the full-length coding sequence of SEQ ID NO: 19.

In one further embodiment the variant comprises a sequence with at least 60% sequence identity to the sequence of SEQ ID NO: 20.

In a further embodiment the polynucleotide of a) comprises the sequence of SEQ ID NO: 20.

In one further embodiment the variant comprises a sequence with at least 60% sequence identity to the full-length coding sequence of SEQ ID NO: 20.

In a further embodiment the polynucleotide of a) comprises the full-length coding sequence of SEQ ID NO: 20.

In one further embodiment the variant comprises a sequence with at least 60% sequence identity to the sequence of SEQ ID NO: 21.

In a further embodiment the polynucleotide of a) comprises the sequence of SEQ ID NO:21.

In one further embodiment the variant comprises a sequence with at least 60% sequence identity to the full-length coding sequence of SEQ ID NO: 21.

In a further embodiment the polynucleotide of a) comprises the full-length coding sequence of SEQ ID NO:21.

In one further embodiment the variant comprises a sequence with at least 60% sequence identity to the sequence of SEQ ID NO: 22.

In a further embodiment the polynucleotide of a) comprises the sequence of SEQ ID NO:22.

In one further embodiment the variant comprises a sequence with at least 60% sequence identity to the full-length coding sequence of SEQ ID NO: 22.

In a further embodiment the polynucleotide of a) comprises the full-length coding sequence of SEQ ID NO:22.

In one further embodiment the variant comprises a sequence with at least 60% sequence identity to the sequence of SEQ ID NO: 23.

In a further embodiment the polynucleotide of a) comprises the sequence of SEQ ID NO:23.

In one further embodiment the variant comprises a sequence with at least 60% sequence identity to the full-length coding sequence of SEQ ID NO: 23.

In a further embodiment the polynucleotide of a) comprises the full-length coding sequence of SEQ ID NO:23.

In a preferred embodiment the method further comprises transformation of the plant cell or plant with a polynucleotide comprising a nucleotide sequence selected from any one the sequences of SEQ ID NO: 38 to 48, or a variant thereof, wherein the variant encodes a polypeptide which has the activity of a GDP-D-Mannose epimerase.

In one embodiment the variant comprises a sequence with at least 70% sequence identity to any one of the sequences of SEQ ID NO: 38 to 48.

In a further embodiment the polynucleotide of a) comprises any one the sequences of SEQ ID NO: 38 to 48.

In a further embodiment the polynucleotide of a) comprises the full-length coding sequence of any one of SEQ ID NO: 38 to 48.

In one further embodiment the variant comprises a sequence with at least 70% sequence identity to the sequence of SEQ ID NO: 38.

In a further embodiment the polynucleotide of a) comprises the sequence of SEQ ID NO: 38.

In one further embodiment the variant comprises a sequence with at least 70% sequence identity to the full-length coding sequence of SEQ ID NO: 38.

In a further embodiment the polynucleotide of a) comprises the full-length coding sequence of SEQ ID NO: 38.

In one further embodiment the variant comprises a sequence with at least 70% sequence identity to the sequence of SEQ ID NO: 39.

In a further embodiment the polynucleotide of a) comprises the sequence of SEQ ID NO: 39.

In one further embodiment the variant comprises a sequence with at least 70% sequence identity to the full-length coding sequence of SEQ ID NO: 39.

In a further embodiment the polynucleotide of a) comprises the full-length coding sequence of SEQ ID NO: 39.

In one further embodiment the variant comprises a sequence with at least 70% sequence identity to the sequence of SEQ ID NO: 40.

In a further embodiment the polynucleotide of a) comprises the sequence of SEQ ID NO: 40.

In one further embodiment the variant comprises a sequence with at least 70% sequence identity to the full-length coding sequence of SEQ ID NO: 40.

In a further embodiment the polynucleotide of a) comprises the full-length coding sequence of SEQ ID NO: 40.

Transformation with the transferase and epimerase may be sequential, in either order. Alternatively transformation with the epimerase and transferase may be simultaneous. When simultaneous, sequences encoding the epimerase and transferase may be on the same or separate constructs or vectors.

In a further aspect the invention provides a method for producing a plant cell or plant with increased GDP-D-Mannose epimerase activity, the method comprising transformation of a plant cell or plant with a polynucleotide encoding a polypeptide with the amino acid sequence of any one of SEQ ID NO: 25 to 35, or a variant of the polypeptide, wherein the variant has the activity of GDP-D-Mannose epimerase.

In one embodiment the variant comprises the amino acid sequence:

```
AADMGGMGFIQSNHSVI.        (SEQ ID NO: 36)
```

In a further embodiment the variant comprises the amino acid sequence:

```
GTWKGGREKAPAAFCRK.        (SEQ ID NO: 37)
```

In a further embodiment the variant comprises the sequences of both SEQ ID NO: 36 and SEQ ID NO: 37.

In a further embodiment the variant has at least 70% sequence identity to a polypeptide with the amino acid sequence of any one of SEQ ID NO: 25 to 35.

In a further embodiment the polynucleotide encodes a polypeptide with the amino acid sequence of any one of SEQ ID NO: 25 to 35.

In a further embodiment the variant has at least 70% sequence identity to a polypeptide with the amino acid sequence of SEQ ID NO: 25.

In a further embodiment the polynucleotide of a) encodes a polypeptide with the amino acid sequence of SEQ ID NO: 25.

In a further embodiment the variant has at least 70% sequence identity to a polypeptide with the amino acid sequence of SEQ ID NO: 26.

In a further embodiment the polynucleotide of a) encodes a polypeptide with the amino acid sequence of SEQ ID NO: 26.

In a further embodiment the variant has at least 70% sequence identity to a polypeptide with the amino acid sequence of SEQ ID NO: 27.

In a further embodiment the polynucleotide of a) encodes a polypeptide with the amino acid sequence of SEQ ID NO: 27.

In a further aspect the invention provides a method of producing a plant cell or plant with increased GDP-D-Mannose epimerase activity, the method comprising transformation of a plant cell or plant with a polynucleotide comprising a nucleotide sequence selected from any one the sequences of SEQ ID NO: 38 to 48, or a variant thereof, wherein the variant encodes a polypeptide which has the activity of a GDP-D-Mannose epimerase.

In one embodiment the variant comprises a sequence with at least 70% sequence identity to any one of the sequences of SEQ ID NO: 38 to 48.

In a further embodiment the polynucleotide of a) comprises any one the sequences of SEQ ID NO: 38 to 48.

In a further embodiment the polynucleotide of a) comprises the full-length coding sequence of any one of SEQ ID NO: 38 to 48.

In one further embodiment the variant comprises a sequence with at least 70% sequence identity to the sequence of SEQ ID NO: 38.

In a further embodiment the polynucleotide of a) comprises the sequence of SEQ ID NO: 38.

In one further embodiment the variant comprises a sequence with at least 70% sequence identity to the full-length coding sequence of SEQ ID NO: 38.

In a further embodiment the polynucleotide of a) comprises the full-length coding sequence of SEQ ID NO: 38.

In one further embodiment the variant comprises a sequence with at least 70% sequence identity to the sequence of SEQ ID NO: 39.

In a further embodiment the polynucleotide of a) comprises the sequence of SEQ ID NO: 39.

In one further embodiment the variant comprises a sequence with at least 70% sequence identity to the full-length coding sequence of SEQ ID NO: 39.

In a further embodiment the polynucleotide of a) comprises the full-length coding sequence of SEQ ID NO: 39.

In one further embodiment the variant comprises a sequence with at least 70% sequence identity to the sequence of SEQ ID NO: 40.

In a further embodiment the polynucleotide of a) comprises the sequence of SEQ ID NO: 40.

In one further embodiment the variant comprises a sequence with at least 70% sequence identity to the full-length coding sequence of SEQ ID NO: 40.

In a further embodiment the polynucleotide of a) comprises the full-length coding sequence of SEQ ID NO: 40.

In a first aspect the invention provides a method for producing a plant cell or plant with increased ascorbate content, the method comprising transformation of a plant cell or plant with a polynucleotide encoding a polypeptide with the amino acid sequence of any one of SEQ ID NO: 25 to 35 or a variant of the polypeptide, wherein the variant has the activity of GDP-D-Mannose epimerase.

In one embodiment the variant comprises the amino acid sequence:

```
AADMGGMGFIQSNHSVI.    (SEQ ID NO: 36)
```

In a further embodiment the variant comprises the amino acid sequence:

```
GTWKGGREKAPAAFCRK.    (SEQ ID NO: 37)
```

In a further embodiment the variant comprises the sequences of both SEQ ID NO: 36 and SEQ ID NO: 37.

In a further embodiment the variant has at least 70% sequence identity to a polypeptide with the amino acid sequence of any one of SEQ ID NO: 25 to 35.

In a further embodiment the polynucleotide encodes a polypeptide with the amino acid sequence of any one of SEQ ID NO: 25 to 35.

In a further embodiment the variant has at least 70% sequence identity to a polypeptide with the amino acid sequence of SEQ ID NO: 25.

In a further embodiment the polynucleotide of a) encodes a polypeptide with the amino acid sequence of SEQ ID NO: 25.

In a further embodiment the variant has at least 70% sequence identity to a polypeptide with the amino acid sequence of SEQ ID NO: 26.

In a further embodiment the polynucleotide of a) encodes a polypeptide with the amino acid sequence of SEQ ID NO: 26.

In a further embodiment the variant has at least 70% sequence identity to a polypeptide with the amino acid sequence of SEQ ID NO: 27.

In a further embodiment the polynucleotide of a) encodes a polypeptide with the amino acid sequence of SEQ ID NO: 27.

In a preferred embodiment of the method for producing a plant cell or plant with increased ascorbate content, the plant cell or plant is also transformed with a polynucleotide encoding a GDP-L-Galactose-Guanyltransferase.

Transformation with the epimerase and transferase may be sequential, in either order. Alternatively transformation with the epimerase and transferase may be simultaneous. When simultaneous, sequences encoding the epimerase and transferase may be on the same or separate constructs or vectors.

Preferably the GDP-L-Galactose Guanyltransferase has the amino acid sequence of any one of SEQ ID NO: 1 to 11, or a variant of the polypeptide, wherein the variant has the activity of an GDP-L-Galactose Guanyltransferase.

In one embodiment the variant comprises the amino acid sequence:

```
AINVSPIEYGHVLLIP.    (SEQ ID NO: 12)
```

In a further embodiment the variant comprises the amino acid sequence:

```
GYNSLGAFATINHLHFQAY.    (SEQ ID NO: 13)
```

In a further embodiment the variant comprises the sequences of both SEQ ID NO: 12 and SEQ ID NO: 13.

In a further embodiment the variant has at least 60% sequence identity to a polypeptide with the amino acid sequence of any one of SEQ ID NO: 1 to 11.

In a further embodiment the polynucleotide encodes a polypeptide with the amino acid sequence of any one of SEQ ID NO: 1 to 11.

In a further embodiment the variant has at least 60% sequence identity to a polypeptide with the amino acid sequence of SEQ ID NO: 1.

In a further embodiment the polynucleotide of a) encodes a polypeptide with the amino acid sequence of SEQ ID NO: 1.

In a further embodiment the variant has at least 60% sequence identity to a polypeptide with the amino acid sequence of SEQ ID NO: 6.

In a further embodiment the polynucleotide of a) encodes a polypeptide with the amino acid sequence of SEQ ID NO: 6.

In a further embodiment the variant has at least 60% sequence identity to a polypeptide with the amino acid sequence of SEQ ID NO: 7.

In a further embodiment the polynucleotide of a) encodes a polypeptide with the amino acid sequence of SEQ ID NO: 7.

In a further embodiment the variant has at least 60% sequence identity to a polypeptide with the amino acid sequence of SEQ ID NO: 8.

In a further embodiment the polynucleotide of a) encodes a polypeptide with the amino acid sequence of SEQ ID NO: 8.

In a further embodiment the variant has at least 60% sequence identity to a polypeptide with the amino acid sequence of SEQ ID NO: 9.

In a further embodiment the polynucleotide of a) encodes a polypeptide with the amino acid sequence of SEQ ID NO: 9.

In a further embodiment the variant has at least 60% sequence identity to a polypeptide with the amino acid sequence of SEQ ID NO: 10.

In a further embodiment the polynucleotide of a) encodes a polypeptide with the amino acid sequence of SEQ ID NO: 10.

In a further aspect the invention provides a method of producing a plant cell or plant with increased ascorbate content, the method comprising transformation of a plant cell or plant with a polynucleotide comprising a nucleotide sequence selected from any one the sequences of SEQ ID NO: 38 to 48, or a variant thereof, wherein the variant encodes a polypeptide which has the activity of a GDP-D-Mannose epimerase.

In one embodiment the variant comprises a sequence with at least 70% sequence identity to any one of the sequences of SEQ ID NO: 38 to 48.

In a further embodiment the polynucleotide of a) comprises any one the sequences of SEQ ID NO: 38 to 48.

In a further embodiment the polynucleotide of a) comprises the full-length coding sequence of any one of SEQ ID NO: 38 to 48.

In one further embodiment the variant comprises a sequence with at least 70% sequence identity to the sequence of SEQ ID NO: 38.

In a further embodiment the polynucleotide of a) comprises the sequence of SEQ ID NO: 38.

In one further embodiment the variant comprises a sequence with at least 70% sequence identity to the full-length coding sequence of SEQ ID NO: 38.

In a further embodiment the polynucleotide of a) comprises the full-length coding sequence of SEQ ID NO: 38.

In one further embodiment the variant comprises a sequence with at least 70% sequence identity to the sequence of SEQ ID NO: 39.

In a further embodiment the polynucleotide of a) comprises the sequence of SEQ ID NO: 39.

In one further embodiment the variant comprises a sequence with at least 70% sequence identity to the full-length coding sequence of SEQ ID NO: 39.

In a further embodiment the polynucleotide of a) comprises the full-length coding sequence of SEQ ID NO: 39.

In one further embodiment the variant comprises a sequence with at least 70% sequence identity to the sequence of SEQ ID NO: 40.

In a further embodiment the polynucleotide of a) comprises the sequence of SEQ ID NO: 40.

In one further embodiment the variant comprises a sequence with at least 70% sequence identity to the full-length coding sequence of SEQ ID NO: 40.

In a further embodiment the polynucleotide of a) comprises the full-length coding sequence of SEQ ID NO: 40.

In a preferred embodiment of the method of producing a plant cell or plant with increased ascorbate content, the plant cell or plant is also transformed with a polynucleotide encoding a GDP-L-Galactose Guanyltransferase.

Transformation with the epimerase and transferase may be sequential, in either order. Alternatively transformation with the epimerase and transferase may be simultaneous. When simultaneous, sequences encoding the epimerase and transferase may be on the same or separate constructs or vectors.

Preferably the polynucleotide encoding the GDP-L-Galactose Guanyltransferase has a nucleotide sequence selected from any one the sequences of SEQ ID NO: 14 to 24, or a variant thereof, wherein the variant encodes a polypeptide which has the activity of an GDP-L-Galactose Guanyltransferase.

In one embodiment the variant comprises a sequence with at least 60% sequence identity to any one of the sequences of SEQ ID NO: 14 to 24.

In a further embodiment the polynucleotide of a) comprises any one the sequences of SEQ ID NO: 14 to 24.

In a further embodiment the polynucleotide of a) comprises the full-length coding sequence of any one of SEQ ID NO: 14 to 24.

In one further embodiment the variant comprises a sequence with at least 60% sequence identity to the sequence of SEQ ID NO: 14.

In a further embodiment the polynucleotide of a) comprises the sequence of SEQ ID NO: 14.

In one further embodiment the variant comprises a sequence with at least 60% sequence identity to the full-length coding sequence of SEQ ID NO: 14.

In a further embodiment the polynucleotide of a) comprises the full-length coding sequence of SEQ ID NO: 14.

In one further embodiment the variant comprises a sequence with at least 60% sequence identity to the sequence of SEQ ID NO: 19.

In a further embodiment the polynucleotide of a) comprises the sequence of SEQ ID NO: 19.

In one further embodiment the variant comprises a sequence with at least 60% sequence identity to the full-length coding sequence of SEQ ID NO: 19.

In a further embodiment the polynucleotide of a) comprises the full-length coding sequence of SEQ ID NO: 19.

In one further embodiment the variant comprises a sequence with at least 60% sequence identity to the sequence of SEQ ID NO: 20.

In a further embodiment the polynucleotide of a) comprises the sequence of SEQ ID NO: 20.

In one further embodiment the variant comprises a sequence with at least 60% sequence identity to the full-length coding sequence of SEQ ID NO: 20.

In a further embodiment the polynucleotide of a) comprises the full-length coding sequence of SEQ ID NO: 20.

In one further embodiment the variant comprises a sequence with at least 60% sequence identity to the sequence of SEQ ID NO: 21.

In a further embodiment the polynucleotide of a) comprises the sequence of SEQ ID NO: 21.

In one further embodiment the variant comprises a sequence with at least 60% sequence identity to the full-length coding sequence of SEQ ID NO: 21.

In a further embodiment the polynucleotide of a) comprises the full-length coding sequence of SEQ ID NO: 21.

In one further embodiment the variant comprises a sequence with at least 60% sequence identity to the sequence of SEQ ID NO: 22.

In a further embodiment the polynucleotide of a) comprises the sequence of SEQ ID NO: 22.

In one further embodiment the variant comprises a sequence with at least 60% sequence identity to the full-length coding sequence of SEQ ID NO: 22.

In a further embodiment the polynucleotide of a) comprises the full-length coding sequence of SEQ ID NO: 22.

In one further embodiment the variant comprises a sequence with at least 60% sequence identity to the sequence of SEQ ID NO: 23.

In a further embodiment the polynucleotide of a) comprises the sequence of SEQ ID NO: 23.

In one further embodiment the variant comprises a sequence with at least 60% sequence identity to the full-length coding sequence of SEQ ID NO: 23.

In a further embodiment the polynucleotide of a) comprises the full-length coding sequence of SEQ ID NO: 23.

In a further aspect the invention provides a method for producing a plant cell or plant with increased ascorbate content, the method comprising transformation of a plant cell or plant with:
a) a polynucleotide encoding a GDP-D-Mannose epimerase; and
b) a polynucleotide encoding a GDP-L-Galactose Guanyltransferase.

In one embodiment GDP-D-Mannose epimerase comprises the amino acid sequence:

```
    AADMGGMGFIQSNHSVI.      (SEQ ID NO: 36)
```

In a further embodiment the GDP-D-Mannose epimerase comprises the amino acid sequence:

```
    GTWKGGREKAPAAFCRK.      (SEQ ID NO: 37)
```

In a further embodiment the GDP-D-Mannose epimerase comprises a sequence with at least 70% sequence identity to the amino acid sequence of any one of SEQ ID NO: 25 to 35.

In a further embodiment the GDP-D-Mannose epimerase comprises the amino acid sequence of any one of SEQ ID NO: 25 to 35.

In one embodiment the GDP-L-Galactose Guanyltransferase comprises the amino acid sequence:

```
    AINVSPIEYGHVLLIP.       (SEQ ID NO: 12)
```

In a further embodiment the GDP-L-Galactose Guanyltransferase comprises the amino acid sequence:

```
    GYNSLGAFATINHLHFQAY.    (SEQ ID NO: 13)
```

In a further embodiment the GDP-L-Galactose Guanyltransferase comprises a sequence with at least 60% sequence identity to a polypeptide with the amino acid sequence of any one of SEQ ID NO:1 to 11.

In a further embodiment the GDP-L-Galactose Guanyltransferase comprises the amino acid sequence of any one of SEQ ID NO:1 to 11.

In a further aspect the invention provides an isolated polynucleotide encoding a polypeptide comprising a sequence selected any one of SEQ ID NO: 1 to 7 or a variant thereof wherein the variant is a GDP-L-Galactose Guanyltransferase.

In one embodiment the variant comprises the sequence AINVSPIEYGHVLLIP (SEQ ID NO: 12).

In a further embodiment the variant comprises the sequence GYNSLGAFATINHLHFQAY (SEQ ID NO: 13).

In a further embodiment the variant comprises the sequence of both SEQ ID NO:12 and SEQ ID NO:13.

In a further embodiment the polypeptide comprises a sequence with at least 72% identity to the sequence of any one of SEQ ID NO: 1 to 7.

In a further embodiment the polypeptide comprises a sequence selected from any one of SEQ ID NO:1 to 7.

In a further embodiment the polypeptide comprises a sequence with at least 75% identity to the sequence of SEQ ID NO: 1.

In a further embodiment the polypeptide comprises the sequence of SEQ ID NO:1.

In a further embodiment the polypeptide comprises a sequence with at least 74% identity to the sequence of SEQ ID NO: 2.

In a further embodiment the polypeptide comprises the sequence of SEQ ID NO:2.

In a further embodiment the polypeptide comprises a sequence with at least 75% identity to the sequence of SEQ ID NO: 3.

In a further embodiment the polypeptide comprises the sequence of SEQ ID NO:3.

In a further embodiment the polypeptide comprises a sequence with at least 78% identity to the sequence of SEQ ID NO: 4.

In a further embodiment the polypeptide comprises the sequence of SEQ ID NO:4.

In a further embodiment the polypeptide comprises a sequence with at least 75% identity to the sequence of SEQ ID NO: 5.

In a further embodiment the polypeptide comprises the sequence of SEQ ID NO:5.

In a further embodiment the polypeptide comprises a sequence with at least 72% identity to the sequence of SEQ ID NO: 6.

In a further embodiment the polypeptide comprises the sequence of SEQ ID NO:6.

In a further embodiment the polypeptide comprises a sequence with at least 73% identity to the sequence of SEQ ID NO: 7.

In a further embodiment the polypeptide comprises the sequence of SEQ ID NO:7.

In a further aspect the invention provides an isolated polynucleotide comprising the full-length coding sequence of any one of SEQ ID NO: 14 to 20, or a variant thereof wherein the variant encodes a GDP-L-Galactose Guanyltransferase.

In one embodiment the variant comprises a sequence with at least 68% sequence identity to the full-length coding sequence of any one of SEQ ID NO:14 to 20.

In one embodiment the polynucleotide comprises the full-length coding sequence of any one of SEQ ID NOs:14 to 20.

In a further embodiment the polynucleotide comprises the sequence of any one of SEQ ID NO:14 to 20.

In a further embodiment the polynucleotide comprises a sequence with at least 68% sequence identity to the full-length coding sequence of SEQ ID NO:14.

In a further embodiment the polynucleotide comprises the full-length coding sequence from within the sequence of SEQ ID NO:14.

In a further embodiment the polynucleotide comprises the sequence of SEQ ID NO: 14.

In a further embodiment the polynucleotide comprises a sequence with at least 69% sequence identity to the full-length coding sequence of SEQ ID NO:15.

In a further embodiment the polynucleotide comprises the full-length coding sequence from within the sequence of SEQ ID NO:15.

In a further embodiment the polynucleotide comprises the sequence of SEQ ID NO: 15.

In a further embodiment the polynucleotide comprises a sequence with at least 66% sequence identity to the full-length coding sequence of SEQ ID NO:16.

In a further embodiment the polynucleotide comprises the full-length coding sequence from within the sequence of SEQ ID NO:16.

In a further embodiment the polynucleotide comprises the sequence of SEQ ID NO: 16.

In a further embodiment the polynucleotide comprises a sequence with at least 69% sequence identity to the full-length coding sequence of SEQ ID NO:17.

In a further embodiment the polynucleotide comprises the full-length coding sequence from within the sequence of SEQ ID NO:17.

In a further embodiment the polynucleotide comprises the sequence of SEQ ID NO: 17.

In a further embodiment the polynucleotide comprises a sequence with at least 69% sequence identity to the full-length coding sequence of SEQ ID NO:18.

In a further embodiment the polynucleotide comprises the full-length coding sequence from within the sequence of SEQ ID NO:18.

In a further embodiment the polynucleotide comprises the sequence of SEQ ID NO: 18.

In a further embodiment the polynucleotide comprises a sequence with at least 68% sequence identity to the full-length coding sequence of SEQ ID NO:19.

In a further embodiment the polynucleotide comprises the full-length coding sequence from within the sequence of SEQ ID NO:19.

In a further embodiment the polynucleotide comprises the sequence of SEQ ID NO: 19.

In a further embodiment the polynucleotide comprises a sequence with at least 70% sequence identity to the full-length coding sequence of SEQ ID NO:20.

In a further embodiment the polynucleotide comprises the full-length coding sequence from within the sequence of SEQ ID NO:20.

In a further embodiment the polynucleotide comprises the sequence of SEQ ID NO: 20.

In a further aspect the invention provides an isolated polypeptide comprising the amino acid sequence of SEQ ID NO:1 to 7, or a variant thereof, wherein the variant has the activity of an GDP-L-Galactose Guanyltransferase.

In one embodiment the variant polypeptide has at least 72% sequence identity to an amino acid sequence selected from any one of SEQ ID NO: 1 to 7, wherein the variant has the activity of an GDP-L-Galactose Guanyltransferase.

In a further embodiment the isolated polypeptide has at least 75% sequence identity to the amino acid sequence of SEQ ID NO:1.

In a further embodiment the isolated polypeptide comprises the amino acid sequence of SEQ ID NO:1.

In a further embodiment the isolated polypeptide has at least 74% sequence identity to the amino acid sequence of SEQ ID NO:2.

In a further embodiment the isolated polypeptide comprises the amino acid sequence of SEQ ID NO:2.

In a further embodiment the isolated polypeptide has at least 75% sequence identity to the amino acid sequence of SEQ ID NO:3.

In a further embodiment the isolated polypeptide comprises the amino acid sequence of SEQ ID NO:3.

In a further embodiment the isolated polypeptide has at least 78% sequence identity to the amino acid sequence of SEQ ID NO:4.

In a further embodiment the isolated polypeptide comprises the amino acid sequence of SEQ ID NO:4.

In a further embodiment the isolated polypeptide has at least 75% sequence identity to the amino acid sequence of SEQ ID NO:5.

In a further embodiment the isolated polypeptide comprises the amino acid sequence of SEQ ID NO:5.

In a further embodiment the isolated polypeptide has at least 72% sequence identity to the amino acid sequence of SEQ ID NO:6.

In a further embodiment the isolated polypeptide comprises the amino acid sequence of SEQ ID NO:6.

In a further embodiment the isolated polypeptide has at least 73% sequence identity to the amino acid sequence of SEQ ID NO:7.

In a further embodiment the isolated polypeptide comprises the amino acid sequence of SEQ ID NO:7.

In a further aspect the invention provides an isolated polynucleotide encoding a polypeptide comprising a sequence selected any one of SEQ ID NO: 25 to 27 or a variant thereof wherein the variant is a GDP-D-Mannose epimerase.

In one embodiment the variant comprises the sequence:

```
AADMGGMGFIQSNHSVI.      (SEQ ID NO: 36)
```

In a further embodiment the variant comprises the sequence:

```
GTWKGGREKAPAAFCRK.      (SEQ ID NO: 37)
```

In a further embodiment the variant comprises the sequence of both SEQ ID NO: 36 and SEQ ID NO: 37.

In a further embodiment the polypeptide comprises a sequence with at least 91% identity to the sequence of any one of SEQ ID NO: 25 to 27.

In a further embodiment the polypeptide comprises a sequence selected from any one of SEQ ID NO: 25 to 27.

In a further embodiment the polypeptide comprises a sequence with at least 91% identity to the sequence of SEQ ID NO: 25.

In a further embodiment the polypeptide comprises the sequence of SEQ ID NO: 25.

In a further embodiment the polypeptide comprises a sequence with at least 91% identity to the sequence of SEQ ID NO: 26.

In a further embodiment the polypeptide comprises the sequence of SEQ ID NO: 26.

In a further embodiment the polypeptide comprises a sequence with at least 91% identity to the sequence of SEQ ID NO: 27.

In a further embodiment the polypeptide comprises the sequence of SEQ ID NO: 27.

In a further aspect the invention provides an isolated polynucleotide comprising the full-length coding sequence of any one of SEQ ID NO: 38 to 40, or a variant thereof wherein the variant encodes a GDP-D-Mannose epimerase.

In one embodiment the variant comprises a sequence with at least 70% sequence identity to the full-length coding sequence of any one of SEQ ID NO: 38 to 40.

In one embodiment the polynucleotide comprises the full-length coding sequence of any one of SEQ ID NOs: 38 to 40.

In a further embodiment the polynucleotide comprises the sequence of any one of SEQ ID NO: 38 to 40.

In a further embodiment the polynucleotide comprises a sequence with at least 70% sequence identity to the full-length coding sequence of SEQ ID NO: 38.

In a further embodiment the polynucleotide comprises the full-length coding sequence from within the sequence of SEQ ID NO: 38.

In a further embodiment the polynucleotide comprises the sequence of SEQ ID NO: 38.

In a further embodiment the polynucleotide comprises a sequence with at least 70% sequence identity to the full-length coding sequence of SEQ ID NO: 39.

In a further embodiment the polynucleotide comprises the full-length coding sequence from within the sequence of SEQ ID NO: 39.

In a further embodiment the polynucleotide comprises the sequence of SEQ ID NO: 39.

In a further embodiment the polynucleotide comprises a sequence with at least 70% sequence identity to the full-length coding sequence of SEQ ID NO: 40.

In a further embodiment the polynucleotide comprises the full-length coding sequence from within the sequence of SEQ ID NO: 40.

In a further embodiment the polynucleotide comprises the sequence of SEQ ID NO: 40.

In a further aspect the invention provides an isolated polypeptide comprising the amino acid sequence of SEQ ID NO: 25 to 27, or a variant thereof, wherein the variant has the activity of an a GDP-D-Mannose epimerase.

In one embodiment the variant polypeptide has at least 91% sequence identity to an amino acid sequence selected from any one of SEQ ID NO: 25 to 27, wherein the variant has the activity of an a GDP-D-Mannose epimerase.

In a further embodiment the isolated polypeptide has at least 91% sequence identity to the amino acid sequence of SEQ ID NO: 25.

In a further embodiment the isolated polypeptide comprises the amino acid sequence of SEQ ID NO: 25.

In a further embodiment the isolated polypeptide has at least 91% sequence identity to the amino acid sequence of SEQ ID NO: 26.

In a further embodiment the isolated polypeptide comprises the amino acid sequence of SEQ ID NO: 26.

In a further embodiment the isolated polypeptide has at least 91% sequence identity to the amino acid sequence of SEQ ID NO: 27.

In a further embodiment the isolated polypeptide comprises the amino acid sequence of SEQ ID NO: 27.

In a further aspect the invention provides an isolated polynucleotide encoding a polypeptide of the invention.

In a further aspect the invention provides an isolated polynucleotide comprising:
a) a polynucleotide comprising a fragment, of at least 15 nucleotides in length, of a polynucleotide of the invention;
b) a polynucleotide comprising a complement, of at least 15 nucleotides in length, of the polynucleotide of the invention; or
d) a polynucleotide comprising a sequence, of at least 15 nucleotides in length, capable of hybridising to the polynucleotide of the invention.

In a further aspect the invention provides a genetic construct which comprises at least one polynucleotide of the invention.

In a further aspect the invention provides an expression construct which comprises at least one polynucleotide of the invention.

In a further aspect the invention provides an RNAi construct which comprises at least one polynucleotide of the invention.

In a further aspect the invention provides a vector comprising an expression construct, genetic construct or RNAi construct of the invention.

In a further aspect the invention provides a host cell comprising at least one expression construct or genetic construct of the invention.

In a further aspect the invention provides a host cell genetically modified to express at least one polynucleotide of the invention, or at least one polypeptide of the invention.

Preferably the host cell is genetically modified to express: a polynucleotide encoding a GDP-L-Galactose Guanyltransferase; and a polynucleotide encoding a GDP-D-Mannose epimerase.

In a further aspect the invention provides a method for producing a GDP-L-Galactose Guanyltransferase polypeptide, the method comprising culturing a host cell comprising an expression construct of the invention or a genetic construct of the invention, capable of expressing an GDP-L-Galactose Guanyltransferase polypeptide.

In a further aspect the invention provides a method for producing the enzymic product of an GDP-L-Galactose Guanyltransferase, the method comprising culturing a host cell including an expression construct of the invention or an genetic construct of the invention, capable of expressing an GDP-L-Galactose Guanyltransferase polypeptide, in the presence of enzymic substrate which may be supplied to, or may be naturally present within the host cell.

In a further aspect the invention provides a method for producing a GDP-D-Mannose epimerase polypeptide, the method comprising culturing a host cell comprising an expression construct of the invention or a genetic construct of the invention, capable of expressing a GDP-D-Mannose epimerase polypeptide.

In a further aspect the invention provides a method for producing the enzymic product of a GDP-D-Mannose epimerase, the method comprising culturing a host cell including an expression construct of the invention or an genetic construct of the invention, capable of expressing a GDP-D-Mannose epimerase polypeptide, in the presence of enzymic substrate which may be supplied to, or may be naturally present within the host cell.

In a further aspect the invention provides a method for the biosynthesis of ascorbate comprising the steps of culturing a host cell comprising an expression construct of the invention or the genetic construct of the invention, capable of expressing a GDP-L-Galactose Guanyltransferase, in the presence of an ascorbate precursor which may be supplied to, or may be naturally present within the host cell.

Preferably the host cell also comprises an expression construct of the invention capable of expressing a GDP-D-Mannose epimerase.

In a further aspect the invention provides a method for the biosynthesis of ascorbate comprising the steps of culturing a host cell comprising an expression construct of the invention or a genetic construct of the invention, capable of expressing a GDP-D-Mannose epimerase, in the presence of an ascorbate precursor which may be supplied to, or may be naturally present within the host cell.

Preferably the host cell also comprises an expression construct of the invention capable of expressing a GDP-L-Galactose Guanyltransferase.

Preferably the host cell is a plant cell. Preferably the plant cell is part of a plant.

In a further aspect the invention provides a plant cell genetically modified to express at least one polynucleotide of the invention, or at least one polypeptide of the invention.

In a further aspect the invention provides a plant cell which comprises at least one expression construct of the invention or at least one genetic construct of the invention.

In a further aspect the invention provides a plant which comprises a plant cell of the invention.

In a further aspect the invention provides a method for selecting a plant altered in GDP-L-Galactose Guanyltransferase activity, the method comprising testing of a plant for altered expression of a polynucleotide of the invention.

In a further aspect the invention provides a method for selecting a plant altered in GDP-L-Galactose Guanyltransferase activity, the method comprising testing of a plant for altered expression of a polypeptide of the invention.

In a further aspect the invention provides a method for selecting a plant altered in GDP-D-Mannose epimerase activity, the method comprising testing of a plant for altered expression of a polynucleotide of the invention.

In a further aspect the invention provides a method for selecting a plant altered in GDP-D-Mannose epimerase activity, the method comprising testing of a plant for altered expression of a polypeptide of the invention.

In a further aspect the invention provides a method for selecting a plant with altered ascorbic acid content; the method comprising testing of a plant for altered expression of a polynucleotide or polypeptide of the invention.

In a further aspect the invention provides a plant cell or plant produced by the method of the invention. Preferably the plant is genetically modified to include or express a polynucleotide or polypeptide of the invention.

In a further aspect the invention provides a plant selected by the method of the invention.

In a further aspect the invention provides a group of plants selected by the method of the invention. Preferably the group comprises at least 2, more preferably at least 3, more preferably at least 4, more preferably at least 5, more preferably at least 6, more preferably at least 7, more preferably at least 8, more preferably at least 9, more preferably at least 10, more preferably at least 11, more preferably at least 12, more preferably at least 13, more preferably at least 14, more preferably at least 15, more preferably at least 16, more preferably at least 17, more preferably at least 18, more preferably at least 19, more preferably at least 20 plants.

In a further aspect the invention provides a method of producing ascorbate, the method comprising extracting ascorbate from a plant cell or plant of the invention.

In a further aspect the invention provides a method for identifying a compound as a candidate for a herbicide, comprising:
  a) contacting said compound with a polypeptide comprising a sequence selected from any one of SEQ ID NO: 1 to 11, or a variant thereof that has the activity of a GDP-L-Galactose Guanyltransferase, and
  b) detecting the presence and/or absence of binding between said compound and said polypeptide; wherein binding indicates that said compound is a candidate for a herbicide.

In a further aspect the invention provides a method for identifying a compound as a candidate for a herbicide, comprising:
  a) contacting said compound with a polypeptide comprising a sequence selected from any one of SEQ ID NO: 1 to 11, or a variant thereof that has the activity of a GDP-L-Galactose Guanyltransferase, and
  b) assessing the effect of the compound on the GDP-L-Galactose Guanyltransferase activity of the polypeptide; wherein a decrease in activity indicates that said compound is a candidate for a herbicide.

In a further aspect the invention provides a method for identifying a compound as a candidate for a herbicide, comprising:
  a) contacting said compound with a polypeptide comprising a sequence selected from any one of SEQ ID NO: 25 to 35, or a variant thereof that has the activity of a GDP-D-Mannose epimerase, and
  b) detecting the presence and/or absence of binding between said compound and said polypeptide; wherein binding indicates that said compound is a candidate for a herbicide.

In a further aspect the invention provides a method for identifying a compound as a candidate for a herbicide, comprising:
  a) contacting said compound with a polypeptide comprising a sequence selected from any one of SEQ ID NO: 25 to 35, or a variant thereof that has the activity of a GDP-D-Mannose epimerase, and
  b) assessing the effect of the compound on the GDP-D-Mannose epimerase activity of the polypeptide; wherein a decrease in activity indicates that said compound is a candidate for a herbicide.

In a further aspect the invention provides a compound identified by a method of the invention.

In a further aspect the invention provides a method for determining whether the compound of the invention has herbicidal activity, comprising: contacting a plant or plant cells with said herbicide candidate and detecting a decrease in growth or viability of said plant or plant cells, wherein said decrease is indicative of herbicidal activity of the compound.

In a further aspect the invention provides an antibody raised against a polypeptide of the invention.

In a further aspect the invention provides method of producing L-Galactose-1-phosphate, the method comprising contacting GDP-L-Galactose and a GDP acceptor including either a Hexose-1-phosphate or phosphate with the expression product of an expression construct comprising a polynucleotide of the invention to obtain L-Galactose-1-phosphate.

In a further aspect the invention provides method of producing GDP-Galactose, the method comprising contacting GDP-Mannose with the expression product of an expression construct comprising a polynucleotide of the invention or a polypeptide of the invention to obtain GDP-Galactose.

In alternative embodiments of all aspects of the invention, the GDP-L-Galactose Guanyltransferase is a GDP-L-Galactose Hexose-1-P-Guanyltransferase. Similarly in alternative embodiments of all aspects of the invention, the GDP-L-Galactose Guanyltransferase activity is GDP-L-Galactose Hexose-1-P-Guanyltransferase activity. A GDP-L-Galactose Hexose-1-P-Guanyltransferase is not necessarily limited to use of Hexose-1-P as an GDP acceptor but may use other GDP acceptors such as phosphate and pyrophosphate. Preferably the other GDP acceptor is phosphate.

The polynucleotides and variants of polynucleotides, of the invention may be derived from any species. The polynucleotides and variants may also be recombinantly produced and also may be the products of "gene shuffling' approaches.

In one embodiment the polynucleotide or variant, is derived from a plant species.

In a further embodiment the polynucleotide or variant, is derived from a gymnosperm plant species.

In a further embodiment the polynucleotide or variant, is derived from an angiosperm plant species.

In a further embodiment the polynucleotide or variant, is derived from a dicotyledonous plant species.

The polypeptides and variants of polypeptides of the invention may be derived from any species. The polypeptides and variants may also be recombinantly produced and also may also be expressed from the products of "gene shuffling' approaches.

In one embodiment the polypeptides or variants of the invention are derived from plant species.

In a further embodiment the polypeptides or variants of the invention are derived from gymnosperm plant species.

In a further embodiment the polypeptides or variants of the invention are derived from angiosperm plant species.

In a further embodiment the polypeptides or variants of the invention are derived from dicotyledonous plant species.

The plant cells and plants of the invention, including those from which the polynucleotides, variant polynucleotides, polypeptide and variant polypeptides are derived may be from any species.

In one embodiment the plants cells and plants are from gymnosperm species.

In a further embodiment the plants cells and plants are from angiosperm species.

In a further embodiment the plants cells and plants are from dicotyledonous species.

In a further embodiment the plants cells and plants are from a fruit species selected from a group comprising but not limited to the following genera: *Actinidia, Malus, Citrus, Fragaria* and *Vaccinium*.

Particularly preferred fruit plant species are: *Actidinia deliciosa, A. chinensis, A. eriantha, A. arguta*, hybrids of the four *Actinidia* species, *Malus domestica* and *Malus sieboldii*.

In a further embodiment the plants cells and plants are from a vegetable species selected from a group comprising but not limited to the following genera: *Brassica, Lycopersicon* and *Solanum*.

Particularly preferred vegetable plant species are: *Lycopersicon esculentum* and *Solanum tuberosum*.

In a further embodiment the plants cells and plants of the invention are from monocotyledonous species.

In a further embodiment the plants cells and plants are from a crop species selected from a group comprising but not limited to the following genera: *Glycine, Zea, Hordeum* and *Oryza*.

Particularly preferred crop plant species are: *Oryza sativa, Glycine max* and *Zea mays*.

BRIEF DESCRIPTION OF THE DRAWINGS

The present invention will be better understood with reference to the accompanying drawings in which:

FIGS. 1A-1B show an alignment of the *Arabidopsis thaliana* sequence VTC2 (SEQ ID NO:8) with the *Actinidia chinensis* 'Hort16A' sequence 319998 (SEQ ID NO:1) and a second *A. thaliana* sequence, At5g55120 (SEQ ID NO:9). Also aligned is the *Arabidopsis* enzyme At5g18200 (SEQ ID NO:49) (coding for a putative UDP-glucose-hexose-1-phosphate uridylyltransferase (EC-Number 2.7.7.12)) and the unnamed mouse protein Mm_74150758 (SEQ ID NO:50) (the number is the GenBank accession number). Identical aligned residues in all five sequences are shown in dark grey, similar residues in light grey. The sequences were aligned using Clustal X (Jeanmougin et al., 1998) with some manual adjustment. The HIT triad sequence is identified at ~amino acid residue 250.

FIGS. 6A-6C show alignment of a range of sequences with significant similarity to At4g26850 (SEQ ID NO:8). Alignments were done using ClustalX (1). 244893_Ac (SEQ ID NO:3) and 319998_Ac (SEQ ID NO:1) are ESTs from *Actinidia chinensis*, 24547_Ae (SEQ ID NO:4) and 276582_Ae (SEQ ID NO:5) ESTs from *A. eriantha*, 82552_Md (SEQ ID NO:2) an EST from *Malus×domesticus*, 315905_Ms (SEQ ID NO:6) an EST from *M. sieboldii* (crab apple) At4g26850 (SEQ ID NO:8) is VTC2 from *Arabidopsis thaliana* and At5g55120 (SEQ ID NO:9) is a homologue also from *A. thaliana*. BT013858_Le (SEQ ID NO:10) is a translation of a Genbank DNA entry from tomato (*Lycopersicon esculentum*), Os12g0190000 (SEQ ID NO:11) is a *Oryza sativa* (rice) sequence. Contig_St (SEQ ID NO:7) is a contig was assembled from 95% identical overlapping *Solanum tuberosum* (potato) ESTs identified Genbank.

FIG. 7 shows % identity between the sequences aligned in FIGS. 6A-6C.

FIGS. 9A-9H show alignments (using ClustalX) of coding sequences, that encode for the polypeptide sequences aligned in FIGS. 6A-6C. Sequence identifiers corresponding to the sequences presented are as follows: 244893_KAIA, SEQ ID NO:16; 24547_KUFA, SEQ ID NO:17; 276582_KAJB_Ae, SEQ ID NO:18; 315905_ABOC, SEQ ID NO:19; 319998_KAZD, SEQ ID NO:14; At4g26850, SEQ ID NO:21; At5g55120, SEQ ID NO:22; BT013858_tomato, SEQ ID NO:23; NM_001072870_Os, SEQ ID NO:24; Potato VTC2 contig from ESTs, SEQ ID NO:20; and 82552_AARA_NNT, SEQ ID NO:51.

FIG. 10 shows percent identities between the coding sequences aligned in FIGS. 9A-9H.

FIGS. 11A-11B show an alignment of the GDP-D-Mannose epimerase polypeptide sequences of SEQ ID NO: 25 to 35. Identical aligned residues in all four sequences are shown in dark grey, similar residues in light grey. The sequences were aligned using Clustal X (Jeanmougin et al., 1998). Sequence identifiers corresponding to the sequences presented in FIG. 11 are as follows: *Actinidia deliciosa* 198296 KALA, SEQ ID NO:26; *Actinidia eriantha* 169164, SEQ ID NO:25; *Arabidopsis thaliana* AT5G28840, SEQ ID NO:28; *Malpighia glabra* DQ229167, SEQ ID NO:29; *Malus pumila* 108403 AAOA, SEQ ID NO:27; *Ostreococcus lucimarinus* XM 001422193, SEQ ID NO:32; *Solanum tuberosum* DO268848, SEQ ID NO:33; *Vitis vinifera* EF554358, SEQ ID NO:34; *Lycopersicon esculentum* BT013590, SEQ ID NO:35; *Oryza sativa* AB193582, SEQ ID NO:30; *Oryza sativa* AB235855, SEQ ID NO:31.

FIG. 12 shows % sequence identities between the sequences aligned in FIGS. 1A-1B.

FIGS. 13A-13C show alignment (using ClustalX) of epimerase polynucleotide sequences of SEQ ID NO: 5 to 8. Sequence identifiers corresponding to the sequences presented in FIG. 13 are as follows: 108403, SEQ ID NO:40; 169164, SEQ ID NO:38; 198296, SEQ ID NO:39; and At5g28840, SEQ ID NO:41.

FIG. 14 shows % identity between the epimerase polynucleotide sequences of SEQ ID NO: 25 to 28.

FIGS. 16A-16B show ascorbate levels in tobacco leaves transiently transformed with a range of GDP-L-Galactose guanyltransferase and epimerase constructs.

FIGS. 17A-17B show ascorbate levels in tobacco leaves transiently transformed with a specialised GDP-L-Galactose guanyltransferase.

FIGS. 18A-18B show segregation of kanamycin resistance in GDP-L-Galactose guanyltransferase 319998 transformed *Arabidopsis* lines. Seeds were grown on Kanamycin plates and numbers of green and dead germinated seed counted. True=multiple copy, False=single copy. Numbers in bold were carried on to the second generation (Table 3).

FIG. 19 shows second generation lines of GDP-L-Galactose guanyltransferase 319998 transformed *Arabidopsis* showing incidence of high ascorbate in leaves. All plants were selected as Kanamycin resistant. Numbers in brackets are standard errors of the mean. Ascorbate (ASC) in mg/100 g.

FIGS. 20A-20B show third generation lines of GDP-L-Galactose guanyltransferase 319998 transformed *Arabidopsis* showing incidence of high ascorbate in leaves. All plants were selected as Kanamycin resistant. Numbers in brackets are standard errors of the mean. Ascorbate (ASC) in mg/100 g.

FIG. 21 shows gene expression and leaf ascorbate concentrations in selected GDP-L-Galactose guanyltransferase 319998 transformed *Arabidopsis* lines. Gene expression was measured by qPCR in selected lines.

FIG. 22 shows stably GDP-L-Galactose guanyltransferase 319998 transformed tobacco ascorbate levels and gene expression. PCR was carried out using qualitative techniques.

FIG. 23 shows GDP-L-Galactose guanyltransferase enzyme activities observed with enzyme expressed in *E coli*. Assays were run in either an older Victor plate reader ("old" using a correction factor of 0.000254517 nmole/F to convert fluorescence units to nmoles) or in a newer Victor 3 ("new" correction factor 2.6565E-05 nmole/F) at 20 C.

DETAILED DESCRIPTION

Figure 2:
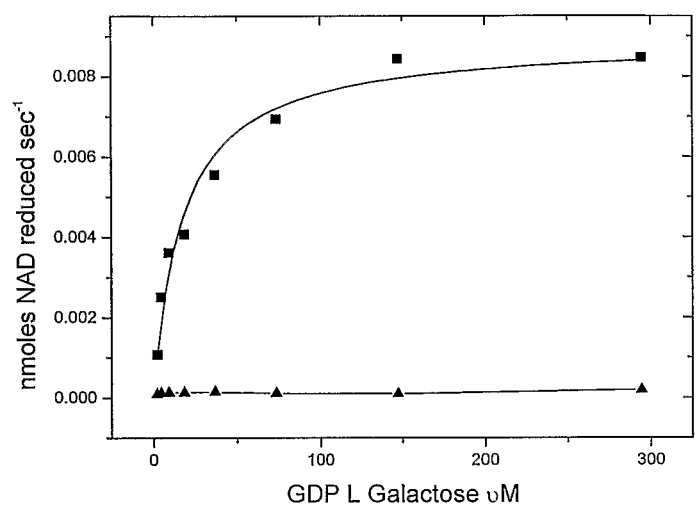
FIG. 2 shows the response of the kiwifruit GDP-Mannose-1-P Guanyl transferase, EST 319998 (SEQ ID NO:1, amino acid sequence, SEQ ID NO:14, nucleotide sequence) to GDP-L-Galactose. GDP-L-Galactose was made from GDP-D-Mannose using the epimerase as described in the methods and the concentration of the mixture that was GDP-L-Galactose determined by HPLC. Assays were conducted using the continuous coupled assay using 0.029 ug of enzyme per assay. Mannose-1-P concentration was 0.93 mM and 1.87 mM $MgCl_2$. Other conditions were as described in the text. Squares represent the reaction minus the background run without mannose-1-P. Triangles represent the background values using HisTrap purified *E coli* extract (0.006 ug) expressing an empty PET30a vector. (time courses 319998 11 10 06.xls).

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

Polynucleotides and Fragments

The term "polynucleotide(s)," as used herein, means a single or double-stranded deoxyribonucleotide or ribonucleotide polymer of any length but preferably at least 15 nucleotides, and include as non-limiting examples, coding and non-coding sequences of a gene, sense and antisense sequences complements, exons, introns, genomic DNA, cDNA, pre-mRNA, mRNA, rRNA, sRNA, miRNA, tRNA, ribozymes, recombinant polypeptides, isolated and purified naturally occurring DNA or RNA sequences, synthetic RNA and DNA sequences, nucleic acid probes, primers and fragments.

A "fragment" of a polynucleotide sequence provided herein is a subsequence of contiguous nucleotides that is capable of specific hybridization to a target of interest, e.g., a sequence that is at least 15 nucleotides in length. The fragments of the invention comprise 15 nucleotides, preferably at least 20 nucleotides, more preferably at least 30 nucleotides, more preferably at least 50 nucleotides, more preferably at least 50 nucleotides and most preferably at least 60 nucleotides of contiguous nucleotides of a polynucleotide of the invention. A fragment of a polynucleotide sequence can be used in antisense, gene silencing, triple helix or ribozyme technology, or as a primer, a probe, included in a microarray, or used in polynucleotide-based selection methods of the invention.

The term "primer" refers to a short polynucleotide, usually having a free 3'OH group, that is hybridized to a template and used for priming polymerization of a polynucleotide complementary to the target.

The term "probe" refers to a short polynucleotide that is used to detect a polynucleotide sequence, that is complementary to the probe, in a hybridization-based assay. The probe may consist of a "fragment" of a polynucleotide as defined herein.

Polypeptides and Fragments

The term "polypeptide", as used herein, encompasses amino acid chains of any length but preferably at least 5 amino acids, including full-length proteins, in which amino acid residues are linked by covalent peptide bonds. Polypeptides of the present invention may be purified natural products, or may be produced partially or wholly using recombinant or synthetic techniques. The term may refer to a polypeptide, an aggregate of a polypeptide such as a dimer or other multimer, a fusion polypeptide, a polypeptide fragment, a polypeptide variant, or derivative thereof.

A "fragment" of a polypeptide is a subsequence of the polypeptide that performs a function that is required for the biological activity and/or provides three dimensional structure of the polypeptide. The term may refer to a polypeptide, an aggregate of a polypeptide such as a dimer or other multimer, a fusion polypeptide, a polypeptide fragment, a polypeptide variant, or derivative thereof capable of performing the above enzymatic activity.

The term "isolated" as applied to the polynucleotide or polypeptide sequences disclosed herein is used to refer to sequences that are removed from their natural cellular environment. An isolated molecule may be obtained by any method or combination of methods including biochemical, recombinant, and synthetic techniques.

The term "recombinant" refers to a polynucleotide sequence that is removed from sequences that surround it in its natural context and/or is recombined with sequences that are not present in its natural context.

A "recombinant" polypeptide sequence is produced by translation from a "recombinant" polynucleotide sequence.

The term "derived from" with respect to polynucleotides or polypeptides of the invention being derived from a particular genera or species, means that the polynucleotide or polypeptide has the same sequence as a polynucleotide or polypeptide found naturally in that genera or species. The polynucleotide or polypeptide, derived from a particular genera or species, may therefore be produced synthetically or recombinantly.

Variants

As used herein, the term "variant" refers to polynucleotide or polypeptide sequences different from the specifically identified sequences, wherein one or more nucleotides or amino acid residues is deleted, substituted, or added. Variants may be naturally occurring allelic variants, or non-naturally occurring variants. Variants may be from the same or from other species and may encompass homologues, paralogues and orthologues. In certain embodiments, variants of the inventive polypeptides and polypeptides possess biological activities that are the same or similar to those of the inventive polypeptides or polypeptides. The term "variant" with reference to polypeptides and polypeptides encompasses all forms of polypeptides and polypeptides as defined herein.

Polynucleotide Variants

Variant polynucleotide sequences preferably exhibit at least 50%, more preferably at least 51%, more preferably at least 52%, more preferably at least 53%, more preferably at least 54%, more preferably at least 55%, more preferably at least 56%, more preferably at least 57%, more preferably at least 58%, more preferably at least 59%, more preferably at least 60%, more preferably at least 61%, more preferably at least 62%, more preferably at least 63%, more preferably at least 64%, more preferably at least 65%, more preferably at least 66%, more preferably at least 67%, more preferably at least 68%, more preferably at least 69%, more preferably at least 70%, more preferably at least 71%, more preferably at least 72%, more preferably at least 73%, more preferably at least 74%, more preferably at least 75%, more preferably at least 76%, more preferably at least 77%, more preferably at least 78%, more preferably at least 79%, more preferably at least 80%, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, and most preferably at least 99% identity to a sequence of the present invention. Identity is found over a comparison window of at least 20 nucleotide positions, preferably at least 50 nucleotide positions, more preferably at least 100 nucleotide positions, and most preferably over the entire length of a polynucleotide of the invention.

Polynucleotide sequence identity can be determined in the following manner. The subject polynucleotide sequence is compared to a candidate polynucleotide sequence using BLASTN (from the BLAST suite of programs, version 2.2.5 [November 2002]) in bl2seq (Tatiana A. Tatusova, Thomas L. Madden (1999), "Blast 2 sequences—a new tool for comparing protein and nucleotide sequences", FEMS Microbiol Lett. 174:247-250), which is publicly available from NCBI via the internet. The default parameters of bl2seq are utilized except that filtering of low complexity parts should be turned off.

The identity of polynucleotide sequences may be examined using the following unix command line parameters:
bl2seq -i nucleotideseq1 -j nucleotideseq2 -F F -p blastn The parameter -F F turns off filtering of low complexity sections. The parameter -p selects the appropriate algorithm for the pair of sequences. The bl2seq program reports sequence identity as both the number and percentage of identical nucleotides in a line "Identities=".

Polynucleotide sequence identity may also be calculated over the entire length of the overlap between a candidate and subject polynucleotide sequences using global sequence alignment programs (e.g. Needleman, S. B. and Wunsch, C. D. (1970) J. Mol. Biol. 48, 443-453). A full implementation of the Needleman-Wunsch global alignment algorithm is found in the needle program in the EMBOSS package (Rice, P. Longden, I. and Bleasby, A. EMBOSS: The European Molecular Biology Open Software Suite, Trends in Genetics June 2000, vol 16, No 6. pp. 276-277) which can be obtained from on the world-wide web, at hgmp<.>mrc<.>ac<.>uk/Software/EMBOSS/. The European Bioinformatics Institute server also provides the facility to perform EMBOSS-needle global alignments between two sequences on line at on the world-wide web, at ebi<.>ac<.>uk/emboss/align/.

Alternatively the GAP program may be used which computes an optimal global alignment of two sequences without penalizing terminal gaps. GAP is described in the following paper: Huang, X. (1994) On Global Sequence Alignment. Computer Applications in the Biosciences 10, 227-235.

A preferred method for calculating polynucleotide % sequence identity is based on aligning sequences to be compared using Clustal X (Jeanmougin et al., 1998, *Trends Biochem. Sci.* 23, 403-5.)

Polynucleotide variants of the present invention also encompass those which exhibit a similarity to one or more of the specifically identified sequences that is likely to preserve the functional equivalence of those sequences and which could not reasonably be expected to have occurred by random chance. Such sequence similarity with respect to polypeptides may be determined using the publicly available bl2seq program from the BLAST suite of programs (version 2.2.5 [November 2002]) from NCBI via the internet.

The similarity of polynucleotide sequences may be examined using the following unix command line parameters:

bl2seq -i nucleotideseq1 -j nucleotideseq2 -F F -p tblastx

The parameter -F F turns off filtering of low complexity sections. The parameter -p selects the appropriate algorithm for the pair of sequences. This program finds regions of similarity between the sequences and for each such region reports an "E value" which is the expected number of times one could expect to see such a match by chance in a database of a fixed reference size containing random sequences. The size of this database is set by default in the bl2seq program. For small E values, much less than one, the E value is approximately the probability of such a random match.

Variant polynucleotide sequences preferably exhibit an E value of less than $1\times10^{-6}$ more preferably less than $1\times10^{-9}$, more preferably less than $1\times10^{-12}$, more preferably less than $1\times10^{-15}$, more preferably less than $1\times10^{-18}$, more preferably less than $1\times10^{-21}$, more preferably less than $1\times10^{-30}$, more preferably less than $1\times10^{-40}$, more preferably less than $1\times10^{-50}$, more preferably less than $1\times10^{-60}$, more preferably less than $1\times10^{-70}$, more preferably less than $1\times10^{-80}$, more preferably less than $1\times10^{-90}$ and most preferably less than $1\times10^{-100}$ when compared with any one of the specifically identified sequences.

Alternatively, variant polynucleotides of the present invention hybridize to the specified polynucleotide sequences, or complements thereof under stringent conditions.

The term "hybridize under stringent conditions", and grammatical equivalents thereof, refers to the ability of a polynucleotide molecule to hybridize to a target polynucleotide molecule (such as a target polynucleotide molecule immobilized on a DNA or RNA blot, such as a Southern blot or Northern blot) under defined conditions of temperature and salt concentration. The ability to hybridize under stringent hybridization conditions can be determined by initially hybridizing under less stringent conditions then increasing the stringency to the desired stringency.

With respect to polynucleotide molecules greater than about 100 bases in length, typical stringent hybridization conditions are no more than 25 to 30° C. (for example, 10° C.) below the melting temperature (Tm) of the native duplex (see generally, Sambrook et aL, Eds, 1987, Molecular Cloning, A Laboratory Manual, 2nd Ed. Cold Spring Harbor Press; Ausubel et al., 1987, Current Protocols in Molecular Biology, Greene Publishing). Tm for polynucleotide molecules greater than about 100 bases can be calculated by the formula Tm=81. 5+0.41% (G+C-log (Na+). (Sambrook et al., Eds, 1987, Molecular Cloning, A Laboratory Manual, 2nd Ed. Cold Spring Harbor Press; Bolton and McCarthy, 1962, PNAS 84:1390). Typical stringent conditions for polynucleotide of greater than 100 bases in length would be hybridization conditions such as prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

With respect to polynucleotide molecules having a length less than 100 bases, exemplary stringent hybridization conditions are 5 to 10° C. below Tm. On average, the Tm of a polynucleotide molecule of length less than 100 bp is reduced by approximately (500/oligonucleotide length)° C.

With respect to the DNA mimics known as peptide nucleic acids (PNAs) (Nielsen et al., Science. 1991 December 6; 254(5037)1497-500) Tm values are higher than those for DNA-DNA or DNA-RNA hybrids, and can be calculated using the formula described in Giesen et al., Nucleic Acids Res. 1998 November 1; 26(21):5004-6. Exemplary stringent hybridization conditions for a DNA-PNA hybrid having a length less than 100 bases are 5 to 10° C. below the Tm.

Variant polynucleotides of the present invention also encompasses polynucleotides that differ from the sequences of the invention but that, as a consequence of the degeneracy of the genetic code, encode a polypeptide having similar activity to a polypeptide encoded by a polynucleotide of the present invention. A sequence alteration that does not change the amino acid sequence of the polypeptide is a "silent variation". Except for ATG (methionine) and TGG (tryptophan), other codons for the same amino acid may be changed by art recognized techniques, e.g., to optimize codon expression in a particular host organism.

Polynucleotide sequence alterations resulting in conservative substitutions of one or several amino acids in the encoded polypeptide sequence without significantly altering its biological activity are also included in the invention. A skilled artisan will be aware of methods for making phenotypically silent amino acid substitutions (see, e.g., Bowie et al., 1990, Science 247, 1306).

Variant polynucleotides due to silent variations and conservative substitutions in the encoded polypeptide sequence may be determined using the publicly available bl2seq program from the BLAST suite of programs (version 2.2.5 [November 2002]) from NCBI via the internet and via the tblastx algorithm as previously described.

The function of a variant polynucleotide of the invention as a GDP-L-Galactose Guanyltransferase may be assessed for example by expressing such a sequence in bacteria and testing activity of the encoded protein as described in the Example section. Function of a variant may also be tested for its ability to alter GDP-L-Galactose Guanyltransferase activity or ascorbate content in plants, also as describe in the Examples section herein.

The function of a variant polynucleotide of the invention as a GDP-D-Mannose epimerase may be assessed for example by expressing such a sequence in bacteria and testing activity of the encoded protein as described in the Example section. Function of a variant may also be tested for its ability to alter GDP-D-Mannose epimerase activity or ascorbate content in plants, also as describe in the Examples section herein.

Polypeptide Variants

The term "variant" with reference to polypeptides encompasses naturally occurring, recombinantly and synthetically produced polypeptides. Variant polypeptide sequences preferably exhibit at least 50%, more preferably at least 51%, more preferably at least 52%, more preferably at least 53%, more preferably at least 54%, more preferably at least 55%, more preferably at least 56%, more preferably at least 57%, more preferably at least 58%, more preferably at least 59%, more preferably at least 60%, more preferably at least 61%, more preferably at least 62%, more preferably at least 63%, more preferably at least 64%, more preferably at least 65%, more preferably at least 66%, more preferably at least 67%, more preferably at least 68%, more preferably at least 69%, more preferably at least 70%, more preferably at least 71%, more preferably at least 72%, more preferably at least 73%, more preferably at least 74%, more preferably at least 75%, more preferably at least 76%, more preferably at least 77%, more preferably at least 78%, more preferably at least 79%, more preferably at least 80%, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, and most preferably at least 99% identity to a sequences of the present invention. Identity is found over a comparison window of at least 20 amino acid positions, preferably at least 50 amino acid positions, more preferably at least 100 amino acid positions, and most preferably over the entire length of a polypeptide of the invention.

Polypeptide sequence identity can be determined in the following manner. The subject polypeptide sequence is compared to a candidate polypeptide sequence using BLASTP (from the BLAST suite of programs, version 2.2.5 [November 2002]) in bl2seq, which is publicly available from NCBI via the internet. The default parameters of bl2seq are utilized except that filtering of low complexity regions should be turned off.

Polypeptide sequence identity may also be calculated over the entire length of the overlap between a candidate and subject polynucleotide sequences using global sequence alignment programs. EMBOSS-needle (available on the world-wide web at ebi<.>ac<.>uk/emboss/align/) and GAP (Huang, X. (1994) On Global Sequence Alignment. Computer Applications in the Biosciences 10, 227-235.) as discussed above are also suitable global sequence alignment programs for calculating polypeptide sequence identity.

A preferred method for calculating polypeptide % sequence identity is based on aligning sequences to be compared using Clustal X (Jeanmougin et al., 1998, *Trends Biochem. Sci.* 23, 403-5.)

Polypeptide variants of the present invention also encompass those which exhibit a similarity to one or more of the specifically identified sequences that is likely to preserve the functional equivalence of those sequences and which could not reasonably be expected to have occurred by random chance. Such sequence similarity with respect to polypeptides may be determined using the publicly available bl2seq program from the BLAST suite of programs (version 2.2.5 [November 2002]) from NCBI via the internet. The similarity of polypeptide sequences may be examined using the following unix command line parameters:

bl2seq -i peptideseq1 -j peptideseq2 -F F -p blastp

Variant polypeptide sequences preferably exhibit an E value of less than $1 \times 10^{-6}$ more preferably less than $1 \times 10^{-9}$, more preferably less than $1 \times 10^{-12}$, more preferably less than $1 \times 10^{-15}$, more preferably less than $1 \times 10^{-18}$, more preferably less than $1 \times 10^{-21}$, more preferably less than $1 \times 10^{-30}$, more preferably less than $1 \times 10^{-40}$, more preferably less than $1 \times 10^{-50}$, more preferably less than $1 \times 10^{-60}$, more preferably less than $1 \times 10^{-70}$, more preferably less than $1 \times 10^{-80}$, more preferably less than $1 \times 10^{-90}$ and most preferably $1 \times 10^{-100}$ when compared with any one of the specifically identified sequences.

The parameter -F F turns off filtering of low complexity sections. The parameter -p selects the appropriate algorithm for the pair of sequences. This program finds regions of similarity between the sequences and for each such region reports an "E value" which is the expected number of times one could expect to see such a match by chance in a database of a fixed reference size containing random sequences. For small E values, much less than one, this is approximately the probability of such a random match.

Conservative substitutions of one or several amino acids of a described polypeptide sequence without significantly altering its biological activity are also included in the invention. A skilled artisan will be aware of methods for making phenotypically silent amino acid substitutions (see, e.g., Bowie et al., 1990, Science 247, 1306).

The function of a polypeptide variant as a GDP-L-Galactose Guanyltransferase may be assessed by the methods described in the Example section herein.

The function of a polypeptide variant as a GDP-D-Mannose epimerase may be assessed by the methods described in the Example section herein.

Constructs, Vectors and Components Thereof

The term "genetic construct" refers to a polynucleotide molecule, usually double-stranded DNA, which may have inserted into it another polynucleotide molecule (the insert polynucleotide molecule) such as, but not limited to, a cDNA molecule. A genetic construct may contain the necessary elements that permit transcribing the insert polynucleotide molecule, and, optionally, translating the transcript into a polypeptide. The insert polynucleotide molecule may be derived from the host cell, or may be derived from a different cell or organism and/or may be a recombinant polynucleotide. Once inside the host cell the genetic construct may become integrated in the host chromosomal DNA. The genetic construct may be linked to a vector.

The term "vector" refers to a polynucleotide molecule, usually double stranded DNA, which is used to transport the genetic construct into a host cell. The vector may be capable of replication in at least one additional host system, such as *E. coli*.

The term "expression construct" refers to a genetic construct that includes the necessary elements that permit transcribing the insert polynucleotide molecule, and, optionally, translating the transcript into a polypeptide. An expression construct typically comprises in a 5' to 3' direction:

a) a promoter functional in the host cell into which the construct will be transformed,
b) the polynucleotide to be expressed, and
c) a terminator functional in the host cell into which the construct will be transformed.

The term "coding region" or "open reading frame" (ORF) refers to the sense strand of a genomic DNA sequence or a cDNA sequence that is capable of producing a transcription product and/or a polypeptide under the control of appropriate regulatory sequences. The coding sequence is identified by the presence of a 5' translation start codon and a 3' translation stop codon. When inserted into a genetic construct, a "coding sequence" is capable of being expressed when it is operably linked to promoter and terminator sequences.

"Operably-linked" means that the sequenced to be expressed is placed under the control of regulatory elements that include promoters, tissue-specific regulatory elements, temporal regulatory elements, enhancers, repressors and terminators.

The term "noncoding region" refers to untranslated sequences that are upstream of the translational start site and downstream of the translational stop site. These sequences are also referred to respectively as the 5' UTR and the 3' UTR. These regions include elements required for transcription initiation and termination and for regulation of translation efficiency.

Terminators are sequences, which terminate transcription, and are found in the 3' untranslated ends of genes downstream of the translated sequence. Terminators are important determinants of mRNA stability and in some cases have been found to have spatial regulatory functions.

The term "promoter" refers to nontranscribed cis-regulatory elements upstream of the coding region that regulate gene transcription. Promoters comprise cis-initiator elements which specify the transcription initiation site and conserved boxes such as the TATA box, and motifs that are bound by transcription factors.

A "transgene" is a polynucleotide that is taken from one organism and introduced into a different organism by transformation. The transgene may be derived from the same species or from a different species as the species of the organism into which the transgene is introduced.

A "transgenic plant" refers to a plant which contains new genetic material as a result of genetic manipulation or transformation. The new genetic material may be derived from a plant of the same species as the resulting transgenic plant or from a different species.

An "inverted repeat" is a sequence that is repeated, where the second half of the repeat is in the complementary strand, e.g.,

```
(5')GATCTA.......TAGATC(3')
(3')CTAGAT.......ATCTAG(5')
```

Read-through transcription will produce a transcript that undergoes complementary base-pairing to form a hairpin structure provided that there is a 3-5 bp spacer between the repeated regions.

The terms "to alter expression of" and "altered expression" of a polynucleotide or polypeptide of the invention, are intended to encompass the situation where genomic DNA corresponding to a polynucleotide of the invention is modified thus leading to altered expression of a polynucleotide or polypeptide of the invention. Modification of the genomic DNA may be through genetic transformation or other methods known in the art for inducing mutations. The "altered expression" can be related to an increase or decrease in the amount of messenger RNA and/or polypeptide produced and may also result in altered activity of a polypeptide due to alterations in the sequence of a polynucleotide and polypeptide produced.

The applicants have identified novel polynucleotides (SEQ ID NO:14 to 20) that encode novel polypeptides (SEQ ID NO:1 to 7 respectively) with activity as GDP-L-Galactose Guanyltransferases (also known as GDP-L-Galactose phosphorylase). The applicants have also shown that additional known, but uncharacterised sequences (polynucleotides of SEQ ID NO:21 to 24 encoding polypeptides of SEQ ID NO:8 to 11 respectively) with previously unknown activity, are also GDP-L-Galactose Guanyltransferase sequences.

The applicants have shown that all of the disclosed polypeptides sequences (SEQ ID NO:1 to 11) show significant sequence conservation and are variants of one another. The applicants have also identified two consensus polypeptide sequence motifs (SEQ ID NO:12 and 13) both of which are present in all of the GDP-L-Galactose Guanyltransferase sequences Similarly the applicants have shown that all of the disclosed polynucleotides sequences (SEQ ID NO:14 to 24) show significant sequence conservation and are variants of one another.

The invention provides genetic constructs, vectors and plants containing the polynucleotide sequences. The invention also provides plants comprising the genetic construct and vectors of the invention.

The invention provides plants altered in GDP-L-Galactose Guanyltransferase activity, relative to suitable control plants, and plants altered in ascorbic acid content relative to suitable control plants. The invention provides plants with increased GDP-L-Galactose Guanyltransferase activity and ascorbic content. The invention also provides methods for the production of such plants and methods of selection of such plants. The invention also provides methods for identifying herbicidal compounds which inhibit the activity of the GDP-L-Galactose Guanyltransferase polypeptides of the invention.

Suitable control plants include non-transformed plants of the same species or variety or plants transformed with control constructs. Suitable control plants do not include plants with mutations that result in altered, such as decreased, GDP-L-Galactose Guanyltransferase content, GDP-L-Galactose Guanyltransferase activity or ascorbate content.

The applicants have also identified novel polynucleotides (SEQ ID NO: 38 to 40) that encode novel polypeptides (SEQ ID NO: 25 to 27 respectively) that have activity as GDP-D-Mannose epimerases.

The applicants have shown that all of the epimerase disclosed polypeptides sequences (SEQ ID NO: 25 to 35) show significant sequence conservation and are variants of one another. The applicants have also identified two consensus polypeptide sequence motifs (SEQ ID NO: 36 and 37) both of which are present in all of the GDP-D-Mannose epimerase sequences.

Similarly the applicants have shown that all of the disclosed epimerase polynucleotides sequences (SEQ ID NO: 38 to 48) show significant sequence conservation and are variants of one another.

The invention provides genetic constructs, vectors and plants containing the novel polynucleotide sequences (SEQ ID NO: 38 to 40) or sequences encoding the novel polypeptide sequences (SEQ ID NO: 25 to 27). The invention also provides plants comprising the genetic construct and vectors of the invention.

The invention provides plants altered in GDP-D-Mannose epimerase activity, relative to suitable control plants, and plants altered in ascorbic acid content relative to suitable control plants. The invention provides plants with increased GDP-D-Mannose epimerase activity and ascorbic content.

The invention also provides methods for the production of such plants and methods of selection of such plants. The invention also provides methods for identifying herbicidal compounds which inhibit the activity of the GDP-D-Mannose epimerase polypeptides of the invention.

Suitable control plants include non-transformed plants of the same species or variety or plants transformed with control constructs.

In addition, the applicants have shown that expression of a combination of GDP-D-Mannose epimerase and GDP-L-Galactose Guanyltransferase in plants, results in an increase in ascorbate content in the plants that is larger than when either enzyme is individually expressed. In addition the applicants have shown, that when both enzymes over-expressed in a plant cell or plant, there is synergy. The increase in ascorbate when both enzymes are over-expressed together in a plant, is greater than the increase produced by over-expressing one enzyme added to the increase in ascorbate produced by over-expressing the other enzyme. The invention provides methods for producing plants with increased ascorbate, relative to control plants, based on expression of this combination. The invention provides plants produced by the method. The invention also provides plants transformed with both an epimerase and a transferase sequence.

Methods for Isolating or Producing Polynucleotides

The polynucleotide molecules of the invention can be isolated by using a variety of techniques known to those of ordinary skill in the art. By way of example, such polypeptides can be isolated through use of the polymerase chain reaction (PCR) described in Mullis et al., Eds. 1994 The Polymerase Chain Reaction, Birkhauser, incorporated herein by reference. The polypeptides of the invention can be amplified using primers, as defined herein, derived from the polynucleotide sequences of the invention.

Further methods for isolating polynucleotides of the invention include use of all, or portions of, the polypeptides having the sequence set forth herein as hybridization probes. The technique of hybridizing labelled polynucleotide probes to polynucleotides immobilized on solid supports such as nitrocellulose filters or nylon membranes, can be used to screen the genomic or cDNA libraries. Exemplary hybridization and wash conditions are: hybridization for 20 hours at 65° C. in 5.0×SSC, 0.5% sodium dodecyl sulfate, 1×Denhardt's solution; washing (three washes of twenty minutes each at 55° C.) in 1.0×SSC, 1% (w/v) sodium dodecyl sulfate, and optionally one wash (for twenty minutes) in 0.5×SSC, 1% (w/v) sodium dodecyl sulfate, at 60° C. An optional further wash (for twenty minutes) can be conducted under conditions of 0.1× SSC, 1% (w/v) sodium dodecyl sulfate, at 60° C.

The polynucleotide fragments of the invention may be produced by techniques well-known in the art such as restriction endonuclease digestion, oligonucleotide synthesis and PCR amplification.

A partial polynucleotide sequence may be used, in methods well-known in the art to identify the corresponding full length polynucleotide sequence. Such methods include PCR-based methods, 5'RACE (Frohman M A, 1993, Methods Enzymol. 218: 340-56) and hybridization-based method, computer/database-based methods. Further, by way of example, inverse PCR permits acquisition of unknown sequences, flanking the polynucleotide sequences disclosed herein, starting with primers based on a known region (Triglia et al., 1998, Nucleic Acids Res 16, 8186, incorporated herein by reference). The method uses several restriction enzymes to generate a suitable fragment in the known region of a gene. The fragment is then circularized by intramolecular ligation and used as a PCR template. Divergent primers are designed from the known region. In order to physically assemble full-length clones, standard molecular biology approaches can be utilized (Sambrook et al., Molecular Cloning: A Laboratory Manual, 2nd Ed. Cold Spring Harbor Press, 1987).

It may be beneficial, when producing a transgenic plant from a particular species, to transform such a plant with a sequence or sequences derived from that species. The benefit may be to alleviate public concerns regarding cross-species transformation in generating transgenic organisms. Additionally when down-regulation of a gene is the desired result, it may be necessary to utilise a sequence identical (or at least highly similar) to that in the plant, for which reduced expression is desired. For these reasons among others, it is desirable to be able to identify and isolate orthologues of a particular gene in several different plant species.

Variants (including orthologues) may be identified by the methods described.

Methods for Identifying Variants

Physical Methods

Variant polypeptides may be identified using PCR-based methods (Mullis et al., Eds. 1994 The Polymerase Chain Reaction, Birkhauser). Typically, the polynucleotide sequence of a primer, useful to amplify variants of polynucleotide molecules of the invention by PCR, may be based on a sequence encoding a conserved region of the corresponding amino acid sequence.

Alternatively library screening methods, well known to those skilled in the art, may be employed (Sambrook et aL, Molecular Cloning: A Laboratory Manual, 2nd Ed. Cold Spring Harbor Press, 1987). When identifying variants of the probe sequence, hybridization and/or wash stringency will typically be reduced relatively to when exact sequence matches are sought.

Polypeptide variants may also be identified by physical methods, for example by screening expression libraries using antibodies raised against polypeptides of the invention (Sambrook et aL, Molecular Cloning: A Laboratory Manual, 2nd Ed. Cold Spring Harbor Press, 1987) or by identifying polypeptides from natural sources with the aid of such antibodies.

Computer Based Methods

The variant sequences of the invention, including both polynucleotide and polypeptide variants, may also be identified by computer-based methods well-known to those skilled in the art, using public domain sequence alignment algorithms and sequence similarity search tools to search sequence databases (public domain databases include Genbank, EMBL, Swiss-Prot, PIR and others). See, e.g., Nucleic Acids Res. 29:1-10 and 11-16, 2001 for examples of online resources. Similarity searches retrieve and align target sequences for comparison with a sequence to be analyzed (i.e., a query sequence). Sequence comparison algorithms use scoring matrices to assign an overall score to each of the alignments.

An exemplary family of programs useful for identifying variants in sequence databases is the BLAST suite of programs (version 2.2.5 [November 2002]) including BLASTN, BLASTP, BLASTX, tBLASTN and tBLASTX, which are publicly available from the NCBI internet site or from the National Center for Biotechnology Information (NCBI), National Library of Medicine, Building 38A, Room 8N805, Bethesda, Md. 20894 USA. The NCBI server also provides the facility to use the programs to screen a number of publicly available sequence databases. BLASTN compares a nucleotide query sequence against a nucleotide sequence database. BLASTP compares an amino acid query sequence against a protein sequence database. BLASTX compares a nucleotide query sequence translated in all reading frames against a protein sequence database. tBLASTN compares a protein query sequence against a nucleotide sequence database dynamically translated in all reading frames. tBLASTX compares the six-frame translations of a nucleotide query sequence against the six-frame translations of a nucleotide sequence database. The BLAST programs may be used with default parameters or the parameters may be altered as required to refine the screen.

The use of the BLAST family of algorithms, including BLASTN, BLASTP, and BLASTX, is described in the publication of Altschul et al., Nucleic Acids Res. 25: 3389-3402, 1997.

The "hits" to one or more database sequences by a queried sequence produced by BLASTN, BLASTP, BLASTX, tBLASTN, tBLASTX, or a similar algorithm, align and identify similar portions of sequences. The hits are arranged in order of the degree of similarity and the length of sequence overlap. Hits to a database sequence generally represent an overlap over only a fraction of the sequence length of the queried sequence.

The BLASTN, BLASTP, BLASTX, tBLASTN and tBLASTX algorithms also produce "Expect" values for alignments. The Expect value (E) indicates the number of hits one can "expect" to see by chance when searching a database of the same size containing random contiguous sequences. The Expect value is used as a significance threshold for determining whether the hit to a database indicates true similarity. For example, an E value of 0.1 assigned to a polynucleotide hit is interpreted as meaning that in a database of the size of the database screened, one might expect to see 0.1 matches over the aligned portion of the sequence with a similar score simply by chance. For sequences having an E value of 0.01 or less over aligned and matched portions, the probability of finding a match by chance in that database is 1% or less using the BLASTN, BLASTP, BLASTX, tBLASTN or tBLASTX algorithm.

Multiple sequence alignments of a group of related sequences can be carried out with CLUSTALW (Thompson, J. D., Higgins, D. G. and Gibson, T. J. (1994) CLUSTALW: improving the sensitivity of progressive multiple sequence alignment through sequence weighting, positions-specific gap penalties and weight matrix choice. Nucleic Acids Research, 22:4673-4680, or on the internet, website of igbmc<.>ustrasbg<.>fr/Biolnfo/ClustalW/Top<.>html or T-COFFEE (Cedric Notredame, Desmond G. Higgins, Jaap Heringa, T-Coffee: A novel method for fast and accurate multiple sequence alignment, J. Mol. Biol. (2000) 302: 205-217)) or PILEUP, which uses progressive, pairwise alignments. (Feng and Doolittle, 1987, J. Mol. Evol. 25, 351).

Pattern recognition software applications are available for finding motifs or signature sequences. For example, MEME (Multiple Em for Motif Elicitation) finds motifs and signature sequences in a set of sequences, and MAST (Motif Alignment and Search Tool) uses these motifs to identify similar or the same motifs in query sequences. The MAST results are provided as a series of alignments with appropriate statistical data and a visual overview of the motifs found. MEME and MAST were developed at the University of California, San Diego.

PROSITE (Bairoch and Bucher, 1994, Nucleic Acids Res. 22, 3583; Hofmann et al., 1999, Nucleic Acids Res. 27, 215) is a method of identifying the functions of uncharacterized proteins translated from genomic or cDNA sequences. The PROSITE database (expasy<.>org/prosite website) contains biologically significant patterns and profiles and is designed so that it can be used with appropriate computational tools to assign a new sequence to a known family of proteins or to determine which known domain(s) are present in the sequence (Falquet et al., 2002, Nucleic Acids Res. 30, 235). Prosearch is a tool that can search SWISS-PROT and EMBL databases with a given sequence pattern or signature.

Methods for Isolating Polypeptides

The polypeptides of the invention, including variant polypeptides, may be prepared using peptide synthesis methods well known in the art such as direct peptide synthesis using solid phase techniques (e.g. Stewart et al., 1969, in Solid-Phase Peptide Synthesis, WH Freeman Co, San Francisco Calif., or automated synthesis, for example using an Applied Biosystems 431A Peptide Synthesizer (Foster City, Calif.). Mutated forms of the polypeptides may also be produced during such syntheses.

The polypeptides and variant polypeptides of the invention may also be purified from natural sources using a variety of techniques that are well known in the art (e.g. Deutscher, 1990, Ed, Methods in Enzymology, Vol. 182, *Guide to Protein Purification*).

Alternatively the polypeptides and variant polypeptides of the invention may be expressed recombinantly in suitable host cells and separated from the cells as discussed below.

Methods for Producing Constructs and Vectors

The genetic constructs of the present invention comprise one or more polynucleotide sequences of the invention and/or polynucleotides encoding polypeptides of the invention, and may be useful for transforming, for example, bacterial, fungal, insect, mammalian or plant organisms. The genetic constructs of the invention are intended to include expression constructs as herein defined.

Methods for producing and using genetic constructs and vectors are well known in the art and are described generally in Sambrook et al., Molecular Cloning: A Laboratory Manual, 2nd Ed. Cold Spring Harbor Press, 1987; Ausubel et al., Current Protocols in Molecular Biology, Greene Publishing, 1987).

Methods for Producing Host Cells Comprising Polynucleotides, Constructs or Vectors The invention provides a host cell which comprises a genetic construct or vector of the invention. Host cells may be derived from, for example, bacterial, fungal, insect, mammalian or plant organisms.

Host cells comprising genetic constructs, such as expression constructs, of the invention are useful in methods well known in the art (e.g. Sambrook et al., Molecular Cloning: A Laboratory Manual, 2nd Ed. Cold Spring Harbor Press, 1987; Ausubel et al., Current Protocols in Molecular Biology, Greene Publishing, 1987) for recombinant production of polypeptides of the invention. Such methods may involve the culture of host cells in an appropriate medium in conditions suitable for or conducive to expression of a polypeptide of the invention. The expressed recombinant polypeptide, which may optionally be secreted into the culture, may then be separated from the medium, host cells or culture medium by methods well known in the art (e.g. Deutscher, Ed, 1990, Methods in Enzymology, Vol 182, Guide to Protein Purification).

Methods for Producing Plant Cells and Plants Comprising Constructs and Vectors

The invention further provides plant cells which comprise a genetic construct of the invention, and plant cells modified to alter expression of a polynucleotide or polypeptide of the invention. Plants comprising such cells also form an aspect of the invention.

Alteration of GDP-L-Galactose Guanyltransferase activity and/or GDP-D-Mannose epimerase and/or ascorbic acid content may also be altered in a plant through methods of the invention. Such methods may involve the transformation of plant cells and plants, with a construct of the invention designed to alter expression of a polynucleotide or polypeptide which modulates GDP-L-Galactose Guanyltransferase activity and/or GDP-D-Mannose epimerase activity and/or ascorbic acid content in such plant cells and plants. Such methods also include the transformation of plant cells and plants with a combination of the construct of the invention and one or more other constructs designed to alter expression of one or more polynucleotides or polypeptides which modulate GDP-L-Galactose Guanyltransferase activity and/or GDP-D-Mannose epimerase activity and/or ascorbic acid content in such plant cells and plants.

Methods for transforming plant cells, plants and portions thereof with polypeptides are described in Draper et al., 1988, Plant Genetic Transformation and Gene Expression. A Laboratory Manual. Blackwell Sci. Pub. Oxford, p. 365; Potrykus and Spangenburg, 1995, Gene Transfer to Plants. Springer-Verlag, Berlin.; and Gelvin et al., 1993, Plant Molecular Biol. Manual. Kluwer Acad. Pub. Dordrecht. A review of transgenic plants, including transformation techniques, is provided in Galun and Breiman, 1997, Transgenic Plants. Imperial College Press, London.

Methods for Genetic Manipulation of Plants

A number of plant transformation strategies are available (e.g. Birch, 1997, Ann Rev Plant Phys Plant Mol Biol, 48, 297, Hellens R P, et al (2000) Plant Mol Biol 42: 819-32, Hellens R et al Plant Meth 1: 13). For example, strategies may be designed to increase expression of a polynucleotide/polypeptide in a plant cell, organ and/or at a particular developmental stage where/when it is normally expressed or to ectopically express a polynucleotide/polypeptide in a cell, tissue, organ and/or at a particular developmental stage which/when it is not normally expressed. The expressed polynucleotide/polypeptide may be derived from the plant species to be transformed or may be derived from a different plant species.

Transformation strategies may be designed to reduce expression of a polynucleotide/polypeptide in a plant cell, tissue, organ or at a particular developmental stage which/when it is normally expressed. Such strategies are known as gene silencing strategies.

Genetic constructs for expression of genes in transgenic plants typically include promoters for driving the expression of one or more cloned polynucleotide, terminators and selectable marker sequences to detest presence of the genetic construct in the transformed plant.

The promoters suitable for use in the constructs of this invention are functional in a cell, tissue or organ of a monocot or dicot plant and include cell-, tissue- and organ-specific promoters, cell cycle specific promoters, temporal promoters, inducible promoters, constitutive promoters that are active in most plant tissues, and recombinant promoters. Choice of promoter will depend upon the temporal and spatial expression of the cloned polynucleotide, so desired. The promoters may be those normally associated with a transgene of interest, or promoters which are derived from genes of other plants, viruses, and plant pathogenic bacteria and fungi. Those skilled in the art will, without undue experimentation, be able to select promoters that are suitable for use in modifying and modulating plant traits using genetic constructs comprising the polynucleotide sequences of the invention. Examples of constitutive plant promoters include the CaMV 35S promoter, the nopaline synthase promoter and the octopine synthase promoter, and the Ubi 1 promoter from maize. Plant promoters which are active in specific tissues, respond to internal developmental signals or external abiotic or biotic stresses are described in the scientific literature. Exemplary promoters are described, e.g., in WO 02/00894, which is herein incorporated by reference.

Exemplary terminators that are commonly used in plant transformation genetic construct include, e.g., the cauliflower mosaic virus (CaMV) 35S terminator, the *Agrobacterium tumefaciens* nopaline synthase or octopine synthase terminators, the *Zea mays* zein gene terminator, the *Oryza sativa* ADP-glucose pyrophosphorylase terminator and the *Solanum tuberosum* PI-II terminator.

Selectable markers commonly used in plant transformation include the neomycin phosphotransferase II gene (NPT II) which confers kanamycin resistance, the aadA gene, which confers spectinomycin and streptomycin resistance, the phosphinothricin acetyl transferase (bar gene) for Ignite (AgrEvo) and Basta (Hoechst) resistance, and the hygromycin phosphotransferase gene (hpt) for hygromycin resistance.

Use of genetic constructs comprising reporter genes (coding sequences which express an activity that is foreign to the host, usually an enzymatic activity and/or a visible signal (e.g., luciferase, GUS, GFP) which may be used for promoter expression analysis in plants and plant tissues are also contemplated. The reporter gene literature is reviewed in Herrera-Estrella et al., 1993, Nature 303, 209, and Schrott, 1995, In: Gene Transfer to Plants (Potrykus, T., Spangenberg. Eds) Springer Verlag. Berline, pp. 325-336.

Gene silencing strategies may be focused on the gene itself or regulatory elements which effect expression of the encoded polypeptide. "Regulatory elements" is used here in the widest possible sense and includes other genes which interact with the gene of interest.

Genetic constructs designed to decrease or silence the expression of a polynucleotide/polypeptide of the invention may include an antisense copy of a polynucleotide of the invention. In such constructs the polynucleotide is placed in an antisense orientation with respect to the promoter and terminator.

An "antisense" polynucleotide is obtained by inverting a polynucleotide or a segment of the polynucleotide so that the transcript produced will be complementary to the mRNA transcript of the gene, e.g.,

```
5'GATCTA 3'        3'CTAGAT 5'  (antisense strand)
(coding strand)

3'CUAGAU 5' mRNA   5'GAUCUCG 3' antisense RNA
```

Genetic constructs designed for gene silencing may also include an inverted repeat. An 'inverted repeat' is a sequence that is repeated where the second half of the repeat is in the complementary strand, e.g.,

```
5'-GATCTA.........TAGATC-3'

3'-CTAGAT.........ATCTAG-5'
```

The transcript formed may undergo complementary base pairing to form a hairpin structure. Usually a spacer of at least 3-5 bp between the repeated region is required to allow hairpin formation.

Another silencing approach involves the use of a small antisense RNA targeted to the transcript equivalent to an mi RNA (Llave et al., 2002, Science 297, 2053). Use of such small antisense RNA corresponding to polynucleotide of the invention is expressly contemplated.

The term genetic construct as used herein also includes small antisense RNAs and other such polypeptides effecting gene silencing.

Transformation with an expression construct, as herein defined, may also result in gene silencing through a process known as sense suppression (e.g. Napoli et al., 1990, Plant Cell 2, 279; de Carvalho Niebel et al., 1995, Plant Cell, 7, 347). In some cases sense suppression may involve overexpression of the whole or a partial coding sequence but may also involve expression of non-coding region of the gene, such as an intron or a 5' or 3' untranslated region (UTR). Chimeric partial sense constructs can be used to coordinately silence multiple genes (Abbott et al., 2002, Plant Physiol. 128(3): 844-53; Jones et al., 1998, Planta 204: 499-505). The use of such sense suppression strategies to silence the expression of a polynucleotide of the invention is also contemplated.

The polynucleotide inserts in genetic constructs designed for gene silencing may correspond to coding sequence and/or non-coding sequence, such as promoter and/or intron and/or 5' or 3' UTR sequence, or the corresponding gene.

Other gene silencing strategies include dominant negative approaches and the use of ribozyme constructs (McIntyre, 1996, Transgenic Res, 5, 257).

Pre-transcriptional silencing may be brought about through mutation of the gene itself or its regulatory elements. Such mutations may include point mutations, frameshifts, insertions, deletions and substitutions.

The following are representative publications disclosing genetic transformation protocols that can be used to genetically transform the following plant species: Rice (Alam et al., 1999, Plant Cell Rep. 18, 572); apple (Yao et al., 1995, Plant Cell Reports 14, 407-412); maize (U.S. Pat. Nos. 5,177,010 and 5,981,840); wheat (Ortiz et al., 1996, Plant Cell Rep. 15, 1996, 877); tomato (U.S. Pat. No. 5,159,135); potato (Kumar et al., 1996 Plant J. 9: 821); cassava (Li et al., 1996 Nat. Biotechnology 14, 736); lettuce (Michelmore et al., 1987, Plant Cell Rep. 6, 439); tobacco (Horsch et al., 1985, Science 227, 1229); cotton (U.S. Pat. Nos. 5,846,797 and 5,004,863); grasses (U.S. Pat. Nos. 5,187,073 and 6,020,539); peppermint (Niu et al., 1998, Plant Cell Rep. 17, 165); citrus plants (Pena et al., 1995, Plant Sci. 104, 183); caraway (Krens et al., 1997, Plant Cell Rep, 17, 39); banana (U.S. Pat. No. 5,792, 935); soybean (U.S. Pat. Nos. 5,416,011; 5,569,834; 5,824, 877; 556,304,455 and 5,968,830); pineapple (U.S. Pat. No. 5,952,543); poplar (U.S. Pat. No. 4,795,855); monocots in general (U.S. Pat. Nos. 5,591,616 and 6,037,522); *brassica* (U.S. Pat. Nos. 5,188,958; 5,463,174 and 5,750,871); cereals (U.S. Pat. No. 6,074,877); pear (Matsuda et al., 2005, Plant Cell Rep. 24(1):45-51); Prunus (Ramesh et al., 2006 Plant Cell Rep. 25(8):821-8; Song and Sink 2005 Plant Cell Rep. 2006; 25(2):117-23; Gonzalez Padilla et al., 2003 Plant Cell Rep. 22(1):38-45); strawberry (Oosumi et al., 2006 Planta. 223(6):1219-30; Folta et al., 2006 Planta April 14; PMID: 16614818), rose (Li et al., 2003), *Rubus* (Graham et al., 1995 Methods Mol Biol. 1995; 44:129-33), tomato (Dan et al., 2006, Plant Cell Reports V25:432-441), apple (Yao et al., 1995, *Plant Cell Rep.* 14, 407-412) and *Actinidia eriantha* (Wang et al., 2006, Plant Cell Rep. 25, 5: 425-31). Transformation of other species is also contemplated by the invention. Suitable methods and protocols are available in the scientific literature.

Several further methods known in the art may be employed to alter expression of a nucleotide and/or polypeptide of the invention. Such methods include but are not limited to Tilling (Till et al., 2003, Methods Mol Biol, 2%, 205), so called "Deletagene" technology (Li et al., 2001, Plant Journal 27(3), 235) and the use of artificial transcription factors such as synthetic zinc finger transcription factors. (e.g. Jouvenot et al., 2003, Gene Therapy 10, 513). Additionally antibodies or fragments thereof, targeted to a particular polypeptide may also be expressed in plants to modulate the activity of that polypeptide (Jobling et al., 2003, Nat. Biotechnol., 21(1), 35). Transposon tagging approaches may also be applied. Additionally peptides interacting with a polypeptide of the invention may be identified through technologies such as phase-display (Dyax Corporation). Such interacting peptides may be expressed in or applied to a plant to affect activity of a polypeptide of the invention. Use of each of the above approaches in alteration of expression of a nucleotide and/or polypeptide of the invention is specifically contemplated.

Methods of Selecting Plants

Methods are also provided for selecting plants with altered GDP-L-Galactose Guanyltransf erase activity and/or GDP-D-Mannose epimerase activity and/or ascorbate content. Such methods involve testing of plants for altered for the expression of a polynucleotide or polypeptide of the invention. Such methods may be applied at a young age or early developmental stage when the altered GDP-L-Galactose Guanyltransf erase activity and/or GDP-D-Mannose epimerase activity and/or ascorbate content may not necessarily be easily measurable.

The expression of a polynucleotide, such as a messenger RNA, is often used as an indicator of expression of a corresponding polypeptide. Exemplary methods for measuring the expression of a polynucleotide include but are not limited to Northern analysis, RT-PCR and dot-blot analysis (Sambrook et al., Molecular Cloning: A Laboratory Manual, 2nd Ed. Cold Spring Harbor Press, 1987). Polynucleotides or portions of the polynucleotides of the invention are thus useful as probes or primers, as herein defined, in methods for the identification of plants with altered levels of GDP-L-Galactose Guanyltransf erase activity, GDP-D-Mannose epimerase activity, or ascorbate. The polynucleotides of the invention may be used as probes in hybridization experiments, or as primers in PCR based experiments, designed to identify such plants.

Alternatively antibodies may be raised against polypeptides of the invention. Methods for raising and using antibodies are standard in the art (see for example: Antibodies, A Laboratory Manual, Harlow A Lane, Eds, Cold Spring Harbour Laboratory, 1998). Such antibodies may be used in methods to detect altered expression of polypeptides which modulate flower size in plants. Such methods may include ELISA (Kemeny, 1991, A Practical Guide to ELISA, NY Pergamon Press) and Western analysis (Towbin & Gordon, 1994, J Immunol Methods, 72, 313).

These approaches for analysis of polynucleotide or polypeptide expression and the selection of plants with altered GDP-L-Galactose Guanyltransferase activity, GDP-D-Mannose epimerase activity, or ascorbate content are useful in conventional breeding programs designed to produce varieties with altered GDP-L-Galactose Guanyltransferase activity, GDP-D-Mannose epimerase activity, or ascorbate content.

Plants

The term "plant" is intended to include a whole plant, any part of a plant, propagules and progeny of a plant.

The term 'propagule' means any part of a plant that may be used in reproduction or propagation, either sexual or asexual, including seeds and cuttings.

The plants of the invention may be grown and either self-ed or crossed with a different plant strain and the resulting hybrids, with the desired phenotypic characteristics, may be identified. Two or more generations may be grown to ensure that the subject phenotypic characteristics are stably maintained and inherited. Plants resulting from such standard breeding approaches also form an aspect of the present invention.

Alteration of GDP-L-Galactose Guanyltransferase activity, and/or CDP-D-Mannose epimerase activity, and/or ascorbic acid content may also be altered in a plant through methods of the invention. Such methods may involve the transformation of plant cells and plants, with a construct of the invention designed to alter expression of a polynucleotide or polypeptide which modulates GDP-L-Galactose Guanyltransferase activity and/or GDP-D-Mannose epimerase activity, and/or ascorbic acid content in such plant cells and plants. Such methods also include the transformation of plant cells and plants with a combination of the construct of the invention and one or more other constructs designed to alter expression of one or more polynucleotides or polypeptides which modulate GDP-L-Galactose Guanyltransferase activity, and/or GDP-D-Mannose epimerase activity, and/or ascorbic acid content in such plant cells and plants.

Methods for Extracting and Measuring Ascorbate from Plants

Methods are also provided for the production of ascorbate by extraction of ascorbate from a plant of the invention. Ascorbate may be extracted from plants as follows:

Frozen tissue samples are ground to a fine powder in a Cryomill at liquid nitrogen temperature. About 200 mg of frozen powdered tissue is then suspended in 4 volumes of 0.5

N HCl containing 4 mM TCEP (Pierce), vortexed for 20 sec and incubated in a heating block for 2 h at 40° C. TCEP is used in the extraction solution, because it is more effective reducing agent under acidic conditions than DTT, ensuring that all of vitamin C is in the ascorbic acid reduced form. The extract is centrifuged at 4° C. and twenty µL of the supernatant is injected into a 7.8×300 mm Aminex HPX-87H HPLC column (BioRad). The column is run with 2.8 mM $H_2SO_4$, at a flow rate of 0.6 mL/min and the amount of ascorbic acid is calculated from absorbance at 245 nm (retention time 9.6 min), using ascorbic acid (Sigma St Louis) as a standard. The peak is authenticated as ascorbic acid by showing that it is completely degraded by ascorbate oxidase at pH 5.5.

This method may be up-scaled for larger scale ascorbate extraction using approaches well-known to those skilled in the art.

Herbicide Screening Methods

Any compound may be screened as a candidate herbicide using the methods of the invention. Examples of compounds that could be screened include inorganic and organic compounds such as, but not limited to, amino acids, peptides, proteins, nucleotides, nucleic acids, glyco-conjugates, oligosaccharides, lipids, alcohols, thiols, aldehydes, alkylators, carbonic ethers, hydrazides, hydrazines, ketones, nitrils, amines, sulfochlorides, triazines, piperizines, sulphonamides and the like. Preferably compound libraries are screened in the methods of the invention. Methods for synthesising and screening compound libraries are known to those skilled in the art. See for example, U.S. Pat. Nos. 5,463,564; 5,574, 656; 5,684,711; and 5,901,069, the contents of which are incorporated by reference.

Methods for identifying compounds which bind to such polypeptides are known and described for example in WO 03/077648. Methods for measuring the activity of polypeptides of the invention are described in the Examples provided herein.

This invention may also be said broadly to consist in the parts, elements and features referred to or indicated in the specification of the application, individually or collectively, and any or all combinations of any two or more said parts, elements or features, and where specific integers are mentioned herein which have known equivalents in the art to which this invention relates, such known equivalents are deemed to be incorporated herein as if individually set forth.

EXAMPLES

The invention will now be illustrated with reference to the following non-limiting example.

Example 1

Identification of a Putative Homologue of Arabidopsis thaliana At4g 26850 from Kiwi Fruit Blast searches using At4g26850 of a Horticultural and Food Research Institute of New Zealand proprietary *Actinidia* EST database revealed 120 ESTs with homology to AT4g26850 out of over 132,000 ESTs. These came from a range of tissues including petals, fruit, buds and meristems and leaves. The applicants selected EST 319998 from an *Actinidia chinensis* young fruit library. The two *Arabidopsis* proteins and the kiwifruit protein showed 71 to 75 percent identity to each other. The sequences were aligned using ClustalX (Clustal X (Jeanmougin et al., 1998) as shown in FIGS. 1A-1B.

Example 2

Use of Bioinformatic Analysis to Reveal a Putative function for At 4g 26850 as a GDP-L-Galactose-guanyltransferase Similarity and Motif Searches.

PSI Blast (Altschul et al., 1997; Schaffer et al., 2001) was run for 6+ iterations and identified genes further examined for their annotations. Motif searching was done using MEME (Bailey and Elkan, 1994) using a set of genes as input selected (At4g26850 and HIT members including GalT).

Through BLASTp searches for genes encoding proteins similar to the predicted protein sequence of the uncharacterised *Arabidopsis* gene At4g26850 the applicants initially detected only other plant genes that were also annotated as similar to At4g26850. However, further into the list of matched genes were members of the Interpro HIT family (IPR001310) of proteins, that are characterised as nucleotide-binding proteins and hydrolases. The family includes diadenosine tetraphosphate (Ap4A) hydrolase and GalT (D-Galactose-1-phosphate uridyl transferase, class I) (Brenner, 2002). For example, a rat gene belonged to this GalT family showed an expect value of 1E-37 with 30% identity and 48% similarity over 364 residues of At4g26850. These HIT proteins are usually characterised by the motif HXHXH (where X is a hydrophobic amino acid) although the GalT subgroup (also interpro IPR001937) has the related motif HXHXQ. GalT has been shown to be a member of the HIT family of proteins based on structural analysis (Brenner et al., 1997).

The applicants refined this search using PSI-BLAST (Altschul et al., 1997; Schaffer et al., 2001) and a major category of aligned sequences were members of the HIT family. For example, after 6 interactions, the first non-plant aligned sequence was a human gene (Genbank 34527348) with 28% identity, 47% similarity (out of 373 residues) and an expect value of 2E-99. Similar alignments were found for genes from a range of species from Mammalia, all with E values <2E-93 and descriptions Diadenosine tetraphosphate (Ap4A) hydrolase and other HIT family hydrolases. At lower similarity, the applicants observed a group of ATP adenylyltransferase-like proteins (expect >E-70). At higher expect (>1E-10) values the applicants then found further genes with HIT annotations.

The applicants then used a selected group of interpro IPRO01310 members of the HIT group, plus AT4g26850, At4g26850 and EST 319998 (see table 1) and searched for motifs using the MEME website (meme<.>sdsc<.>edu) (Bailey and Elkan, 1994). The applicants identified six significant motifs that were present in all five plant sequences. Five of these motifs that were present in four animal sequences and the remaining animal sequence had four motifs (Table 1). This shows that these proteins are clearly related and belong to the HIT superfamily.

TABLE 1

Motifs present in a selected range of homologues to kiwifruit est 319998.

| Genbank Accession | Description | E-value | Length | Motiv (in linear order) | | | | | |
|---|---|---|---|---|---|---|---|---|---|
| | | | | 2 | 5 | 3 | 1 | 6 | 4 |
| At4g26850 | *Arabidopsis thaliana* VTC2 | 9.00E–228 | 442 | + | + | + | + | + | + |
| At5g55120 | *Arabidopsis thaliana* | 1.10E–226 | 431 | + | + | + | + | + | + |
| 319998 | Kiwfruit enzyme used in this paper | 3.30E–225 | 450 | + | + | + | + | + | + |
| ABA96028 | Rice VTC2 like | 3.30E–210 | 438 | + | + | + | + | + | + |
| NP_915203 | Rice unnamed protein | 2.40E–156 | 352 | + | + | + | + | + | + |
| BAC85370 | *Homo sapiens* unnamed protein HIT | 4.30E–140 | 385 | + | + | + | + | | + |
| BAE25508 | *Mus musculus* unnamed protein HIT | 5.00E–139 | 386 | + | + | + | + | | + |
| XP_689388 | *Danio rerio* VTC2 like | 3.70E–138 | 343 | + | + | + | + | | + |
| AAI21599 | *Xenopus tropicalis* unnamed protein | 7.60E–135 | 399 | + | + | + | + | | + |
| CAG03444 | *Tetraodon nigroviridis* unnamed protein | 1.80E–102 | 288 | | + | + | + | | + |

Motif 1 included the diagnostic pattern HxHxQ (of HxHxH) (see FIGS. 1A-1B). Interestingly, the GalT subfamily of the HIT family also shares this HxHxQ pattern, although were unable to discover motifs in common with this sequence.

From these bioinformatics analyses, it appeared possible that the gene responsible for the ascorbic acid mutant VTC2 (At4g26850) and its kiwifruit homologue encoded a guanyltransferase.

Example 3

Expression of Kiwifruit GDP-L-Galactose Guanyltransferase EST 319998 and *Arabidopsis thaliana* At4g26850 in *E. coli* and Characterization of Enzymatic Activity Materials and Methods Expression of genes in *E. coli*. The EST 319998 from young fruit of *Actinidia chinensis* and At4g26850 were each cloned into pET30A (Novagene, USA), their sequence checked and expressed in *E. coli*. The N terminal $His_6$ tag was used to purify the protein. An empty vector control was expressed and purified in parallel. Techniques were essentially as described earlier (Laing et al., 2004). In much of this work the His-protein was further purified on a 5 mL HiTrap Q FF column (GE Healthcare), and identical results were obtained with both preparations.

Coupling Enzymes:

L-Galactose dehydrogenase (Gen Bank accession AA018639 (EST 56121), 1.5 ug/assay was cloned from an EST derived from an *A. deliciosa* (kiwifruit) shoot bud library with a maltose binding protein presequence and assayed as described previously (Laing et al., 2004). L-Galactose-1-Phosphate phosphatase was cloned from *Arabidopsis thaliana* (At3g02870, 3.1 ug/assay) and assayed as described (Laing et al., 2004). GDP-D-Mannose 3',5'-Epimerase (198296) was cloned from dormant kiwifruit (*A. deliciosa*) buds three days after hydrogen cyanamide treatment and assayed as described (Wolucka et al., 2001). The former two enzymes are highly specific as to their substrates (Laing et al., 2004; Laing et al., 2004).

GDP-L-Galactose (~50% pure, contaminated with the breakdown products GDP and L-Galactose-1-Phosphate as shown by HPLC and LCMS) and L-Galactose-1-Phosphate were purchased from Glycoteam, Hamburg, Germany. The applicants found GDP-L-Galactose was extremely acid labile and the applicants did not attempt to purify it further. Other biochemicals were purchased from Sigma.

Activity Assays:

The assay for GDP-L-Galactose-1-Phosphate Guanyltransferase was run in 20 mM TrisCl, pH 8.0, GDP-L-Galactose, with 1 mM D-Mannose-1-Phosphate. GDP-L-Galactose was either used directly from the Glycoteam product (in which case high backgrounds were observed due to contaminating L-Galactose-1-Phosphate) or GDP-L-Galactose was generated using the epimerase. In the latter case, 0.21 mg of epimerase was incubated with GDP-D-Mannose in 20 mM Tris Cl pH 8 in a total volume of 400 µL (see Wolucka et al., 2001) for 30 minutes at 20 C and then used directly in the assay at a 1 to 20 dilution. Assays were either terminated after 10 minutes by heating to 100 C for three minutes, or directly coupled to the phosphatase and L-Galactose dehydrogenase to measure product formation during the assay. Heat terminated assays were cooled on ice, centrifuged to remove precipitated protein and L-Galactose assayed using the coupling enzymes described above (see also (Laing et al., 2004)). Assays for L-Galactose were linear with added L-Galactose-1-Phosphate over the range measured. Backgrounds were run using the empty vector control, which gave the same result as a boiled enzyme control.

As an alternative assay, LCMS was used to identify the forward reaction described above as well measure as the reverse pyrophosphorylase reaction where GTP (1 mM) and L-Galactose-1-Phosphate were incubated as above and the formation of GDP-L-Galactose followed. GDP-D-Mannose and GDP-L-Galactose were separated by HPLC before MS. LC-MS employed an LTQ linear ion trap mass spectrometer fitted with an ESI interface (ThermoQuest, Finnigan, San Jose, Calif., USA) coupled to an EttanTM MDLC (GE Healthcare Bio-Sciences). Separation of GDP-D-Mannose and GDP-L-Galactose was achieved using a Hypercarb column (Thermo Electron, USA), 100×2.1 mm maintained at 40 C. Solvents were (A) 50 mM ammonium acetate and (B) acetonitrile and the flow rate was 200 uL/min. The initial mobile phase, 5% B was held for 3 min, then ramped linearly to 20% B at 11 min, held for 5 min, then ramped linearly to 70% B at 19 min and held for 5 min before resetting to the original conditions. Retention times for GDP-D-Mannose and GDP-L-Galactose were 16.8 min and 17.5 min, respectively.

MS data was acquired in the negative mode using both a selective reaction monitoring (SRM) method SRM m/z 604>m/z 344, 362, 424, 442 and a selected ion monitoring (SIM) method SIM m/z 604. This SIM method monitors only the (M-H)— ion for GDP-D-Mannose and GDP-L-Galactose while the SRM method monitors the distinctive daughter ions formed by fragmenting the precursor ion (M-H)— for both compounds. Both methods maximise sensitivity by screening out any chemical noise from other compounds present. The ESI voltage, capillary temperature, sheath gas pressure, sweep gas and auxiliary gas were set at −10 V, 350° C., 25 psi, 3 psi, and 3 psi, respectively. Separation of D-Mannose-1-Phosphate and L-Galactose-1-Phosphate was achieved isocratically using a Hypercarb column (Thermo Electron, USA), 100×2.1 mm maintained at 40° C. Solvents were (A) 20 mM ammonium acetate and (B) methanol and the flow rate was 200 uL/min. Using a mobile phase of 2% B the retention times for D-Mannose-1-Phosphate and L-Galactose-1-Phosphate were 4.3 min and 4.9 min, respectively. MS data was acquired in the negative mode using both a selective reaction monitoring (SRM) method SRM m/z 259>m/z 79, 97 and a selected ion monitoring (SIM) method SIM m/z 259.

The transferase activity in tobacco leaves was measured by extracting liquid nitrogen ground leaves in approximately five volumes of TrisCI pH 8.0, 2 mM DTT and 1 mM EDTA, centrifuging, desalting the supernatant using a NAP desalting column equilibrated with the same buffer and assaying the enzyme using the coupled assay described above. Protein in the extracts was measured using the Biorad Bradford Coumassie assay (Bradford, 1976) using BSA as a standard.

Results

The applicants expressed these genes in E. coli in the pET30 vector and purified the protein using the His tag and a Ni chelating column. The protein appeared on an SDS gel at ~55KD and constituted about 90% of the protein isolated. Controls containing the empty pET30 vector were also treated in the same manner.

The applicants used two assays to characterise the enzyme, using two sources of the substrate GDP-L-Galactose. The first assay used the E. coli expressed coupling enzymes L-Galactose-1-Phosphate phosphatase and L-Galactose dehydrogenase. The phosphatase is highly specific to L-Galactose-1-Phosphate, otherwise only significantly dephosphorylating myo-inositol-1-P (Laing et al., 2004). The dehydrogenase is specific to L-Galactose, not reacting with D-Mannose or D-Galactose or a range of other sugars (Gatzek et al., 2002; Laing et al., 2004) except for L-Gulose. With this latter substrate, L-Galactose dehydrogenase showed approximately 2.5 fold higher maximum velocity and 30 times the $K_M$ (substrate) resulting in about 8% activity with L-Gulose compared with L-Galactose at limiting substrate concentrations. Consequently, our coupled assay would measure primarily L-Galactose and also L-Gulose. The applicants either measured the product formed by adding the coupling enzymes in the assay and measuring the time course of NADH formed, or by stopping the reaction after 10 minutes by boiling for 3 minutes and centrifuging. To this latter fixed time assay, the applicants then either adding coupling enzymes to measure L-Galactose production or using the LCMS to measure the products. The LCMS was used only to confirm the results of the coupled enzyme reaction and to measure the reverse reaction.

Figure 3:
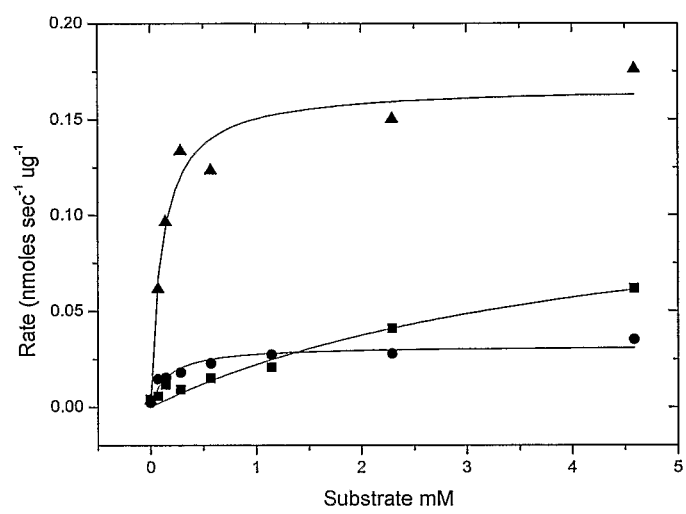
FIG. 3 shows the response of the enzyme, EST319998 (SEQ ID NO:1, amino acid sequence, SEQ ID NO:14, nucleotide sequence) to potential guanyl acceptors. Assays were carried out using the continuous coupled assay with varying concentrations of inorganic phosphate (square), inorganic pyrophosphate (circle) or D-Mannose-1-P (triangle) as the guanyl acceptor. The vamax values were 0.12±0.03, 0.032±0.002 and 0.17±0.009 nmoles $sec^{-1}$ $ug^{-1}$ protein for the substrates phosphate, pyrophosphate and D-mannose-1-P respectively. $K_M$ values were 4.4±2, 0.16±0.05 and 0.11±0.03 mM respectively. Assays were carried out three times with similar results.

Using both the LCMS and the coupled reaction to measure products it was clear that E. coli expressed kiwifruit EST 319998 and At4g26 could catalyse the conversion of GDP-L-Galactose to L-Galactose-1-P. Depending on enzyme concentration, time courses were linear for up to ~10 minutes and the rate of reaction was linear with added enzyme over the range assayed (data not shown). No reaction occurred in the presence of boiled enzyme or empty vector (FIG. 2). D-mannose-1-P was a better acceptor for the guanyl moiety than phosphate or pyrophosphate, but reaction was seen with these latter two compounds at physiological concentrations of these substrates (FIG. 3). No NAD reduction activity was seen with GDP-D-Mannose without epimerase or with either substrate and without the coupling enzymes (data not shown). Reactions using commercially purchased GDP-L-Galactose-1-Phosphate had high backgrounds because of the contaminating L-Galactose-1-Phosphate and were assayed using the fixed time procedure. This substrate showed a slightly higher rate than that seen with the epimerase generated substrate. Other guanyl acceptors were tested and the enzyme was found to accept a wide range of Hexose-1-P substrates although D-Glucose-6-P reacted at only about 25% the rate of the best acceptors (Table 2). The reaction did not require Mg (data not shown) although Mg was included in the coupled assay as the phosphatase required Mg.

Coupled assays using the expressed Arabidopsis sequence (At4g26850) also showed transferase activity (data not shown) with similar properties to the kiwi fruit EST 319998.

TABLE 2

Effect of different sugar phosphates to act as guanyl acceptors for the transferase activity. Enzyme was assayed using the epimerase generated substrate and the continuous coupled assay with other conditions as described in the methods. N = 6.
(time courses 319998 11 10 06.xls)

| Substrate | Rate nmoles/ sec/ug protein | Std Error | % of D-mannose-1P |
|---|---|---|---|
| D-Glucose-1-P | 0.35 | 0.036 | 106 |
| D-Glucose-6-P | 0.08 | 0.002 | 24 |
| D-Glucose-1-P | 0.24 | 0.05 | 74 |
| L-Myoinositol-1-P | 0.42 | 0.07 | 126 |
| D-Galactose-1-P | 0.38 | 0.01 | 113 |
| D-Mannose-1-P | 0.33 | 0.07 | 100 |

The products of the reaction were confirmed using LC mass spectrometry to be L-Galactose-1-Phosphate (Table 3). This involved separation of the products of the reaction using liquid chromatography, which separated L-Galactose from D-Mannose and GDP-L-Galactose from GDP-D-Mannose and confirmation of the identity of the products by their measured mass. Little to no back reaction was detected.

TABLE 3

Measurement of transferase activity by LCMS. Activity was measured using a fixed time assay at either high or low protein concentration and different acceptor and substrate combinations as shown in the table. Assays were killed by boiling and aliquots either measured using coupling enzymes or by LCMS.

| | | | nmoles/sec/ug protein | |
|---|---|---|---|---|
| substrate | acceptor | ug protein | Coupled assay | LCMS |
| GDPMan/epim | Mannose-1-P | 0.057 | 0.012 | 0.0094 |
| GDPMan/epim | None | 1.14 | 0.00038 | 0.00031 |
| GDPMan/epim | none | 0.057 | 0.00012 | 0 |
| GDPGal | Mannose-1-P | 0.057 | 0.017 | high BG |
| GDPMan/epim | PPi | 1.14 | 0.00095 | 0.0013 |
| GDPMan/epim | PPi | 0.057 | 0.0026 | 0.0031 |
| GDPMan | Gal1P | 1.14 | nm | 0 |
| GDPMan | Gal1P | 0.057 | nm | 0 |
| GTP | Gal1P | 1.14 | nm | 0 |
| GTP | Gal1P | 0.057 | nm | 0 | nm is not measured.

Example 4

Increasing GDP-L-Galactose Guanyltransferase Activity and Ascorbate Production in Plants by Expression of Transferase Polynucleotides of the invention Transient Transformation of Tobacco Leaves.

Tobacco (*Nicotiana benthamiana*) was transiently transformed with *Agrobacterium* containing the kiwifruit gene for GDP-L-Galactose Guanyltransferase (EST 319998) cloned in pGreen (Hellens et al., 2000) mixed with *Agrobacterium* containing the gene for the silencing suppressor P19 as previously described (Hellens et al., 2005). Controls were run using *Agrobacterium* containing P19 in pGreen alone. Tobacco leaves were harvested 9 days after transformation and frozen in liquid nitrogen.

Ascorbate Measurement.

Ascorbate was extracted as described previously in metaphosphoric acid without reducing agent (Davey et al., 2003; Rassam and Laing, 2005).

Figure 4:
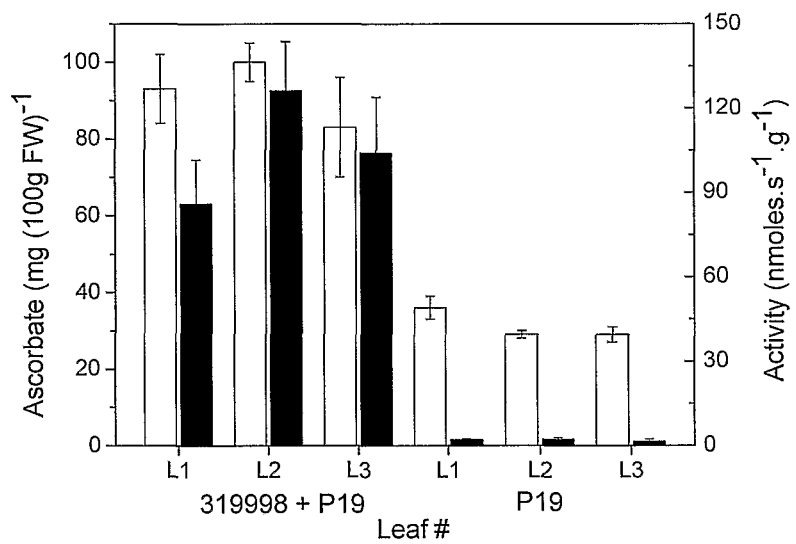
FIG. 4 shows the effect of transiently expressed kiwi fruit EST 319998 (SEQ ID NO: 1) on ascorbate content and enzyme activity in tobacco leaves. See methods for details. White bars represent ascorbate concentration (expressed on a fresh weight basis) in the leaf, black bars the GDP-L-Galactose Guanyltransferase activity (expressed on a g protein basis). L1, L2 and L3 represent three leaves from the top that were injected. Error bars are the standard error of the mean (n=3 to 6).
Figure 5:
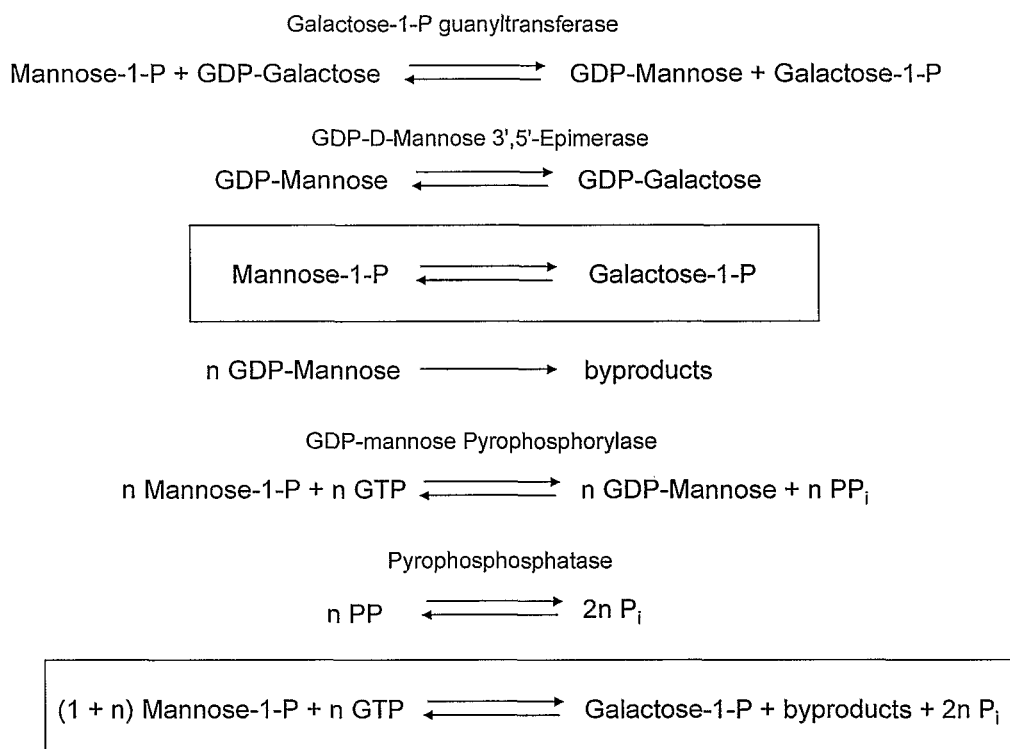
FIG. 5 shows reactions converting D-Mannose-1-Phosphate to L-Galactose-1-Phosphate.

When tobacco leaves were transiently transformed with an *Agrobacterium* clone containing kiwifruit EST 319998 in the vector pGreen mixed with P19 as a suppressor of silencing, measurable activity could be measured in the extract of the leaves (FIG. 4A). Little activity (~2% of transformed) was seen in the tobacco leaves transformed only with P19 alone (FIG. 4). The low enzyme level in the controls is typical of other enzymes in the L-Galactose pathway of ascorbate biosynthesis (W Laing, unpublished observations).

The activity was present in a range of leaves of different ages injected with *Agrobacterium*. The same 319998 transformed leaves showed a highly significant three fold increase in ascorbate compared to the control leaves (FIG. 4).

Example 5

Gene Expression Analysis of Ascorbate Pathway Genes in Kiwi Fruit Shows that High Expression of GDP-L-Galactose Guanyltransferase is Associated with Increased Ascorbate Production Gene expression of genes for committed steps in the L-galactose pathway of ascorbate biosynthesis from developing fruit of two species of kiwifruit were measured using qPCR. *Actinidia deliciosa* has 100 mg/100 g FW ascorbate and *A. eriantha* has 10 fold more ascorbate. The only step showing a strong increase in gene expression, in parallel with the increase in ascorbate, is the gene for the GDP-L-Galactose-1-Phosphate transferase (Table 1s). This supports the observation that over-expression of this same gene in tobacco leaves results in a three-fold increase in ascorbate levels.

TABLE 1s

Relative level of expression of L-galactose ascorbic acid biosynthetic pathway members compared to a housekeeper gene (PPPRSA; expression set to 1) in Hayward and *A. eriantha* fruit at four weeks after anthesis.

| Enzyme | Substrate | *A. deliciosa* (Hayward) | *A. eriantha* (11-4-18a) | Fold change |
|---|---|---|---|---|
| GDP-mannose-3',5'-epimerase | GDP-mannose | 1.8 | 2.4 | 1.3 |
| GDP-L-Galactose Guanyltransferase | GDP-L-galactose | 4.1 | 31.2* | 7.6 |
| L-galactose-1-phosphate phosphatase | L-galactose-1-phosphate | 0.7 | 1.8* | 2.6 |
| L-galactose dehydrogenase | L-galactose | 1.5 | 1.2* | 0.8 |
| L-galactono-1,4-lactone dehydrogenase | L-galactono-1,4-lactone | Not assayed | Not assayed | — |
| L-ascorbic acid in 4 weeks after anthesis fruit (mg/100 mg fresh weight) | L-ascorbic acid | 100 | 1085 | 10.9 |

*significantly different to Hayward (p = 0.05)

Example 6

Variants of kiwifruit EST for GDP-L-Galactose Guanyltransferase

Several variant sequences of the kiwi fruit EST for GDP-L-Galactose Guanyltransferase disclosed were identified essentially as described in Example 2, either from Genbank or from the proprietary HortResearch EST databases of *Actinidia* and *Malus* sequences. All eleven protein sequences were aligned by Clustal X (Jeanmougin et al., 1998, *Trends Biochem. Sci.* 23, 403-5.) as shown in FIGS. 6A-6C.

The sequences all show regions of strong homology and include two completely conserved motifs: AINVSPIEYGH-VLLIP (SEQ ID NO:12) and GYNSLGAFATINHLHFQAY (SEQ ID NO:13) that were identified visual inspection of the aligned sequences.

When either sequence (SEQ ID NO:12 or 13) was used in a blastp (Altschul, S. F., Gish, W., Miller, W., Myers, E. W. & Lipman, D. J. (1990) "Basic local alignment search tool." J. Mol. Biol. 215:403-410) search of the GenBank translated protein database (NCBI, internet) on 3rd March 2007, no further plant sequences that contained the perfectly conserved motifs, were identified, other than those disclosed in the sequence listing of the present application.

Either sequence motif therefore appears to be diagnostic of the GDP-L-Galactose Guanyltransferase of the invention or used in the methods of the invention.

The % identity between all polypeptide sequences is shown in FIG. 7.

Figure 8:
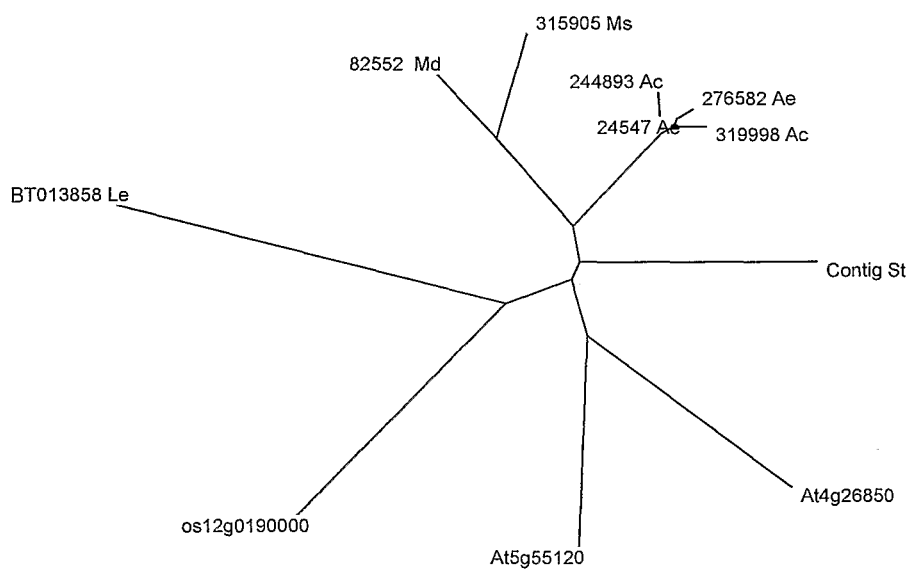
FIG. 8 shows an unrooted tree of sequences aligned above showing clustering of the different species sequences.

FIG. 8, shows the unrooted tree where the apple and kiwifruit sequences cluster together and the rice and tomato sequences are more isolated. Sequences were identified using Blastp searches of Genbank and HortResearch databases and aligned using ClustalX and visualised using Treeview.

The DNA sequences for the coding region of each polynucleotide sequence were also aligned using Clustal X as shown in FIGS. 9A-9H. The % sequence identity between all of the polynucleotide coding sequences is shown if FIG. 10.

Example 7

Identification of a GDP-D-Mannose epimerase sequence from kiwifruit and apple

Figure 11A:
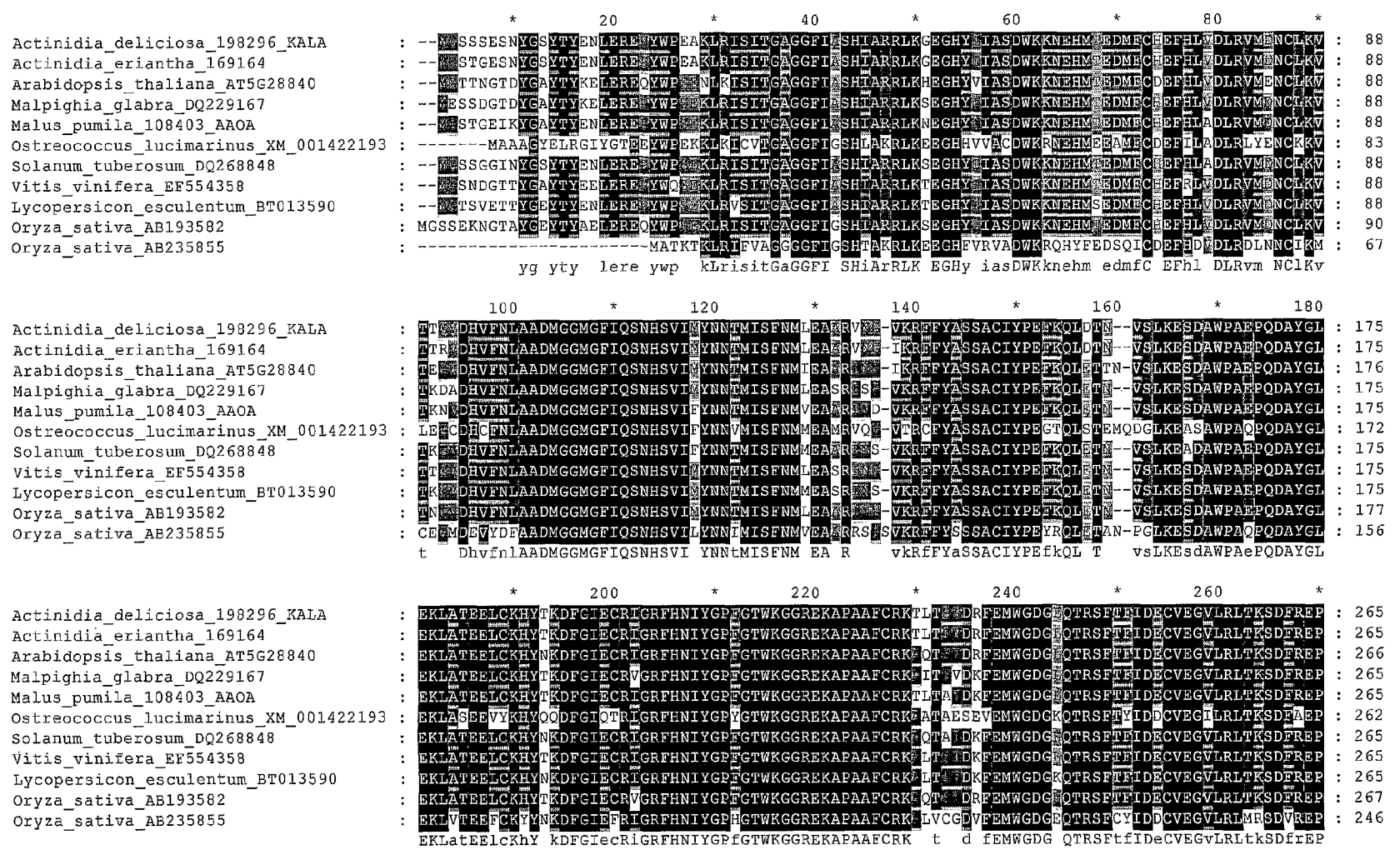
Figure 11B:
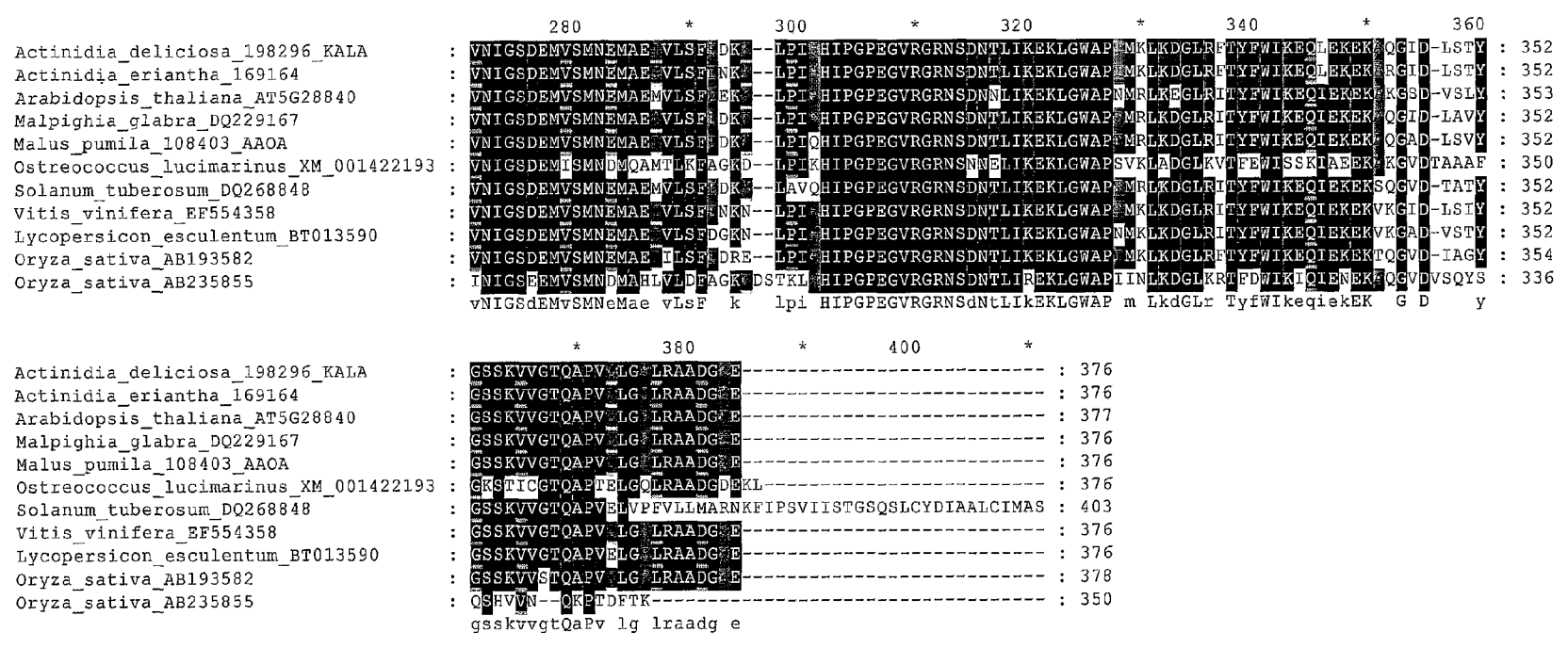

The applicants performed Blast searches of Horticultural and Food Research Institute of New Zealand proprietary *Actinidia* and *Malus* EST databases to identify ESTs with homology to At5g28840. The applicants selected three sequences, two from kiwifruit (169164_KUFA: SEQ ID NO: 38 and 1998296_KALA: SEQ ID NO: 39) and one from apple (108403_AAOA: SEQ ID NO: 40) as potential GDP-D-Mannose epimerase encoding sequences. The corresponding polypeptide sequences are shown in SEQ ID NOs: 25, 26 and 27 respectively. The applicants also identified other GDP-D-Mannose epimerase sequences from public databases with the polynucleotide sequences of SEQ ID NO: 42 to 48, encoding the polypeptide sequences of SEQ ID NO: 29 to 35. The polypeptide sequences were aligned using ClustaLX (Clustal X (Jeanmougin et al., 1998) as shown in FIGS. 11A-11B. The level of % sequence identity between the sequences is shown in FIG. 12.

The applicants also identified two sequence motifs (SEQ ID NO: 36 and 37) that are completely conserved in all of the aligned sequences.

Example 8

Expression of kiwifruit GDP-D-Mannose epimerase sequence in *E. coli* and characterization of enzymatic activity Materials and Methods The 198296_KALA sequence (SEQ ID NO: 39) of *Actinidia deliciosa* was cloned using standard techniques into pET30A (Novagene, USA), and expressed in *E. colI*. The N terminal $His_6$ tag was used to purify the protein. An empty vector control was expressed and purified in parallel. Techniques were essentially as described earlier (Laing et al., 2004). The His-protein was desalted on a 5 mL HiTrap Q FF column (GE Healthcare).

Methods were as described in Example 3.

Enzyme activity was assayed as described (Wolucka et al., 2001).

0.21 mg of epimerase was incubated with GDP-D-Mannose in 20 mM Tris Cl pH 8 in a total volume of 400 µL (see Wolucka et al., 2001) for 30 minutes at 20° C. The products of the reaction were separated by HPLC to identify newly synthesised GDP-L-Galactose, the product of the reaction. Typically a reverse phase column was used.

Results

The protein appeared on an SDS gel at ~50 KD and constituted about 90% of the protein isolated. Controls containing the empty pET30 vector were also treated in the same manner.

Example 9

Increasing GDP-D-Mannose epimerase activity and Ascorbate Production in Plants by Expression of the Epimerase Polynucleotide of the Invention Transient Transformation of Tobacco Leaves.

Tobacco (*Nicotiana benthamiana*) was transiently transformed with separate *Agrobacterium* cultures containing the kiwifruit genes for GDP-D-Mannose epimerase (169164_KUFA: SEQ ID NO: 38) and/or GDP-L-Galactose Guanyltransferase (EST 319998_Ac SEQ ID NO: 14) cloned in pGreen (Hellens et al., 2000) mixed with *Agrobacterium* containing the gene for the silencing suppressor P19 as previously described (Hellens et al., 2005). Controls were run using *Agrobacterium* containing P19 in pGreen alone. Tobacco leaves were harvested 9 days after transformation and frozen in liquid nitrogen.

Ascorbate Measurement.

Ascorbate was extracted as described previously in metaphosphoric acid without reducing agent (Davey et al., 2003; Rassam and Laing, 2005).

When tobacco leaves were transiently transformed with an *Agrobacterium* clone containing kiwifruit EST 319998 in the vector pGreen mixed with P19 as a suppressor of silencing, measurable activity could be measured in the extract of the leaves. Little activity (~2% of transformed) was seen in the tobacco leaves transformed only with P19 alone.

Leaf infiltration with *Agrobacterium* containing the pGreen vector carrying the epimerase, or P19, or injection with water containing only aceto-syringinone, had no effect on leaf ascorbate levels. Infiltration of tobacco leaves with *Agrobacterium* carrying the gene for the transferase resulted in ascorbate levels in the tobacco leaf rising ~3 fold as previously shown (Laing et al., 2007). However, injection of the leaf with a mixture of epimerase and transferase raised the ascorbate levels another 2 fold (Table 2) for a total of ~6 fold, as shown in Table 2 below.

TABLE 2

Leaf ascorbate levels found after transient expression of the genes for the GDP-L-Galactose Guanyl Transferase (319998), or the GDP-D-Mannose Epimerase (169164) either separately or together. In every case, the gene for the viral suppressor protein, P19, was also expressed with the other two genes. Controls either used P19 alone, or the aceto-syringone *Agrobacterium* infection agent alone (identical results). Data represents the mean of three plants, three leaves per plant (9 measurements, except the controls where the data represent 18 measurements).

| Treatment | average | SE | Relative amount of ascorbate |
| --- | --- | --- | --- |
| Controls | 34.2 | 2.7 | 1.0 |
| Epimerase | 33.3 | 2.3 | 1.0 |
| Transferase | 102.0 | 7.4 | 3.0 |
| Epim + Trans | 194.2 | 22.6 | 5.7 |

These experiments show that over-expression of the epimerase sequence of the invention can increase ascorbate production in plants. This is demonstrated by a further two-fold increase in ascorbate levels in plants already increased (3-fold) in ascorbate, due to over expression of a GDP-L-Galactose Guanyltransferase.

Example 10

Varying the Ratio of the Transferase and Epimerase Sequences of the Invention Expressed in Plants to Manipulate Ascorbate Production Transient Over Expression in Tobacco.

The transient expression system (Hellens et al., 2005) was used to transform *Nicotiana benthamiana* by injecting suspended *Agrobacterium* cultures containing the gene of interest. The GDP-Mannose epimerase was the EST 169164 from *A. eriantha* and the transferase was the EST 319998 from *A. chinensis*.

The leaves were then harvested and ascorbate levels measured. In addition in some cases, enzyme activity was also measured.

Methods used were as described in Example 9.

Interaction and synergy between the epimerase and transferase sequences of the invention was studied by a titration of both the genes injected into tobacco leaves as mixtures. The volumes of transferase (EST 319998) and epimerase (169164) containing *Agrobacterium* suspensions were varied from zero added, 0.01, 0.1 and 1 mL in all combinations of each enzyme with the other. P19 was also added in all cases to avoid gene silencing.

Figure 15:
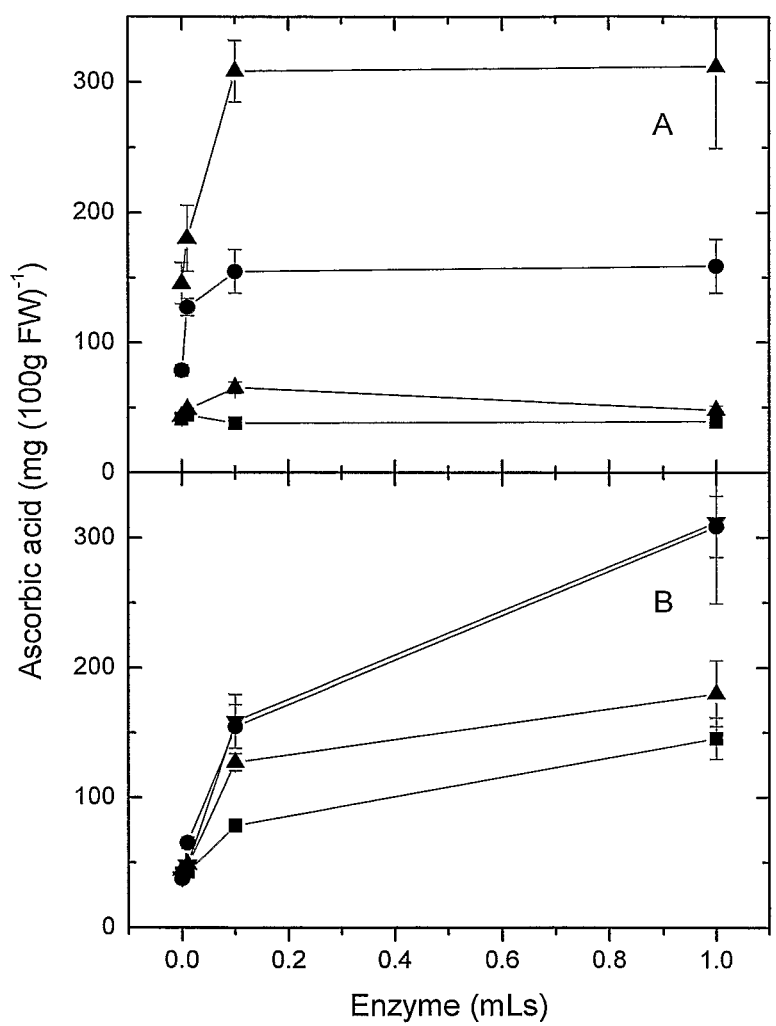
FIG. 15 shows ascorbate in tobacco leaves as a function of the amount of GDP-L-Galactose guanyltransferase (319998) and epimerase (169164) injected into the leaf. Tobacco was transiently transformed with *Agrobacterium* containing one of either of the two genes. Different amounts were mixed before injection, a constant amount of *Agrobacterium* containing P19 added and the volume made up to a constant level for all mixtures. Ascorbate was measured after ~8 days. Titration of epimerase (A) and transferase (B) is shown at different levels of the other gene.

The results (FIG. 15) show that increased levels of the epimerase in the absence of the transferase has no effect of leaf ascorbate. However, in the presence of transferase, ascorbate responds to increased epimerase in a curve that saturates. On the other hand, as the transferase is increased in the presence of different amounts of epimerase, saturation is not reached. This data shows that the two genes act synergistically, but that greater volumes of transferase is needed to reach maximal concentrations of leaf ascorbate than epimerase. In this experiment, the applicants observed a 7.5 fold increase in leaf ascorbate at the maximal amounts of the two enzymes used. Fitting a simple hyperbolic model to the data predicts more than 9 fold increase of leaf ascorbate at saturating transferase and epimerase.

Example 11

Expression of an Epimerase Sequence of the Invention in Combination with a Variety of Transferase Sequences of the Invention Increases Ascorbate Production in Plants Ascorbate production was measured in tobacco leaves transiently transformed (by methods described in Example 8) with either a kiwifruit (319998_Ac), tomato (BT013858_Lc) and apple (82552_Md) GDP-L-Galactose transferase gene in the presence of the kiwifruit epimerase (169164). The kiwifruit 319998 transformation was also performed in three different vector construct/*Agrobacterium* strain combinations. The results are shown in FIGS. 16A-16B. For all the species shown, the transferase increased ascorbate levels in the leaf, and adding epimerase further increased the ascorbate in a synergistic fashion. EST 319998 usually was the most effective gene at doing this. All three different vectors and *Agrobacterium* clones worked similarly.

The applicants also checked that two specialised constructs of 319998.

The first was the 319998 transferase cloned into pGreenII 0229 62-SK (Hellens R P, Edwards E A, Leyland N R, Bean S, Mullineaux P M (2000) pGreen: a versatile and flexible binary Ti vector for *Agrobacterium*-mediated plant transformation. Plant Mol. Biol. 42: 819-32) which provided bialaphos resistance. This construct can be used to produce doubly transformed plants with both transferase and epimerase in the same plant, but with two different selectable markers, allowing selection of both genes. The results in FIGS. 17A-17B show that this construct is fully functional. This experiment also compared the kiwifruit (169164) and apple (108403) epimerases and showed that both were effective in synergistically increasing ascorbate with the transferase.

The second construct included a His tag in front of the 31998 transferase sequence gene in pGreen, in order to facilitate purification of the protein from a plant source. When transiently transformed into tobacco leaves, this was active in increasing leaf ascorbate (FIGS. 17A-17B).

Example 12

Expression of the Transferase Sequence of the Invention in Transgenic Plants Increases Ascorbate Production The applicants generated *Arabidopsis* plants transformed by floral dipping with *Agrobacterium* containing the transferase 319998 in pGreen (Clough S J and Bent A F, 1998. Floral dip: a simplified method for *Agrobacterium*-mediated transformation of *Arabidopsis thaliana*. Plant J 16:735-7430. Seed was collected and kanamycin resistant lines selected. 44 kanamycin resistant lines were recovered, of which 19 were tested for the kanamycin resistance segregation ratio. This data is shown in FIGS. 18A-18B.

On the basis of this data the following lines were selected for further study; 2, 6, 8, 16, 21, 34, 37, 40, 41, 43, 44 three of which had only one insert.

In the second generation, up to 12 plants from each line, selected from the kanamycin plates, were grown to a standard size of a complete rosette of leaves in the glasshouse and ascorbate measured (FIG. 19). Of the 11 lines selected on the basis of Kanamycin resistance, 9 showed significantly increased ascorbate. The increased ascorbate ranged up to over 4 times the normal level of ascorbate in *Arabidopsis* leaves. Some plants showed reduced ascorbate compared to the control plants (eg lines 8 and 16) suggesting gene silencing was occurring. These lines had a mixture of high and low ascorbate plants within the line.

Selected plants from the second generation were taken on to the next generation. Plants were checked by growing on Kanamycin plates for presence of the selectable marker and were shown to be kanamycin resistant. Again the applicants observed plants with leaf ascorbate over 4 times the control level (FIGS. 20A-20B), but again within a line with high ascorbate progeny, there were always plants with high and low ascorbate in spite of all plants coming from a high ascorbate kanamycin resistant parent. Again this suggests gene silencing is occurring. This is especially the case as the levels of ascorbate fell below the leaf ascorbate in untransformed plants also suggesting the endogenous gene was also silenced. Regions of complete sequence identity are found, when the 319998 and *Arabidopsis* sequence is aligned (data not shown). This could account for the apparent silencing seen.

The applicants checked the third generation plants for gene expression of the 319998 (FIG. 21). In every case, plants with high ascorbate relative to controls also showed enhanced expression of 319998. In one case, a plant with a low ascorbate (no plants in this line had high ascorbate) also showed high expression of 319998. This may be interpreted to mean that during gene silencing in this line, some gene expression, as measured by our qPCR method, was occurring.

Example 13

Expression of the Transferase Gene of the Invention in Transgenic Tobacco Results in Increase Ascorbate Content Tobacco was transformed with 319998 and Kanamycin resistant lines selected. These plants were transferred to soil and grown until several leaves were expanded. Ascorbate and gene expression was measured in these leaves (FIG. 22). Many lines showed gene expression, and two lines also showed a significant increase in leaf ascorbate of 60%.

*Nicotiana tabacum* 'Samsun' was transformed using *Agrobacterium tumefaciens* strain GV101 carrying the pHex vector containing EST 319998. Methods used were as described by Guerineau et al (1990), except kanamycin was used instead of sulphonamide selective agents at the rate of 100 mg.L-1.

Example 14

Expression of Transferase and Epimerase Sequences of the Invention in *E. coli*, and Demonstration of Enzyme Activity Various transferase genes were cloned into the pET30 vector and transformed into *E. coli*. Protein with a His-Trap tag was expressed, extracted, purified by metal ion chromatography and desalted using a G25 column, Activity was measured using a coupled assay where assays were run using a GDP-D-Mannose/GDP-L-Galactose mix (generated by mixing expressed GDP-Mannose epimerase protein from EST 198296 with GDP-mannose) as the substrate. This substrate mix was incubated with the transferase being assayed, with an excess of coupling enzymes (more epimerase, L-Galactose phosphatase, L-Galactose dehydrogenase) and 50 mM Bis tris propane, pH 7.5, 0.5 mM NAD and 2.5 mM $MgCl_2$. Assays were linear over time and amount of transferase added.

Measured activity was in the range of 0.1 to 0.7 nmoles/mg protein/sec (FIG. 23). All expressed genes tested showed transferase activity. In addition, *E coli* expressed ESTs 198296 and 108403 also showed epimerase activity (data not shown) as measured by HPLC and direct coupling assay.

It is not the intention to limit the scope of the invention to the abovementioned examples only. As would be appreciated by a skilled person in the art, many variations are possible without departing from the scope of the invention.

REFERENCES

Agius F, Gonzalez-Lamothe R, Caballero J L, Munoz-Blanco J, Botella M A, Valpuesta V (2003) Engineering increased vitamin C levels in plants by overexpression of a D-galacturonic acid reductase. Nat Biotechnol 21: 177-181.

Altschul S F, Madden T L, Schaffer A A, Zhang J, Zhang Z, Miller W, Lipman D J (1997) Gapped BLAST and PSI-BLAST: a new generation of protein database search programs. Nucleic Acids Res 25: 3389-3402.

Bailey T L, Elkan C (1994) Fitting a mixture model by expectation maximization to discover motifs in biopolymers. In Proceedings of the Second International Conference on Intelligent Systems for Molecular Biology. AAAI Press, Menlo Park, Calif., pp 28-36.

Bartoli C G, Guiamet J J, Kiddie G, Pastori G M, Di Cagno R, Theodoulou F L, Foyer C H (2005) Ascorbate content of wheat leaves is not determined by maximal l-galactono-1, 4-lactone dehydrogenase (GalLDH) activity under drought stress. Plant, Cell and Environment 28: 1073-1081.

Bradford M (1976) A rapid and sensitive method for the quantitation of microgram quantities of protein utilizing the principal of protein-dye binding. Analytical Biochemistry 72: 248-254.

Brenner C (2002) Hint, Fhit, and GalT: Function, Structure, Evolution, and Mechanism of Three Branches of the Histidine Triad Superfamily of Nucleotide Hydrolases and Transferases. Biochemistry 41: 9003-9014.

Brenner C, Garrison P, Gilmour J, Peisach D, Ringe D, Petsko G A, Lowenstein J M (1997) Crystal structures of HINT demonstrate that histidine triad proteins are GalT-related nucleotide-binding proteins. Nat Struct Biol 4: 231-238.

Chen Z, Young T E, Ling J, Chang S C, Gallie D R (2003) Increasing vitamin C content of plants through enhanced ascorbate recycling. Proc Natl Acad Sci 100: 3525-3530.

Conklin P L (1998) Vitamin C: a new pathway for an old antioxidant. Trends Plant Sci 3: 329-330.

Conklin P L, Gatzek S, Wheeler G L, Dowdle J, Raymond M J, Rolinski S, Isupoy M, Littlechild J A, Smirnoff N (2006) *Arabidopsis thaliana* VTC4 Encodes L-Galactose-1-P Phosphatase, a Plant Ascorbic Acid Biosynthetic Enzyme. J. Biol. Chem. 281: 15662-15670.

Conklin P L, Norris S R, Wheeler G L, Williams E H, Smirnoff N, Last R L (1999) Genetic evidence for the role of GDP-mannose in plant ascorbic acid (vitamin C) biosynthesis. Proc Natl Acad Sci USA 96: 4198-4203.

Conklin P L, Saracco S A, Norris S R, Last R L (2000) Identification of Ascorbic Acid-Deficient *Arabidopsis thaliana* Mutants. Genetics 154: 847-856.

Davey M W, Dekempeneer E, Keulemans J (2003) Rocket-powered high-performance liquid chromatographic analysis of plant ascorbate and glutathione. Analytical Biochemistry 316: 74-81.

Ferguson A R, MacRae E A (1992) Vitamin C in *Actinidia*. Acta Horticulture 297: 481-487.

Gatzek S, Wheeler G L, Smirnoff N (2002) Antisense suppression of l-galactose dehydrogenase in *Arabidopsis thaliana* provides evidence for its role in ascorbate synthesis and reveals light modulated l-galactose synthesis. Plant Journal 30: 541-553.

Guerineau F, Brooks L, Meadows J, Lucy A, Robinson C, Mullineaux P (1990) Sulfonamide resistance gene for plant transformation. Plant Molecular Biology 15: 127-136

Hellens R, Allan A, Friel E, Bolitho K, Grafton K, Templeton M, Karunairetnam S, Gleave A, Laing W (2005) Transient expression vectors for functional genomics, quantification of promoter activity and RNA silencing in plants. Plant Methods 1: 13.

Hellens R P, Edwards E A, Leyland N R, Bean S, Mullineaux P M (2000) pGreen: a versatile and flexible binary Ti vector for *Agrobacterium*-mediated plant transformation. Plant Mol Biol 42: 819-832.

Holden H M, Rayment I, Thoden J B (2003) Structure and Function of Enzymes of the Leloir Pathway for Galactose Metabolism. J. Biol. Chem. 278: 43885-43888.

Imai T, Karita S, Shiratori G, Hattori M, Nunome T, Oba K, Hirai M (1998) L-galactono-gamma-lactone dehydrogenase from sweet potato: Purification and cDNA sequence analysis. Plant and Cell Physiology 39: 1350-1358.

Ishikawa T, Dowdle J, Smirnoff N (2006) Progress in manipulating ascorbic acid biosynthesis and accumulation in plants. Physiologia Plantarum 126: 343-355.

Jander G, Norris S R, Rounsley S D, Bush D F, Levin I M, Last R L (2002) *Arabidopsis* Map-Based Cloning in the Post-Genome Era. Plant Physiol. 129: 440-450.

Jeanmougin F, Thompson J D, Gouy M, Higgins D G, Gibson T J (1998) Multiple sequence alignment with Clustal X. Trends Biochem Sci 23: 403-405.

Keller R, Renz F S, Kossmann J (1999) Antisense inhibition of the GDP-mannose pyrophosphorylase reduces the ascorbate content in transgenic plants leading to developmental changes during senescence. Plant J 19: 131-141.

Laing W A, Barraclough D, Bulley S, Cooney J, Wright M, Macrae E (2004) A specific L-Galactose-1-Phosphate phosphatase on the path to ascorbate biosynthesis. Proceedings of the National Academy of Sciences (USA) 101: 16976-16981.

Laing W A, Frearson N, Bulley S, MacCrae E (2004) Kiwifruit L-Galactose dehydrogenase; molecular, biochemical and physiological aspects of the enzyme. Functional Plant Biology 31: 1015-1025.

Laing, W. A., Wright, M., Cooney, J. & Bulley, S. (2007) *Proceedings of the National Academy of Sciences (USA)* 104:9534-9.

Lorence A, Chevone B I, Mendes P, Nessler C L (2004) myo-lnositol Oxygenase Offers a Possible Entry Point into Plant Ascorbate Biosynthesis. Plant Physiol. 134: 1200-1205.

Piro G, Zuppa A, Dalessandro G, Northcote D H (1993) Glucomannan synthesis in pea epicotyls: the mannose and glucose transferases. Planta 190: 206-220.

Radzio J A, Lorence A, Chevone B I, Nessler C L (2003) L-Gulono-1,4-lactone oxidase expression rescues vitamin C-deficient *Arabidopsis* (vtc) mutants. Plant Mol Biol 53: 837-844.

Rassam M, Laing W (2005) Variation in Ascorbic Acid and Oxalate Levels in the Fruit of *Actinidia chinensis* Tissues and Genotypes. J. Agric. Food Chem. 53: 2322-2326.

Redgwell R J (1983) Composition of *Actinidia* mucilage. Phytochemistry 22: 951-956.

Redgwell R J, Melton L D, Brasch D J (1990) Cell wall changes in kiwifruit following post harvest ethylene treatment. Phytochemistry 29: 399-407.

Schaffer A A, Aravind L, Madden T L, Shavirin S, Spouge J L, Wolf Y I, Koonin E V, Altschul S F (2001) Improving the accuracy of PSI-BLAST protein database searches with composition-based statistics and other refinements. Nucleic Acids Res 29: 2994-3005.

Seifert G J (2004) Nucleotide sugar interconversions and cell wall biosynthesis: how to bring the inside to the outside. Current Opinion in Plant Biology 7: 277-284.

Smirnoff N (2001) L-ascorbic acid biosynthesis. Vitam Norm 61: 241-266.

Tokunaga T, Miyahara K, Tabata K, Esaka M (2005) Generation and properties of ascorbic acid-overproducing transgenic tobacco cells expressing sense RNA for I-galactono-1,4-lactone dehydrogenase. Planta 220: 854-863.

Valpuesta V, Botella M A (2004) Biosynthesis of L-ascorbic acid in plants: new pathways for an old antioxidant. Trends in Plant Science 9: 573-577.

Watanabe K, Suzuki K, Kitamura S (2006) Characterization of a GDP-d-mannose 3",5"-epimerase from rice. Phytochemistry 67: 338-346.

Wheeler G L, Jones M A, Smirnoff N (1998) The biosynthetic pathway of vitamin C in higher plants. Nature 393: 365-369.

Wolucka B A, Davey M W, Boerjan W (2001) A high-performance liquid chromatography radio method for determination of L-ascorbic acid and guanosine 5'-diphosphate-1-galactose, key metabolites of the plant vitamin C pathway. Anal Biochem 294: 161-168.

Wolucka B A, Persiau G, Van Doorsselaere J, Davey M W, Demol H, Vandekerckhove J, Van Montagu M, Zabeau M, Boerjan W (2001) Partial purification and identification of GDP-mannose 3",5"-epimerase of *Arabidopsis thaliana*, a key enzyme of the plant vitamin C pathway. Proceedings of the National Academy of Sciences of the United States of America 98: 14843-14848.

Wolucka B A, Van Montagu M (2003) GDP-Mannose 3',5'-Epimerase Forms GDP-L-gulose, a Putative Intermediate for the de Novo Biosynthesis of Vitamin C in Plants. J. Biol. Chem. 278: 47483-47490.

SUMMARY OF SEQUENCES

| SEQ ID NO. | Comment | Molecule type | Species | Reference |
| --- | --- | --- | --- | --- |
| 1 | transferase | polypeptide | *Actinidia chinensis* | EST 319998_Ac |
| 2 | transferase | polypeptide | *Malus x domesticus* | EST 82552_Md |
| 3 | transferase | polypeptide | *Actinidia chinensis* | EST 244893_Ac |
| 4 | transferase | polypeptide | *Actinidia eriantha* | EST 24547_Ae |
| 5 | transferase | polypeptide | *Actinidia eriantha* | EST 276582_Ae |
| 6 | transferase | polypeptide | *Malus sieboldii* | EST 315905_Ms |
| 7 | transferase | polypeptide | *Solanum tuberosum* | contig_st |
| 8 | transferase | polypeptide | *Arabidopsis thaliana* | At4g26850 |
| 9 | transferase | polypeptide | *Arabidopsis thaliana* | At5g55120 |
| 10 | transferase | polypeptide | *Lycopersicon esculentum* | BTO13858_Le |
| 11 | transferase | polypeptide | *Oryza sativa* | Os12g0190000 |
| 12 | transferase | polypeptide | — | conserved transferase motif 1 |
| 13 | transferase | polypeptide | — | conserved transferase motif 2 |
| 14 | transferase | polynucleotide | *Actinidia chinensis* | EST 319998_Ac |
| 15 | transferase | polynucleotide | *Malus x domesticus* | EST 82552_Md |
| 16 | transferase | polynucleotide | *Actinidia chinensis* | EST 244893_Ac |
| 17 | transferase | polynucleotide | *Actinidia eriantha* | EST 24547_Ae |
| 18 | transferase | polynucleotide | *Actinidia eriantha* | EST 276582_Ae |
| 19 | transferase | polynucleotide | *Malus sieboldii* | EST 315905_Ms |
| 20 | transferase | polynucleotide | *Solanum tuberosum* | contig_st |
| 21 | transferase | polynucleotide | *Arabidopsis thaliana* | At4g26850 |

-continued

SUMMARY OF SEQUENCES

| SEQ ID NO. | Comment | Molecule type | Species | Reference |
|---|---|---|---|---|
| 22 | transferase | polynucleotide | *Arabidopsis thaliana* | At5g55120 |
| 23 | transferase | polynucleotide | *Lycopersicon esculentum* | BTO13858_Le |
| 24 | transferase | polynucleotide | *Oryza sativa* | Os12g0190000 |
| 25 | epimerase | polypeptide | *Actinidia eriantha* | 169164_KUFA |
| 26 | epimerase | polypeptide | *Actinidia deliciosa* | 198296_KALA |
| 27 | epimerase | polypeptide | *Malus x domesticus* | 108403_AAOA |
| 28 | epimerase | polypeptide | *Arabidopsis thaliana* | At5g28840 |
| 29 | epimerase | polypeptide | *Malpighia glabra* | DQ229167 |
| 30 | epimerase | polypeptide | *Oryza sativa* | AB193582 |
| 31 | epimerase | polypeptide | *Oryza sativa* | AB235855 |
| 32 | epimerase | polypeptide | *Ostreococcus lucimarinus* | XM_001422193 |
| 33 | epimerase | polypeptide | *Solanum tuberosum* | DQ268848 |
| 34 | epimerase | polypeptide | *Vitis vinifera* | EF554358 |
| 35 | epimerase | polypeptide | *Lycopersicon esculentum* | BT013590 |
| 36 | epimerase | polypeptide | — | conserved epimerase motif 1 |
| 37 | epimerase | polypeptide | — | conserved epimerase motif 2 |
| 38 | epimerase | polynucleotide | *Actinidia eriantha* | 169164_KUFA |
| 39 | epimerase | polynucleotide | *Actinidia deliciosa* | 198296_KALA |
| 40 | epimerase | polynucleotide | *Malus x domesticus* | 108403_AAOA |
| 41 | epimerase | polynucleotide | *Arabidopsis thaliana* | At5g28840 |
| 42 | epimerase | polynucleotide | *Malpighia glabra* | DQ229167 |
| 43 | epimerase | polynucleotide | *Oryza sativa* | AB193582 |
| 44 | epimerase | polynucleotide | *Oryza sativa* | AB235855 |
| 45 | epimerase | polynucleotide | *Ostreococcus lucimarinus* | XM_001422193 |
| 46 | epimerase | polynucleotide | *Solanum tuberosum* | DQ268848 |
| 47 | epimerase | polynucleotide | *Vitis vinifera* | EF554358 |
| 48 | epimerase | polynucleotide | *Lycopersicon esculentum* | BT013590 |
| 49 | transferase | polypeptide | *Arabidopsis thaliana* | At5g18200 |
| 50 | transferase | polypeptide | *Mus musculus* | Mm_74150758 |
| 51 | transferase | polynucleotide | *Malus xdomestica* | 82552_AARA_NNT |

Transferase = GDP-L-Galactose Guanyltransferase
Epimerase = GDP-D-Mannose epimerase

---

The invention claimed is:

1. A method for producing a plant cell or plant with increased ascorbate relative to a control plant, the method comprising transformation of a plant cell or plant with a polynucleotide encoding at least one of:
   a) a polypeptide with the amino acid sequence of SEQ ID NO:1, and
   b) a polypeptide with an amino acid sequence with at least 72% identity to SEQ ID NO:1 and having GDP-L-Galactose Guanyltransferase activity,
   wherein the polypeptide in b) further comprises the amino acid sequences of SEQ ID NO:12 and SEQ ID NO:13,
   wherein the control plant is not a plant with a mutation that results in decreased ascorbate, and wherein the control plant has not been transformed with the polynucleotide.

2. The method of claim 1 in which the plant cell or plant is transformed with a polynucleotide encoding a polypeptide with the amino acid sequence of SEQ ID NO:1.

3. The method of claim 1 in which the plant cell or plant is also transformed with a polynucleotide encoding a GDP-D-Mannose epimerase.

4. A method for producing a plant cell or plant with increased ascorbate content, the method comprising transformation of a plant cell or plant with:

a) a polynucleotide encoding a GDP-D-Mannose epimerase comprising amino acid sequences of SEQ ID NO:36 and SEQ ID NO: 37; and
b) a polynucleotide encoding a GDP-L-Galactose Guanyltransferase comprising amino acid sequences of SEQ ID NO:12 and SEQ ID NO: 13 wherein the increase in ascorbate content produced when both the epimerase and the transferase are over-expressed together is greater than the increase produced by over-expressing the epimerase alone added to the increase produced by over-expressing the transferase alone.

5. The method of claim 4 in which the GDP-D-Mannose epimerase comprises a sequence with at least 70% sequence identity to the amino acid sequence of SEQ ID NO: 25.

6. The method of claim 4 in which the GDP-D-Mannose epimerase comprises the amino acid sequence of SEQ ID NO: 25.

7. The method of claim 4 in which the GDP-L-Galactose Guanyltransferase comprises a sequence with at least 72% sequence identity to a polypeptide with the amino acid sequence of SEQ ID NO:1.

8. The method of claim 4 in which the GDP-L-Galactose Guanyltransferase comprises the amino acid sequence of SEQ ID NO:1.

9. A genetic construct comprising a polynucleotide encoding a polypeptide comprising a sequence with at least 78% identity to the sequence of SEQ ID NO: 1, wherein the polypeptide is a GDP-L-Galactose Guanyltransferase, wherein percent identity is calculated over amino acids 1 to 450 of SEQ ID NO: 1, wherein the polypeptide comprises the sequences of SEQ ID NO: 12 and SEQ ID NO:13, and wherein the polynucleotide is operably linked to at least one of:
   a) a heterologous promoter, and
   b) a promoter to which the polynucleotide is not operably linked in nature.

10. The genetic construct of claim 9 wherein the polypeptide comprises the sequence of SEQ ID NO:1.

11. A silencing construct which comprises a promoter polynucleotide sequence operably linked to:
   a) a polynucleotide comprising a fragment, of at least 21 nucleotides in length, of the polynucleotide encoding a polypeptide comprising a sequence with at least 78% identity to the sequence of SEQ ID NO: 1, wherein the polypeptide is a GDP-L-Galactose Guanyltransferase, and wherein percent identity is calculated over amino acids 1 to 450 of SEQ ID NO: 1;
   b) a polynucleotide comprising a complement, of at least 21 nucleotides in length, of the polynucleotide encoding a polypeptide comprising a sequence with at least 78% identity to the sequence of SEQ ID NO: 1, wherein the polypeptide is a GDP-L-Galactose Guanyltransferase, and wherein percent identity is calculated over amino acids 1 to 450 of SEQ ID NO: 1; or
   c) a polynucleotide comprising a sequence, of at least 21 nucleotides in length, capable of hybridising to the polynucleotide encoding a polypeptide comprising a sequence with at least 78% identity to the sequence of SEQ ID NO: 1, wherein the polypeptide is a GDP-L-Galactose Guanyltransferase, and wherein percent identity is calculated over amino acids 1 to 450 of SEQ ID NO: 1,
   wherein the promoter is at least one of:
   a) a heterologous promoter, and
   b) a promoter to which the polynucleotide is not operably linked in nature.

12. A host cell, plant cell or plant, wherein the host cell, plant cell or plant comprises the genetic construct of claim 9.

13. A host cell, plant cell or plant genetically modified to express at least one polynucleotide encoding a polypeptide comprising a sequence with at least 78% identity to the sequence of SEQ ID NO:1, wherein the polypeptide is a GDP-L-Galactose Guanyltrasnferase, wherein percent identity is calculated over amino acids 1 to 450 of SEQ ID NO:1, wherein the polypeptide comprises the sequences of SEQ ID NO: 12 and SEQ ID NO:13, and wherein the polynucleotide is operably linked to at least one of:
   a) a heterologous promoter, ar and
   b) a promoter to which the polynucleotide is not operably linked in nature.

14. The host cell, plant cell or plant of claim 13 which is further modified to express a polynucleotide encoding a GDP-D-Mannose epimerase.

15. A method for the biosynthesis of ascorbate comprising the step of culturing the host cell, plant cell or plant of claim 13 in the presence of an ascorbate precursor which is supplied to, or is naturally present within the host cell, plant cell or plant.

16. A method for selecting a plant having increased GDP-L-Galactose Guanyltransferase activity or ascorbic acid content relative to that in a control plant, the method comprising testing of a plant for an increase in expression, relative to that in the control plant, of a polynucleotide encoding a polypeptide comprising a sequence with at least 78% identity to the sequence of SEQ ID NO: 1, wherein the polypeptide is a GDP-L-Galactose Guanyltransferase, wherein percent identity is calculated over amino acids 1 to 450 of SEQ ID NO: 1, wherein the polypeptide comprises the sequences of SEQ ID NO: 12 and SEQ ID NO: 13, wherein the control plant is not transformed with the polynucleotide and the control plant is not a plant with a mutation that results in decreased ascorbate.

17. A plant cell or plant produced by the method of claim 1.

18. A method of producing L-Galactose-1-phosphate, the method comprising contacting GDP-L-Galactose and a GDP acceptor, including either a Hexose-1-phosphate or phosphate, with the expression product of the expression construct of claim 9 to obtain L-Galactose-1-phosphate.

19. A host cell, plant cell or plant, wherein the host cell, plant cell or plant comprises the genetic construct of claim 10.

20. A host cell, plant cell or plant, wherein the host cell, plant cell or plant comprises the silencing construct of claim 11.

21. A method for producing a plant cell or plant with increased ascorbate relative to a control plant cell or plant, the method comprising the steps:
   1) transformation of a plant cell or plant with a polynucleotide encoding at least one of:
      a) a polypeptide with the amino acid sequence of SEQ ID NO:1, and
      b) a polypeptide with an amino acid sequence with at least 72% identity to SEQ ID NO:1 and having GDP-L-Galactose Guanyltransferase activity,
   wherein the polypeptide in b) further comprises the amino acid sequences of SEQ ID NO:12 and SEQ ID NO:13, and
   2) testing the plant cell or plant cell for increased ascorbate relative to the control plant cell or plant,
   wherein the control plant cell or plant is not a plant cell or plant with a mutation that results in decreased ascorbate, and wherein the control plant cell or plant has not been transformed with the polynucleotide.

* * * * *